US012522669B2

(12) United States Patent
Nezu et al.

(10) Patent No.: US 12,522,669 B2
(45) **Date of Patent: *Jan. 13, 2026**

(54) CYTOTOXICITY-INDUCING THERAPEUTIC AGENT

(71) Applicant: Chugai Seiyaku Kabushiki Kaisha, Tokyo (JP)

(72) Inventors: Junichi Nezu, Shizuoka (JP); Takahiro Ishiguro, Kanagawa (JP); Atsushi Narita, Shizuoka (JP); Akihisa Sakamoto, Shizuoka (JP); Yumiko Kawai, Kanagawa (JP); Tomoyuki Igawa, Shizuoka (JP); Taichi Kuramochi, Shizuoka (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 18/590,651

(22) Filed: Feb. 28, 2024

(65) Prior Publication Data

US 2024/0294672 A1 Sep. 5, 2024

Related U.S. Application Data

(62) Division of application No. 17/367,909, filed on Jul. 6, 2021, which is a division of application No. 13/990,088, filed as application No. PCT/JP2011/077603 on Nov. 30, 2011, now Pat. No. 11,066,483.

(30) Foreign Application Priority Data

Nov. 30, 2010 (JP) ................................ 2010-266760
May 31, 2011 (JP) ................................ 2011-121771
Oct. 31, 2011 (JP) ................................ 2011-238818

(51) Int. Cl.

| | |
|---|---|
| ***C07K 16/46*** | (2006.01) |
| ***C07K 16/28*** | (2006.01) |
| ***C07K 16/30*** | (2006.01) |
| *A61K 39/00* | (2006.01) |

(52) U.S. Cl.

CPC .......... *C07K 16/46* (2013.01); *C07K 16/2809* (2013.01); *C07K 16/2863* (2013.01); *C07K 16/30* (2013.01); *C07K 16/303* (2013.01); *A61K 2039/505* (2013.01); *C07K 2317/31* (2013.01); *C07K 2317/35* (2013.01); *C07K 2317/41* (2013.01); *C07K 2317/52* (2013.01); *C07K 2317/55* (2013.01); *C07K 2317/56* (2013.01); *C07K 2317/60* (2013.01); *C07K 2317/622* (2013.01); *C07K 2317/64* (2013.01); *C07K 2317/71* (2013.01); *C07K 2317/73* (2013.01); *C07K 2317/94* (2013.01); *C07K 2319/00* (2013.01); *C07K 2319/30* (2013.01)

(58) Field of Classification Search

CPC ............ C07K 16/2809; C07K 16/2863; C07K 2317/31; C07K 2317/71

USPC ...................................................... 424/133.1

See application file for complete search history.

(56) References Cited

U.S. PATENT DOCUMENTS

| | | | | |
|---|---|---|---|---|
| 4,658,019 | A | 4/1987 | Kung et al. | |
| 5,474,771 | A | 12/1995 | Lederman et al. | |
| 5,585,097 | A | 12/1996 | Bolt et al. | |
| 5,595,756 | A | 1/1997 | Bally et al. | |
| 5,601,819 | A | 2/1997 | Wong et al. | |
| 5,624,821 | A | 4/1997 | Winter et al. | |
| 5,648,260 | A | 7/1997 | Winter et al. | |
| 5,859,205 | A | 1/1999 | Adair et al. | |
| 5,945,311 | A | 8/1999 | Lindhofer et al. | |
| 6,025,165 | A | 2/2000 | Whitlow et al. | |
| 6,129,914 | A | 10/2000 | Weiner | |
| 6,143,297 | A | 11/2000 | Bluestone | |
| 6,737,056 | B1 | 5/2004 | Presta | |
| 8,080,250 | B1 | 12/2011 | Govindan et al. | |
| 8,735,545 | B2 | 5/2014 | Lazar et al. | |
| 9,096,651 | B2 | 8/2015 | Igawa et al. | |
| 9,315,567 | B2 | 4/2016 | Chang et al. | |
| 9,334,331 | B2 | 5/2016 | Igawa et al. | |
| 9,644,025 | B2 | 5/2017 | Black et al. | |
| 9,670,269 | B2 | 6/2017 | Igawa et al. | |
| 9,751,942 | B2 * | 9/2017 | Kawai | A61K 39/3955 |
| 9,861,633 | B2 | 1/2018 | Mahamed et al. | |
| 9,975,966 | B2 | 5/2018 | Nezu et al. | |
| 10,301,391 | B2 | 5/2019 | Raum et al. | |
| 10,421,807 | B2 | 9/2019 | Gonzales et al. | |
| 10,435,458 | B2 | 10/2019 | Kuramochi et al. | |
| 10,544,220 | B2 * | 1/2020 | Engelberts | C07K 16/30 |
| 10,759,870 | B2 | 9/2020 | Teranishi et al. | |

(Continued)

FOREIGN PATENT DOCUMENTS

| | | | |
|---|---|---|---|
| CA | 2658557 | A1 * | 2/2008 |
| CA | 2819530 | A1 | 6/2012 |

(Continued)

OTHER PUBLICATIONS

U.S. Appl. No. 18/611,460, filed Jul. 20, 2021, Nezu Junichi.*
Almagro & Franssen, Frontiers in Bioscience, 13:1619-33 (2008).*
Edwards et al., J Mol Biol 334:103-118 (2003).*
Marchalonis et al., Dev & Comp Immunol. 30:223-247 (2006).*
Lippow et al., Nature Biotechnology, 25(10):1171-1176 (2007).*
Sulea et al., Scientific Reports, 8(260):1-11 (2018).*
Hasegawa et al., MABS, vol. 9, No. 5, pp. 854-873 (2017).*
Altshuler et al., Biochemistry (Moscow), 75(13):1584-1605 (2010).*
Lutterbuese, R. et al., Proc. Natl. Acad. Sci. USA 107, 12605-12610 (2010)).*
Vajda et al., Current Opinion in Structural Biology, 67 pp. 226-231 (2021).*

(Continued)

*Primary Examiner* — Lynn A Bristol
(74) *Attorney, Agent, or Firm* — Fish & Richardson P.C.

(57) ABSTRACT

Disclosed are bispecific antibodies with heavy chain constant regions having the sequence of an IgG1 constant region with one or more mutations including one or more substitutions that reduce the ability of the heavy chain constant regions to bind to a human Fcγ receptor.

25 Claims, 26 Drawing Sheets

Specification includes a Sequence Listing.

(56) References Cited

U.S. PATENT DOCUMENTS 10,934,344 B2 3/2021 Igawa et al.
11,001,643 B2 5/2021 Nezu et al.
11,066,483 B2 * 7/2021 Nezu .................... C07K 16/303
11,072,666 B2 7/2021 Kinoshita et al.
11,130,808 B2 9/2021 Yan et al.
11,485,790 B2 * 11/2022 Igawa ..................... A61P 35/00
11,505,605 B2 11/2022 Igawa et al.
11,649,262 B2 5/2023 Tanaka et al.
11,649,293 B2 5/2023 Igawa et al.
11,660,340 B2 5/2023 Tsunenari et al.
11,667,713 B2 * 6/2023 Kamikawaji .......... C07K 16/28 424/136.1
11,685,781 B2 * 6/2023 Bonvini ............. C07K 16/2809 424/136.1
11,718,680 B2 * 8/2023 Bacac ..................... A61P 43/00 424/154.1
11,851,476 B2 12/2023 Kuramochi et al.
2002/0102278 A1 8/2002 Guo
2002/0137897 A1 9/2002 Stevens et al.
2002/0164668 A1 11/2002 Durham et al.
2003/0035798 A1 2/2003 Fang et al.
2003/0078385 A1 4/2003 Arathoon et al.
2003/0190311 A1 10/2003 Dall'Aqua et al.
2003/0207346 A1 11/2003 Arathoon et al.
2003/0216551 A1 11/2003 Delovitch
2003/0232049 A1 12/2003 Jung
2004/0002587 A1 1/2004 Watkins et al.
2004/0236080 A1 11/2004 Aburatani et al.
2005/0118174 A1 6/2005 Presta
2005/0130224 A1 6/2005 Saito et al.
2005/0191293 A1 9/2005 Deshpande et al.
2006/0134709 A1 6/2006 Stavenhagen et al.
2006/0134805 A1 6/2006 Berg et al.
2006/0159673 A1 7/2006 Kojima et al.
2006/0160184 A1 7/2006 Hoogenboom et al.
2006/0177896 A1 8/2006 Mach et al.
2006/0204493 A1 9/2006 Huang et al.
2006/0235208 A1 10/2006 Lazar et al.
2006/0275282 A1 12/2006 Moore et al.
2007/0054354 A1 3/2007 Humphreys et al.
2007/0110757 A1 5/2007 Wei et al.
2007/0178092 A1 8/2007 Bolt et al.
2007/0224188 A1 9/2007 Allan et al.
2007/0231329 A1 10/2007 Lazar et al.
2007/0254831 A1 11/2007 Mezo et al.
2007/0287170 A1 12/2007 Davis et al.
2008/0025979 A1 1/2008 Honjo et al.
2008/0095755 A1 4/2008 Kink et al.
2008/0220000 A1 9/2008 Moore et al.
2008/0317758 A9 12/2008 Presta
2009/0053211 A9 2/2009 Lazar et al.
2009/0053233 A1 2/2009 De Romeuf et al.
2009/0068192 A1 3/2009 Jure-Kunkel et al.
2009/0226466 A1 9/2009 Fong et al.
2009/0274649 A1 11/2009 Qu et al.
2009/0324589 A1 12/2009 Igawa et al.
2010/0004431 A1 1/2010 Bernett et al.
2010/0015133 A1 1/2010 Igawa et al.
2010/0105874 A1 4/2010 Schuurman et al.
2010/0178298 A1 7/2010 Lindhofer et al.
2010/0221252 A1 9/2010 Bigler et al.
2010/0286374 A1 11/2010 Kannan et al.
2010/0298542 A1 11/2010 Igawa et al.
2010/0322935 A1 12/2010 Croasdale et al.
2010/0331527 A1 12/2010 Davis et al.
2011/0021755 A1 1/2011 Lazar et al.
2011/0059076 A1 3/2011 McDonagh et al.
2011/0059469 A1 3/2011 Aburatani et al.
2011/0081354 A1 4/2011 Korman et al.
2011/0123532 A1 5/2011 Gurney et al.
2011/0150892 A1 6/2011 Thudium et al.
2011/0236374 A1 9/2011 Shitara et al.
2011/0287009 A1 11/2011 Scheer et al.
2011/0293513 A1 12/2011 Govindan et al.
2012/0021409 A1 1/2012 McWhirter et al.
2012/0034228 A1 2/2012 Kufer et al.
2012/0065379 A1 3/2012 Igawa et al.
2012/0076727 A1 3/2012 McBride et al.
2012/0100140 A1 4/2012 Reyes et al.
2012/0149876 A1 6/2012 Von Kreudenstein et al.
2012/0184718 A1 7/2012 Peter et al.
2012/0213781 A1 8/2012 Hilbert
2012/0269826 A1 10/2012 Mckee et al.
2013/0018174 A1 1/2013 Igawa et al.
2013/0039913 A1 2/2013 Labrijn et al.
2013/0058937 A1 3/2013 Auer et al.
2013/0085199 A1 4/2013 Tamori et al.
2013/0115208 A1 5/2013 Ho et al.
2013/0129730 A1 5/2013 Kufer et al.
2014/0051833 A1 2/2014 Fischer et al.
2014/0093496 A1 4/2014 Mimoto et al.
2014/0112914 A1 4/2014 Nezu et al.
2014/0154270 A1 6/2014 Wang et al.
2014/0294759 A1 10/2014 Chu et al.
2014/0302037 A1 10/2014 Borges et al.
2014/0348832 A1 11/2014 Zhu et al.
2014/0370020 A1 12/2014 Kuramochi et al.
2014/0377253 A1 12/2014 Harding et al.
2015/0166661 A1 6/2015 Chen et al.
2015/0297820 A1 10/2015 Kawai
2015/0337053 A1 11/2015 McCarthy et al.
2016/0024147 A1 1/2016 Tustian et al.
2016/0152722 A1 6/2016 Sharp et al.
2016/0168259 A1 6/2016 Igawa et al.
2016/0229915 A1 8/2016 Igawa et al.
2016/0333095 A1 11/2016 Van et al.
2017/0015758 A1 1/2017 Hammond et al.
2017/0022287 A1 1/2017 Igawa et al.
2017/0260271 A1 9/2017 Igawa et al.
2017/0267783 A1 9/2017 Nezu et al.
2017/0275332 A1 9/2017 Igawa et al.
2018/0162902 A1 6/2018 Igawa et al.
2018/0192623 A1 7/2018 Jishage et al.
2018/0244805 A1 8/2018 Nezu et al.
2018/0326058 A1 11/2018 Tsunenari et al.
2018/0346605 A1 12/2018 Chiu et al.
2019/0062368 A1 2/2019 Igawa et al.
2019/0077872 A1 3/2019 Igawa
2019/0330268 A1 10/2019 Tanaka et al.
2019/0352334 A1 11/2019 Igawa et al.
2019/0352421 A1 11/2019 Adams et al.
2020/0087380 A1 3/2020 Kuramochi et al.
2020/0123256 A1 4/2020 Hoshino et al.
2020/0190213 A1 6/2020 Preyer et al.
2020/0207805 A1 7/2020 Igawa et al.
2020/0223940 A1 7/2020 Teranishi et al.
2020/0354473 A1 11/2020 Teranishi et al.
2021/0040147 A1 2/2021 Igawa et al.
2021/0054076 A1 2/2021 Kimura et al.
2021/0155713 A1 * 5/2021 Didonato ........... C07K 16/2896
2021/0292360 A1 9/2021 Igawa et al.
2022/0041756 A1 * 2/2022 Nezu ...................... C07K 16/30
2022/0135618 A1 5/2022 Igawa et al.
2022/0348651 A1 * 11/2022 DiDonato .......... C07K 16/2818
2022/0348658 A1 11/2022 Ishiguro et al.
2022/0389054 A1 12/2022 Igawa et al.
2023/0057904 A1 2/2023 Kimura et al.
2023/0075499 A1 3/2023 Kim et al.
2023/0151112 A1 5/2023 Igawa et al.
2023/0227498 A1 7/2023 Igawa et al.
2023/0235056 A1 7/2023 Tanaka et al.
2024/0083939 A1 3/2024 Igawa et al.
2024/0150465 A1 * 5/2024 Kamikawaji ........... A61P 35/00
2024/0239890 A1 7/2024 Hoshino et al.
2024/0262933 A1 * 8/2024 Nezu ...................... C07K 16/46
2024/0391952 A1 11/2024 Igawa et al.

FOREIGN PATENT DOCUMENTS

CA 2830972 A1 10/2012
CN 1842540 A 10/2006
CN 1984931 A 6/2007
CN 101198698 A 6/2008
CN 1763097 B 4/2011

(56) References Cited

FOREIGN PATENT DOCUMENTS

| | | | |
|---|---|---|---|
| CN | 102471378 | A | 5/2012 |
| CN | 102574921 | A | 7/2012 |
| CN | 103429737 | A | 12/2013 |
| CN | 103833852 | A | 6/2014 |
| CN | 107002068 | A | 8/2017 |
| EP | 0 637 593 | A1 | 2/1995 |
| EP | 1 378 520 | A1 | 1/2004 |
| EP | 1 510 943 | A1 | 3/2005 |
| EP | 1 605 058 | A1 | 12/2005 |
| EP | 1 674 111 | A1 | 6/2006 |
| EP | 1 449 238 | B1 | 11/2006 |
| EP | 1 870 459 | A1 | 12/2007 |
| EP | 1 876 236 | A1 | 1/2008 |
| EP | 2 009 101 | A1 | 12/2008 |
| EP | 2 107 115 | A1 | 10/2009 |
| EP | 2 194 006 | A1 | 6/2010 |
| EP | 2 194 066 | A1 | 6/2010 |
| EP | 2 196 541 | A1 | 6/2010 |
| EP | 2 241 578 | A1 | 10/2010 |
| EP | 2 270 051 | A2 | 1/2011 |
| EP | 2 431 393 | A1 | 3/2012 |
| EP | 2 445 936 | A1 | 5/2012 |
| EP | 2 522 724 | A1 | 11/2012 |
| EP | 2 543 730 | A1 | 1/2013 |
| EP | 2 576 621 | A1 | 4/2013 |
| EP | 1 776 384 | B1 | 6/2013 |
| EP | 2 644 698 | A1 | 10/2013 |
| EP | 2 647 707 | A1 | 10/2013 |
| EP | 2 698 431 | A1 | 2/2014 |
| EP | 1 931 709 | B1 | 12/2016 |
| EP | 3 130 606 | A1 | 2/2017 |
| EP | 2 368 911 | B1 | 5/2017 |
| EP | 3 199 628 | A1 | 8/2017 |
| EP | 1 141 024 | B1 | 8/2018 |
| EP | 3 378 488 | A1 | 9/2018 |
| EP | 3 434 767 | A1 | 1/2019 |
| EP | 3 690 050 | A1 | 8/2020 |
| JP | 9-506001 | A | 6/1997 |
| JP | 2002-521053 | A | 7/2002 |
| JP | 2002-540771 | A | 12/2002 |
| JP | 2003-512019 | A | 4/2003 |
| JP | 2004-508036 | A | 3/2004 |
| JP | 2004-321100 | A | 11/2004 |
| JP | 2005-537009 | A | 12/2005 |
| JP | 2007-503206 | A | 2/2007 |
| JP | 2007-532095 | A | 11/2007 |
| JP | 2008-503449 | A | 2/2008 |
| JP | 2008-505174 | A | 2/2008 |
| JP | 2008-522600 | A | 7/2008 |
| JP | 2008-523140 | A | 7/2008 |
| JP | 2008-523783 | A | 7/2008 |
| JP | 2009-500458 | A | 1/2009 |
| JP | 2009-507838 | A | 2/2009 |
| JP | 2009-526823 | A | 7/2009 |
| JP | 2009-527499 | A | 7/2009 |
| JP | 4511035 | B | 7/2010 |
| JP | 2010-200768 | A | 9/2010 |
| JP | 2010-532369 | A | 10/2010 |
| JP | 2011-508604 | A | 3/2011 |
| JP | 2012-504970 | A | 3/2012 |
| JP | 2012-515160 | A | 7/2012 |
| JP | 2012-515556 | A | 7/2012 |
| JP | 2012-521759 | A | 9/2012 |
| JP | 2012-522512 | A | 9/2012 |
| JP | 2012-224631 | A | 11/2012 |
| JP | 2012-528092 | A | 11/2012 |
| JP | 2012-531439 | A | 12/2012 |
| JP | 2013-039131 | A | 2/2013 |
| JP | 2013-505732 | A | 2/2013 |
| JP | 2013-508392 | A | 3/2013 |
| JP | 2013-512258 | A | 4/2013 |
| JP | 2013-528569 | A | 7/2013 |
| JP | 2015-510764 | A | 4/2015 |
| JP | 2015-535828 | A | 12/2015 |
| JP | 5912436 | B2 | 4/2016 |
| JP | 2016-69329 | A | 5/2016 |
| JP | 2016-538275 | A | 12/2016 |
| JP | 2017-504314 | A | 2/2017 |
| JP | 2017-513011 | A | 5/2017 |
| JP | 2018-531599 | A | 11/2018 |
| JP | 6773929 | B2 | 10/2020 |
| KR | 2008/0013875 | A | 2/2008 |
| KR | 2009/0107091 | A | 10/2009 |
| KR | 2010/0056467 | A | 5/2010 |
| KR | 2012/0123055 | A | 11/2012 |
| KR | 2013/0130765 | A | 12/2013 |
| KR | 2014/0014167 | A | 2/2014 |
| KR | 2014/0084249 | A | 7/2014 |
| MX | 349057 | B | 7/2017 |
| RU | 94028282 | A | 8/1994 |
| RU | 2179862 | C1 | 2/2002 |
| RU | 2006/104842 | A | 8/2007 |
| RU | 2323737 | C2 | 5/2008 |
| RU | 2337107 | C2 | 10/2008 |
| RU | 2355705 | C2 | 5/2009 |
| RU | 2009/149451 | A | 12/2009 |
| RU | 2012/112067 | A | 10/2013 |
| SG | 11201701119 | R | 3/2017 |
| TW | 2012/49872 | A1 | 12/2012 |
| TW | 2016/02132 | A | 1/2016 |
| TW | 2016/19193 | A | 6/2016 |
| WO | WO 95/33844 | A1 | 12/1995 |
| WO | WO 96/27011 | A1 | 9/1996 |
| WO | WO 98/50431 | A2 | 11/1998 |
| WO | WO 99/51642 | A1 | 10/1999 |
| WO | WO 99/58572 | A1 | 11/1999 |
| WO | WO 99/61057 | A2 | 12/1999 |
| WO | WO 00/06605 | A2 | 2/2000 |
| WO | WO 00/18806 | A1 | 4/2000 |
| WO | WO 00/42072 | A2 | 7/2000 |
| WO | WO 01/90192 | A2 | 11/2001 |
| WO | WO 02/20615 | A2 | 3/2002 |
| WO | WO 03/035835 | A2 | 5/2003 |
| WO | WO 03/074679 | A2 | 9/2003 |
| WO | WO 2004/003019 | A2 | 1/2004 |
| WO | WO 2004/010951 | A2 | 2/2004 |
| WO | WO 2004/020579 | A2 | 3/2004 |
| WO | WO 2004/029207 | A2 | 4/2004 |
| WO | WO 2004/035607 | A2 | 4/2004 |
| WO | WO 2004/052397 | A1 | 6/2004 |
| WO | WO 2004/063351 | A2 | 7/2004 |
| WO | WO 2004/065611 | A1 | 8/2004 |
| WO | WO 2004/099249 | A2 | 11/2004 |
| WO | WO 2004/103404 | A1 | 12/2004 |
| WO | WO 2005/000900 | A1 | 1/2005 |
| WO | WO 2005/018572 | A2 | 3/2005 |
| WO | WO 2005/035584 | A1 | 4/2005 |
| WO | WO 2005/040220 | A1 | 5/2005 |
| WO | WO 2005/044859 | A2 | 5/2005 |
| WO | WO 2005/061547 | A1 | 7/2005 |
| WO | WO 2005/063815 | A2 | 7/2005 |
| WO | WO 2005/092927 | A1 | 10/2005 |
| WO | WO 2005/115451 | A2 | 12/2005 |
| WO | WO 2005/118635 | A2 | 12/2005 |
| WO | WO 2006/019447 | A1 | 2/2006 |
| WO | WO 2006/020114 | A2 | 2/2006 |
| WO | WO 2006/061219 | A2 | 6/2006 |
| WO | WO 2006/065208 | A1 | 6/2006 |
| WO | WO 2006/105338 | A2 | 10/2006 |
| WO | WO 2006/106905 | A1 | 10/2006 |
| WO | WO 2006/109592 | A1 | 10/2006 |
| WO | WO 2006/113767 | A2 | 10/2006 |
| WO | WO 2007/009065 | A2 | 1/2007 |
| WO | WO 2007/033230 | A2 | 3/2007 |
| WO | WO 2007/041635 | A2 | 4/2007 |
| WO | WO 2007/053659 | A2 | 5/2007 |
| WO | WO 2007/093630 | A1 | 8/2007 |
| WO | WO 2007/110205 | A2 | 10/2007 |
| WO | WO 2007/114325 | A1 | 10/2007 |
| WO | WO 2007/141280 | A2 | 12/2007 |
| WO | WO 2007/145941 | A2 | 12/2007 |
| WO | WO 2007/147901 | A1 | 12/2007 |
| WO | WO 2008/051424 | A2 | 5/2008 |
| WO | WO 2008/079713 | A2 | 7/2008 |

(56) References Cited

FOREIGN PATENT DOCUMENTS

| | | | |
|---|---|---|---|
| WO | WO 2008/090960 | A1 | 7/2008 |
| WO | WO 2008/118970 | A2 | 10/2008 |
| WO | WO 2008/119565 | A2 | 10/2008 |
| WO | WO 2008/119567 | A2 | 10/2008 |
| WO | WO 2009/011941 | A2 | 1/2009 |
| WO | WO 2009/012394 | A1 | 1/2009 |
| WO | WO 2009/041613 | A1 | 4/2009 |
| WO | WO 2009/053368 | A1 | 4/2009 |
| WO | WO 2009/080252 | A1 | 7/2009 |
| WO | WO 2009/080253 | A1 | 7/2009 |
| WO | WO 2009/087978 | A1 | 7/2009 |
| WO | WO 2009/089004 | A1 | 7/2009 |
| WO | WO 2009/095478 | A1 | 8/2009 |
| WO | WO 2009/099829 | A1 | 8/2009 |
| WO | WO 2009/120922 | A2 | 10/2009 |
| WO | WO 2009/126920 | A2 | 10/2009 |
| WO | WO 2009/134776 | A2 | 11/2009 |
| WO | 2010006060 | * | 1/2010 |
| WO | WO 2010/028797 | A1 | 3/2010 |
| WO | WO 2010/034441 | A1 | 4/2010 |
| WO | WO 2010/037395 | A2 | 4/2010 |
| WO | WO 2010/037836 | A2 | 4/2010 |
| WO | WO 2010/042904 | A2 | 4/2010 |
| WO | WO 2010/065882 | A1 | 6/2010 |
| WO | WO 2010/066803 | A2 | 6/2010 |
| WO | WO 2010/075249 | A2 | 7/2010 |
| WO | WO 2010/080065 | A1 | 7/2010 |
| WO | WO 2010/085682 | A2 | 7/2010 |
| WO | WO 2010/102251 | A2 | 9/2010 |
| WO | WO 2010/111367 | A1 | 9/2010 |
| WO | WO 2010/120561 | A1 | 10/2010 |
| WO | WO 2010/129304 | A2 | 11/2010 |
| WO | WO 2010/131733 | A1 | 11/2010 |
| WO | WO 2010/136172 | A1 | 12/2010 |
| WO | WO 2010/151792 | A1 | 12/2010 |
| WO | WO 2011/025964 | A2 | 3/2011 |
| WO | WO 2011/039126 | A1 | 4/2011 |
| WO | WO 2011/050106 | A2 | 4/2011 |
| WO | WO 2011/057788 | A1 | 5/2011 |
| WO | WO 2011/066501 | A1 | 6/2011 |
| WO | WO 2011/078332 | A1 | 6/2011 |
| WO | WO 2011/108714 | A1 | 9/2011 |
| WO | WO 2011/121110 | A1 | 10/2011 |
| WO | WO 2011/125674 | A1 | 10/2011 |
| WO | WO 2011/147986 | A1 | 12/2011 |
| WO | WO 2012/003956 | A1 | 1/2012 |
| WO | WO 2012/067176 | A1 | 5/2012 |
| WO | WO 2012/073985 | A1 | 6/2012 |
| WO | WO 2012/088290 | A2 | 6/2012 |
| WO | WO 2012/095412 | A1 | 7/2012 |
| WO | WO 2012/115241 | A1 | 8/2012 |
| WO | WO 2012/131555 | A2 | 10/2012 |
| WO | WO 2012/145183 | A2 | 10/2012 |
| WO | WO 2012/156018 | A1 | 11/2012 |
| WO | WO 2012/175751 | A2 | 12/2012 |
| WO | WO 2013/026833 | A1 | 2/2013 |
| WO | WO 2013/065708 | A1 | 5/2013 |
| WO | WO 2013/070468 | A1 | 5/2013 |
| WO | WO 2013/072523 | A1 | 5/2013 |
| WO | WO 2013/092001 | A1 | 6/2013 |
| WO | WO 2013/136186 | A2 | 9/2013 |
| WO | WO 2013/158856 | A2 | 10/2013 |
| WO | WO 2013/181543 | A1 | 12/2013 |
| WO | WO 2014/047231 | A1 | 3/2014 |
| WO | WO 2014/051433 | A1 | 4/2014 |
| WO | WO 2014/075697 | A1 | 5/2014 |
| WO | WO 2014/075788 | A1 | 5/2014 |
| WO | WO 2014/089113 | A1 | 6/2014 |
| WO | WO 2014/108483 | A1 | 7/2014 |
| WO | WO 2014/116846 | A2 | 7/2014 |
| WO | WO 2014/138306 | A1 | 9/2014 |
| WO | WO 2014/145907 | A1 | 9/2014 |
| WO | WO 2014/165818 | A2 | 10/2014 |
| WO | WO 2015/046467 | A1 | 4/2015 |
| WO | WO 2015/046554 | A1 | 4/2015 |
| WO | WO 2015/063339 | A1 | 5/2015 |
| WO | WO 2015/069794 | A2 | 5/2015 |
| WO | WO 2015/095392 | A1 | 6/2015 |
| WO | WO 2015/124715 | A1 | 8/2015 |
| WO | WO 2015/149077 | A1 | 10/2015 |
| WO | WO 2015/156268 | A1 | 10/2015 |
| WO | WO 2015/164392 | A2 | 10/2015 |
| WO | WO 2015/174439 | A1 | 11/2015 |
| WO | WO 2016/047722 | A1 | 3/2016 |
| WO | WO 2016/105503 | A1 | 6/2016 |
| WO | WO 2016/179003 | A1 | 11/2016 |
| WO | WO 2016/194992 | A1 | 12/2016 |
| WO | WO 2017/060304 | A1 | 4/2017 |
| WO | WO 2017/086367 | A1 | 5/2017 |
| WO | WO 2017/086419 | A1 | 5/2017 |
| WO | WO 2017/115773 | A1 | 7/2017 |
| WO | WO 2017/159287 | A1 | 9/2017 |
| WO | WO 2018/054973 | A1 | 3/2018 |
| WO | WO 2018/093821 | A1 | 5/2018 |
| WO | WO 2018/191438 | A1 | 10/2018 |
| WO | WO 2018/203567 | A1 | 11/2018 |
| WO | WO 2019/131988 | A1 | 7/2019 |
| WO | WO 2019/135404 | A1 | 7/2019 |
| WO | WO 2020/095866 | A1 | 5/2020 |
| WO | WO 2020/153467 | A1 | 7/2020 |
| WO | WO 2020/250915 | A1 | 12/2020 |
| WO | WO 2021/006328 | A1 | 1/2021 |
| WO | WO 2021/010326 | | 1/2021 |
| WO | WO 2021/200896 | A1 | 10/2021 |
| WO | WO 2021/256555 | A1 | 12/2021 |

OTHER PUBLICATIONS

Marks et al., J. Biol. Chem. 295(29) 9823-9837 (2020 ).*
Akbar et al., Cell Reports 34, 108856, Mar. 16, 2021.*
Lo et al., BMC Genomics vol. 22, Article No. 116 (2021).*
Singh et al (British Journal of Cancer (2021) 124:1037-1048).*
Shin et al (Int. J. Mol. Sci. 2022, 23, 5686).*
Zhou et al (Biomarker Research (2021) 9:38).*
Middleburg et al (Cancers (2021) 13:287).*
Belmontes et al (Sci Transl. Med. 13:1-19 (2021)).*
Alarcon et al (J. Biol. Chem. (2020) 295(29) 10076-10076).*
Perosa et al (J Immunol (2009) 182 (1): 416-423).*
U.S. Appl. No. 18/176,201, Igawa et al., filed Feb. 28, 2023.
U.S. Appl. No. 15/617,008, Igawa et al., filed Jun. 8, 2017 (abandoned).
U.S. Appl. No. 15/875,847, Igawa et al., filed Jan. 19, 2018 (abandoned).
U.S. Appl. No. 16/155,673, Igawa et al., filed Oct. 9, 2018 (abandoned).
U.S. Appl. No. 16/448,088, Igawa et al., filed Jun. 21, 2019 (abandoned).
U.S. Appl. No. 16/815,089, Igawa et al., filed Mar. 11, 2020 (abandoned).
U.S. Appl. No. 17/076,938, Igawa et al., filed Oct. 22, 2020 (abandoned).
U.S. Appl. No. 17/336,538, Igawa et al., filed Jun. 2, 2021 (abandoned).
U.S. Appl. No. 17/574,614, Igawa et al., filed Jan. 13, 2022 (abandoned).
U.S. Appl. No. 17/821,494, Igawa et al., filed Aug. 23, 2022 (abandoned).
U.S. Appl. No. 18/193,697, Igawa et al., filed Mar. 31, 2023 (abandoned).
U.S. Appl. No. 18/505,180, Igawa et al., filed Nov. 9, 2023.
U.S. Appl. No. 16/692,676, Kuramochi et al., filed Nov. 22, 2019.
U.S. Appl. No. 16/605,556, Hoshino et al., filed Oct. 16, 2019.
U.S. Appl. No. 18/535,310, Hoshino et al., filed Dec. 11, 2023.
U.S. Appl. No. 15/578,931, Taniguchi et al., filed Dec. 1, 2017 (abandoned).
U.S. Appl. No. 17/225,273, Nezu et al., filed Apr. 8, 2021.
U.S. Appl. No. 17/290,439, Kodama et al., filed Apr. 30, 2021.
U.S. Appl. No. 17/352,652, Kinoshita et al., filed Jun. 21, 2021.
U.S. Appl. No. 17/424,603, Nezu et al., filed Jul. 21, 2021.
U.S. Appl. No. 17/625,868, Kamikawaji et al., filed Jan. 10, 2022.
U.S. Appl. No. 17/616,373, Ishiguro et al., filed Dec. 3, 2021.

(56) References Cited

OTHER PUBLICATIONS

U.S. Appl. No. 17/622,118, Kimura et al., filed Dec. 22, 2021.
U.S. Appl. No. 17/933,879, Igawa et al., filed Sep. 21, 2022.
U.S. Appl. No. 18/010,615, Tanaka et al., filed Dec. 15, 2022.
U.S. Appl. No. 14/351,654, filed Apr. 14, 2014, Kuramochi et al.
U.S. Appl. No. 15/302,439, filed Oct. 6, 2016, Igawa et al.
U.S. Appl. No. 15/310,162, filed Nov. 10, 2016, Igawa et al.
U.S. Appl. No. 15/467,654, filed Mar. 23, 2017, Nezu et al.
U.S. Appl. No. 15/490,936, filed Apr. 19, 2017, Igawa et al.
U.S. Appl. No. 15/578,931, filed Dec. 1, 2017, Taniguchi et al.
U.S. Appl. No. 15/617,008, filed Jun. 8, 2017, Igawa et al.
U.S. Appl. No. 15/776,541, filed May 16, 2018, Igawa.
U.S. Appl. No. 15/776,587, filed May 16, 2018, Tsunenari et al.
U.S. Appl. No. 15/875,847, filed Jan. 19, 2018, Igawa et al.
U.S. Appl. No. 15/963,221, filed Apr. 26, 2018, Nezu et al.
U.S. Appl. No. 16/061,454, filed Jun. 12, 2018, Tanaka et al.
U.S. Appl. No. 16/083,975, filed Sep. 11, 2018, Kinoshita et al.
U.S. Appl. No. 16/155,673, filed Oct. 9, 2018, Igawa et al.
U.S. Appl. No. 16/448,088, filed Jun. 21, 2019, Igawa et al.
U.S. Appl. No. 16/605,556, filed Oct. 16, 2019, Hoshino et al.
U.S. Appl. No. 16/692,676, filed Nov. 22, 2019, Kuramochi et al.
U.S. Appl. No. 16/815,089, filed Mar. 11, 2020, Igawa et al.
U.S. Appl. No. 17/076,938, filed Oct. 22, 2020, Igawa et al.
U.S. Appl. No. 17/225,273, filed Apr. 8, 2021, Nezu et al.
U.S. Appl. No. 17/290,439, filed Apr. 30, 2021, Kodama et al.
U.S. Appl. No. 17/336,538, filed Jun. 2, 2021, Igawa et al.
U.S. Appl. No. 17/352,652, filed Jun. 21, 2021, Kinoshita et al.
U.S. Appl. No. 17/424,603, filed Jul. 21, 2021, Nezu et al.
U.S. Appl. No. 17/616,373, filed Dec. 3, 2021, Ishiguro et al.
U.S. Appl. No. 17/622,118, filed Dec. 22, 2021, Kimura et al.
U.S. Appl. No. 17/574,614, filed Jan. 13, 2022, Igawa et al.
U.S. Appl. No. 17/625,868, filed Jan. 10, 2022, Kamikawaji et al.
U.S. Appl. No. 17/821,494, filed Aug. 23, 2022, Igawa et al.
U.S. Appl. No. 17/933,879, filed Sep. 21, 2022, Igawa et al.
U.S. Appl. No. 18/010,615, filed Dec. 15, 2022, Tanaka et al.
U.S. Appl. No. 18/176,201, filed Feb. 28, 2023, Igawa et al.
U.S. Appl. No. 18/193,697, filed Mar. 31, 2023, Igawa et al.
U.S. Appl. No. 18/505,180, filed Nov. 9, 2023, Igawa et al.
U.S. Appl. No. 18/535,310, filed Dec. 11, 2023, Hoshino et al.
U.S. Appl. No. 61/467,727, filed Mar. 25, 2011, Blein et al.
Abe et al., "Purification of monoclonal antibodies with light-chain heterogeneity produced by mouse hybridomas raised with NS-1 myelomas: application of hydrophobic interaction high-performance liquid chromatography," J Biochem Biophys Methods, Oct. 1993, 27(3):215-227.
Abe et al., "Novel Protein A Resin: Synthetic Polymer Matrix Design Impact on Antibody Binding Capacity," JSR Technical Review, No. 119, 2012, pp. 1-5, retrieved from the Internet on Feb. 17, 2017 at URL:http://www.jsr.co.jp/pdf/rd/tec119-1.pdf (with English translation).
Abuazza et al., "Claudins 6, 9, and 13 are developmentally expressed renal tight junction proteins," Am J Physiol Renal Physiol, Dec. 2006, 291(6):F1132-F1141.
Akbar et al., "A compact vocabulary of paratope-epitope interactions enables predictability of antibody-antigen binding," Cell Reports, Mar. 16, 2021, 34:108856, 21 pages.
Al Qaraghuli et al., "Antibody-protein binding and conformational changes: identifying allosteric signalling pathways to engineer a better effector response," Nature Scientific Reports, 2020, 10:13969, 10 pages.
Alarcon et al., "The CD3-γ and CD3-δ subunits of the T cell antigen receptor can be expressed within distinct functional TCR/CD3 complexes," EMBO J, Apr. 1991, 10(4):903-912.
Alignment of Fc domain sequences of catumaxomab and SEQ ID Nos. 23, 24, 25 and 26, 2 pages (cited in EPO opposition proceedings of European Patent No. 2 647 707 on May 31, 2019 and Jun. 12, 2019).
Allard et al., "Antigen binding properties of highly purified bispecific antibodies," Mol Immunol, Oct. 1992, 29(10):1219-1227.
Alley et al., "Antibody-drug conjugates: targeted drug delivery for cancer," Curr Opin Chem Biol, Aug. 2010, 14(4):529-537. doi: 10.1016/j.cbpa.2010.06.170. Epub Jul. 17, 2010.
Amann et al., "Therapeutic window of an EpCAM/CD3-specific BiTE antibody in mice is determined by a subpopulation of EpCAM-expressing lymphocytes that is absent in humans," Cancer Immunol Immunother, Jan. 2009, 58(1):95-109. Epub Jul. 2, 2008.
Amersham Biosciences, "Protein Purification Handbook," ed. AD, 2002, 137:16-18.
Amigorena et al., "Cytoplasmic Domain Heterogeneity and Functions of IgG Fc Receptors in B Lymphocytes," Science, Jun. 26, 1992, 256(5065):1808-1812.
Amigorena et al., "FcγRII expression in resting and activated B lymphocytes," Eur J Immunol, Aug. 1989, 19(8):1379-1385.
An et al., "IgG2m4, an engineered antibody isotype with reduced Fc function," mAbs, Nov.-Dec. 2009, 1(6):572-579.
Annex I. Analysis of the Examples of EP 2 787 078 (document submitted in EPO opposition proceedings of EP 2 787 078 on Feb. 28, 2020).
Arguments filed on Oct. 12, 2016 on U.S. Appl. No. 14/351,654 (document submitted in EPO opposition proceedings of EP 2 787 078 on Feb. 28, 2020).
Armour et al., "Differential binding to human FcγRIIa and FcγRIIb receptors by human IgG wildtype and mutant antibodies," Mol Immunol, Dec. 2003, 40(9):585-593.
Armour et al., "Recombinant human IgG molecules lacking Fcgamma receptor I binding and monocyte triggering activities," Eur J Immunol, 1999, 29(8):2613-2624.
Asano et al., "Highly Effective Recombinant Format of a Humanized IgG-like Bispecific Antibody for Cancer Immunotherapy with Retargeting of Lymphocytes to Tumor Cells," J Biol Chem, Sep. 2007, 282:27659-27665.
Asano et al., "Diabody-based Recombinant Formats of Humanized IgG-like Bispecific Antibody with Effective Retargeting of Lymphocytes to Tumor Cells," J Immunother, Oct. 2008, 31(8):752-761 (Abstract only).
Aschermann et al., "The other side of immunoglobulin G: suppressor of inflammation," Clin Exp Immunol, May 2010, 160(2):161-167. doi: 10.1111/j.1365-2249.2009.04081.x. Epub Dec. 16, 2009.
Ascierto et al., "Clinical Experiences With Anti-CD137 and Anti-PD1 Therapeutic Antibodies," Semin Oncol, Oct. 2010, 37(5):508-516.
Assi et al., "Safety and Efficacy of Blinatumomab in Combination With a Tyrosine Kinase Inhibitor for the Treatment of Relapsed Philadelphia Chromosome-positive Leukemia," Clin Lymphoma Myeloma Leuk, Dec. 2017, 17(12):897-901.
Auerbach et al., "Angiogenesis assays: Problems and pitfalls," Cancer Metastasis Rev, 2000 Jun. 2000, 19(1-2):167-172.
Bannerji et al., "Emerging Clinical Activity of REGN1979, an Anti-CD20 x Anti-CD3 Bispecific Antibody, in Patients with Relapsed/Refractory Follicular Lymphoma (FL), Diffuse Large B-Cell Lymphoma (DLBCL), and Other B-Cell Non-Hodgkin Lymphoma (B-NHL) Subtypes," Blood, 2018, 132(Supplement 1):1690, 21 pages.
Barach et al., "T cell coinhibition in prostate cancer: new immune evasion pathways and emerging therapeutics," Trends Mol Med, Jan. 2011, 17(1):47-55. doi: 10.1016/j.molmed.2010.09.006.
Bargou et al., "Tumor regression in cancer patients by very low doses of a T cell-engaging antibody," Science, 2008, 321(5891):974-977.
Baselga et al., "Novel anticancer targets: revisiting ERBB2 and discovering ERBB3," Nat Rev Cancer, Jul. 2009, 9(7):463-475.
Bastid et al., "ENTPD1/CD39 is a promising therapeutic target in oncology," Oncogene, Apr. 4, 2013:32(14):1743-1751. doi: 10.1038/onc.2012.269. Epub Jul. 2, 2012.
Bates et al., "Quantification of Regulatory T Cells Enables the Identification of High-Risk Breast Cancer Patients and Those at Risk of Late Relapse," J Clin Oncol, Dec. 1, 2006, 24(34):5373-5380.
Baeuerle et al., "Bispecific T-Cell Engaging Antibodies for Cancer Therapy," Cancer Res, Jun. 15, 2009, 69(12):4941-4944. doi: 10.1158/0008-5472.CAN-09-0547. Epub Jun. 9, 2009.

(56) References Cited

OTHER PUBLICATIONS

Baeuerle et al., "BiTE: Teaching antibodies to engage T-cells for cancer therapy," Curr Opin Mol Ther, Feb. 2009, 11(1):22-30.
Baudler et al., "Insulin-Like Growth Factor-1 Controls Type 2 T Cell-Independent B Cell Response," J Immunol, May 1, 2005, 174(9):5516-5525.
Beckman et al., "Antibody Constructs in Cancer Therapy—Protein Engineering Strategies to Improve Exposure in Solid Tumors," Cancer, 2007, 109(2):170-179. doi:10.1002/cncr.22402.
Bekeredjian-Ding et al., "Toll-like receptors—sentries in the B-cell response," Immunology, Nov. 2009, 128(3):311-323. doi: 10.1111/j.1365-2567.2009.03173.x.
Belmontes et al., "Immunotherapy combinations overcome resistance to bispecific T cell engager treatment in T cell-cold solid tumors," Sci Transl Med, Aug. 25, 2021, 13:1-19.
Bendig, "Humanization of Rodent Monoclonal Antibodies by CDR Grafting," Methods: A Companion to Methods in Enzymology, 1995, 8:83-93.
Berglund et al., "The epitope space of the human proteome," Protein Science, Apr. 2008, 17:606-613.
Bhatia et al., "CTLA4 Blockade Enhances the Anti-Tumor Activity of Therapy with an Anti-CD3-Based Bispecific Antibody," J Investig Med, Sep. 1997, 45(7):346A.
Bi et al., "Treatment of hepatocellular carcinoma with a GPC3-targeted bispecific T cell engager," Oncotarget, May 16, 2017, 8(32):52866-52876. doi: 10.18632/oncotarget.17905. eCollection Aug. 8, 2017.
Bluemel et al., "Epitope distance to the target cell membrane and antigen size determine the potency of T cell-mediated lysis by BiTE antibodies specific for a large melanoma surface antigen," Cancer Immunol Immunother, Aug. 2010, 59(8):1197-1209.
Bodelon et al., "Immunoglobulin domains in *Escherichia coli* and other enterobacteria: from pathogenesis to applications in antibody technologies," FEMS Microbiol Rev, Mar. 2013, 37(2):204-250. doi: 10.1111/j.1574-6976.2012.00347.x. Epub Jul. 23, 2012.
Bokemeyer, "Catumaxomab—trifunctional anti-EpCAM antibody used to treat malignant ascites," Expert Opin Biol Ther, 2010, 10(8):1259-1269.
Bolt et al., "The generation of a humanized, non-mitogenic CD3 monoclonal antibody which retains in vitro immunosuppressive properties," Eur J Immunol, Feb. 1993, 23(2):403-411.
Bono et al., "ING-1, a monoclonal antibody targeting Ep-CAM in patients with advanced adenocarcinomas," Clin Cancer Res, Nov. 15, 2004, 10(22):7555-7565.
Borch et al., "Reorienting the immune system in the treatment of cancer by using anti-PD-1 and anti-PD-L1 antibodies," Drug Discov Today, Sep. 2015, 20(9):1127-1134. doi: 10.1016/j.drudis.2015.07.003. Epub Jul. 17, 2015.
Bose et al., "Activating HER2 mutations in HER2 gene amplification negative breast cancer," Cancer Discov, Feb. 2013, 3(2):224-237.
Bowie et al., "Deciphering the Message in Protein Sequences: Tolerance to Amino Acid Substitutions," Science, Mar. 16, 1990, 247:1306-1310.
Branden et al., "Recognition of Foreign Molecules by the Immune System," Introduction to Protein Structure, $2^{nd}$ ed., 1999, pp. 299-323.
Brandl et al., "The effect of dexamethasone on polyclonal T cell activation and redirected target cell lysis as induced by a CD19/CD3-bispecific single-chain antibody construct," Cancer Immunol, Immunother, Oct. 2007, 56(10):1551-1563. Epub Feb. 20, 2007.
Brennan et al., "Safety and immunotoxicity assessment of immunomodulatory monoclonal antibodies," mAbs, May-Jun. 2010, 2(3):233-255. Epub May 23, 2010.
Brezski et al., "The origins, specificity, and potential biological relevance of human anti-IgG hinge autoantibodies," Scientific World Journal, May 26, 2011, 11:1153-1167.
Brischwein et al., "MT110: A novel bispecific single-chain antibody construct with high efficacy in eradicating established tumors," Mol Immunol, Mar. 2006, 43(8):1129-1143. doi: 10.1016/j.molimm.2005.07.034. Epub Sep. 1, 2005.
Brown et al., "Tolerance to Single, but not Multiple, Amino Acid Replacements in Antibody $V_H$ CDR2," J Immunol, May 1, 1996, 156(9):3285-3291.
Bruhns et al., "Specificity and affinity of human Fcγ receptors and their polymorphic variants for human IgG subclasses," Blood, Apr. 16, 2009, 113(16):3716-3725. Epub Nov. 18, 2008.
Bugelski et al., "Monoclonal antibody-induced cytokine-release syndrome," Expert Rev Clin Immunol, Sep. 2009, 5(5):499-521.
Buque et al., "Trial Watch: Immunomodulatory monoclonal antibodies for oncological indications," Oncoimmunology, Mar. 2, 2015, 4(4):e1008814. eCollection 2015.
Burges et al., "Effective relief of malignant ascites in patients with advanced ovarian cancer by a trifunctional anti-EpCAM x anti-CD3 antibody: a phase I/II study," Clin Cancer Res, Jul. 1, 2007, 13(13):3899-3905.
Burgess et al., "Possible dissociation of the heparin-binding and mitogenic activities of heparin-binding (acidic fibroblast) growth factor-1 from its receptor-binding activities by site-directed mutagenesis of a single lysine residue," J Cell Biol, Nov. 1990, 111(5 Pt 1):2129-2138.
Buszko et al., "Differential depletion of total T cells and regulatory T cells and prolonged allotransplant survival in CD38 humanized mice treated with polyclonal anti human thymocyte globulin," PLoS One, Mar. 3, 2017:12(3):e0173088. doi: 10 A33.1371/journal.pone.0173088. eCollection 2017.
Campoli et al., "Immunotherapy of malignant disease with tumor antigen-specific monoclonal antibodies," Clin Cancer Res, Jan. 1, 2010, 16(1):11-20. Epub Dec. 22, 2009.
Canfield et al., "The Binding Affinity of Human IgG for its High Affinity Fc Receptor is Determined by Multiple Amino Acids in the $C_H2$ Domain and Is Modulated by the Hinge Region," J Exp Med, Jun. 1, 1991, 173(6):1483-1491.
Carpenter et al., "Non-Fc Receptor-Binding Humanized Anti-CD3 Antibodies Induce Apoptosis of Activated Human T Cells," J Immunol, 2000, 165(11):6205-6213. doi:10.4049/jimmunol.165.11.6205.
Carter, "Bispecific human IgG by design," J Immunol Methods, Feb. 1, 2001, 248(1-2):7-15.
Carter et al., "Potent antibody therapeutics by design," Nat Rev Immunol, May 2006, 6(5):343-357.
Cespedes et al., "Mouse models in oncogenesis and cancer therapy," Clin Transl Oncol, 2006, 8(5):318-329. doi:10.1007/s12094-006-0177-7.
Chae et al., "Inhibition of the fibroblast growth factor receptor (FGFR) pathway: the current landscape and barriers to clinical application," Oncotarget, Feb. 28, 2017, 8(9):16052-16074.
Chamow et al., "A humanized, bispecific immunoadhesin-antibody that retargets CD3+ effectors to kill HIV-1-infected cells," J Immunol, Nov. 1, 1994, 153(9):4268-4280.
Chan, "The pre-ligand binding assembly domain: a potential target of inhibition of tumour necrosis factor receptor function," Ann Rheum Dis, Nov. 2000, 59(Suppl 1):i50-i53.
Chan et al., "Therapeutic antibodies for autoimmunity and inflammation," Nat Rev Immunol, May 2010, 10(5):301-316. doi: 10.1038/nri 2761.
Chandramohan et al., "Antibody, T-cell and dendritic cell immunotherapy for malignant brain tumors," Future Oncol, Jul. 2013, 9(7):977-990. doi: 10.2217/fon.13.47.
Chappel et al., "Identification of the Fcγ receptor class I binding site in human IgG through the use of recombinant IgG1/IgG2 hybrid and point-mutated antibodies," Proc Natl Acad Sci USA, Oct. 15, 1991, 88(20):9036-9040.
Chelius et al., "Structural and functional characterization of the trifunctional antibody catumaxomab," mAbs, May-Jun. 2010, 2(3):309-319. Epub May 16, 2010.
Chen et al., "Bispecific antibodies in cancer immunotherapy," Hum Vaccin Immunother, Oct. 2, 2016, 12(10):2491-2500. doi:10.1080/21645515.2016.1187802. Epub Jun. 1, 2016.

(56) References Cited

OTHER PUBLICATIONS

Cheng et al., "Interleukin-6 Induces Gr-1+CD11b+ Myeloid Cells to Suppress CD8+ T Cell-Mediated Liver Injury in Mice," PLoS One. Mar. 4, 2011;6(3):e17631. doi: 10.1371/journal.pone.0017631.
Chothia et al., "Domain Association in Immunoglobulin Molecules—The Packing of Variable Domains," J Mol Biol, Dec. 5, 1985, 186(3):651-663. doi: 10.1016/0022-2836(85)90137-8.
Choudhry et al., "A Retrospective Review of Tocilizumab for the Management of Blinatumomab (a Bispecific T Cell Engager)-Induced Cytokine Release Syndrome (CRS)," Blood, 2018, 132(Supplement 1):5211, 18 pages.
Christiansen et al., "Biological impediments to monoclonal antibody-based cancer immunotherapy," Mol Cancer Ther, Nov. 2004, 3(11):1493-501.
Claims filed on Sep. 5, 2018 in U.S. Appl. No. 14/351,654 (document submitted in EPO opposition proceedings of EP 2 787 078 on Feb. 28, 2020).
Clayton et al., "Unligated Epidermal Growth Factor Receptor Forms Higher Order Oligomers within Microclusters on A431 Cells That are Sensitive to Tyrosine Kinase Inhibitor Binding," Biochemistry, Apr. 17, 2007, 46(15):4589-4597. Epub Mar. 24, 2007.
Cole et al., "Human IgG2 variants of chimeric anti-CD3 are nonmitogenic to T cells," J Immunol, Oct. 1, 1997, 159(7):3613-3621.
Colman, "Effects of amino acid sequence changes on antibody-antigen interactions," Research in Immunology, Jan. 1994, 145:33-36.
Cong et al., "Ion transporters in brain tumors," Curr Med Chem, 2015, 22(10):1171-1181.
Annex 1, submitted by the patentee during examination proceedings on Sep. 18, 2015, 5 pages (cited in EPO opposition proceedings of EP 2 647 707 on May 31, 2019 and Jun. 12, 2019).
Curiel et al., "Specific recruitment of regulatory T cells in ovarian carcinoma fosters immune privilege and predicts reduced survival," Nat Med, Sep. 2004, 10(9):942-949. Epub Aug. 22, 2004.
Curriculum vitae of Dr. K. Philipp Holliger, 12 pages (submitted by the opponent in the EPO opposition proceedings of EP 2 787 078 on Mar. 4, 2021).
D'Arena et al., "Regulatory T-cell number is increased in chronic lymphocytic leukemia patients and correlates with progressive disease," Leuk Res, Mar. 2011, 35(3):363-368. doi: 10.1016/j.leukres.2010.08.010. Epub Sep. 28, 2010.
Dall'Acqua, "Modulation of the Effector Functions of a Human IgG1 through Engineering of Its Hinge Region," J Immunol, 2006, 177:1129-1138.
Dall'Acqua et al., "Increasing the Affinity of a Human IgGI for the Neonatal Fc Receptor: Biological Consequences," J Immunol, Nov. 1, 2002, 169(9):5171-5180.
Das et al., "Producing Bispecific and Bifunctional Antibodies," Methods Mol Med, 2005, 109:329-346.
D'Avis et al., "Constitutive Activation of Fibroblast Growth Factor Receptor 3 by Mutations Responsible for the Lethal Skeletal Dysplasia Thanatophoric Dysplasia Type 1," Cell Growth Differ, Jan. 1998, 9(1):71-78.
Davis et al., "Abatacept binds to the Fc receptor CD64 but does not mediate complement-dependent cytotoxicity or antibody-dependent cellular cytotoxicity," J Rheumatol, Nov. 2007, 34(11):2204-2210.
De Gast et al., "CD8 T cell activation after intravenous administration of CD3xCD19 bispecific antibody in patients with non-Hodgkin lymphoma," Cancer Immunol Immunother, Jun. 1995, 40(6):390-396.
De Vos Van Steenwijk et al., "Tumor-infiltrating CD14-positive myeloid cells and CD8-positive T-cells prolong survival in patients with cervical carcinoma," Int J Cancer, Dec. 15, 2013, 133(12):2884-2894. doi: 10.1002/ijc.28309. Epub Jul. 5, 2013.
Declaration of Dr. K. Philipp Holliger, 15 pages (submitted by the opponent in the EPO opposition proceedings of EP 2 787 078 on Mar. 4, 2021).
Deluca et al., "Fine-tuning of dendritic cell biology by the TNF superfamily," Nat Rev Immunol, Apr. 10, 2012, 12(5):339-351.
Demanet et al., "Treatment of murine B cell lymphoma with bispecific monoclonal antibodies (anti-idiotype x anti-CD3)," J Immunol, Aug. 1, 1991, 147(3):1091-1097.
Dennis, "Cancer: Off by a whisker," Nature, 2006, 442(7104):739-741. doi:10.1038/442739a.
Desjarlais et al., "Optimizing engagement of the immune system by anti-tumor antibodies: an engineer's perspective," Drug Discov Today, Nov. 2007, 12(21-22):898-910. Epub Oct. 22, 2007.
Dillon et al., "Structural and Functional Characterization of Disulfide Isoforms of the Human IgG2 Subclass," J Biol Chem, 2008, 283(23):16206-16215.
Di Martino et al., "Mutant fibroblast growth factor receptor 3 induces intracellular signaling and cellular transformation in a cell type- and mutation-specific matter," Oncogene, Dec. 3, 2009, 28(48):4306-4316.
Ding et al., "GSE1 predicts poor survival outcome in gastric cancer patients by SLC7A5 enhancement of tumor growth and metastasis," J Biol Chem, Mar. 16, 2018, 293(11):3949-3964.
Do et al., "A rapid method for determining dynamic binding capacity of resins for the purification of proteins," Protein Expr Purif, Aug. 2008, 60(2):147-150. doi: 10.1016/j.pep.2008.04.009. Epub May 3, 2008.
Document from file history of EP 2787078, submitted on Sep. 16, 2021, by opposer in EPO opposition proceedings of EP 2 787 078, 3 pages.
Dong et al., "Increased expression of MMP14 correlates with the poor prognosis of Chinese patients with gastric cancer," Gene, May 25, 2015, 563(1):29-34.
Drake, "Combined Immune Checkpoint Blockade," Semin Oncol, Aug. 2015, 42(4):656-662. doi: 10.1053/j.seminoncol.2015.05.002. Epub Jun. 3, 2015.
Dreier et al., "Extremely potent, rapid and costimuation-independent cytotoxic t-cell response against lymphoma cells catalyzed by a single-chain bispecific antibody," Int J Cancer, Aug. 20, 2002, 100(6):690-697.
Dubrot et al., "Treatment with anti-CD 137 mAbs causes intense accumulations of liver T cells without selective antitumor immunotherapeutic effects in this organ," Cancer Immunol Immunother, Aug. 2010, 59(8):1223-1233.
Dumont et al., "Monomeric Fc fusions: impact on pharmacokinetic and biological activity of protein therapeutics," BioDrugs, 2006, 20(3):151-160.
Edelman et al., "The covalent structure of an entire γG immunoglobulin molecule," Proc Natl Acad Sci USA, May 1969, 63(1):78-85.
Edwards et al., "The Remarkable Flexibility of the Human Antibody Repertoire; Isolation of Over One Thousand Different Antibodies to a Single Protein, Blys," J Mol Biol, Nov. 14, 2003, 334(1):103-118.
El Andaloussi et al., "Prolongation of survival following depletion of CD4+CD25+ regulatory T cells in mice with experimental brain tumors," J Neurosurg, Sep. 2006, 105(3):430-437.
Endo et al., "HER2 mutation status in Japanese HER2-positive breast cancer patients," Breast Cancer, Nov. 2016, 23(6):902-907.
English translation of the application as filed for EP 11845786, 123 pages (cited in the EPO opposition proceedings of EP 2 647 707 on May 31, 2019 and Jun. 12, 2019).
English translation of JP 2010-266760, 279 pages (submitted by Opponent 3 on Mar. 26, 2020 in EPO opposition proceedings of EP 2 647 707).
EPO opposition preliminary decision in opposition of EP 2 647 707, dated May 13, 2020, 23 pages.
EPO Opposition Division, Consolidated List of cited references submitted in EPO opposition proceedings of EP 2 647 707, dated Feb. 18, 2021, 5 pages.
EPO Opposition Division, Grounds for Decision and Minutes of Oral Proceedings in opposition of EP 2 647 707, dated Apr. 1, 2021, 51 pages.
Examination report in 18192844.1, dated Dec. 5, 2019, 6 pages (submitted by Opponent 3 on Mar. 26, 2020 in EPO opposition proceedings of EP 2 647 707).
Feige et al., "An Unfolded CH1 Domain Controls the Assembly and Secretion of IgG Antibodies," Mol Cell, Jun. 12, 2009, 34(5):569-579. doi: 0.1016/j.molcel.2009.04.028.

(56) References Cited

OTHER PUBLICATIONS

Feng et al., "Glypican-3 antibodies: A new therapeutic target for liver cancer," FEBS Lett, Jan. 21, 2014, 588(2):377-382. doi: 10.1016/j.febslet.2013.10.002. Epub Oct. 15, 2013.
Feucht et al., "T-cell responses against CD19+ pediatric acute lymphoblastic leukemia mediated by bispecific T-cell engager (BiTE) are regulated contrarily by PD-L1 and CD80/CD86 on leukemic blasts," Oncotarget, 2016, 7(47):76902-76919.
Filmus et al., "Protein family review—Glypicans," Genome Biol, May 22, 2008, 9(5):224. doi:10.1186/GB-2008-9-5-224.
Filmus et al., "Glypicans," J Clin Invest, Aug. 2001, 108(4):497-501.
Fischer et al., "Bispecific Antibodies: Molecules That Enable Novel Therapeutic Strategies," Pathobiology, 2007, 74(1):3-14.
Fisher et al., "Targeting of 4-1BB by monoclonal antibody PF-05082566 enhances T-cell function and promotes anti-tumor activity," Cancer Immunol Immunother, Oct. 2012, 61(10):1721-1733.
Form posted on EPO website and dated Mar. 2, 2021, disclosing that EP 2 647 707 was revoked in an oral proceeding that occurred on Feb. 25 and 26, 2021, 1 page.
French et al., "Tumor-Associated Lymphocytes and Increased FoxP3+ Regulatory T Cell Frequency Correlate with More Aggressive Papillary Thyroid Cancer," J Clin Endocrinol Metab, May 2010, 95(5):2325-2333. doi: 10.1210/jc.2009-2564. Epub Mar. 5, 2010.
Fujimori et al., "A Modeling Analysis of Monoclonal Antibody Percolation Through Tumors: A Binding-Site Barrier," J Nucl Med, 1990, 31(7):1191-1198.
Fukushima et al., "Aberrant methylation and silencing of the SPINT2 gene in high-grade gliomas," Cancer Sci, Sep. 2018, 109(9):2970-2979.
Furuse et al., "Claudins in occluding junctions of humans and flies," Trends Cell Biol, Apr. 2006, 16(4):181-188. Epub Mar. 14, 2006.
Furness et al., "Impact of tumour microenvironment and Fe receptors on the activity of immunomodulatory antibodies," Trends Immunol, Jul. 2014, 35(7):290-298. doi:10.1016/j.it.2014.05.002. Epub Jun. 18, 2014.
Gajewski et al., "Innate and adaptive immune cells in the tumor microenvironment," Nat Immunol, Oct. 2013, 14(10):1014-1022. doi: 10.1038/ni.2703.
Gao et al., "Ring finger protein 43 associates with gastric cancer progression and attenuates the stemness of gastric cancer stem-like cells via the Wnt-β/catenin signaling pathway," Stem Cell Res Ther, Apr. 26, 2017, 8(1):98, 11 pages.
Garber et al., "Bispecific antibodies rise again," Nat Rev Drug Discov, Nov. 2014, 13(11):799-801.
Garcia Roche et al., "Cytokine release syndrome. Reviewing a new entity in the intensive care unit," Med Intensiva (Engl ed.), Nov. 2019, 43(8):480-488.
GE Healthcare Life Sciences, "Dynamic binding capacity study on MabSelect SuRe™ LX for capturing high-titer monoclonal antibodies," Application Note 28-9875-25-AA, 2011, retrieved from the Internet on Feb. 17, 2017 at <http://www.processdevelopmentforum.com/images/articles/28-9875-25_AA_AN_DBC_study_on_MabSelect_SuRe_LX_final.pdf>.
GenBank NP_001070977.1, "Tumor necrosis factor receptor superfamily member 9 isoform 1 precursor [Mus musculus]," Mar. 23, 2014, 3 pages.
GenBank NP_001552.2, "Tumor necrosis factor receptor superfamily member 9 precursor [*Homo sapiens*]," Mar. 16, 2014, 3 pages.
Gerber et al., "High expression of FOXP3 in primary melanoma is associated with tumour progression," Br J Dermatol, Jan. 2014, 170(1):103-109. doi: 10.1111/bjd.12641.
Gillies et al., "Antigen binding and biological activities of engineered mutant chimeric antibodies with human tumor specificities," Hum Antibodies Hybridomas, 1990, 1(1):47-54.
Gobert et al., "Regulatory T Cells Recruited through CCL22/CCR4 are Selectively Activated in Lymphoid Infiltrates Surrounding Primary Breast Tumors and Lead to an Adverse Clinical Outcome," Cancer Res, Mar. 1, 2009, 69(5):2000-2009. doi: 10.1158/0008-5472.CAN-08-2360. Epub Feb. 24, 2009.
Goel et al., "Plasticity within the Antigen-Combining Site May Manifest as Molecular Mimicry in the Humoral Immune Response," J Immunol, 2004, 173:7358-7367.
Goel et al., "Genetically Engineered Tetravalent Single-Chain Fv of the Pancarcinoma Monoclonal Antibody CC49: Improved Biodistribution and Potential for Therapeutic Application," Cancer Res, Dec. 15, 2000, 60(24):6964-6971.
Goldstein et al., "Adoptive Cell Therapy for Lymphoma with CD4 T Cells Depleted of CD137-Expressing Regulatory T Cells," Cancer Res, Mar. 1, 2012, 72(5):1239-1247. doi: 10.1158/0008-5472.CAN-11-3375. Epub Jan. 9, 2012.
Gomes et al., "Knockdown of STEAP1 inhibits cell growth and induces apoptosis in LNCaP prostate cancer cells counteracting the effect of androgens," Med Oncol, Feb. 20, 2018, 35(3):40.
Gorbenko et al., "Generation of Monoclonal Antibody Targeting Fibroblast Growth Factor Receptor 3," Hybridoma, Aug. 2009, 28(4):295-300.
Graca, "Anti-CD3: from T cell depletion to tolerance induction," The Immune Synapse as a Novel Target for Therapy, 2008:59-61.
Gunasekaran et al., "Enhancing Antibody Fc Heterodimer Formation through Electrostatic Steering Effects," J Biol Chem, Jun. 18, 2010, 285(25):19637-19646.
Guo et al., "Extracellular domain of 4-1BBL enhanced the antitumoral efficacy of peripheral blood lymphocytes mediated by anti-CD3 × anti-Pgp bispecific diabody against human multidrug-resistant leukemia," Cell Immunol, Feb. 2008, 251(2):102-108. doi: 10.1016/j.cellimm.2008.04.006. Epub May 14, 2008.
Gupta et al., "Affinity chromatography and co-chromatography of bispecific monoclonal antibody immunoconjugates," J Biochem Biophys Methods, May 31, 2002, 51(3):203-216.
Gura, "Cancer Models—Systems for Identifying New Drugs are Often Faulty," Science, Nov. 7, 1997, 278(5340):1041-1042.
Haagen et al., "Unprimed CD4+ and CD8+ T cells can be rapidly activated by a CD3xCD19 bispecific antibody to proliferate and become cytotoxic," Cancer Immunol Immunother, Dec. 1994, 39(6):391-396.
Haagen et al., "Evaluation of Fcγ receptor mediated T-cell activation by two purified CD3xCD19 bispecific monoclonal antibodies with hybrid Fc domains," Ther Immunol, Oct. 1994, 1(5):279-87.
Haagen et al., "Interaction of human monocyte Fcγ receptors with rat IgG2b. A new indicator for the FcγRIIa (R-H131) polymorphism," J Immunol, Feb. 15, 1995, 154(4):1852-60.
Haiman et al., "Genome-Wide Testing of Putative Functional Exonic Variants in Relationship with Breast and Prostate Cancer Risk in a Multiethnic Population," PLoS Genet, Mar. 2013, 9(3):e1003419, 15 pages.
Hamid et al., "Anti-programmed death-1 and anti-programmed death-ligand 1 antibodies in cancer therapy," Expert Opin Biol Ther, Jun. 2013, 13(6):847-861. doi:10.1517/14712598.2013.770836. Epub Feb. 19, 2013.
Hammond et al., "Selective Targeting and Potent Control of Tumor Growth Using an EphA2/CD3-Bispecific Single-Chain Antibody Construct," Cancer Res, Apr. 15, 2007, 67(8):3927-3935. doi: 10.1158/0008-5472.CAN-06-2760.
Hanahan et al., "Hallmarks of Cancer: The Next Generation," Cell., Mar. 4, 2011, 144(5):646-674. doi: 10.1016/j.cell.2011.02.013.
Harada et al., "In vitro toxicological support to establish specification limit for anti-CD3 monospecific impurity in a bispecific T cell engager drug, ERY974," Toxicol In Vitro, Aug. 2020, 66:104841, 7 pages. doi: 10.1016/j.tiv.2020.104841. Epub Apr. 1, 2020.
Hart et al., "Identification of Tyrosine Residues in Constitutively Activated Fibroblast Growth Factor Receptor 3 Involved in Mitogenesis, Stat Activation, and Phosphatidylinositol 3-Kinase Activation," Mol Biol Cell, Apr. 2001, 12(4):931-942.
Hashizume et al., "Expression Patterns of Claudin Family of Tight Junction Membrane Proteins in Developing Mouse Submandibular Gland," Dev Dyn, Oct. 2004, 231(2):425-431.
Hausler et al., " Anti-CD39 and anti-CD73 antibodies A1 and 7G2 improve targeted therapy in ovarian cancer by blocking adenosine-dependent immune evasion," Am J Transl Res, 2014, 6(2):129-139.

(56) References Cited

OTHER PUBLICATIONS

Heiss et al., "The trifunctional antibody catumaxomab for the treatment of malignant ascites due to epithelial cancer: results of a prospective randomized phase II/III trial," Int J Cancer, 2010, 127:2209-2221.
Hernandez et al., "FGFR3 mutations in prostate cancer: association with low-grade tumors," Mod Pathol, Jun. 2009, 22(6):848-856.
Hess et al., "Cancer therapy with trifunctional antibodies: linking innate and adaptive immunity," Future Oncol, Jan. 2012, 8(1):73-85. doi: 10.2217/ fon.11.138.
Hessell et al., "Fc receptor but not complement binding is important in antibody protection against HIV," Nature, Sep. 6, 2007, 449(7158):101-104.
Heyman, "Feedback regulation by IgG antibodies," Immunol Lett, Aug. 5, 2003, 88(2):157-161.
Hezareh et al., "Effector Function Activities of a Panel of Mutants of a Broadly Neutralizing Antibody against Human Immunodeficiency Virus Type 1," J Virol, Dec. 2001, 75(24):12161-12168.
Hinton et al., "An engineered human IgG1 antibody with longer serum half-life," J Immunol, Jan. 1, 2006, 176:346-356.
Hiraoka et al., "Prevalence of FOXP3+ Regulatory T Cells Increases During the Progression of Pancreatic Ductal Adenocarcinoma and Its Premalignant Lesions," Clin Cancer Res, Sep. 15, 2006, 12(18):5423-5434.
Ho et al., "Glypican-3: A new target for cancer immunotherapy," Eur J Cancer, Feb. 2011, 47(3):333-338. doi: 10.1016/j.ejca.2010.10.024. Epub Nov. 26, 2010.
Hombach et al., "A CD16/CD30 bispecific monoclonal antibody induces lysis of Hodgkin's cells by unstimulated natural killer cells in vitro and in vivo," Int J Cancer, 1993, 55:830-836.
Horne et al., "Noncovalent Association of Heavy and Light Chains of Human Immunoglobulins, III. Specific Interactions between $V_H$ and $V_L$," J Immunol, Aug. 1982, 129(2):660-664.
Hoseini et al., "Immunotherapy of hepatocellular carcinoma using chimeric antigen receptors and bispecific antibodies," Cancer Lett, Jul. 28, 2017, 399:44-52. doi: 10.1016/j.canlet.2017.04.013. Epub Apr. 17, 2017.
Houot et al., "Therapeutic effect of CD137 immunomodulation in lymphoma and its enhancement by $T_{reg}$ depletion," Blood, Oct. 15, 2009, 114(16):3431-3438.
Hornig et al., "Evaluating combinations of costimulatory antibody-ligand fusion proteins for targeted cancer immunotherapy," Cancer Immunol Immunother, 2013, 62(8):1369-1380. doi: 10.1007/s00262-013 1441-7. Epub May 30, 2013.
Hornig et al., "Combination of a Bispecific Antibody and Costimulatory Antibody-Ligand Fusion Proteins for Targeted Cancer Immunotherapy," J Immunother, Jun. 2012, 35(5):418-429. doi: 10.1097/CJI.Ob013e3182594387.
Huang et al., "Recombinant immunotherapeutics: current state and perspectives regarding the feasibility and market," Appl Microbiol Biotechnol, 2010, 87(2):401-410. doi: 10.1007/s00253-010-2590-7.
Hutchins et al., "Improved biodistribution, tumor targeting, and reduced immunogenicity in mice with a gamma 4 variant of Campath-1H," Proc Natl Acad Sci USA, Dec. 19, 1995, 92(26):11980-11984.
Hyman et al., "HER kinase inhibition in patients with HER2- and HER3-mutant cancers," Nature, Feb. 8, 2018, 554(7691):189-194.
Ibragimova et al., "Stability of the beta-sheet of the WW domain: A molecular dynamics simulation study," Biophys J, Oct. 1999, 77(4):2191-2198.
IMGT Scientific charts depicting the correspondence between Eu and Kabat numberings for the human IgG constant region, created May 17, 2001 and last updated Aug. 13, 2014.
Immunoglobin G—Review, 2011, https://www.invivogen.com/review-antibodygeneration2011.
Ishiguro et al., "An anti-glypican 3/CD3 bispecific T cell-redirecting antibody for treatment of solid tumors," Sci Transl Med, Oct. 4, 2017, 9(410). pii: eaal4291. doi: 10.1126/scitranslmed.aal4291.
Ishikawa et al., "Characterization of SEZ6L2 cell-surface protein as a novel prognostic marker for lung cancer," Cancer Sci, Aug. 2006, 97(8):737-745.
Iwai et al., "Therapeutic Agents for Gastric Cancer," Igan Chiryoyaku, Yakkyoku, Jan. 5, 2016, 67(1)138-141 (with English translation).
Iwata et al., "Daily ascending dosing in cynomolgus monkeys to mitigate cytokine release syndrome induced by ERY22, surrogate for T-cell redirecting bispecific antibody ERY974 for cancer immunotherapy," Toxicol Appl Pharmacol, Sep. 15, 2019, 379:114657. doi: 0.1016/j.taap.2019.114657. Epub Jul. 19, 2019.
Jackman et al., "Development of a two-part strategy to identify a therapeutic human bispecific antibody that inhibits IgE receptor signaling," J Biol Chem, Jul. 2, 2010, 285(27):20850-20859. doi: 10.1074/jbc.M110.113910. Epub May 5, 2010.
Jacobs et al., "Dendritic Cell Vaccination in Combination with Anti-CD25 Monoclonal Antibody Treatment: A Phase 1/11 Study in Metastatic Melanoma Patients," Clin Cancer Res, Oct. 15, 2010, 16(20):5067-5078. doi: 10.1158/1078-0432.CCR-10-1757. Epub Aug. 2010.
Jacobs et al., "Management of Cytokine Release Syndrome in AML Patients Treated with Flotetuzumab, a CD123xCD3 Bispecific Dart® Molecule for T-Cell Redirected Therapy," Blood, 2018, 132(Supplement 1):2738.
Jaeger, Clinical Immunology and Allergology, 2nd ed., M.: Medicina, 1990, 2:484-485 (with English translation).
Jain et al., "Engineering antibodies for clinical applications," Trends Biotechnol, 2007, 25(7):307-316.
Jain, "Barriers to Drug Delivery in Solid Tumors," Sci Am, Jul. 1994, 271(1):58-65.
Jefferis et al., "Interaction sites on human IgG-Fc for FcγR: current models," Immunol Lett, Jun. 3, 2002, 82(1-2):57-65.
Jendeberg et al., "Engineering of $FC_1$ and $Fc_3$ from human immunoglobulin G to analyse subclass specificity for staphylococcal protein A," J Immunol Methods, 1997, 201(1):25-34.
Johnson et al., "Kabat database and its applications: 30 years after the first variability plot," Nucleic Acids Res, Jan. 1, 2000, 28(1):214-218.
Jones et al., "Growth factor receptor interplay and resistance in cancer," Endocr Relat Cancer, Dec. 2006, 13(1):S45-S51.
Jure-Kunkel et al., "Synergy between chemotherapeutic agents and CTLA-4 blockade in preclinical tumor models," Cancer Immunol Immunother, Sep. 2013, 62(9):1533-1545. doi: 10.1007/s00262-013-1451-5. Epub Jul. 20, 2013.
Kabat et al., "Identical V Region Amino Acid Sequences and Segments of Sequences in Antibodies of Different Specificities," J Immunol, Sep. 1, 1991, 147(5):1709-1719.
Kabat et al., Sequences of proteins of immunological interest, 5th ed., 1991, vol. 1, pp. 647-652 and 661-669.
Kadauke et al., "Early Administration of Tocilizumab (TOCI) for the Prevention of Grade 4 Cytokine Release Syndrome (CRS) After CD19-Directed CAR T-Cell Therapy (CTL019)," Cytotherapy, 2019, 21(5 Supplement):e2-e3.
Karshtedt et al., "Limits on Hard-to-Reproduce Inventions: Process Elements and Biotechnology's Compliance with the Enablement Requirement," Hastings Sci & Tech L J, 2011, 3(1):109-155.
Kasthuri et al., "Role of Tissue Factor in Cancer," J Clin Oncol, Oct. 10, 2009, 27(29):4834-4838. doi: 10.1200/JCO.2009.22.6324. Epub Sep. 8, 2009.
Kauer et al., "Tocilizumab, but not dexamethasone, prevents CRS without affecting antitumor activity of bispecific antibodies," J Immunother Cancer, May 2020, 8(1):e000621, 6 pages.
Kavuri et al., "HER2 activating mutations are targets for colorectal cancer treatment," Cancer Discov, Aug. 2015, 5(8):832-841.
Kawaida et al., "Distribution of CD4(+)CD25$^{high}$ regulatory T-cells in tumor-draining lymph nodes in patients with gastric cancer," J Surg Res, Mar. 2005, 124(1):151-157.
Kelleher et al., "Fibroblast growth factor receptors, developmental corruption and malignant disease," Carcinogenesis, Oct. 2013, 34(10):2198-2205.
Kenanova et al., "Tailoring the pharmacokinetics and positron emission tomography imaging properties of anti-carcinoembryonic antigen single-chain Fv-Fc antibody fragments," Cancer Res, Jan. 15, 2005, 65(2):622-631.

(56) References Cited

OTHER PUBLICATIONS

Khadka et al., "Management of cytokine release syndrome: an update on emerging antigen-specific T cell engaging immunotherapies," Immunotherapy, Jul. 2019, 11(10):851-857.
Khan et al., "Tumor infiltrating regulatory T cells: tractable targets for immunotherapy," Int Rev Immunol, Oct. 2010, 29(5):461-484. doi: 10.3109/08830185.2010.508854.
Khan et al., "Adjustable Locks and Flexible Keys: Plasticity of Epitope-Paratope Interactions in Germline Antibodies," J Immunol, 2014, 192:5398-5405.
Khantasup et al., "Design and Generation of Humanized Single-chain Fv Derived from Mouse Hybridoma for Potential Targeting Application," Monoclonal Antibodies in Immununodiagnosis and Immunotherapy, Dec. 2015, 34(6):404-417.
Kiewe et al., "Ertumaxomab: a trifunctional antibody for breast cancer treatment," Expert Opinion on Investigational Drugs, 2008, 17(10):1553-1558.
Kim et al., "TMPRSS4 induces invasion and epithelial-mesenchymal transition through upregulation of integrin α5 and its signaling pathways," Carcinogenesis, Apr. 2010, 31(4):597-606.
Kim et al., "Antibody Engineering for the Development of Therapeutic Antibodies," Mol Cells, Aug. 31, 2005, 20(1):17-29.
Kim et al., "Anti-CD137 mAb Deletes Both Donor CD4+ and CD8+ T Cells in Acute Graft-versus-host Disease," Immune Netw, Dec. 2011, 11(6):428-430. doi: 10.4110/in.2011.11.6.428. Epub Dec. 31, 2011.
Kim et al., "Antibody light chain variable domains and their biophysically improved versions for human immunotherapy," mAbs, Jan.-Feb. 2014, 6(1):219-235. doi: 10.4161/mabs 26844.
Kim et al., "Mapping the site on human IgG for binding of the MHC class I-related receptor, FcRn," Eur J Immunol, Sep. 1999, 29(9):2819-2825.
King, Applications and Engineering of Monoclonal Antibodies, 2005, pp. 146-147.
Klein et al., "Progress in overcoming the chain association issue in bispecific heterodimeric IgG antibodies," mAbs, Nov.-Dec. 2012, 4(6):653-663. doi: 10.4161/mabs.21379. Epub Aug. 27, 2012.
Klinger et al., "Harnessing T cells to fight cancer with BiTE® antibody constructs—past developments and future directions," Immunol Rev, Mar. 2016, 270(1):193-208. doi:10.1111/imr.12393.
Kobayashi et al., "FOXP3+ Regulatory T Cells Affect the Development and Progression of Hepatocarcinogenesis," Clin Cancer Res, Feb. 1, 2007, 13(3):902-911.
Kohnke et al., "Increase of PD-L1 expressing B-precursor ALL cells in a patient resistant to the CD19/CD3-bispecific T cell engager antibody blinatumomab," J Hematol Oncol, Oct. 8, 2015, 8:111. doi:10.1186/s13045-015-0213-6.
Kojima et al., "Downregulation of tight junction-associated Marvel protein marvelD3 during epithelial-mesenchymal transition in human pancreatic cancer cells," Exp Cell Res, Oct. 1, 2011, 317(16):2288-2298.
Kono et al., "CD4(+)CD25$^{high}$ regulatory T cells increase with tumor stage in patients with gastric and esophageal cancers," Cancer Immunol Immunother, Sep. 2006, 55(9):1064-1071. Epub Nov. 23, 2005.
Kontermann, "Dual targeting strategies with bispecific antibodies," mAbs, Mar.-Apr. 2012, 4(2):182-197. doi: 10.4161/mabs.4.2.19000. Epub Mar. 1, 2012.
Kontermann, "The Role of the Fc Region," Bispecific Antibodies, 2011, pp. 296-298.
Kontermann, "Recombinant bispecific antibodies for cancer therapy," Acta Pharmacol Sin, Jan. 2005, 26(1):1-9.
Kontermann, "Strategies to Extend Plasma Half-Lives of Recombinant Antibodies," BioDrugs, 2009, 23(2):93-109. doi: 10.2165/00063030-200923020-00003.
Koo et al., "Tumour suppressor RNF43 is a stem-cell E3 ligase that induces endocytosis of Wnt receptors," Nature, Aug. 30, 2012, 488(7413):665-669. doi: 10.1038/nature11308.
Koriskta et al., "Retargeting of Human Regulatory T Cells by Single-Chain Bispecific Antibodies," J Immunol, Feb. 1, 2012, 188(3):1551-1558. doi:10.4049/jimmunol.1101760. Epub Dec. 19, 2011.
Kraft et al., "FcεRI-Mediated Activation of Transcription Factors in Antigen-Presenting Cells," Int Arch Allergy Immunol, May 2001, 125(1):9-15.
Kranenborg et al., "Development and characterization of anti-renal cell carcinoma x antichelate bispecific monoclonal antibodies for two-phase targeting of renal cell carcinoma," Cancer Res, Dec. 1, 1995, 55(23 Suppl):5864s-5867s.
Kreutz et al., "Efficient bispecific monoclonal antibody purification using gradient thiophilic affinity chromatography," J Chromatogr B Biomed Sci Appl, Sep. 4, 1998, 714(2):161-170.
Kroesen et al., "Bispecific antibodies for treatment of cancer in experimental animal models and man," Adv Drug Deliv Rev, Apr. 6, 1998, 31(1-2):105-129.
Kufer et al., "A revival of bispecific antibodies," Trends Biotechnol, 2004, 22(5):238-244.
Kumagai et al., "Humanized bispecific antibodies that recognize lymphocytes and cancer cells," Drug Delivery System, 2008, 23(5):518-525 (with English translation).
Kumar et al., "Molecular Cloning and Expression of the Fabs of Human Autoantibodies in *Escherichia coli*," J Biol Chem, 2000, 275:35129-35136.
Kunik et al., "Structural Consensus among Antibodies Defines the Antigen Binding Site," PLoS Comput Biol, 2012, 8(2):e1002388, 12 pages. doi: 10.1371/journal.pcbi.1002388. Epub Feb. 23, 2012.
Labrijn et al., "Efficient generation of stable bispecific IgG1 by controlled Fab-arm exchange," Proc Natl Acad Sci USA, Mar. 26, 2013, 110(13):5145-5150. doi: 10.1073/pnas.1220145110. Epub Mar. 11, 2013.
Lansdorp et al., "Purification and analysis of bispecific tetrameric antibody complexes," Mol Immunol, Jul. 1990, 27(7):659-666.
Larkin et al., "Combined Nivolumab and Ipilimumab or Monotherapy in Untreated Melanoma," N Engl J Med, Jul. 2, 2015, 373(1):23-34. doi: 10.1056/NEJMoa1504030. Epub May 31, 2015.
Laurent et al., "Nox1 is over-expressed in human colon cancers and correlates with activating mutations in K-Ras," Int J Cancer, Jul. 1, 2008, 123(1):100-107.
Lazar et al., "Transforming growth factor alpha: mutation of aspartic acid 47 and leucine 48 results in different biological activities," Mol Cell Biol, Mar. 1988, 8(3):1247-1252.
Lazar et al., "Engineered antibody Fc variants with enhanced effector function," Proc Natl Acad Sci USA, Mar. 14, 2006, 103(11):4005-4010. Epub Mar. 6, 2006.
Lebégue et al., "Production and characterization of hybrid monoclonal antibodies with IgG1/IgG3 double isotype," C R Acad Sci III, 1990, 310(9):377-382.
Lejeune et al., "Bispecific, T-Cell-Recruiting Antibodies in B-Cell Malignancies," Frontiers in Immunology, May 7, 2020, 11:762, 20 pages.
Lewis et al., "Differential responses of human tumor cell lines to anti-p185$^{HER2}$ monoclonal antibodies," Cancer Immunol Immunother, Sep. 1993, 37(4):255-263.
Li et al., "Construction and characterization of a humanized anti-human CD3 monoclonal antibody 12F6 with effective immunoregulation functions," Immunology, Dec. 2005, 116(4):487-98.
Li et al., "Framework selection can influence pharmacokinetics of a humanized therapeutic antibody through differences in molecule charge," mAbs, 2014, 6(5):1255-1264. doi: 10.4161/mabs29809. Epub Oct. 30, 2014.
Li et al., "Antitumor activities of agonistic anti-TNFR antibodies require differential FcγRIIB coengagement in vivo," Proc Natl Acad Sci USA, Nov. 26, 2013, 110(48):19501-19506. doi: 10.1073/pnas.1319502110. Epub Nov. 11, 2013.
Li et al., "Phosphorylated ERM Is Responsible for Increased T Cell Polarization, Adhesion, and Migration in Patients with Systemic Lupus Erythematosus," J Immunol, 2007, 178:1938-1947.
Lin et al., "Structure-function relationships in glucagon: properties of highly purified des-His-1-, monoiodo-, and (des-Asn-28, Thr-29)(homoserine lactone-27)-glucagon," Biochemistry, Apr. 22, 1975, 14(8):1559-1563.

(56) References Cited

OTHER PUBLICATIONS

Lindhofer et al., "Preferential species-restricted heavy/light chain pairing in rat/mouse quadromas. Implications for a single-step purification of bispecific antibodies," J Immunol, Jul. 1, 1995, 155(1):219-225.
Link et al., "Anti-CD-3-Based Bispecific Antibody Designed for Therapy of Human B-Cell Malignancy Can Induce T-Cell Activation by Antigen-Dependent and Antigen-Independent Mechanisms," Int J Cancer, Jul. 17, 1998, 77(2):251-256.
Linnenbach et al., "Sequence investigation of the major gastrointestinal tumor-associated antigen gene family, GA733," Proc Natl Acad Sci USA, Jan. 1989, 86:27-31.
Little, Recombinant Antibodies for Immunotherapy, 2009, pp. 133-134.
Liu et al., "Efficient Inhibition of Human B-cell Lymphoma in SCID Mice by Synergistic Antitumor Effect of Human 4-1BB Ligand/Anti-CD20 Fusion Proteins and Anti-CD3/Anti-CD20 Diabodies," J Immunother, Jun. 2010, 33(5):500-509. doi: 10.1097/CJI.0b013e3181d75c20.
Liotta et al., "Frequency of regulatory T cells in peripheral blood and in tumour-infiltrating lymphocytes correlates with poor prognosis in renal cell carcinoma," BJU Int, May 2011, 107(9):1500-1506. doi: 10.1111/j.1464-410X.2010.09555.x. Epub Aug. 24, 2010.
Lloyd et al., "The production of a bispecific anti-CEA, anti-hapten (4-amino-phthalate) hybrid-hybridoma," J Natl Med Assoc, Oct. 1991, 83(10):901-904.
Lloyd et al., "Modelling the human immune response: performance of a $10^{11}$ human antibody repertoire against a broad panel of therapeutically relevant antigens," Protein Eng Des Sel, Mar. 2009, 22(3):159-168. doi: 10.1093/protein/gzn058. Epub Oct. 29, 2008.
Lo et al., "Conformational epitope matching and prediction based on protein surface spiral features," BMC Genomics, 2021, 22(Suppl 2): 116, 16 pages.
Loffler et al., "A recombinant bispecific single-chain antibody, CD19xCD3, induces rapid and high lymphoma-directed cytotoxicity by unstimulated T lymphocytes," Blood, Mar. 15, 2000, 95(6):2098-2103.
Lund et al., "Multiple Interactions of IgG with its Core Oligosaccharide can Modulate Recognition by Complement and Human Fcγ Receptor 1 and Influence the Synthesis of its Oligosaccharide Chains," J Immunol, Dec. 1, 1996, 157(11):4963-4969.
Lutterbuese et al., "T cell-engaging BiTe antibodies specific for EGFR potently eliminate KRAS- and BRAF-mutated colorectal cancer cells," Proc Natl Acad Sci USA, Jul. 13, 2010, 107(28):12605-12610. doi: 10.1073/pnas.1000976107. Epub Jun. 28, 2010.
Lutterbuese et al., "Potent tumor killing and inhibition of tumor growth by CEA/CD3-bispecific single chain antibodies that are resistant to inhibition by soluble CEA," Proc Am Assoc Cancer Res, from 98th AACR Annual Meeting, May 2007, vol. 67, Issue 9, Abstract 4106.
Lutterbuese et al., "Conversion of Cetuximab and Trastuzumab into T cell-engaging BiTE antibodies creates novel drug candidates with superior anti-tumor activity," Proc Am Assoc Cancer Res, from 99th AACR Annual Meeting, May 2008, vol. 68, Issue 9, Abstract 2402.
Mack et al., "A small bispecific antibody construct expressed as a functional single-chain molecule with high tumor cell cytotoxicity," Proc Natl Acad Sci USA, 1995, 92(15):7021-7025.
Male et al., "Antibodies," Immunology, $7^{th}$ ed., published by Elsevier Ltd., 2006, pp. 59-86.
Manz et al., "Biomolecules," Bioanalytical Chemistry, World Scientific Publishing Co., 2003, p. 7.
Manzke et al., "Single-step purification of bispecific monoclonal antibodies for immunotherapeutic use by hydrophobic interaction chromatography," J Immunol Methods, 1997, 208:65-73.
Mariuzza, "The Structural Basis of Antigen-Antibody Recognition," Annu Rev Biophys Biophys Chem, 1987, 16:139-159.
Marks et al., "How repertoire data are changing antibody science," J Biol Chem, 2020, 295(29):9823-9837.
Marme et al., "Intraperitoneal Bispecific Antibody (HEA125XOKT3) Therapy Inhibits Malignant Ascites Production in Advanced Ovarian Carcinoma," Int J Cancer, Sep. 10, 2002, 101(2):183-189.
Marvin et al., "Recombinant approaches to IgG-like bispecific antibodies," Acta Pharmacol Sin, Jun. 2005, 26(6):649-658.
Marvin et al., "Redesigning an antibody fragment for faster association with its antigen," Biochemistry, Jun. 17, 2003, 42(23):7077-7083.
Masharani et al., "Teplizumab therapy for type 1 diabetes," Expert Opin Biol Ther, Mar. 2010, 10(3):459-465.
Matzku et al., Antibodies in Diagnosis and Therapy—Technologies, Mechanisms and Clinical Data, 1999, p. 7.
Mau-Sorensen et al., "A phase I trial of intravenous catumaxomab: a bispecific monoclonal antibody targeting EpCAM and the T cell coreceptor CD3," Cancer Chemother Pharmacol, May 2015, 75(5):1065-1073.
Maude et al., "Managing Cytokine Release Syndrome Associated with Novel T Cell-Engaging Therapies," Cancer J, Mar.-Apr. 2014, 20(2):119-122.
McDermott et al., "PD-1 as a potential target in cancer therapy," Cancer Med, Oct. 2013, 2(5):662-673. doi: 10.1002/cam4.106. Epub Jul. 21, 2013.
McEarchern et al., "Engineered anti-CD70 antibody with multiple effector functions exhibits in vitro and in vivo antitumor activities," Blood, Feb. 1, 2007, 109(3):1185-1192. Epub Oct. 12, 2006.
Medesan et al., "Delineation of the amino acid residues involved in transcytosis and catabolismof mouse IgG1," J Immunol, Mar. 1, 1997, 158(5):2211-2217.
Melero et al., "Multi-layered action mechanisms of CD137 (4-1BB)-targeted immunotherapies," Trends Pharmacol Sci, Aug. 2008, 29(8):383-390.
Melero et al., "Agonist antibodies to TNFR molecules that costimulate T and NK cells," Clin Cancer Res, Mar. 1, 2013, 19(5):1044-1053. doi: 10.1158/1078-0432.CCR-12-2065.
Merchant et al., "An efficient route to human bispecific IgG," Nat Biotechnol, 1998, 16(7):677-681.
Mezzanzanica et al., "Human ovarian carcinoma lysis by cytotoxic T cells targeted by bispecific monoclonal antibodies: analysis of the antibody components," Int J Cancer, 1988, 41(4):609-615.
Michaelsen et al., "A mutant human IgG molecule with only one C1q binding site can activate complement and induce lysis of target cells," Eur J Immunol, Jan. 2006, 36(1):129-138.
Micke et al., "Aberrantly activated claudin 6 and 18.2 as potential therapy targets in non-small-cell lung cancer," Int J Cancer, Nov. 1, 2014, 135(9):2206-2214.
Middelburg et al., "Overcoming Challenges for CD3-Bispecific Antibody Therapy in Solid Tumors," Cancers, 2021, 13:287.
Midorikawa et al., "Glypican-3, overexpressed in hepatocellular carcinoma, modulates FGF2 and BMP-7 signaling," Int J Cancer, Feb. 10, 2003, 103(4):455-465.
Milstein et al., "Hybrid hybridomas and their use in immunohistochemistry," Nature, Oct. 6-12, 1983, 305(5934):537-540.
Moiseenko, "Monoclonal Antibodies in the Treatment of Malignant Tumors," Practical Oncology, 2003, 4(3):148-156 (with what are believed to be the corresponding pages from an English language edition of Practical Oncology).
Molhoj et al., "CD19-/CD3-bispecific antibody of the BiTE class is far superior to tandem diabody with respect to redirected tumor cell lysis," Mol Immunol, 2007, 44(8):1935-1943.
Morgan et al., "The N-terminal end of the $C_H2$ domain of chimeric human IgG1 anti-HLA-DR is necessary for C1q, FcγRI and FcγRIII binding," Immunology, Oct. 1995, 86(2):319-324.
Morimoto et al., "Single-step purification of F(ab')2 fragments of mouse monoclonal antibodies (immunoglobulins G1) by hydrophobic interaction high performance liquid chromatography using TSKgel Phenyl-5PW," J Biochem Biophys Methods, Mar. 1992, 24(1-2):107-117.
Morita et al., "Claudin multigene family encoding four-transmembrane domain protein components of tight junction strands," Proc Natl Acad Sci USA, Jan. 19, 1999, 96(2):511-516.
Morell et al., "Metabolic properties of IgG subclasses in man," J Clin Invest, Apr. 1970, 49(4):673-680.

(56) References Cited

OTHER PUBLICATIONS

Mueller et al., "Humanized Porcine VCAM-Specific Monoclonal Antibodies with Chimeric IgG2/G4 Constant Regions Block Human Leukocyte Binding to Porcine Endothelial Cells," Mol Immunol, Apr. 1997, 34(6):441-352.
Muller et al., "A Novel Antibody—4-1BBL Fusion Protein for Targeted Costimulation in Cancer Immunotherapy," J Immunother, Oct. 2008, 31(8):714-722. doi: 10.1097/CJI.0b013e31818353e9.
Muller et al., "The first constant domain ($C_H1$ and $C_L$) of an antibody used as heterodimerization domain for bispecific miniantibodies," FEBS Lett, Jan. 30, 1998, 422(2):259-264.
Muller et al., "Bispecific antibodies for cancer immunotherapy: Current perspectives," BioDrugs, Apr. 1, 2010, 24(2):89-98.
Muller et al., "Recombinant bispecific antibodies for cellular cancer immunotherapy," Curr Opin Mol Ther, Aug. 2007, 9(4):319-326.
Munz et al., "Side-by-Side analysis of five clinically tested anti-EpCAM monoclonal antibodies," Cancer Cell International, Nov. 2, 2010, 10:44.
Muta et al., "A 13-amino-acid motif in the cytoplasmic domain of FcγRIIB modulates B-cell receptor signalling," Nature, Mar. 3, 1994, 368(6466):70-73.
Nakano et al., "Anti-glypican 3 antibodies cause ADCC against human hepatocellular carcinoma cells," Biochem Biophys Res Commun, Jan. 9, 2009, 378(2):279-284. doi: 10.1016/j.bbrc.2008.11.033. Epub Nov. 18, 2008.
Natsume et al., "Improving effector functions of antibodies for cancer treatment: Enhancing ADCC and CDC," Drug Des Devel Ther, 2009, 3:7-16.
NCT01307267: A Study of PF-05082566 as a Single Agent and In Combination With Rituximab, Submitted: Mar. 3, 2014 (v26), 8 pages.
NCT02401542: Dose Escalation, Expansion Study of Vofatamab (B-701) in Treatment of Locally Advanced or Metastatic Urothelial Cell Carcinoma (Fierce-21), First submitted: Mar. 16, 2015, 9 pages.
Nelson et al., "5.2 Complementary Interactions between Proteins and Ligands: The Immune System and Immunoglobulins," Lehninger, Principles of Biochemistry, $5^{th}$ ed., 2008, p. 171.
Nicholas et al., "Regulation of the Immune Response. I. Reduction in Ability of Specific Antibody to Inhibit Long-Lasting IgG Immunological Priming After Removal of the Fc Fragment," J Exp Med, Jun. 1, 1969, 129(6):1183-1201.
Nimmerjahn et al., "Fcγ receptors as regulators of immune responses," Nat Rev Immunol, Jan. 2008, 8(1):34-47.
Nishikawa et al., "Perspectives on Clinical Applications of Regulatory T Cells," Inflammation & Immunology, 2013, 21(1):66-72 (with English translation).
Nissim et al., "Historical Development of Monoclonal Antibody Therapeutics," Therapeutic Antibodies, ed. Chernajovsky et al., Springer-Verlag, 2008, pp. 3-7.
Nitta et al., "Bispecific $F(ab')_2$ monomer prepared with anti-CD3 and anti-tumor monoclonal antibodies is most potent in induction of cytolysis of human T cells," Eur J Immunol, Aug. 1989, 19(8):1437-1441.
Niu et al., "RNF43 Inhibits Cancer Cell Proliferation and Could be a Potential Prognostic Factor for Human Gastric Carcinoma," Cell Physiol Biochem, 2015, 36(5):1835-1846.
O'Brien et al., "Biophysical characterization and molecular simulation of electrostatically driven self-association of a single-chain antibody," Protein Sci, Jul. 2018, 27(7):1275-1285.
Oganesyan et al., "Structural characterization of a human Fc fragment engineered for lack of effector functions," Acta Crystallogr D Biol Crystallogr, Jun. 2008, 64(Pt 6):700-704. doi: 10.1107/S0907444908007877. Epub May 14, 2008.
Onda et al., "Lowering the Isoelectric Point of the Fv Portion of Recombinant Immunotoxins Leads to Decreased Nonspecific Animal Toxicity without Affecting Antitumor Activity," Cancer Res, 2001, 61:5070-5077.
Pabst et al., "Engineering of novel Staphylococcal Protein A ligands to enable milder elution pH and high dynamic binding capacity," J Chromatogr A, Oct. 3, 2014, 1362:180-185. doi: 10.1016/j.chroma.2014.08.046. Epub Aug. 19, 2014.
Pabst et al., "Evaluation of recent Protein A stationary phase innovations for capture of biotherapeutics," J Chromatogr A, Jun. 15, 2018, 1554:45-60. doi: 10.1016/j.chroma.2018.03.060. Epub Apr. 7, 2018.
Padlan et al., "Antibody Fab assembly: the interface residues between CH1 and CL," Mol Immunol, 1986, 23(9):951-960.
Padlan, "X-Ray Crystallography of Antibodies," Advances in Protein Chemistry, 1996, 49:57-133.
Palazon et al., "The HIF-1α Hypoxia Response in Tumor-Infiltrating T Lymphocytes Induces Functional CD137 (4-1BB) for Immunotherapy," Cancer Discov, Jul. 2012, 2(7):608-623. doi: 10.1158/2159-8290.CD-11-0314. Epub Jun. 19, 2012.
Pan et al., "Blocking neuropilin-1 function has an additive effect with anti-VEGF to inhibit tumor growth," Cancer Cell, Jan. 2007, 11(1):53-67.
Parren et al., "Induction of T-cell proliferation by recombinant mouse and chimeric mouse/human anti-CD3 monoclonal antibodies," Res Immunol, Nov.-Dec. 1991, 142(9):749-763.
Pastor et al., "Targeting 4-1BB Costimulation to Disseminated Tumor Lesions With Bi-specific Oligonucleotide Aptamers," Mol Ther, Oct. 2011, 19(10):1878-1886. doi: 10.1038/mt.2011.145. Epub Aug. 9, 2011.
Paul, "Structure and Function of Immunoglobulins," Fundamental Immunology, $3^{rd}$ ed., 1993, pp. 292-295.
Paul et al., "7.9. Comparison of properties of constant regions—7.9.1. Disulphide bonds," Immunology, M.:Mir, 1987-1988, vol. 1, p. 231 (with English translation).
Pavlou et al., "The therapeutic antibodies market to 2008," Eur J Pharm Biopharm, 2005, 59:389-396.
Peng et al., "FLVCR1 promotes the proliferation and tumorigenicity of synovial sarcoma through inhibiting apoptosis and autophage," Int J Oncol, May 2018, 52(5):1559-1568.
Percival-Alwyn et al., "Generation of potent mouse monoclonal antibodies to self-proteins using T-cell epitope 'tags'," mAbs, 2015, 7(1):129-137. doi: 10.4161/19420862.2014.985489.
Pere et al., "Comprehensive analysis of current approaches to inhibit regulatory T cells in cancer," Oncoimmunology, May 1, 2012, 1(3):326-333.
Poosarla et al., "Computational *de novo* Design of Antibodies binding to a Peptide with High Affinity," Biotechn Bioeng, 2017, 114(6):1331-1342.
Postow et al., "Nivolumab and Ipilimumab versus Ipilimumab in Untreated Melanoma," N Engl J Med, May 21, 2015, 372(21):2006-2017. doi: 10.1056/NEJMoa1414428. Epub Apr. 20, 2015.
Presta, "Molecular engineering and design of therapeutic antibodies," Curr Opin Immunol, Aug. 2008, 20(4):460-470. doi: 10.1016/j.coi.2008.06.012.
Prieto et al., "CTLA-4 Blockade with Ipilimumab: Long-term Follow-up of 177 Patients with Metastatic Melanoma," Clin Cancer Res, Apr. 1, 2012, 18(7):2039-2047.
Pritsch et al., "Can Immunoglobulin CHI Constant Region Domain Modulate Antigen Binding Affinity of Antibodies?," J Clin Invest, Nov. 15, 1996, 98(10):2235-2243.
Porter et al., "Chimeric Antigen Receptor-Modified T Cells in Chronic Lymphoid Leukemia," N Engl J Med, Aug. 25, 2011, 365(8):725-733. doi.1056/NEJMoa1103849. Epub Aug. 10, 2011.
Queen et al., "A humanized antibody that binds to the interleukin 2 receptor," Proc Natl Acad Sci USA, Dec. 1989, 86(24):10029-10033.
Qing et al., "Antibody-based targeting of FGFR3 in bladder carcinoma and t(4;14)-positive multiple myeloma in mice," J Clin Invest, May 2009, 119(5):1216-1229.
Radaev et al., "The Structure of a Human Type III Fcγ Receptor in Complex with Fc," J Biol Chem, May 11, 2001, 276(19):16469-16477. Epub Jan. 31, 2001.
Rahner et al., "Heterogeneity in Expression and Subcellular Localization of Claudins 2, 3, 4, and 5 in the Rat Liver, Pancreas, and Gut," Gastroenterology, Feb. 2001, 120(2):411-422.
Ravetch et al., "Fc Receptors," Annu Rev Immunol, Apr. 1991, 9:457-492.

(56) References Cited

OTHER PUBLICATIONS

Ravetch et al., "Immune Inhibitory Receptors," Science, Oct. 6, 2000, 290(5489):84-89.
Reichert et al., "Monoclonal antibody successes in the clinic," Nat Biotechnol, 2005, 23:1073-1078.
Reinhard et al., "An RNA vaccine drives expansion and efficacy of claudin-CAR-T cells against solid tumors," Science, Jan. 24, 2020, 367(6476):446-453.
Remer et al., "Therapeutic mechanisms of anti-4-1BB antibodies in cancer: agonism versus regulatory T cell depletion," Cancer Immunol Res, 2016, 4(11 Suppl): Abstract B046.
Renders et al., "Engineered CD3 antibodies for immunosuppression," Clin Exp Immunol, Sep. 2003, 133(3):307-309.
Rendon-Huerta et al., "Distribution and Expression Pattern of Claudins 6, 7, and 9 in Diffuse- and Intestinal-Type Gastric Adenocarcinomas," J Gastrointest Cancer, Mar. 2010, 41(1):52-59.
Renkvist et al., "A listing of human tumor antigens recognized by T cells," Cancer Immunol Immunother, Mar. 2001, 50:3-15.
Representative abstracts allegedly showing long-term administration of a variety of anti-cancer antibodies in the prior art, 5 pages (document submitted by the Opponents in the EPO opposition proceedings of EP 2 647 707 and reported in the EPO Communication issued Jan. 20, 2021; the document cites publication dates of the abstracts ranging from May 2006 to Feb. 2010).
Ridgway et al., "'Knobs-into-holes' engineering of antibody CH3 domains for heavy chain heterodimerization," Protein Eng, 1996, 9(7):617-621.
Riechelmann et al., "Adoptive therapy of head and neck squamous cell carcinoma with antibody coated immune cells: a pilot clinical trial," Cancer Immunol Immunother, Sep. 2007, 56(9):1397-1406. Epub Feb. 2, 2007.
Riechelmann et al., "Phase 1 trial with the CD44v6-targeting immunoconjugate bivatuzumab mertansine in head and neck squamous cell carcinoma," Oral Oncol, Sep. 2008, 44(9):823-829. doi: 10.1016/j.oraloncology.2007.10.009. Epub Jan. 18, 2008.
Roguska et al., "Humanization of murine monoclonal antibodies through variable domain resurfacing," Proc Natl Acad Sci USA, 1994, 91:969-973.
Roitt et al., Immunology, M., Mir, 5th ed., 2000, pp. 110, 150, and 537-539 (with English translation).
Roitt et al., Immunology, M., Mir, 5th ed., 2000, pp. 97-113 (with what are believed to be the corresponding pages from an English language edition of Immunology).
Rosty et al., "Clinical and biological characteristics of cervical neoplasias with FGFR3 mutation," Mol Cancer, May 3, 2005, 4(1):15.
Rothe et al., "Recombinant proteins in rheumatology—recent advances," N Biotechnol, Sep. 2011, 28(5):502-510. doi: 10.1016/j.nbt.2011.03.019. Epub Apr. 5, 2011.
Rother et al., "Discovery and development of the complement inhibitor eculizumab for the treatment of paroxysmal nocturnal hemoglobinuria," Nat Biotechnol, Nov. 2007, 25(11):1256-1264.
Rothlisberger et al., "Domain interactions in the Fab fragment: a comparative evaluation of the single-chain Fv and Fab format engineered with variable domains of different stability," J Mol Biol, 2005, 347(4):773-789.
Routledge et al., "A humanized monovalent CD3 antibody which can activate homologous complement," Eur J Immunol, Nov. 1991, 21(11):2717-2725.
Rudikoff et al., "Single amino acid substitution altering antigen-binding specificity," Proc Natl Acad Sci USA, 1982, 79(6):1979-1983.
Rudnick et al., "Affinity and Avidity in Antibody-Based Tumor Targeting," Cancer Biother Radiopharm, 2009, 24(2):155-161. doi:10.1089/cbr.2009.0627.
Ruf et al., "Induction of a long-lasting antitumor immunity by a trifunctional bispecific antibody," Blood, Oct. 15, 2001, 98(8):2526-2534.
Ruf et al., "Pharmacokinetics in in vivo stability of intraperitoneally administered therapeutic antibody catumaxomab," J Clin Oncol, 2008 ASCO Annual Meeting Proceedings (Post-Meeting Edition), 2008, vol. 25, No. 15S(May 20 Supplement):14006.
Ruf et al., "Ganglioside GD2-specific trifunctional surrogate antibody Surek demonstrates therapeutic activity in a mouse melanoma model," Journal of Translational Medicine, Nov. 7, 2012, 10:219, 10 pages.
Rui et al., "In vitro Cytolysis of B-Lymphoma Cells Mediated by an Anti-CD3/Anti-CD20 Bispecific Single-chain Antibody," Chin J Biotech, May 2006, 22(3):384-390.
Runcie et al., "Bi-specific and tri-specific antibodies—the next big thing in solid tumor therapeutics," Molecular Medicine, 2018, 24:50, 15 pages.
Saichaemchan et al., "Fibroblast Growth Factor Receptors: From the Oncogenic Pathway to Targeted Therapy," Curr Mol Med, 2016, 16(1):40-62.
Salfeld, "Isotype selection in antibody engineering," Nat Biotechnol, Dec. 2007, 25(12):1369-1372.
Sal-Man et al., "Arginine mutations within a transmembrane domain of Tar, an *Escherichia coli* aspartate receptor, can drive homodimer dissociation and heterodimer association in vivo," Biochem J, Jan. 1, 2005, 385(Pt. 1):29-36.
Salnikov et al., "Targeting of cancer stem cell marker EpCAM by bispecific antibody EpCAMxCD3 inhibits pancreatic carcinoma," J Cell Mol Med, Sep. 2009, 13(9B):4023-4033. doi: 10.1111/j.1582-4934.2009.00723.x.
Sakamoto et al., "Clinicopathological significance of somatic RNF43 mutation and aberrant expression of ring finger protein 43 in intraductal papillary mucinous neoplasms of the pancreas," Mod Pathol, Feb. 2015, 28(2):261-267. doi: 10.1038/modpathol.2014.98. Epub Aug. 1, 2014.
Sampei et al., "Identification and multidimensional optimization of an asymmetric bispecific IgG antibody mimicking the function of factor VIII cofactor activity," PLoS One, 2013, 8(2):e57479. doi: 10.1371/journal.pone.0057479. Epub Feb. 28, 2013.
Sandin et al., "Local CTLA4 blockade effectively restrains experimental pancreatic adenocarcinoma growth in vivo," Oncoimmunology, Jan. 1, 2014, 3(1):e27614. Epub Jan. 16, 2014.
Santos et al., "Development of more efficacious antibodies for medical therapy and diagnosis," Prog Nucleic Acid Res Mol Biol, 1998, 60:169-194.
Satoh et al., "Non-fucosylated therapeutic antibodies as next-generation therapeutic antibodies," Expert Opin Biol Ther, Nov. 2006, 6(11):1161-1173.
Sato et al., "Intraepithelial CD8+ tumor-infiltrating lymphocytes and a high CD8+/regulatory T cell ratio are associated with favorable prognosis in ovarian cancer," Proc Natl Acad Sci USA, Dec. 20, 2005, 102(51):18538-18543. Epub Dec. 12, 2005.
Saunders et al., "Conceptual Approaches to Modulating Antibody Effector Functions and Circulation Half-Life," Front Immunol, Jun. 7, 2019, 10(1296):1-20.
Schabowsky et al., "A Novel Form of 4-1BBL Has Better Immunomodulatory Activity than an Agonistic Anti-4-1BB Ab without Ab Associated Severe Toxicity," Vaccine, Dec. 11, 2009, 28(2):512-522. doi: 10.1016/j.vaccine.2009.09.127. Epub Oct. 29, 2009.
Schaefer et al., "Immunoglobulin domain crossover as a generic approach for the production of bispecific IgG antibodies," Proc Natl Acad Sci USA, Jul. 5, 2011, 108(27):11187-11192. doi: 10.1073/pnas.1019002108. Epub Jun. 20, 2011.
Schaefer et al., "Heavy and light chain pairing of bivalent quadroma and knobs-into-holes antibodies analyzed by UHR-ESI-QTOF mass spectrometry," mAbs, Jan. 2016, 8(1):49-55.
Schlereth et al., "T-cell activation and B-cell depletion in chimpanzees treated with a bispecific anti-CD19/anti-CD3 single-chain antibody construct," Cancer Immunol Immunother, May 2006, 55(5):503-514. Epub Jul. 20, 2005.
Schneider et al., "In vitro and in vivo properties of a dimeric bispecific single-chain antibody IgG-fusion protein for depletion of CCR2+ target cells in mice," Eur J Immunol, 2005, 35:987-995 https://onlinelibrary.wiley.com/doi/full/10.1002/eji.200425512.
Schwartz et al., "A superactive insulin: [B10-aspartic acid]insulin(human)," Proc Natl Acad Sci USA, Sep. 1987, 84(18):6408-6411.

(56) References Cited

OTHER PUBLICATIONS

Sebastian et al., "Treatment of non-small cell lung cancer patients with the trifunctional monoclonal antibody catumaxomab (anti-EpCAM x anti-CD3): a phase I study," Cancer Immunol Immunother, 2007, 56(10):1637-1644.
Segal et al., "Bispecific antibodies in cancer therapy," Curr Opin Immunol, 1999, 11(5):558-562.
Segal et al., "Production of Bispecific Antibodies," Current Protocols in Immunology, 1995, Unit 2.13.1-2.13.16.
Seimetz et al., "Development and approval of the trifunctional antibody catumaxomab (anti-EpCAM x anti-CD3) as a targeted cancer immunotherapy," Cancer Treat Rev, 2010, 36(6):458-467.
Seiwert et al., "Integrative and Comparative Genomic Analysis of HPV-Positive and HPV-Negative Head and Neck Squamous Cell Carcinomas," Clin Cancer Res, Feb. 1, 2015, 21(3):632-641.
Selby et al., "Anti-CTLA-4 Antibodies of IgG2a Isotype Enhance Antitumor Activity through Reduction of Intratumoral Regulatory T Cells," Cancer Immunol Res, Jul. 2013, 1(1):32-42. doi: 10.1158/2326-6066.CIR-13-0013. Epub Apr. 7, 2013.
Sequence Alignments, 6 pages (cited in EPO opposition proceedings of EP 2 647 707 on May 31, 2019 and Jun. 12, 2019).
Sequence Alignments (comparison of heavy chain constant region), 1 page (submitted by the Patentee (Chugai Seiyaku Kabushiki Kaisha) in the EPO opposition proceedings of EP 2 647 707 on Dec. 23, 2020).
Shahabuddin et al., "Lymphocyte subset reference ranges in healthy Saudi Arabian children," Pediatr Allergy Immunol, Feb. 1998, 9(1):44-48.
Shao et al., "Characterisation of soluble murine CD137 and its association with systemic lupus," Mol Immunol, Sep. 2008, 45(15):3990-3999.
Shaul et al., "Exploring the charge space of protein-protein association: a proteomic study," Proteins, Aug. 15, 2005, 60(3):341-352.
Shields et al., "High resolution mapping of the binding site on human IgG1 for FcγRI, FcγRII, FcγRIII, and FcRn and design of IgG1 variants with improved binding to the FcγR," J Biol Chem, 2001, 276:6591-6604. Epub Nov. 28, 2000.
Shimabukuro-Vornhagen et al., "Cytokine release syndrome," J Immunother Cancer, Jun. 15, 2018, 6(1):56.
Shiraiwa et al., "Engineering a bispecific antibody with a common light chain: Identification and optimization of an anti-CD3 epsilon and anti-GPC3 bispecific antibody, ERY974," Methods, Feb. 1, 2019, 154:10-20. doi: 10.1016/j.ynneth.2018.10.005. Epub Oct. 13, 2018.
Shirakawa et al., "Glypican-3 is a useful diagnostic marker for a component of hepatocellular carcinoma in human liver cancer," Int J Oncol, Mar. 2009, 34(3):649-656.
Shreshtha et al., "Cytokine Release Syndrome: An Overview on its Features and Management," J Pure Appl Microbiol, 2019, 13(1):133-140.
Simpson et al., "Fc-dependent depletion of tumor-infiltrating regulatory T cells co-defines the efficacy of anti-CTLA-4 therapy against melanoma," J Exp Med, Aug. 26, 2013, 210(9):1695-1710. doi: 10.1084/jem.20130579. Epub Jul. 29, 2013.
Singer et al., Genes & Genomes, 1998, 1:63-64 (with what are believed to be the corresponding pages from an English language edition of Genes & Genomes, pp. 67-70).
Smans et al., "Bispecific antibody-mediated lysis of primary cultures of ovarian carcinoma cells using multiple target antigens," Int J Cancer, 1999, 83:270-277.
Smith et al., "FcγRIIB in autoimmunity and infection: evolutionary and therapeutic implications," Nat Rev Immunol, May 2010, 10(5):328-343.
Smith-Gill et al., "Contributions of Immunoglobulin Heavy and Light Chains to Antibody Specificity for Lysozyme and Two Haptens," J Immunol, 1987, 139:4135-4144.
Son et al., "Humanization of agonistic anti-human 4-1BB monoclonal antibody using a phage-displayed combinatorial library," J Immunol Methods, Mar. 2004, 286(1-2):187-201.
Sondermann et al., "The 3.2-Åcrystal structure of the human IgGI Fc fragment-FcγRIII complex," Nature, Jul. 20, 2000, 406(6793):267-273.
Song et al., "Light Chain of Natural Antibody Plays a Dominant Role in Protein Antigen Binding," Biochem Biophys Res Comm, 2000, 268:390-394.
Spiess et al., "Bispecific antibodies with natural architecture produced by co-culture of bacteria expressing two distinct half-antibodies," Nat Biotechnol, Aug. 2013, 31(8):753-758. doi: 10.1038/nbt.2621. Epub Jul. 7, 2013.
Sporn et al., "Chemoprevention of cancer," Carcinogenesis, Mar. 2000, 21(3):525-523.
Stadler et al., "Characterization of the first-in-class T-cell-engaging bispecific single-chain antibody for targeted immunotherapy of solid tumors expressing the oncofetal protein claudin 6," Oncoimmunology, Oct. 29, 2015, 5(3):e1091555. eCollection Mar. 2016.
Stadler et al., "Elimination of large tumors in mice by mRNA-encoded bispecific antibodies," Nat Med, 2017, 23(7):815-817. doi:10.1038/nm.4356.
Staerz et al., "Hybrid antibodies can target sites for attack by T cells," Nature, 1985, 314(6012):628-631.
Staerz et al., "Hybrid hybridoma producing a bispecific monoclonal antibody that can focus effector T-cell activity," Proc Natl Acad Sci USA, 1986, 83:1453-1457.
Stanglmaier et al., "Bi20 (FBTA05), a novel trifunctional bispecific antibody (anti-CD20 x anti-CD3), mediates efficient killing of B-cell lymphoma cells even with very low CD20 expression levels," Int J Cancer, Sep. 1, 2008, 123:1181-1189.
Strauss et al., "Without Prior Stimulation, Tumor-associated Lymphocytes from Malignant Effusions Lyse Autologous Tumor Cells in the Presence of Bispecific Antibody HEA125xOKT3," Clin Cancer Res, Jan. 1999, 5(1):171-180.
Stroehlein et al., "Induction of anti-tumor immunity by trifunctional antibodies in patients with peritoneal carcinomatosis," Journal of Experimental & Clinical Cancer Research, 2009, 28(1):18, 10 pages.
Strohl, "Optimization of Fc-mediated effector functions of monoclonal antibodies," Curr Opin Biotechnol, Dec. 2009, 20(6):685-691. doi: 10.1016/j.copbio.2009.10.011. Epub Nov. 4, 2009.
Sugiyama et al., "Anti-CCR4 mAb selectively depletes effector-type $FoxP3^+CD4^+$regulatory T cells, evoking antitumor immune responses in humans," Proc Natl Acad Sci USA, Oct. 29, 2013, 110(44):17945-17950. doi: A15210.1073/pnas.1316796110. Epub Oct. 14, 2013.
Suresh et al., "Bispecific monoclonal antibodies from hybrid hybridomas," Methods Enzymol, 1986, 121:210-228.
Suzuki, "Research and Development of Antibody Pharmaceuticals," NIBS Letter, 2010, 56(4):45-51 (with English translation).
Szoor et al., "T Cell-Activating Mesenchymal Stem Cells as a Biotherapeutic for HCC," Mol Ther Oncolytics, Jul. 28, 2017, 6:69-79. doi: 10.1016/j.onnto.2017.07.002. eCollection Sep. 15, 2017.
Talmadge et al., "Murine Models to Evaluate Novel and Conventional Therapeutic Strategies for Cancer," Am J Pathol, 2007, 170(3):793-804. doi:10.2353/ajpath.2007.060929.
Taniguchi et al., "Phase 1 study of OCV-C02, a peptide vaccine consisting of two peptide epitopes for refractory metastatic colorectal cancer," Cancer Sci, May 2017, 108(5):1013-1021. doi: 10.1111/cas.13227. Epub May 11, 2017.
Tarditi et al., "Selective high-performance liquid chromatographic purification of bispecific monoclonal antibodies," J Chromatogr, May 22, 1992, 599(1-2):13-20.
Teachey et al., "Cytokine release syndrome after blinatumomab treatment related to abnormal macrophage activation and ameliorated with cytokine-directed therapy," Blood, Jun. 27, 2013, 121(26):5154-5157.
Teerinen et al., "Structure-based stability engineering of the mouse IgG1 Fab fragment by modifying constant domains," J Mol Biol, 2006, 361(4):687-697.
Teschner et al., "In Vitro Stimulation and Expansion of Human Tumour-Reactive $CD8^+$Cytotoxic T Lymphocytes by Anti-CD3/CD28/CD137 Magnetic Beads," Scand J Immunol, Aug. 2011, 74(2):155-164. doi: 10.1111/j.1365-3083.2011.02564.x.

(56) References Cited

OTHER PUBLICATIONS

Thakur et al., “Cancer therapy with bispecific antibodies: Clinical experience,” Curr Opin Mol Ther, 2010, 12(3):340-349.
Thomas et al., “A Cell-Based Artificial Antigen-Presenting Cell Coated with Anti-CD3 and CD28 Antibodies Enables Rapid Expansion and Long-Term Growth of CD4 T Lymphocytes,” Clin Immunol, Dec. 2002, 105(3):259-272.
Thurber et al., “Antibody tumor penetration: Transport opposed by systemic and antigen-mediated clearance,” Adv Drug Deliv Rev, 2008, 60(12):1421-1434. doi:10.1016/j.addr.2008.04.012.
Topp et al., “Antibody transport in cultured tumor cell layers,” J Control Release, Apr. 30, 1998, 53(1-3):15-23.
Tosti et al., “Anti-cytotoxic T lymphocyte antigen-4 antibodies in melanoma,” Clin Cosmet Investig Dermatol, Oct. 17, 2013, 6:245-256. doi: 10.2147/CCID.S24246.
Tzartos et al., “Epitope mapping by antibody competition. Methodology and Evaluation of the validity of the technique,” Methods in Molecular Biology, 1996, 66:55-66.
Uekita et al., “Roles of CUB domain-containing protein 1 signaling in cancer invasion and metastasis,” Cancer Sci, Nov. 2011, 102(11):1943-1948.
Unkeless et al., “Structure and Function of Human and Murine Receptors for IgG,” Annu Rev Immunol, 1988, 6:251-281.
Uno et al., “Expression of CD3 antigen on individual adult T cell leukemia cells detected by immunocytochemistry,” Acta Haematol, 1995, 94(1):55-57.
Ushiku et al., “Distinct expression pattern of claudin-6, a primitive phenotype tight junction molecule, in germ cell tumours and visceral carcinomas,” Histopathology, Dec. 2012, 61(6):1043-1056.
Vajda et al., “Progress toward improved understanding of antibody maturation,” Current Opinion in Structural Biology, 2021, 67:226-231.
Vajdos et al., “Comprehensive Functional Maps of the Antigen-binding Site of an Anti-ErbB2 Antibody Obtained with Shotgun Scanning Mutagenesis,” J Mol Biol, Jul. 5, 2002, 320(2):415-428.
Van Loghem et al., “Staphylococcal protein A and human IgG subclasses and allotypes,” Scand J Immunol, 1982, 15(3):275-278.
Viardot et al., “Treatment of Patients With Non-Hodgkin Lymphoma With CD19/CD3 Bispecific Antibody Blinautumomab (MT103),” Dec. 6, 2010, 1 page, printed at the Internet at <http://www.bloodjournal.org/content/116/21/2880?sso-checked=true>.
Vinay et al., “TNF superfamily: costimulation and clinical applications,” Cell Biol Int, Apr. 2009, 33(4):453-465.
Vinay et al., “4-1BB signaling beyond T cells,” Cell Mol Immunol, Jul. 2011, 8(4):281-284. doi: 10.1038/cmi.2010.82. Epub Jan. 10, 2011.
Voskoglou-Nomikos et al., “Clinical Predictive Value of the in Vitro Cell Line, Human Xenograft, and Mouse Allograft Preclinical Cancer Models,” Clin Cancer Res, 2003, 9(11):4227-4239.
Waaijer et al., “Preclinical PET imaging of bispecific antibody ERY974 targeting CD3 and glypican 3 reveals that tumor uptake correlates to T cell infiltrate,” J Immunother Cancer, Mar. 2020, 8(1):e000548. doi: 10.1136/jitc-2020-000548.
Wainwright et al., “Targeting Tregs in malignant brain cancer: overcoming IDO,” Front Immunol, May 15, 2013, 4:116, 17 pages. doi: 10.3389/fimmu.2013.00116. eCollection 2013.
Wang et al., “Conserved amino acid networks involved in antibody variable domain interactions,” Proteins, Jul. 2009, 76(1):99-114. doi: 10.1002/prot.22319.
Wang et al., “The variation of $CD4^+CD25^+$regulatory T cells in the periphery blood and tumor microenvironment of non-small cell lung cancer patients and the downregulation effects induced by CpG ODN,” Target Oncol, Sep. 2011, 6(3):147-154. doi: 10.1007/s11523-011-0182-9. Epub May 25, 2011.
Wang et al., “A New Recombinant Single Chain Trispecific Antibody Recruits T Lymphocytes to Kill CEA (Carcinoma Embryonic Antigen) Positive Tumor Cells In Vitro Efficiently,” J Biochem, Apr. 2004, 135(4):555-565.
Wang et al., “The ubiquitin ligase RNF43 downregulation increases membrane expression of frizzled receptor in pancreatic ductal adenocarcinoma,” Tumour Biol, Jan. 2016, 37(1):627-631. doi: 10.1007/s13277-015-3499-7. Epub Aug. 5, 2015.
Wang et al., “Evidence for Segregation of Heterologous GPI-anchored Proteins into Separate Lipid Rafts within the Plasma Membrane,” J Membr Biol, Sep. 1, 2002, 189(1):35-43. doi: 10.1007/s00232-002-1002-z. PMID: 12202950.
Wang et al., “Comprehensive investigation of oncogenic driver mutations in Chinese non-small cell lung cancer patients,” Oncotarget, Oct. 27, 2015, 6(33):34300-34308.
Ward et al., “Binding activities of a repertoire of single immunoglobulin variable domains secreted from *Escherichia coli*,” Nature, 1989, 341:544-546.
Warnaar et al., “Purification of bispecific F(ab')2 from murine trinoma OC/TR with specificity for CD3 and ovarian cancer,” Hybridoma, Dec. 1994, 13(6):519-526.
Weiner et al., “The Role of T Cell Activation in Anti-CD3 x Antitumor Bispecific Antibody Therapy,” J Immunol, Mar. 1, 1994, 152(5):2385-2392.
Weiner et al., “Monoclonal antibodies: versatile platforms for cancer immunotherapy,” Nat Rev Immunol, May 2010, 10(5):317-327. doi: 10.1038/nri2744.
Wester Velt et al., “Phase 1 First-in-Human Trial of AMV564, a Bivalent Bispecific (2x2) CD33/CD3 T-Cell Engager, in Patients with Relapsed/Refractory Acute Myeloid Leukemia (AML),” Blood, 2018, 132(Supplement 1):1455.
Wherry et al., “T cell exhaustion,” Nat Immunol, Jun. 2011, 12(6):492-499.
Wikipedia entry for “Fc receptor” obtained from Wayback machine entry on May 29, 2010, 8 pages (submitted by Opponent 4 in the EPO opposition proceedings of EP 2 647 707 on Dec. 31, 2021).
Wilcox et al., “Mutations in the Gene Encoding Tight Junction Claudin-14 Cause Autosomal Recessive Deafness *DFNB29*,” Cell, Jan. 12, 2001, 104(1):165-172.
Wines et al., “The IgG Fc contains distinct Fc receptor (FcR) binding sites: the leukocyte receptors FcγRI and FcγRIIa bind to a region in the Fc distinct from that recognized by neonatal FcR and protein A,” J Immunol, May 15, 2000, 164(10):5313-5318.
Wing et al., “Mechanism of First-Dose Cytokine-Release Syndrome by Campath 1-H: Involvement of CD16 (FcγRIII) and CD11a/CD18 (LFA-1) on NK Cells,” J Clin Invest, Dec. 15, 1996, 98(12):2819-2826.
Witte et al., “Monoclonal antibodies targeting the VEGF receptor-2 (Flk1/KDR) as an anti-angiogenic therapeutic strategy,” Cancer Metastasis Rev, Jun. 1998, 17(2):155-161.
Wolf et al., “BiTEs: bispecific antibody constructs with unique anti-tumor activity,” Drug Discov Today, 2005, 10(18):1237-1244.
Wozniak-Knopp et al., “Introducing antigen-binding sites in structural loops of immunoglobulin constant domains: Fc fragments with engineered HER2/neu-binding sites and antibody properties,” Protein Eng Des Sel, Apr. 2010, 23(4):289-297. do i: 10. 1093/ prote in/gzq005. Epub Feb. 11, 2010.
Wu et al., “Upregulated miR-20a-5p expression promotes proliferation and invasion of head and neck squamous cell carcinoma cells by targeting of TNFRSF21,” Oncol Rep, Aug. 2018, 40(2):1138-1146.
Wu et al., “Humanization of a Murine Monoclonal Antibody by Simultaneous Optimization of Framework and CDR Residues,” J Mol Biol, Nov. 19, 1999, 294(1):151-162.
Xing et al., “Reversing Effect of Ring Finger Protein 43 Inhibition on Malignant Phenotypes of human Hepatocellular Carcinoma,” Mol Cancer Ther, Jan. 2013, 12(1):94-103. doi: 10.1158/1535-7163.MCT-12-0672. Epub Nov. 6, 2012.
Xu et al., “In Vitro Characterization of Five Humanized OKT3 Effector Function Variant Antibodies,” Cell Immunol, Feb. 25, 2000, 200(1):16-26.
Yagyu et al., “A novel oncoprotein RNF43 functions in an autocrine manner in colorectal cancer,” Int J Oncol, Nov. 2004, 25(5):1343-1348.
Yamauchi et al., “The glypican 3 oncofetal protein is a promising diagnostic marker for hepatocellular carcinoma,” Mod Pathol, Dec. 2005, 18(12):1591-1598.

(56) References Cited

OTHER PUBLICATIONS

Yang et al., "Attenuation of CD8+T-Cell Function by CD4+CD25+ Regulatory T Cells in B-Cell Non-Hodgkin's Lymphoma," Cancer Res, Oct. 15, 2006, 66(20):10145-10152.
Yang et al., "Intratumoral CD4+CD25+regulatory T-cell-mediated suppression of infiltrating CD4+T cells in B-cell non-Hodgkin lymphoma," Blood, May 1, 2006, 107(9):3639-3646. Epub Jan. 10, 2006.
Yang et al., "Anti-CD3 scFv-B7.1 fusion protein expressed on the surface of HeLa cells provokes potent T-lymphocyte activation and cytotoxicity," Biochem Cell Biol, Apr. 2007, 85(2):196-202.
Yano et al., "Ipilimumab augments antitumor activity of bispecific antibody-armed T cells," Journal of Translational Medicine, 2014, 12(1):191.
Yarilin, Chapter 3 "Molecular and cellular basis of adaptive immunity," Immunology Basics, M:Medicina, 1999, pp. 169-174 (with English translation).
Yonezawa et al., "Boosting Cancer Immunotherapy with Anti-CD137 Antibody Therapy," Clin Cancer Res, Jul. 15, 2015, 21(14):3113-3120. doi 10.1158/1078-0432. CCR-15-0263. Epub Apr. 23, 2015.
Yorita et al., "Prognostic significance of circumferential cell surface immunoreactivity of glypican-3 in hepatocellular carcinoma," Liver Int, Jan. 2011, 31(1):120-131. Epub Oct. 21, 2010.
Yu et al., "Simultaneous inhibition of two regulatory T-cell subsets enhanced Interleukin-15 efficacy in a prostate tumor model," Proc Natl Acad Sci USA, Apr. 17, 2012, 109(16):6187-6192. doi: 10.1073/pnas.1203479109. Epub Apr. 2, 2012.
Yu et al., "Interaction between Bevacizumab and Murine VEGF-A: A Reassessment," Invest Ophthalmol Vis Sci, Feb. 2008, 49(2):522-527. doi: 10.1167/iovs.07-1175.
Yu et al., "T cell-redirecting bispecific antibodies in cancer immunotherapy: recent advances," Jour Cancer Research and Clinical Oncology, 2019, 145:941-956.
Yu et al., "A novel targeted GPC3/CD3 bispecific antibody for the treatment hepatocellular carcinoma," Can Biol Ther, Jul. 2, 2020, 21(7):597-603. doi: 10.1080/15384047.2020.1743158. Epub Apr. 2, 2020.
Zalevsky et al., "The impact of Fc engineering on an anti-CD 19 antibody: increased Fcγ receptor affinity enhances B-cell clearing in nonhuman primates," Blood, Apr. 16, 2009, 113(16):3735-3743. Epub Dec. 24, 2008.
Zeidler et al., "Simultaneous Activation of T Cells and Accessory Cells by a New Class of Intact Bispecific Antibody Results in Efficient Tumor Cell Killing," J Immunol, Aug. 1, 1999, 163(3):1246-1252.
Zeidler et al., "The Fc-region of a new class of intact bispecific antibody mediates activation of accessory cells and NK cells and induces direct phagocytosis of tumour cells," Br J Cancer, Jul. 2000, 83(2):261-266.
Zhao et al., "A Bispecific Protein Capable of Engaging CTLA-4 and MHCII Protects Non-Obese Diabetic Mice from Autoimmune Diabetes," PLoS One, May 21, 2013, 8(5):e63530, 11 pages. doi: 10.1371/journal.pone.0063530.
Zhao et al., "Targeting CD37-positive lymphoid malignancies with a novel engineered small modular immunopharmaceutical," Blood, Oct. 1, 2007, 110(7):2569-2577.
Zheng et al., "YB-1 immunization combined with regulatory T-cell depletion induces specific T-cell responses that protect against neuroblastoma in the early stage," Acta Biochim Biophys Sin (Shanghai), Dec. 2012, 44(12):1006-1014. doi:10.1093/abbs/gms089.
Zhu et al., "Enhanced glypican-3 expression differentiates the majority of hepatocellular carcinomas from benign hepatic disorders," Gut, Apr. 2001, 48(4):558-564.
Zhu et al., "Remodeling domain interfaces to enhance heterodimer formation," Protein Sci, Apr. 1997, 6(4):781-788.
Zirngibl et al., "GD2-directed bispecific trifunctional antibody outperforms dinutuximab beta in a murine model for aggressive metastasized neuroblastoma," Journal for Immuno Therapy of Cancer, Jul. 2021, 9:e002923, 20 pages (including online supplementary material). doi:10.1136/jitc-2021-002923.
International Preliminary Report on Patentability for App. Ser. No. PCT/JP2011/077603, dated Jun. 4, 2013, 10 pages.
International Search Report for App. Ser. No. PCT/JP2011/077603, mailed Mar. 13, 2012, 8 pages.
International Search Report for App. Ser. No. PCT/JP2016/066331, mailed Jul. 19, 2016, 2 pages.
Fish & Richardson P.C., Substance of the Interview in U.S. Appl. No. 13/990,088, dated Nov. 25, 2015, 1 page.
USPTO Restriction Requirement in U.S. Appl. No. 13/990,088, dated Nov. 27, 2015, 9 pages.
USPTO Applicant-Initiated Interview Summary in U.S. Appl. No. 13/990,088, dated Jan. 29, 2016, 3 pages.
Fish & Richardson P.C., Response to Restriction Requirement dated Nov. 27, 2015 in U.S. Appl. No. 13/990,088, filed Feb. 29, 2016, 23 pages.
USPTO Office Action in U.S. Appl. No. 13/990,088, dated Apr. 29, 2016, 33 pages.
Fish & Richardson P.C., Response to Office Action dated Apr. 29, 2016 in U.S. Appl. No. 13/990,088, filed Sep. 28, 2016, 26 pages.
USPTO Final Office Action in U.S. Appl. No. 13/990,088, dated Nov. 25, 2016, 30 pages.
Fish & Richardson P.C., Response to Final Office Action in U.S. Appl. No. 13/990,088, dated May 24, 2017, 16 pages.
USPTO Non-Final Office Action in U.S. Appl. No. 13/990,088, dated Aug. 21, 2017, 16 pages.
USPTO Response to Final Office Action in U.S. Appl. No. 13/990,088, dated Dec. 19, 2017, 17 pages.
USPTO Final Office Action in U.S. Appl. No. 13/990,088, dated Mar. 21, 2018, 19 pages.
USPTO Applicant-Initiated Interview Summary in U.S. Appl. No. 13/990,088, dated Aug. 10, 2018, 6 pages.
Fish & Richardson P.C., Response to Final Office Action in U.S. Appl. No. 13/990,088, dated Aug. 20, 2018, 15 pages.
USPTO Non-Final Office Action in U.S. Appl. No. 13/990,088, dated Oct. 1, 2018, 26 pages.
Fish & Richardson P.C., Response to Final Office Action in U.S. Appl. No. 13/990,088, dated Mar. 11, 2019, 75 pages.
USPTO Final Office Action in U.S. Appl. No. 13/990,088, dated Jun. 5, 2019, 15 pages.
Fish & Richardson P.C., Response to Final Office Action in U.S. Appl. No. 13/990,088, dated Oct. 7, 2019, 9 pages.
USPTO Advisory Action U.S. Appl. No. 13/990,088, dated Oct. 23, 2019, 3 pages.
USPTO Afcp 2.0 Decision in U.S. Appl. No. 13/990,088, dated Oct. 23, 2019, 2 pages.
USPTO Notice of Allowance and Examiner-Initiated Interview Summary in U.S. Appl. No. 13/990,088, dated Jan. 13, 2020, 33 pages.
USPTO Non-Final Office Action in U.S. Appl. No. 13/990,088, dated Jun. 9, 2020, 19 pages.
USPTO Applicant-Initiated Interview Summary in U.S. Appl. No. 13/990,088, dated Jul. 31, 2020, 20 pages.
USPTO Examiner-Initiated Interview Summary in U.S. Appl. No. 13/990,088, dated Aug. 17, 2020, 5 pages.
Fish & Richardson P.C., Response to Final Office Action in U.S. Appl. No. 13/990,088, dated Oct. 6, 2020, 22 pages.
USPTO Final Office Action in U.S. Appl. No. 13/990,088, dated Dec. 1, 2020, 20 pages.
Fish & Richardson P.C., Response to Final Office Action in U.S. Appl. No. 13/990,088, dated Jan. 27, 2021, 19 pages.
USPTO AFCP 2.0 Decision and Notice of Allowance in U.S. Appl. No. 13/990,088, dated Feb. 11, 2021, 14 pages.
Fish & Richardson P.C., Reply to Notice of Allowance in U.S. Appl. No. 13/990,088, dated Mar. 24, 2021, 4 pages.
USPTO Applicant-Initiated Interview Summary in U.S. Appl. No. 13/990,088, dated Apr. 5, 2021, 2 pages.
Fish & Richardson P.C., Amendment after Payment of Issue Fee in U.S. Appl. No. 13/990,088, dated Apr. 14, 2021, 13 pages.
USPTO Notice of Allowance in U.S. Appl. No. 13/990,088, dated Apr. 26, 2021, 22 pages.

(56) References Cited

OTHER PUBLICATIONS

Fish & Richardson P.C., Reply to Notice of Allowance in U.S. Appl. No. 13/990,088, dated May 18, 2021, 3 pages.
USPTO Non-Final Office Action in U.S. Appl. No. 12/295,075, dated Jun. 7, 2013, 17 pages.
International Search Report for App. Ser. No. PCT/JP2012/078103, mailed Jan. 22, 2013, 6 pages.
International Preliminary Report on Patentability for App. Ser. No. PCT/JP2012/078103, dated May 6, 2014, 6 pages.
Chinese Search Report for App. Ser. No. 201180068471.0, dated May 13, 2014, 2 pages.
USPTO Restriction Requirement in U.S. Appl. No. 14/351,654, dated Apr. 29, 2015, 14 pages.
USPTO Applicant-Initiated Interview Summary in U.S. Appl. No. 14/351,654, dated Jul. 31, 2015, 3 pages.
USPTO Applicant-Initiated Interview Summary in U.S. Appl. No. 14/351,654, dated Aug. 4, 2015, 3 pages.
USPTO Non-Final Office Action in U.S. Appl. No. 14/351,654, dated Sep. 8, 2015, 9 pages.
USPTO Final Office Action in U.S. Appl. No. 14/351,654, dated Apr. 14, 2016, 12 pages.
USPTO Non-Final Office Action in U.S. Appl. No. 14/351,654, dated Nov. 9, 2016, 15 pages.
USPTO Notice of Allowance in U.S. Appl. No. 14/351,654, dated Apr. 10, 2017, 15 pages.
USPTO Non-Final Office Action in U.S. Appl. No. 14/351,654, dated Aug. 22, 2017, 9 pages.
USPTO Final Office Action in U.S. Appl. No. 14/351,654, dated May 11, 2018, 12 pages.
USPTO Notice of Allowance in U.S. Appl. No. 14/351,654, dated Sep. 27, 2018, 12 pages.
USPTO Notice of Allowance in U.S. Appl. No. 14/351,654, dated Jan. 23, 2019, 12 pages.
USPTO Notice of Allowance in U.S. Appl. No. 14/351,654, dated Jul. 10, 2019, 10 pages.
USPTO Applicant-Initiated Interview Summary in U.S. Appl. No. 14/351,654, dated May 24, 2019, 4 pages.
USPTO Notice of Allowance in U.S. Appl. No. 14/351,654, dated Sep. 30, 2019, 15 pages.
USPTO Notice of Allowance in U.S. Appl. No. 14/351,654, dated Jan. 29, 2020, 10 pages.
USPTO Non-Final Office Action in U.S. Appl. No. 14/351,654, dated Apr. 16, 2020, 15 pages.
USPTO Final Office Action in U.S. Appl. No. 14/351,654, dated Dec. 1, 2020, 16 pages.
USPTO Non-Final Office Action in U.S. Appl. No. 14/351,654, dated Nov. 24, 2021, 26 pages.
USPTO Final Office Action in U.S. Appl. No. 14/351,654, dated Jun. 14, 2022, 14 pages.
USPTO Non-Final Office Action in U.S. Appl. No. 14/351,654, dated Jan. 24, 2023 11 pages.
U.S. Appl. No. 13/518,861, Igawa et al., filed Oct. 4, 2012.
U.S. Appl. No. 16/959,288, Kimura et al., filed Jun. 30, 2020.
U.S. Appl. No. 17/367,909, Nezu et al., filed Jul. 6, 2021.
U.S. Appl. No. 13/518,861, filed Oct. 4, 2012, Igawa et al.
U.S. Appl. No. 16/959,288, filed, Jun. 30, 2020, Kimura et al.
U.S. Appl. No. 17/367,909, filed Jul. 6, 2021, Nezu et al.
Anti-CD3 antibodies, 62 pages, printed from the Internet on Mar. 15, 2023 at <https://www.abcam.com/products?sortOptions=Relevance&keywords=CD3&selected.reactivity=Human&selected.conjugate=Unconjugated&selected.clonality=Monoclonal>.
Anti-human BRCA1 antibody, 6 pages, printed from the Internet on Mar. 15, 2023 at <https://www.abcam.com/products?sortOptions=Relevance&keywords=BRCA1&selected.c1%20assification-Primary%20antibodies&selected.reactivity=Human>.
Anti-human EGFR antibody, 26 pages, printed from the Internet on Mar. 15, 2023 at <https://www.abcam.com/products?sortOptions=Relevance&keywords=epcam&selected.im%20munogenSpecies=Human>.
Anti-human MUC1 antibody, 21 pages, printed from the Internet on Mar. 15, 2023 at <https://www.abcam.com/products?sortOptions=Relevance&keywords=MUC1&selected.cla%20ssification=Primary%20antibodies&selected.reactivity=Human>.
Anti-human PSA (prostate-specific antigen) antibody, 7 pages, printed from the Internet on Mar. 15, 2023 at <https://www.abcam.com/products?sortOptions=Relevance&keywords=Prostate%20Specific%20Antigen&selected.classification-Primary20antibodies&selected.reactivity=Human>.
USPTO Non-Final Office Action in U.S. Appl. No. 17/367,909, dated Oct. 10, 2023, 107 pages.
USPTO Applicant-Initiated Interview Summary in U.S. Appl. No. 17/367,909, dated Oct. 17, 2023, 3 pages.
Fish & Richardson P.C., Amendment and Reply to Action of Oct. 10, 2023 in U.S. Appl. No. 17/367,909, filed Feb. 21, 2024, 218 pages.
U.S. Appl. No. 18/611,460, Nezu et al., filed Mar. 20, 2024.
U.S. Appl. No. 18/611,460, Nezu et al.
Al Qaraghuli et al., "Antibody-protein binding and conformational changes: identifying allosteric signalling pathways to engineer a better effector response," Nature Scientific Reports, 2020, 10:13696, 10 pages.
Amersham Biosciences, "Protein Purification Handbook," ed. AC, 2001, 98 pages.
ClinicalTrials.gov [online], "A Study of ERY974 in Patient with Advanced Solid Tumors," NCT02748837, date of first posting to ClinicalTrials.gov: Apr. 22, 2016; date of last update: Aug. 22, 2019, pp. 1-7.
ClinicalTrials.gov [online], "A Phase 1 Study of ERY974 in Patients with Hepatocellular Carcinoma," NCT05022927, date of first posting to ClinicalTrials.gov: Aug. 26, 2021; date of last update: Feb. 12, 2024, pp. 1-13.
USPTO Final Office Action in U.S. Appl. No. 17/367,909, dated Apr. 18, 2024, 10 pages.
Almagro et al., "Humanization of antibodies," Frontiers in Bioscience, Jan. 1, 2008, 13:1619-1633.
Altshuler et al., "Generation of Recombinant Antibodies and Means for Increasing Their Affinity," Biochemistry (Moscow), Dec. 2010, 75(13): 1584-1605.
Hasegawa et al., "Single amino acid substitution in LC-CDR1 induces Russell body phenotype that attenuates cellular protein synthesis through eIF2α phosphorylation and thereby downregulates IgG secretion despite operational secretory pathway traffic," mAbs, Jul. 2017, 9(5):854-873.
Lippow et al., "Computational design of antibody-affinity improvement beyond in vivo maturation," Nature Biotechnology, Oct. 2007, 25(10):1171-1176.
Marchalonis et al., "The antibody repertoire in evolution: Chance, selection, and continuity," Dev & Comp Immunol, 2006, 30:223-247.
McDonagh et al., "Engineered anti-CD70 antibody-drug conjugate with increased therapeutic index," Mol Cancer Ther, Sep. 2008, 7(9):2913-2923.
Sulea et al., "Application of Assisted Design of Antibody and Protein Therapeutics (ADAPT) improves efficacy of a Clostridium difficile toxin A single-domain antibody," Scientific Reports, 2018, 8(260):1-11.
Fish & Richardson P.C., Reply to Action of Apr. 18, 2024 in U.S. Appl. No. 17/367,909, filed May 22, 19 pages.
USPTO Non-Final Office Action in U.S. Appl. No. 17/367,909, dated Jun. 20, 2024, 21 pages.
USPTO Non-Final Office Action in U.S. Appl. No. 18/611,460, dated Jun. 5, 2024, 25 pages.
Dickopf et al., "Format and geometries matter: Structure-based design defines the functionality of bispecific antibodies," Comput Struct Biotechnol J, May 14, 2020, 18:1221-1227.
Engelberts et al., "DuoBody-CD3xCD20 induces potent T-cell-mediated killing of malignant B cells in preclinical models and provides opportunities for subcutaneous dosing," EBioMedicine, Feb. 2020, 52:102625, 13 pages.
Gilliland et al., "Universal bispecific antibody for targeting tumor cells for destruction by cytotoxic T cells," Proc Natl Acad Sci USA, Oct. 1988, 85(20):7719-7723.

(56) References Cited

OTHER PUBLICATIONS

Kipriyanov et al., "Recent advances in the generation of bispecific antibodies for tumor immunotherapy," Curr Opin Drug Discov Devel, Mar. 2004, 7(2):233-242.
U.S. Appl. No. 18/748,951, Igawa et al., filed Jun. 20, 2024.
U.S. Appl. No. 18/748,951, filed Jun. 20, 2024, Igawa et al.
Abcam,"anti-CD3 antibodies," 254 pages, printed from the Internet on Sep. 30, 2024 at https://www.abcam.com/en-us/search?facets.categoryType=Primary%20Antibodies&productSorting=relevance&resourceSorting=relevance&keywords=anti-CD3.
Abcam, "CD20 antibodies," 21 pages, printed from the Internet on Sep. 30, 2024 at https://www.abcam.com/en-us/search?facets.target=CD20&facets.categoryType=Primary+Antibodies&sorting=relevance.
"Blinatumomab," WHO Drug Information, Dec. 9, 2008, 22(4):316, printed from the Internet on Sep. 5, 2024 at https://cdn.who.int/media/docs/default-source/international-nonproprietary-names-(inn)/pl100.pdf?sfvrsn=acdb5b98_7&download=true.
"Foralumab," WHO Drug Information, Jun. 9, 2007, 24(2):143, printed from the Internet on Sep. 5, 2024 at https://cdn.who.int/media/docs/default-source/international-nonproprietary-names-(inn)/pl103.pdf?sfvrsn=c81f905b_7&download=true.
"Otelixizumab," WHO Drug Information, Dec. 9, 2007, 21(4):343, printed from the Internet on Sep. 5, 2024 at https://cdn.who.int/media/docs/default-source/international-nonproprietary-names-(inn)/p198.pdf?sfvrsn=8282121d_3&download=true.
"Teplizumab," WHO Drug Information, Jun. 9, 2007, 21(2):165, printed from the Internet on Sep. 5, 2024 at https://cdn.who.int/media/docs/default-source/international-nonproprietary-names-(inn)/p197.pdf?sfvrsn=c8a12630_3&download=true.
"Veltuzumab," WHO Drug Information, Dec. 9, 2007, 21(4):352, printed from the Internet on Sep. 5, 2024 at https://cdn.who.int/media/docs/default-source/international-nonproprietary-names-(inn)/p198.pdf?sfvrsn=8282121d_3&download=true.
Lim et al. "Anti-CD20 monoclonal antibodies: historical and future perspectives," haematologica, 2010, 95(1):135.
"Scheme of alternatives (i)-(v) in claim 5," 5 pages (document submitted in the corresponding European Application No. EP 23200969.6 on Aug. 26, 2024).
Taylor et al., "Immunotherapeutic mechanisms of anti-CD20 monoclonal antibodies," Curr Opin Immunol, Aug. 2008, 20(4):444-449.
Weiβmüller et al., "TGN1412 Induces Lymphopenia and Human Cytokine Release in a Humanized Mouse Model," PLOS ONE, Mar. 9, 2016, 11(3):e0149093, 19 pages.
USPTO Final Office Action in U.S. Appl. No. 18/611,460, dated Sep. 25, 2024, 16 pages.
USPTO Restriction Requirement in U.S. Appl. No. 15/302,439, dated Jun. 15, 2018, 8 pages.
USPTO Non-Final Office Action in U.S. Appl. No. 15/302,439, dated Dec. 4, 2018, 20 pages.
USPTO Restriction Requirement in U.S. Appl. No. 15/302,439, dated Aug. 1, 2019, 5 pages.
USPTO Final Office Action in U.S. Appl. No. 15/302,439, dated Nov. 7, 2019, 11 pages.
USPTO Non-Final Office Action in U.S. Appl. No. 15/302,439, dated Oct. 30, 2020, 21 pages.
USPTO Final Office Action in U.S. Appl. No. 15/302,439, dated May 18, 2021, 14 pages.
"A. Allotype," Pharmaceutical Immunology, 3rd ed., 2nd impression, Ueda et al. (eds.), Sep. 30, 2018, cover page, p. 27, and copyright page (in Japanese, with English translation of cover page, boxed portion of p. 27, and copyright page).
Abbas et al., Cellular and Molecular Immunology, 1st ed., 2nd impression, Jan. 30, 2016, cover page, p. 117, and copyright page (in Japanese, with English translation of cover page, boxed portion of first column on p. 117, and copyright page).
Chames et al., "Bispecific antibodies for cancer therapy—The light at the end of the tunnel?," mAbs, Nov./Dec. 2009, 1(6):539-547.
Giffin et al., "AMG 757, a Half-Life Extended, DLL3-Targeted Bispecific T-Cell Engager, Shows High Potency and Sensitivity in Preclinical Models of Small-Cell Lung Cancer," Clin Cancer Res, Mar. 1, 2021; 27(5):1526-1537.
Imdelltra (AMG757)—tarlatamab-dlle, Amgen Inc., Highlights of prescribing information, FDA label, May 2024, 39 pages.
Matsuzawa et al., "Measurement of Tissue Factor by Enzyme Immunoassay," Japanese Journal of Thrombosis and Hemostasis, 1993, 4(6):441-447 (in Japanese, with English translation of boxed portion of second column on p. 441).
The Chemical Unabridged, 1st ed., 7th impression, Oki et al. (eds.), Jul. 1, 2005, cover page, p. 127, and copyright page (in Japanese, with English translation of cover page, boxed portion of second column on p. 127, and copyright page).
Vojacek et al., "Plasma Tissue Factor in Coronary Artery Disease: Further Step to the Understanding of the Basic Mechanisms of Coronary Artery Thrombosis," Physiol Res, 2008, 57(1):1-5.
www.imgt.org, IMGT Repertoire (IG and TR)—Allotypes: Human (*Homo sapiens*) IGHC, retrieved on Nov. 21, 2024 from URL <https://www.imgt.org/IMGTrepertoire/Proteins/allotypes/human/IGH/IGHC/G1m_allotypes.html>, 4 pages.
Yoshimura et al., The Chemical Dictionary, 2nd ed., pocket edition, 1st impression, Nov. 15, 2012, cover page, p. 103, and copyright page (in Japanese, with English translation of cover page, boxed portion of second column on p. 103, and copyright page).
U.S. Appl. No. 18/884,329, Kinoshita et al., filed Sep. 13, 2024.
U.S. Appl. No. 18/887,180, Nezu et al., filed Sep. 17, 2024.
U.S. Appl. No. 18/884,329, filed Sep. 13, 2024, Kinoshita et al.
U.S. Appl. No. 18/887,180, filed Sep. 17, 2024, Nezu et al.
abysis.org [online], "Key Annotation," retrieved on Feb. 20, 2025, retrieved from URL <http://www.abysis.org/abysis/sequence_input/key_annotation/key_annotation.cgi>, 1 page.
Alegre et al., "A non-activating 'humanized' anti-CD3 monoclonal antibody retains immunosuppressive properties in vivo," Transplantation, Jun. 15, 1994, 57(11):1537-1543.
"Amgen to Acquire Micromet," Press Release, Amgen, Inc., Jan. 26, 2012, 3 pages.
"Amino Acids Reference Chart," Merck KGaA, 2025, 8 pages.
Baudino et al., "Crucial role of aspartic acid at position 265 in the CH2 domain for murine IgG2a and IgG2b Fc-associated effector functions," J Immunol, Nov. 1, 2008, 181(9):6664-6669.
Chames et al., "Bispecific antibodies for cancer therapy," Curr Opin Drug Discov Devel, Mar. 2009, 12(2):276-283.
Clynes et al., "Inhibitory Fc Receptors Modulate In Vivo Cytoxicity Against Tumor Targets," Nat Med, Apr. 2000, 6(4):443-446.
Dondelinger et al., "Understanding the Significance and Implications of Antibody Numbering and Antigen-Binding Surface/Residue Definition," Frontiers in Immunology, Oct. 2018, 9:2278, 15 pages.
Firestone et al. "An Embarrassment of Riches: Three FDA-Approved Bispecific Antibodies for Relapsed Refractory Multiple Myeloma." Blood Cancer Discov, Oct. 12, 2023, 4(6):433-436. doi: 10.1158/2643-3230.BCD-23-0176.
"Guidance for Quality Assessment of Antibody Drugs," Announcement from Director of the Inspection and Control Division, Pharmaceuticals and Food Safety Bureau, Ministry of Health, Labour and Welfare, Dec. 14, 2012, 1(1214):1-16 (with English translation).
Gutcher et al., "APC-derived cytokines and T cell polarization in autoimmune inflammation," J Clin Invest, May 2007, 117(5):1119-1127.
Heiss et al., "Immunotherapy of malignant ascites with trifunctional antibodies," Int J Cancer, Nov. 10, 2005, 117(3):435-443.
Herold et al., "Teplizumab: A Disease-Modifying Therapy for Type 1 Diabetes That Preserves β-Cell Function," Diabetes Care, 2023, 46(10):1848-1856. doi: 10.2337/dc23-0675.
Huang, "Receptor-Fc fusion therapeutics, traps, and Mimetibody™ technology," Curr Opin Biotechnol, Dec. 2009, 20(6):692-699.
Ishii-Watabe et al., "Molecular Design of Antibody Drugs," Journal of Pharmaceutical Science and Technology, 2014, 74(1):4-11 (with English translation).
Izutsu et al., "IV. Recent Topics—1. Antibody Therapies," Nihon Naika Gakkai Zasshi, 2008, 97(7):1620-1626 (108-114) (with English translation).

(56) References Cited

OTHER PUBLICATIONS

Lazar et al., "Optimization of Fc Domains to Enhance Antibody Therapeutics," Recombinant Antibodies for Immunotherapy, 2009, pp. 124-143.

Lwaleed et al., "The biology and tumour-related properties of monocyte tissue factor," J Pathol, Jan. 2001, 193(1):3-12.

Moreira et al., "Nasal administration of anti-CD3 mAb (Foralumab) downregulates NKG7 and increases TGFB1 and GIMAP7 expression in T cells in subjects with COVID-19," Proc Natl Acad Sci USA, 2023, 120(11):e2220272120, 7 pages. doi: 10.1073/pnas.2220272120.

Morrison et al., "Combinatorial alanine-scanning," Curr Opin Chem Biol, Jun. 1, 2001, 5(3):302-307.

Nash et al., "The role of the coagulation system in tumour angiogenesis," Lancet Oncol, Oct. 2001, 2(10):608-613.

nihs.go.jp [online], "Structural Schematic Diagram of Human IgG1," Aug. 15, 2024, retrieved from URL <https://www.nihs.go.jp/dbcb/mabs.html>, 2 pages (with English translation).

Nimmerjahn et al., "FcγRIV: a novel FcR with distinct IgG subclass specificity," Immunity, Jul. 2005, 23(1):41-51.

novoprolabs.com [online], "Antibody CDR annotation," retrieved on Feb. 20, 2025, retrieved from URL <https://www.novoprolabs.com/tools/cdr>, 3 pages.

Panowski et al., "Preclinical Efficacy and Safety Comparison of CD3 Bispecific and ADC Modalities Targeting BCMA for the Treatment of Multiple Myeloma," Mol Cancer Ther, Nov. 1, 2019, 18(11):2008-2020.

Petri, "Coagulation Abnormalities and Oncology," Sysmex Journal Web, 2004, 5(3):1-5 (with English translation).

Price et al., "Tissue Factor and Tissue Factor Pathway Inhibitor," Anaesthesia, May 2004, 59(5):483-492.

Rickles et al., "Tissue Factor, Thrombin, and Cancer," Chest, Sep. 2003, 124(3 Suppl):58S-68S.

Roitt et al., "Chapter 4 Antibodies," Immunology, 6th edition, 2001, p. 67.

Shalaby et al., "Development of Humanized Bispecific Antibodies Reactive with Cytotoxic Lymphocytes and Tumor Cells Overexpressing the HER2 Protooncogene," J Exp Med, Jan. 1, 1992, 175(1):217-225.

Taylor et al., "Immunosuppressive agents in solid organ transplantation: Mechanisms of action and therapeutic efficacy," Critical Reviews in Oncology/Hematology, Oct. 2005, 56(1):23-46.

Tsumura, "Preparation of antibodies of various sizes against tissue factor (TF) and examination of tumor accumulation," Master's Thesis, Department of Advanced Life Sciences, Graduate School of Frontier Sciences, The University of Tokyo, FY2012, Jan. 31, 2013, 7 pages (with English translation).

Versteeg et al., "Tissue factor and cancer metastasis: the role of intracellular and extracellular signaling pathways," Mol Med, Jan.-Jun. 2004, 10(1-6):6-11.

Wolf et al., "Induction of anergy in resting human T lymphocytes by immobilized anti-CD3 antibodies," Eur J Immunol, Jun. 1994, 24(6):1410-1417.

Arakawa et al, "Cloning and Sequencing of the $V_H$ and $Y_K$ Genes of an Anti-CD3 Monoclonal Antibody, and Construction of a Mouse/Human Chimeric Antibody," J Biochem, Sep. 1996, 120(3):657-662.

De Jonge et al., "In Vivo Retargeting of T Cell Effector Function by Recombinant Bispecific Single Chain FV (Anti-CD3 x Anti-Idiotype) Induces Long-Term Survival in the Murine BCL 1 Lymphoma Model," J Immunol, Aug. 1, 1998, 161(3):1454-1461.

Idusogie et al., "Mapping of the C1q Binding Site on Rituxan, a Chimeric Antibody with a Human IgG1 Fc," J Immunol, Apr. 15, 2000, 164(8):4178-4184.

Kabat et al., "Tabulation and Analysis of Amino Acid Sequences of Precursors, V-Regions, C-Regions, J-Chain and β-2-Microglobulins," Sequence of Immunoglobulin Chains, 1979, pp. 144 and 153.

Kabat et al., Sequence of Proteins of Immunological Interest, 1991, vol. 1, 5th ed., pp. 680 and 718.

Magdelaine-Beuzelin et al., "IgG1 heavy chain-coding gene polymorphism (G1m allotypes) and development of antibodies-to-infliximab," Pharmacogenet Genomics, May 2009, 19(5):383-387.

Nitta et al., "Immunotherapy against malignant brain tumor using bispecific (antibody)—Application of immunotherapy for glioma to aid surgical treatment," Juntendo Medical Journal, 1995, 40(4):413-416 (with English translation).

Pharmaceuticals and Medical Devices Agency, "Report on the Results of Deliberations and Review Report—Generic Name Cetuximab," May 7, 2008; Pharmaceutical and Food Safety Bureau, Inspection and Licensing Division, Jun. 2, 2008, 7 pages (with English translation).

www.blincyto.jp, "Blincyto—Action Mechanism," Mar. 21, 2025, retrieved on Apr. 11, 2025, retrieved from URL <https://www.blincyto.jp/documents/mechanism>, 5 pages (with English translation).

www.imgt.org, IMGT Scientific Chart, created May 17, 2002, last updated Jun. 12, 2024, retrieved from URL <https://www.imgt.org/IMGTScientificChart/Numbering/Hu_IGHGnber.html>, 4 pages.

www.miltenyibiotec.com, "T-Cell Activation/Expansion Kit, human," Apr. 8, 2025, retrieved on Apr. 11, 2025, retrieved from URL <https://www.miltenyibiotec.com/UN-en/products/t-cell-activation>, 3 pages.

Hale et al., "Systematic analysis of Fc mutations designed to reduce binding to Fc-gamma receptors," mAbs, Jan.-Dec. 2024, 16(1):2402701.

* cited by examiner

```
Kabat     1                                                                                 2
EU index  1-2---------3---------4---------5---------6---------7---------8---------9---------0---------1---------2--
          8-0---------0---------0---------0---------0---------0---------0---------0---------0---------0---------0--
IgG1      ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCD-
IgG2      ASTKGPSVFPLAPCSRSTSESTAALGCLVKDYFPEPVTVSWNSGALTSGVHTFPAVLQSSGLYSLSSVVTVPSSNFGTQTYTCNVDHKPSNTKVDKTVERK--CC
IgG3      ASTKGPSVFPLAPCSRSTSGGTAALGCLVKDYFPEPVTVSWNSGALTSGVHTFPAVLQSSGLYSLSSVVTVPSSSLGTQTYTCNVNHKPSNTKVDKRVELKTPLG
IgG4      ASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYG--

Kabat      2
EU index   2---------------------------------------------------3---------4---------5---------6---------7---------8
           2-----8---------------------------------------------0---------0---------0---------0---------0---------0
IgG1      -KTHTCPP---------------------------------------------CPAPELLGGPSVFLFPPKPKDTLMISRTPEVTCVVVDVSHEDPEVKFNWYVD
IgG2      -V-E-CPP---------------------------------------------CPAPPVA-GPSVFLFPPKPKDTLMISRTPEVTCVVVDVSHEDPEVQFNWYVD
IgG3      DTTHTCPRCPEPKSCDTPPPCPRCPEPKSCDTPPPCPRCPEPKSCDTPPPCPRCPAPELLGGPSVFLFPPKPKDTLMISRTPEVTCVVVDVSHEDPEVQFKWYVD
IgG4      ---PPCPS---------------------------------------------CPAPEFLGGPSVFLFPPKPKDTLMISRTPEVTCVVVDVSQEDPEVQFNWYVD

Kabat     2                  3
EU index  8--------9---------0---------1---------2---------3---------4---------5---------6---------7---------8-----
          1--------0---------0---------0---------0---------0---------0---------0---------0---------0---------0-----
IgG1      GVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNG
IgG2      GVEVHNAKTKPREEQFNSTFRVVSVLTVVHQDWLNGKEYKCKVSNKGLPAPIEKTISKTKGQPREPQVYTLPPSREEMTKNQVSLTCLVKGFYPSDIAVEWESNG
IgG3      GVEVHNAKTKPREEQYNSTFRVVSVLTVLHQDWLNGKEYKCKVSNKALPAPIEKTISKTKGQPREPQVYTLPPSREEMTKNQVSLTCLVKGFYPSDIAVEWESSG
IgG4      GVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNG

Kabat     3             4
EU index  8---9---------0---------1---------2---------3---------4
          6---0---------0---------0---------0---------0---------0------7
IgG1      QPENNYKTTPPVLDSDGSFFLYSKLTVDKSRWQQGNVFSCSVMHEALHNHYTQKSLSLSPGK (SEQ ID NO: 23)
IgG2      QPENNYKTTPPMLDSDGSFFLYSKLTVDKSRWQQGNVFSCSVMHEALHNHYTQKSLSLSPGK (SEQ ID NO: 24)
IgG3      QPENNYNTTPPMLDSDGSFFLYSKLTVDKSRWQQGNIFSCSVMHEALHNRFTQKSLSLSPGK (SEQ ID NO: 25)
IgG4      QPENNYKTTPPVLDSDGSFFLYSRLTVDKSRWQEGNVFSCSVMHEALHNHYTQKSLSLSLGK (SEQ ID NO: 26)
```

FIG. 18

CYTOTOXICITY-INDUCING THERAPEUTIC AGENT

CROSS-REFERENCE TO RELATED APPLICATIONS

This application is a divisional of U.S. application Ser. No. 17/367,909, filed on Jul. 6, 2021, which is a divisional of U.S. application Ser. No. 13/990,088, filed on Dec. 19, 2013 (now U.S. Pat. No. 11,066,483), which is the National Stage of International Patent Application No. PCT/JP2011/077603, filed on Nov. 30, 2011, which claims the benefit of Japanese Patent Application No. 2010-266760, filed on Nov. 30, 2010, Japanese Patent Application No. 2011-121771, filed on May 31, 2011, and Japanese Patent Application No. 2011-238818, filed on Oct. 31, 2011. The entire content of parent application Ser. No. 17/367,909 is hereby incorporated by reference.

SEQUENCE LISTING

This application contains a Sequence Listing that has been submitted electronically as an XML file named 38856-0225003_SL_ST26. The XML file, created on Feb. 26, 2024, is 118,754 bytes in size. The material in the XML file is hereby incorporated by reference in its entirety.

TECHNICAL FIELD

The present invention relates to polypeptide complexes that enable cancer treatment by having T cells close to target cancer cells and using the cytotoxic activity of T cells against the target cancer cells, methods for producing the polypeptide complexes, and therapeutic agents that contain such a polypeptide complex as an active ingredient for inducing cellular cytotoxicity. The present invention also relates to pharmaceutical compositions for treating or preventing various cancers, which contain an above-mentioned therapeutic agent for inducing cellular cytotoxicity as an active ingredient, and therapeutic methods using such pharmaceutical compositions.

BACKGROUND ART

To date, multiple therapeutic antibodies having an excellent anti-tumor effect have been developed as pharmaceuticals for treating cancer (Non-patent Document 1). These therapeutic antibodies are known to exert their anti-tumor effect on cancer cells through inhibition of signals essential for cancer cell growth, induction of cell death signals, antibody dependent cell-mediated cytotoxicity (ADCC), or complement dependent cytotoxicity (CDC) (Non-patent Document 2). ADCC is a cytotoxicity exerted by effector cells such as NK cells and macrophages against antibody-bound target cancer cells when the Fc region of an antibody binds to an Fc receptor on the effector cells. Meanwhile, a complement complex binds to the complement-binding site in an antibody structure. CDC is cytotoxicity that occurs when a complement component in the complex forms a pore through the cell membrane of an antibody-bound cell, enhancing water or ion influx into the cell. Although conventional therapeutic antibodies show excellent activities, to date administration of such antibodies led to only unsatisfactory therapeutic outcomes. Thus, it is desirable to develop therapeutic antibodies that exert a greater cell-killing activity against cancer.

In addition to the above-mentioned antibodies which adopt ADCC as their anti-tumor mechanism by recruiting NK cells or macrophages as effector cells, T cell-recruiting antibodies (TR antibodies) which adopt cytotoxicity as their anti-tumor mechanism by recruiting T cells as effector cells have been known since the 1980s (Non-patent Documents 3 to 5). A TR antibody is a bispecific antibody that contains an antibody against any one of the subunits forming a T-cell receptor (TCR) complex on T cells, in particular an antibody that binds to the CD3 epsilon chain, and an antibody that binds to an antigen on target cancer cells. A T cell gets near a cancer cell when the TR antibody binds to both the CD3 epsilon chain and cancer antigen at the same time, and this causes an anti-tumor effect against the cancer cell due to the cytotoxic activity of the T cell.

An antibody called "trifunctional antibody" is also known as a TR antibody (Non-patent Documents 6 and 7). A trifunctional antibody is a whole IgG-type bispecific antibody in which one arm contains an Fab that binds to a cancer antigen and the other arm contains an Fab that binds to the CD3 epsilon chain. Therapeutic effect against malignant ascites has been demonstrated by administering catumaxomab, which is a trifunctional antibody against EpCAM, into the peritoneal cavities of malignant ascites patients having EpCAM expression-positive cancer cells. The use of catumaxomab has been approved in the EU for the above treatment.

Furthermore, a TR antibody called "bispecific T-cell engager (BiTE)" has been recently found to exhibit a strong anti-tumor effect (Non-patent Documents 8 and 9). BiTE is a TR antibody with a molecular form in which the scFv of an antibody against a cancer antigen is linked to the scFv of an antibody against the CD3 epsilon chain via a short polypeptide linker. BiTE has been reported to have an anti-tumor activity superior to those of the various known TR antibodies (Non-patent Documents 9 and 10). Specifically, as compared to other TR antibodies, BiTE exerts an anti-tumor effect even at a significantly lower concentration and lower effector cell/cancer cell ratio (ET ratio). It has been also demonstrated that the effect can be exerted without the need to activate effector cells using IL-2, a CD28 agonistic antibody or such in advance. Blinatumomab (MT103), which is a BiTE against CD19, exhibits a much stronger cytotoxic activity against cancer cells in vitro than that of RITUXAN® (rituximab) which is known to produce an excellent clinical effect. Furthermore, blinatumomab has been reported to show an extremely superior anti-tumor effect in phase I and II clinical trials conducted recently (Non-patent Document 11).

The fact that catumaxomab has been approved as a therapeutic agent that demonstrates clinical drug effect, and that multiple BiTEs including blinatumomab exert a strong anti-tumor effect, suggests that TR antibodies that recruit T cells as effector cells have a significantly higher potential as an anti-tumor agent as compared to conventional antibodies that use ADCC as their mechanism of action.

However, it is known that a trifunctional antibody binds to both a T cell and a cell such as an NK cell or macrophage at the same time in a cancer antigen-independent manner, and as a result receptors expressed on the cells are cross-linked, and expression of various cytokines is induced in a cancer antigen-independent manner. Systemic administration of a trifunctional antibody is thought to cause cytokine storm-like side effects as a result of such induction of cytokine expression. In fact, it has been reported that, in the phase I clinical trial, a very low dose of 5 μg/body was the maximum tolerance dose for systemic administration of catumaxomab to patients with non-small cell lung cancer, and that administration of a higher dose causes various severe side effects (Non-patent Document 12). When administered at such a low dose, catumaxomab can never reach the effective blood level. That is, the expected anti-tumor effect cannot be achieved by administrating catumaxomab at such a low dose.

Meanwhile, unlike catumaxomab, BiTE has no Fcγ receptor-binding site, and therefore it does not cross-link the receptors expressed on T cells and cells such as NK cells and macrophages in a cancer antigen-dependent manner. Thus, it has been demonstrated that BiTE does not cause cancer antigen-independent cytokine induction which is observed when catumaxomab is administered. However, since BiTE is a modified low-molecular-weight antibody molecule without an Fc region, the problem is that its blood half-life after administration to a patient is significantly shorter than IgG-type antibodies conventionally used as therapeutic antibodies. In fact, the blood half-life of BiTE administered in vivo has been reported to be about several hours (Non-patent Documents 13 and 14). In the clinical trials of blinatumomab, it is administered by continuous intravenous infusion using a minipump. This administration method is not only extremely inconvenient for patients but also has the potential risk of medical accidents due to device malfunction or the like. Thus, it cannot be said that such an administration method is desirable.

PRIOR ART DOCUMENTS

Non-Patent Documents

[Non-patent Document 1] Clin Cancer Res. (2010) 16 (1), 11-20

[Non-patent Document 2] Drug Des Devel Ther (2009) 3, 7-16

[Non-patent Document 3] Nature (1985) 314 (6012), 628-31

[Non-patent Document 4] Int J Cancer (1988) 41 (4), 609-15

[Non-patent Document 5] Proc Natl Acad Sci USA (1986) 83 (5), 1453-7

[Non-patent Document 6] Cancer Treat Rev. (2010) 36 (6), 458-67

[Non-patent Document 7] Expert Opin Biol Ther (2010) 10 (8), 1259-69

[Non-patent Document 8] Proc Natl Acad Sci USA. (1995) 92 (15), 7021-5

[Non-patent Document 9] Drug Discov Today (2005), 10 (18), 1237-44

[Non-patent Document 10] Trends Biotechnol (2004) 22 (5), 238-44

[Non-patent Document 11] Science (2008), 321 (5891), 974-7

[Non-patent Document 12] Cancer Immunol Immunother (2007) 56 (10), 1637-44

[Non-patent Document 13] Cancer Immunol Immunother. (2006) 55 (5), 503-14

[Non-patent Document 14] Cancer Immunol Immunother. (2009) 58 (1), 95-109

SUMMARY OF THE INVENTION

Problems to be Solved by the Invention

The present invention was achieved in view of the above circumstances. An objective of the present invention is to provide polypeptide complexes that enable cancer treatment by having T cells close to target cancer cells and using the cytotoxicity of T cells against the target cancer cells, methods for producing the polypeptide complexes, and therapeutic agents containing such a polypeptide complex as an active ingredient for inducing cellular cytotoxicity. Another objective of the present invention is to provide pharmaceutical compositions for treating or preventing various cancers, which comprise an above-mentioned therapeutic agent for inducing cellular cytotoxicity as an active ingredient, and therapeutic methods using the pharmaceutical compositions.

Means for Solving the Problems

The present inventors discovered novel polypeptide complexes that retain the strong anti-tumor activity possessed by BiTE and have a long half-life in blood, as well as excellent safety properties that result in no induction of cancer antigen-independent cytokine storm or such. The present inventors also found that the polypeptide complexes can damage various target cells when antigen-binding domains of the polypeptide complexes are substituted. Based on the above findings, the present inventors demonstrated that the polypeptide complexes of the present invention damage cancer cells. The present inventors also revealed that more efficient cellular cytotoxicity is achieved by regulating the CH1/CL interface association and introducing Knobs-into-Holes (KiH) modifications into the polypeptide complexes. In addition, the present inventors demonstrated that various cancers can be treated or prevented using therapeutic agents for inducing cellular cytotoxicity comprising a polypeptide complex of the present invention as an active ingredient.

More specifically, the present invention provides the following:

[1] a polypeptide complex which comprises:
 (1) an antigen-binding domain;
 (2) a domain comprising an Fc region that has reduced Fcγ receptor-binding activity; and
 (3) a T cell receptor complex-binding domain;

[2] the polypeptide complex of [1], wherein the T cell receptor complex-binding domain is a T cell receptor-binding domain;

[3] the polypeptide complex of [1], wherein the T cell receptor complex-binding domain is a CD3-binding domain;

[4] the polypeptide complex of any one of [1] to [3], wherein the antigen-binding domain is a bivalent antigen-binding domain;

[5] the polypeptide complex of [4], wherein the bivalent antigen-binding domain is a domain having an F(ab')2 structure;

[6] the polypeptide complex of [5], in which two polypeptides forming a heavy chain constant region of the domain having the F(ab')2 structure are individually linked to either of the two polypeptides forming an Fc domain;

[7] the polypeptide complex of [6], in which a CD3-binding domain is linked to either or both of the two CH3s forming the Fc domain;

[8] the polypeptide complex of [7], in which a heavy chain Fv fragment forming the CD3-binding domain is linked to one of the CH3s forming the Fc domain and a light chain Fv fragment forming the CD3-binding domain is linked to the other CH3 forming the Fc domain;

[9] the polypeptide complex of [8], in which an antibody CH1 domain is linked to the heavy chain Fv fragment forming the CD3-binding domain and an antibody CL domain is linked to the light chain Fv fragment;

[10] the polypeptide complex of [6], in which the CD3-binding domain is linked to either or both of the two CLs forming the F(ab')2;

[11] the polypeptide complex of [6], in which the CD3-binding domain is linked to either or both of the two VHs forming the F(ab')2;

[12] the polypeptide complex of [6], in which the CD3-binding domain is linked to either or both of the two VLs forming the F(ab')2;

[13] the polypeptide complex of any one of [1] to [12], wherein the CD3-binding domain is Fv;

[14] the polypeptide complex of any one of [1] to [7] and to [12], wherein the CD3-binding domain is Fab;

[15] the polypeptide complex of any one of [1] to [7] and to [12], wherein the CD3-binding domain is scFv;

[16] the polypeptide complex of any one of [1] to [15], wherein the CD3-binding domain is monovalent;

[17] the polypeptide complex of any one of [1] to [3], wherein the antigen-binding domain is a monovalent scFv and a monovalent Fab;

[18] the polypeptide complex of [17], in which the monovalent scFv is linked to one of the polypeptides forming the Fc domain via the scFv that forms the CD3-binding domain; the heavy chain Fv fragment of the monovalent Fab is linked to one of the polypeptides forming the Fc domain via a CH1 domain; and the light chain Fv fragment of the Fab is linked to the CL domain;

[19] the polypeptide complex of any one of [1] to [3], wherein the antigen-binding domain is a bivalent scFv;

[20] the polypeptide complex of [19], in which one monovalent scFv is linked to one of the polypeptides forming the Fc domain via the heavy chain Fv fragment forming the CD3-binding domain, and the other monovalent scFv is linked to the other polypeptide forming the Fc domain via the light chain Fv fragment forming the CD3-binding domain;

[21] the polypeptide complex of [19], wherein one monovalent scFv is linked to one of the polypeptides forming the Fc domain via the scFv forming the CD3-binding domain, and the other monovalent scFv is linked to the other polypeptide forming the Fc domain;

[22] the polypeptide complex of any one of [1] to [3], wherein the antigen-binding domain and T cell receptor complex-binding domain are each a monovalent Fab;

[23] the polypeptide complex of [22], in which the heavy chain Fv fragment of a monovalent Fab forming the antigen-binding domain is linked to one of the polypeptides forming the Fc domain via a CH1 domain and the light chain Fv fragment of the Fab is linked to a CL domain; and the heavy chain Fv fragment of Fab forming the T cell receptor-binding domain is linked to the other polypeptide forming the Fc domain via a CH1 domain and the light chain Fv fragment of the Fab is linked to a CL domain;

[24] the polypeptide complex of [22], in which the heavy chain Fv fragment of a monovalent Fab forming the antigen-binding domain is linked to one of the polypeptides forming the Fc domain via a CH1 domain and the light chain Fv fragment of the Fab is linked to a CL domain; and the light chain Fv fragment of Fab forming the T cell receptor-binding domain is linked to the other polypeptide forming the Fc domain via a CH1 domain and the heavy chain Fv fragment of the Fab is linked to a CL domain;

[25] the polypeptide complex of [22], in which the heavy chain Fv fragment of a monovalent Fab forming the antigen-binding domain is linked to one of the polypeptides forming the Fc domain via a CH1 domain and the light chain Fv fragment of the Fab is linked to a CL domain; and the heavy chain Fv fragment of the Fab forming the T cell receptor-binding domain is linked to the other polypeptide forming the Fc domain via a CL domain and the light chain Fv fragment of the Fab is linked to a CH1 domain;

[26] the polypeptide complex of [22], in which the heavy chain Fv fragment of a monovalent Fab forming the T cell receptor-binding domain is linked to one of the polypeptides forming the Fc domain via a CH1 domain and the light chain Fv fragment of the Fab is linked to a CL domain; and the light chain Fv fragment of Fab forming the antigen-binding domain is linked to the other polypeptide forming the Fc domain via a CH1 domain and the heavy chain Fv fragment of the Fab is linked to a CL domain;

[27] the polypeptide complex of [22], in which the heavy chain Fv fragment of a monovalent Fab forming the T cell receptor-binding domain is linked to one of the polypeptide forming the Fc domain via a CH1 domain and the light chain Fv fragment of the Fab is linked to a CL domain; and the heavy chain Fv fragment of the Fab forming the antigen-binding domain to the other polypeptide forming the Fc domain via a CL domain and the light chain Fv fragment of the Fab is linked to a CH1 domain;

[28] the polypeptide complex of comprising:

(1) an antigen-binding domain in which the heavy chain Fv fragment of a monovalent Fab structure that binds to an antigen is linked via a CH1 domain to one of the polypeptides forming the Fc domain, and the light chain Fv fragment of the Fab structure is linked to a CL domain; and (2) a T cell receptor complex-binding domain in which the heavy chain Fv fragment of a monovalent Fab structure that binds to a T cell receptor complex is linked via a CH1 domain to the other polypeptide forming the Fc domain, and the light chain Fv fragment of the Fab structure is linked to a CL domain;

wherein electric charges of the CH1 and CL domains are controlled so that the heavy chain Fv fragment of the antigen-binding domain assembles with the light chain Fv fragment of the antigen-binding domain, or the heavy chain Fv fragment of the T cell receptor-binding domain assembles with the light chain Fv fragment of the T cell receptor-binding domain;

[29] the polypeptide complex of [28], wherein an amino acid residue in the CH1 domain linked to the heavy chain Fv fragment of the T cell receptor complex-binding domain has the same type of electric charge as an amino acid residue in the CL domain linked to the light chain Fv fragment of the antigen-binding domain;

[30] the polypeptide complex of [28], wherein an amino acid residue in the CH1 domain linked to the heavy chain Fv fragment of the antigen-binding domain has the same type of electric charge as an amino acid residue in the CL domain linked to the light chain Fv fragment of the T cell receptor complex-binding domain;

[31] the polypeptide complex of [28], wherein an amino acid residue in the CH1 domain linked to the heavy chain Fv fragment of the T cell receptor complex-binding domain has the same type of electric charge as an amino acid in the CL domain linked to the light chain Fv fragment of the antigen-binding domain, and an amino acid residue in the CH1 domain linked to the heavy chain Fv fragment of the antigen-binding domain has the same type of electric charge as an amino acid in the CL domain linked to the light chain Fv fragment of the T cell receptor complex-binding domain;

[32] the polypeptide complex of [29] or [31], wherein an amino acid residue in the CH1 domain linked to the heavy chain Fv fragment of the T cell receptor complex-binding domain has an electric charge opposite to that of an amino acid residue in the CL domain linked to the light chain Fv fragment of the T cell receptor-binding domain;

[33] the polypeptide complex of [30] or [31], wherein an amino acid residue in the CH1 domain linked to the heavy chain Fv fragment of the antigen-binding domain has an electric charge opposite to that of an amino acid residue in the CL domain linked to the light chain Fv fragment of the antigen-binding domain;

[34] the polypeptide complex of any one of [22] to [33], wherein the T cell receptor complex-binding domain is a T cell receptor-binding domain;

[35] the polypeptide complex of [34], wherein the T cell receptor-binding domain is a CD3-binding domain;

[36] the polypeptide complex of [32] or [33], wherein the amino acid residues in the CH1 and CL domains are one, two, or more combinations of amino acid residues selected from the group consisting of the combinations of:

(a) the amino acid residue at position 147 (EU numbering) in the CH1 domain, and the amino acid residue at position 180 (EU numbering) in the CL domain;

(b) the amino acid residue at position 147 (EU numbering) in the CH1 domain, and the amino acid residue at position 131 (EU numbering) in the CL domain;

(c) the amino acid residue at position 147 (EU numbering) in the CH1 domain, and the amino acid residue at position 164 (EU numbering) in the CL domain;

(d) the amino acid residue at position 147 (EU numbering) in the CH1 domain, and the amino acid residue at position 138 (EU numbering) in the CL domain;

(e) the amino acid residue at position 147 (EU numbering) in the CH1 domain, and the amino acid residue at position 123 (EU numbering) in the CL domain; and (f) the amino acid residue at position 175 (EU numbering) in the CH1 domain, and the amino acid residue at position 160 (EU numbering) in the CL domain;

and in which the amino acid residue in the CH1 domain has an electric charge opposite to that of the amino acid residue in the CL domain;

[37] the polypeptide complex of [36], wherein the amino acid residues are selected from the group additionally comprising the combination of amino acid residues:

(g) the amino acid residue at position 213 (EU numbering) in the CH1 domain, and the amino acid residue at position 123 (EU numbering) in the CL domain;

[38] the polypeptide complex of [36] or [37], wherein the amino acid residue having an opposite electric charge is selected from an amino acid residue in either group:

(X) glutamic acid (E) and aspartic acid (D); or (Y) lysine (K), arginine (R), and histidine (H);

[39] the polypeptide complex of any one of [36] to [38], wherein the amino acid residues having an opposite electric charge are:

Lys at position 175 (EU numbering) in the CH1 domain, and Glu at positions 131, 160, and 180 (EU numbering) in the CL domain;

[40] the polypeptide complex of any one of [36] to [38], wherein the amino acid residues having an opposite electric charge are:

Glu at positions 147 and 175 (EU numbering) in the CH1 domain, and Lys at positions 131, 160, and 180 (EU numbering) in the CL domain;

[41] the polypeptide complex of [40], wherein the amino acid residue at position 213 (EU numbering) in the CH1 domain is Glu, and the amino acid residue of position 123 (EU numbering) in the CL domain is Lys;

[42] the polypeptide complex of any one of [1] to [41], wherein the Fc domain exhibits impaired Fcγ receptor-binding activity to FcγI, FcγIIA, FcγIIB, FcγIIIA, and/or FcγIIIB;

[43] the polypeptide complex of any one of [1] to [42], wherein the Fc domain is any one of the Fc domains of SEQ ID NOs: 23, 24, 25, and 26 in which an amino acid(s) forming the Fc domain is mutated;

[44] the polypeptide complex of [43], wherein the Fc domain comprises any one of the amino acids below:

the amino acid sequence of positions 118 to 260 (EU numbering) is the sequence of SEQ ID NO: 24; or the amino acid sequence at positions 261 to 447 (EU numbering) is the sequence of SEQ ID NO: 26;

[45] the polypeptide complex of [43], wherein the amino acids forming the Fc domain comprises a mutation at any one of the following positions:

220, 226, 229, 231, 232, 233, 234, 235, 236, 237, 238, 239, 240, 264, 265, 266, 267, 269, 270, 295, 296, 297, 298, 299, 300, 325, 327, 328, 329, 330, 331, and 332 (EU numbering);

[46] the polypeptide complex of [45], wherein the Fc domain comprises a mutation in the amino acids of SEQ ID NO: 23 forming the Fc domain;

[47] the polypeptide complex of [46], wherein the Fc domain is an Fc domain comprising a substitution of the amino acid at position 233, 234, 235, 236, 237, 327, 330, or 331 (EU numbering) by the amino acid at a corresponding position (EU numbering) in the corresponding IgG2 or IgG4;

[48] the polypeptide complex of [46], wherein the Fc domain comprises an amino acid mutation at position 234, 235, or 297 (EU numbering);

[49] the polypeptide complex of [48], in which the amino acid(s) at position 234, 235, and/or 297 is substituted with alanine;

[50] the polypeptide complex of any one of [43] to [49], wherein the sequences of two polypeptides forming the Fc domain are different from each other;

[51] the polypeptide complex of any one of [1] to [50], wherein the amino acid at position 349 is substituted with cysteine and the amino acid at position 366 (EU numbering) is substituted with tryptophan among the amino acid residues of one of the two polypeptides forming the Fc domain; and wherein the amino acid at position 356 is substituted with cysteine, the amino acid at position 366 is substituted with serine, the amino acid at position 368 is substituted with alanine, and the amino acid at position 407 (EU numbering) is substituted with valine among the amino acid residues of the other polypeptide;

[52] the polypeptide complex of any one of [1] to [50], wherein the amino acid at position 356 (EU numbering) is substituted with lysine among the amino acid residues of one of the two polypeptides forming the Fc domain; the amino acid at position 439 (EU numbering) is substituted with glutamic acid in the other polypeptide; and the amino acid at position 435 (EU numbering) is substituted with arginine among the amino acid residues of either of the two polypeptides;

[53] the polypeptide complex of [51] or [52], wherein the sequence GK is deleted from the carboxyl termini of two polypeptides forming the Fc domain;

[54] the polypeptide complex of any one of [1] to [53], wherein the antigen-binding domains bind to the same epitope;

[55] the polypeptide complex of [54], wherein the same epitope is present in a protein comprising the amino acid sequence of SEQ ID NO: 2;

[56] the polypeptide complex of [54], wherein the same epitope is present in a protein comprising the amino acid sequence of SEQ ID NO: 4;

[57] the polypeptide complex of any one of [1] to [53], wherein the antigen-binding domains each bind to a different epitope;

[58] the polypeptide complex of [57], wherein the different epitope is present in a protein comprising the amino acid sequence of SEQ ID NO: 2;

[59] the polypeptide complex of [57], wherein the different epitope is present in a protein comprising the amino acid sequence of SEQ ID NO: 4;

[60] a polynucleotide encoding the polypeptide complex of any one of [1] to [59];

[61] a vector comprising the polynucleotide of [60];

[62] a cell comprising the vector of [61];

[63] a method for producing a polypeptide complex, which comprises culturing the cell of and isolating the polypeptide complex from the culture supernatant;

[64] a therapeutic agent for inducing cellular cytotoxicity, which comprises as an active ingredient the polypeptide complex of any one of [1] to [59];

[65] the therapeutic agent of [64], wherein the therapeutic agent for inducing cellular cytotoxicity is a therapeutic agent for cancer;

[66] the therapeutic agent of [65], wherein the cancer is liver cancer or lung cancer;

[67] a method for treating or preventing cancer, in which the polypeptide complex of any one of [1] to [59] is administered to a patient in need thereof; and

[68] the therapeutic or preventive method of [67], wherein the cancer is liver cancer or lung cancer.

The present invention also relates to kits for use in a method of the present invention, which contain a polypeptide complex of the present invention or a polypeptide complex produced by a method of the present invention. The present invention also relates to use of a polypeptide complex of the present invention or a polypeptide complex produced by a method of the present invention in producing a therapeutic agent for inducing cellular cytotoxicity. The present invention also relates to polypeptide complexes of the present invention or polypeptide complexes produced by methods of the present invention for use in a method of the present invention.

Effects of the Invention

The present invention provides novel polypeptide complexes that retain the strong anti-tumor activity of BiTE and have a long half-life in blood, as well as excellent safety properties that result in no induction of cancer antigen-independent cytokine storm or such. When the antigen-binding domain of a polypeptide complex of the present invention is substituted, therapeutic agents that comprise the polypeptide complex as an active ingredient for inducing cellular cytotoxicity can target and damage various cells including cancer cells. Thus, various cancers can be treated or prevented. This allows desirable treatments that are highly safe and convenient, and reduce the physical burden for patients.

BRIEF DESCRIPTION OF THE DRAWINGS

FIG. 18 shows the amino acid residues forming the Fc domains of IgG1, IgG2, IgG3, and IgG4 and their Kabat EU numbering (herein, also called "EU INDEX").

MODE FOR CARRYING OUT THE INVENTION

Figure 1:
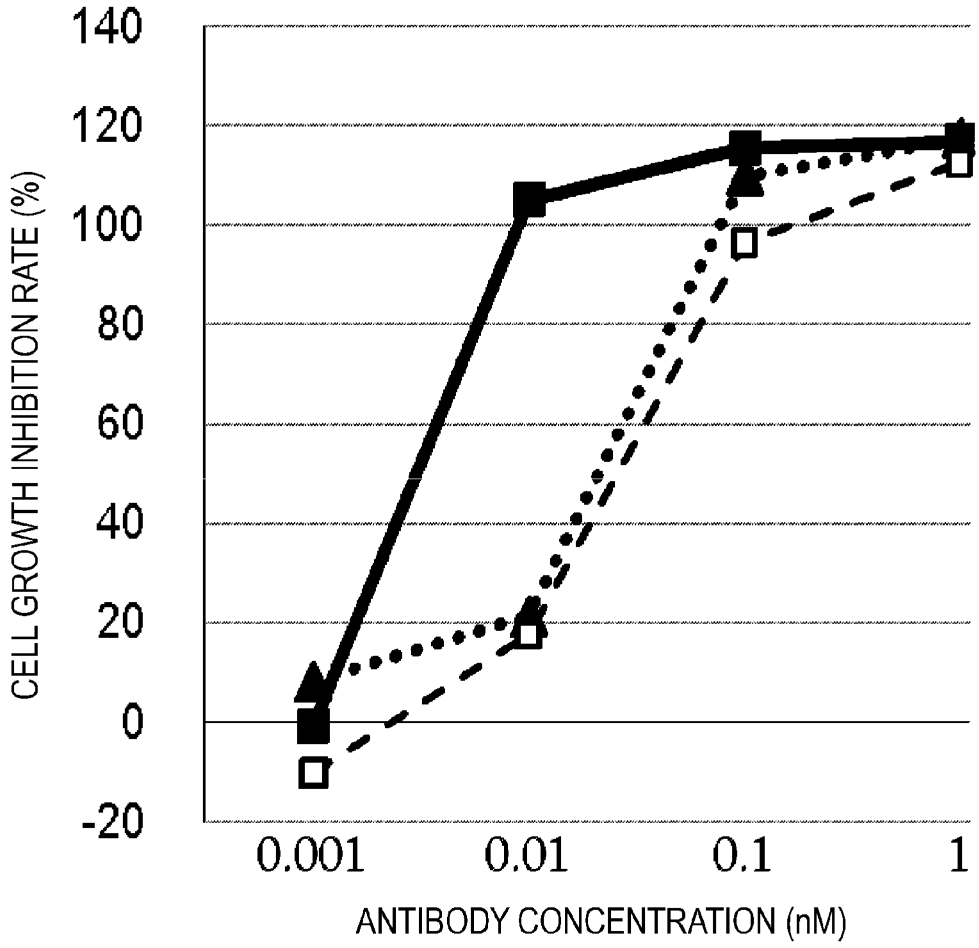
FIG. 1 is a graph showing comparison of the cytotoxic activities of GPC3 ERY1 (GPC3 BITE), GPC3 ERY2, and an IgG-type anti-GPC3 antibody. Closed square (■), closed triangle (▲), and open square (□) represent the cytotoxic activities of GPC3 ERY1 (GPC3 BITE), GPC3 ERY2, the IgG-type anti-GPC3 antibody, respectively.

The definitions below are provided to aid understanding of the present invention.

Antibody

Herein, "antibody" refers to a natural immunoglobulin or an immunoglobulin produced by partial or complete synthesis. Antibodies can be isolated from natural sources such as naturally-occurring plasma and serum, or culture supernatants of antibody-producing hybridomas.

Alternatively, antibodies can be partially or completely synthesized using techniques such as genetic recombination. Preferred antibodies include, for example, antibodies of an immunoglobulin isotype or subclass belonging thereto. Known human immunoglobulins include antibodies of the following nine classes (isotypes): IgG1, IgG2, IgG3, IgG4, IgA1, IgA2, IgD, IgE, and IgM. Of these isotypes, antibodies of the present invention include IgG1, IgG2, IgG3, and IgG4.

Methods for producing an antibody with desired binding activity are known to those skilled in the art. Below is an example that describes a method for producing an antibody (anti-GPC3 antibody) that binds to GPC3, which belongs to the GPI-anchored receptor family (Int J Cancer. (2003) 103(4), 455-65). Antibodies that bind to an antigen other than GPC3 can also be produced according to the example described below.

Anti-GPC3 antibodies can be obtained as polyclonal or monoclonal antibodies using known methods. The anti-GPC3 antibodies preferably produced are monoclonal antibodies derived from mammals. Such mammal-derived monoclonal antibodies include antibodies produced by hybridomas or host cells transformed with an expression vector carrying an antibody gene by genetic engineering techniques.

Monoclonal antibody-producing hybridomas can be produced using known techniques, for example, as described below. Specifically, mammals are immunized by conventional immunization methods using a GPC3 protein as a sensitizing antigen. Resulting immune cells are fused with known parental cells by conventional cell fusion methods. Then, hybridomas producing an anti-GPC3 antibody can be selected by screening for monoclonal antibody-producing cells using conventional screening methods.

Specifically, monoclonal antibodies are prepared as mentioned below. First, the GPC3 gene whose nucleotide sequence is disclosed in RefSeq accession number NM_001164617.1 (SEQ ID NO: 1) can be expressed to produce a GPC3 protein shown in RefSeq accession number NP_001158089.1 (SEQ ID NO: 2), which will be used as a sensitizing antigen for antibody preparation. That is, a gene sequence encoding GPC3 is inserted into a known expression vector, and appropriate host cells are transformed with this vector. The desired human GPC3 protein is purified from the host cells or their culture supernatants by known methods. For example, to prepare soluble GPC3 from culture supernatants, amino acids at positions 564 to 580 that form the hydrophobic region corresponding to the GPI-anchor sequence used to anchor GPC3 on the cell membrane are deleted from the GPC3 polypeptide sequence of SEQ ID NO: 2, and then the resulting protein is expressed instead of the GPC3 protein of SEQ ID NO: 2. Alternatively, it is possible to use a purified natural GPC3 protein as a sensitizing antigen.

The purified GPC3 protein can be used as a sensitizing antigen for immunization of mammals. A partial GPC3 peptide may also be used as a sensitizing antigen. In this case, a partial peptide can be prepared by chemical synthesis based on the amino acid sequence of human GPC3, or by inserting a partial GPC3 gene into an expression vector for expression. Alternatively, a partial peptide can be produced by degrading a GPC3 protein with a protease. The length and region of the partial GPC3 peptide are not limited to particular embodiments. A preferred region can be arbitrarily selected from the amino acid sequence at amino acid positions 564 to 580 in the amino acid sequence of SEQ ID NO: 2. The number of amino acids forming a peptide to be used as a sensitizing antigen is preferably at least five or more, six or more, or seven or more. More specifically, a peptide of 8 to 50 residues, more preferably 10 to 30 residues can be used as a sensitizing antigen.

For sensitizing antigen, alternatively it is possible to use a fusion protein prepared by fusing a desired partial polypeptide or peptide of the GPC3 protein with a different polypeptide. For example, antibody Fc fragments and peptide tags are preferably used to produce fusion proteins to be used as sensitizing antigens. Vectors for expression of such fusion proteins can be constructed by fusing in frame genes encoding two or more desired polypeptide fragments and inserting the fusion gene into an expression vector as described above. Methods for producing fusion proteins are described in Molecular Cloning 2nd ed. (Sambrook, J et al., Molecular Cloning 2nd ed., 9.47-9.58 (1989) Cold Spring Harbor Lab. Press). Methods for preparing GPC3 to be used as a sensitizing antigen, and immunization methods using GPC3 are specifically described in WO 2003/000883, WO 2004/022754, and WO 2006/006693.

There is no particular limitation on the mammals to be immunized with the sensitizing antigen. However, it is preferable to select the mammals by considering their compatibility with the parent cells to be used for cell fusion. In general, rodents such as mice, rats, and hamsters, rabbits, and monkeys are preferably used.

The above animals are immunized with a sensitizing antigen by known methods. Generally performed immunization methods include, for example, intraperitoneal or subcutaneous injection of a sensitizing antigen into mammals. Specifically, a sensitizing antigen is appropriately diluted with PBS (Phosphate-Buffered Saline), physiological saline, or the like. If desired, a conventional adjuvant such as Freund's complete adjuvant is mixed with the antigen, and the mixture is emulsified. Then, the sensitizing antigen is administered to a mammal several times at 4- to 21-day intervals. Appropriate carriers may be used in immunization with the sensitizing antigen. In particular, when a low-molecular-weight partial peptide is used as the sensitizing antigen, it is sometimes desirable to couple the sensitizing antigen peptide to a carrier protein such as albumin or keyhole limpet hemocyanin for immunization.

Alternatively, hybridomas producing a desired antibody can be prepared using DNA immunization as mentioned below. DNA immunization is an immunization method that confers immunostimulation by expressing a sensitizing antigen in an animal immunized as a result of administering a vector DNA constructed to allow expression of an antigen protein-encoding gene in the animal. As compared to conventional immunization methods in which a protein antigen is administered to animals to be immunized, DNA immunization is expected to be superior in that:

immunostimulation can be provided while retaining the structure of a membrane protein such as GPC3; and there is no need to purify the antigen for immunization.

In order to prepare a monoclonal antibody of the present invention using DNA immunization, first, a DNA expressing a GPC3 protein is administered to an animal to be immunized. The GPC3-encoding DNA can be synthesized by known methods such as PCR. The obtained DNA is inserted into an appropriate expression vector, and then this is administered to an animal to be immunized. Preferably used expression vectors include, for example, commercially-available expression vectors such as pcDNA3.1. Vectors can be administered to an organism using conventional methods. For example, DNA immunization is performed by using a gene gun to introduce expression vector-coated gold particles into cells in the body of an animal to be immunized. Antibodies that recognized GPC3 can also be produced by the methods described in WO 2003/104453.

After immunizing a mammal as described above, an increase in the titer of a GPC3-binding antibody is confirmed in the serum. Then, immune cells are collected from the mammal, and then subjected to cell fusion. In particular, splenocytes are preferably used as immune cells.

A mammalian myeloma cell is used as a cell to be fused with the above-mentioned immunocyte. The myeloma cells preferably comprise a suitable selection marker for screening. A selection marker confers characteristics to cells for their survival (or death) under a specific culture condition. Hypoxanthine-guanine phosphoribosyltransferase deficiency (hereinafter abbreviated as HGPRT deficiency) and thymidine kinase deficiency (hereinafter abbreviated as TK deficiency) are known as selection markers. Cells with HGPRT or TK deficiency have hypoxanthine-aminopterin-thymidine sensitivity (hereinafter abbreviated as HAT sensitivity). HAT-sensitive cells cannot synthesize DNA in a HAT selection medium, and are thus killed. However, when the cells are fused with normal cells, they can continue DNA synthesis using the salvage pathway of the normal cells, and therefore they can grow even in the HAT selection medium.

HGPRT-deficient and TK-deficient cells can be selected in a medium containing 6-thioguanine, 8-azaguanine (hereinafter abbreviated as 8AG), or 5'-bromodeoxyuridine, respectively. Normal cells are killed because they incorporate these pyrimidine analogs into their DNA. Meanwhile, cells that are deficient in these enzymes can survive in the selection medium, since they cannot incorporate these pyrimidine analogs. In addition, a selection marker referred to as G418 resistance provided by the neomycin-resistant gene confers resistance to 2-deoxystreptamine antibiotics (gentamycin analogs). Various types of myeloma cells that are suitable for cell fusion are known.

For example, myeloma cells including the following cells can be preferably used:

P3(P3x63Ag8.653) (J. Immunol. (1979) 123 (4), 1548-1550);

P3x63Ag8U.1 (Current Topics in Microbiology and Immunology (1978) 81, 1-7);

NS-1 (C. Eur. J. Immunol. (1976) 6 (7), 511-519);

MPC-11 (Cell (1976) 8 (3), 405-415);

SP2/0 (Nature (1978) 276 (5685), 269-270);

FO (J. Immunol. Methods (1980) 35 (1-2), 1-21);

S194/5.XX0.BU.1 (J. Exp. Med. (1978) 148 (1), 313-323);

R210 (Nature (1979) 277 (5692), 131-133), etc.

Cell fusions between the immunocytes and myeloma cells are essentially carried out using known methods, for example, a method by Kohler and Milstein et al. (Methods Enzymol. (1981) 73:3-46).

More specifically, cell fusion can be carried out, for example, in a conventional culture medium in the presence of a cell fusion-promoting agent. The fusion-promoting agents include, for example, polyethylene glycol (PEG) and Sendai virus (HVJ). If required, an auxiliary substance such as dimethyl sulfoxide is also added to improve fusion efficiency.

The ratio of immunocytes to myeloma cells may be determined at one's own discretion, preferably, for example, one myeloma cell for every one to ten immunocytes. Culture media to be used for cell fusions include, for example, media that are suitable for the growth of myeloma cell lines, such as RPMI1640 medium and MEM medium, and other conventional culture medium used for this type of cell culture. In addition, serum supplements such as fetal calf serum (FCS) may be preferably added to the culture medium.

For cell fusion, predetermined amounts of the above immune cells and myeloma cells are mixed well in the above culture medium. Then, a PEG solution (for example, the average molecular weight is about 1,000 to 6,000) pre-warmed to about 37° C. is added thereto at a concentration of generally 30% to 60% (w/v). This is gently mixed to produce desired fusion cells (hybridomas). Then, an appropriate culture medium mentioned above is gradually added to the cells, and this is repeatedly centrifuged to remove the supernatant. Thus, cell fusion agents and such which are unfavorable to hybridoma growth can be removed.

The hybridomas thus obtained can be selected by culture using a conventional selective medium, for example, HAT medium (a culture medium containing hypoxanthine, aminopterin, and thymidine). Cells other than the desired hybridomas (non-fused cells) can be killed by continuing culture in the above HAT medium for a sufficient period of time. Typically, the period is several days to several weeks. Then, hybridomas producing the desired antibody are screened and singly cloned by conventional limiting dilution methods.

The hybridomas thus obtained can be selected using a selection medium based on the selection marker possessed by the myeloma used for cell fusion. For example, HGPRT- or TK-deficient cells can be selected by culture using the HAT medium (a culture medium containing hypoxanthine, aminopterin, and thymidine). Specifically, when HAT-sensitive myeloma cells are used for cell fusion, cells successfully fused with normal cells can selectively proliferate in the HAT medium. Cells other than the desired hybridomas (non-fused cells) can be killed by continuing culture in the above HAT medium for a sufficient period of time. Specifically, desired hybridomas can be selected by culture for generally several days to several weeks. Then, hybridomas producing the desired antibody are screened and singly cloned by conventional limiting dilution methods.

Desired antibodies can be preferably selected and singly cloned by screening methods based on known antigen/antibody reaction. For example, a GPC3-binding monoclonal antibody can bind to GPC3 expressed on the cell surface. Such a monoclonal antibody can be screened by fluorescence activated cell sorting (FACS). FACS is a system that assesses the binding of an antibody to cell surface by analyzing cells contacted with a fluorescent antibody using laser beam, and measuring the fluorescence emitted from individual cells.

To screen for hybridomas that produce a monoclonal antibody of the present invention by FACS, GPC3-expressing cells are first prepared. Cells preferably used for screening are mammalian cells in which GPC3 is forcedly expressed. As control, the activity of an antibody to bind to cell-surface GPC3 can be selectively detected using non-transformed mammalian cells as host cells. Specifically, hybridomas producing an anti-GPC3 monoclonal antibody can be isolated by selecting hybridomas that produce an antibody which binds to cells forced to express GPC3, but not to host cells.

Alternatively, the activity of an antibody to bind to immobilized GPC3-expressing cells can be assessed based on the principle of ELISA. For example, GPC3-expressing cells are immobilized to the wells of an ELISA plate. Culture supernatants of hybridomas are contacted with the immobilized cells in the wells, and antibodies that bind to the immobilized cells are detected. When the monoclonal antibodies are derived from mouse, antibodies bound to the cells can be detected using an anti-mouse immunoglobulin antibody. Hybridomas producing a desired antibody having the antigen-binding ability are selected by the above screening, and they can be cloned by a limiting dilution method or the like.

Monoclonal antibody-producing hybridomas thus prepared can be passaged in a conventional culture medium, and stored in liquid nitrogen for a long period.

The above hybridomas are cultured by a conventional method, and desired monoclonal antibodies can be prepared from the culture supernatants. Alternatively, the hybridomas are administered to and grown in compatible mammals, and monoclonal antibodies are prepared from the ascites. The former method is suitable for preparing antibodies with high purity.

Antibodies encoded by antibody genes that are cloned from antibody-producing cells such as the above hybridomas can also be preferably used. A cloned antibody gene is inserted into an appropriate vector, and this is introduced into a host to express the antibody encoded by the gene. Methods for isolating antibody genes, inserting the genes into vectors, and transforming host cells have already been established, for example, by Vandamme et al. (Eur. J. Biochem. (1990) 192 (3), 767-775). Methods for producing recombinant antibodies are also known as described below.

For example, a cDNA encoding the variable region (V region) of an anti-GPC3 antibody is prepared from hybridoma cells expressing the anti-GPC3 antibody. For this purpose, total RNA is first extracted from hybridomas. Methods used for extracting mRNAs from cells include, for example:

the guanidine ultracentrifugation method (Biochemistry (1979) 18 (24), 5294-5299), and the AGPC method (Anal. Biochem. (1987) 162 (1), 156-159)

Extracted mRNAs can be purified using the mRNA Purification Kit (GE Healthcare Bioscience) or such. Alternatively, kits for extracting total mRNA directly from cells, such as the QuickPrep™ mRNA Purification Kit (GE Healthcare Bioscience), are also commercially available. mRNAs can be prepared from hybridomas using such kits. cDNAs encoding the antibody V region can be synthesized from the prepared mRNAs using a reverse transcriptase. cDNAs can be synthesized using the AMV Reverse Transcriptase First-strand cDNA Synthesis Kit (Seikagaku Co.) or such. Furthermore, the SMART™ RACE cDNA amplification kit (Clontech) and the PCR-based 5'-RACE method (Proc. Natl. Acad. Sci. USA (1988) 85 (23), 8998-9002; Nucleic Acids Res. (1989) 17 (8), 2919-2932) can be appropriately used to synthesize and amplify cDNAs. In such a cDNA synthesis process, appropriate restriction enzyme sites described below may be introduced into both ends of a cDNA.

The cDNA fragment of interest is purified from the resulting PCR product, and then this is ligated to a vector DNA. A recombinant vector is thus constructed, and introduced into *E. coli* or such. After colony selection, the desired recombinant vector can be prepared from the colony-forming *E. coli*. Then, whether the recombinant vector has the cDNA nucleotide sequence of interest is tested by a known method such as the dideoxy nucleotide chain termination method.

The 5'-RACE method which uses primers to amplify the variable region gene is conveniently used for isolating the gene encoding the variable region. First, a 5'-RACE cDNA library is constructed by cDNA synthesis using RNAs extracted from hybridoma cells as a template. A commercially available kit such as the SMART™ RACE cDNA amplification kit is appropriately used to synthesize the 5'-RACE cDNA library.

The antibody gene is amplified by PCR using the prepared 5'-RACE cDNA library as a template. Primers for amplifying the mouse antibody gene can be designed based on known antibody gene sequences. The nucleotide sequences of the primers vary depending on the immunoglobulin subclass. Therefore, it is preferable that the subclass is determined in advance using a commercially available kit such as the IsoStrip™ mouse monoclonal antibody isotyping kit (Roche Diagnostics).

Specifically, for example, primers that allow amplification of genes encoding γ1, γ2a, γ2b, and γ3 heavy chains and κ and λ light chains are used to isolate mouse IgG-encoding genes. In general, a primer that anneals to a constant region site close to the variable region is used as a 3'-side primer to amplify an IgG variable region gene. Meanwhile, a primer attached to a 5' RACE cDNA library construction kit is used as a 5'-side primer.

PCR products thus amplified are used to reshape immunoglobulins composed of a combination of heavy and light chains. A desired antibody can be selected using the GPC3-binding activity of a reshaped immunoglobulin as an indicator. For example, when the objective is to isolate an antibody against GPC3, it is more preferred that the binding of the antibody to GPC3 is specific. A GPC3-binding antibody can be screened, for example, by the following steps:

(1) contacting a GPC3-expressing cell with an antibody comprising the V region encoded by a cDNA isolated from a hybridoma;

(2) detecting the binding of the antibody to the GPC3-expressing cell; and (3) selecting an antibody that binds to the GPC3-expressing cell.

Methods for detecting the binding of an antibody to GPC3-expressing cells are known. Specifically, the binding of an antibody to GPC3-expressing cells can be detected by the above-described techniques such as FACS. Immobilized samples of GPC3-expressing cells are appropriately used to assess the binding activity of an antibody.

Preferred antibody screening methods that use the binding activity as an indicator also include panning methods using phage vectors. Screening methods using phage vectors are advantageous when the antibody genes are isolated from heavy-chain and light-chain subclass libraries from a polyclonal antibody-expressing cell population. Genes encoding the heavy-chain and light-chain variable regions can be linked by an appropriate linker sequence to form a single-chain Fv (scFv). Phages presenting scFv on their surface can be produced by inserting a gene encoding scFv into a phage vector. The phages are contacted with an antigen of interest. Then, a DNA encoding scFv having the binding activity of interest can be isolated by collecting phages bound to the antigen. This process can be repeated as necessary to enrich scFv having the binding activity of interest.

After isolation of the cDNA encoding the V region of the anti-GPC3 antibody of interest, the cDNA is digested with restriction enzymes that recognize the restriction sites introduced into both ends of the cDNA. Preferred restriction enzymes recognize and cleave a nucleotide sequence that occurs in the nucleotide sequence of the antibody gene at a low frequency. Furthermore, a restriction site for an enzyme that produces a sticky end is preferably introduced into a vector to insert a single-copy digested fragment in the correct orientation. The cDNA encoding the V region of the anti-GPC3 antibody is digested as described above, and this is inserted into an appropriate expression vector to construct an antibody expression vector. In this case, if a gene encoding the antibody constant region (C region) and a gene encoding the above V region are fused in-frame, a chimeric antibody is obtained. Herein, "chimeric antibody" means that the origin of the constant region is different from that of the variable region. Thus, in addition to mouse/human heterochimeric antibodies, human/human allochimeric antibodies are included in the chimeric antibodies of the present invention. A chimeric antibody expression vector can be constructed by inserting the above V region gene into an expression vector that already has the constant region. Specifically, for example, a recognition sequence for a restriction enzyme that excises the above V region gene can be appropriately placed on the 5' side of an expression vector carrying a DNA encoding a desired antibody constant region (C region). A chimeric antibody expression vector is constructed by fusing in frame the two genes digested with the same combination of restriction enzymes.

To produce an anti-GPC3 monoclonal antibody, antibody genes are inserted into an expression vector so that the genes are expressed under the control of an expression regulatory region. The expression regulatory region for antibody expression includes, for example, enhancers and promoters. Furthermore, an appropriate signal sequence may be attached to the amino terminus so that the expressed antibody is secreted to the outside of cells. In the Examples described below, a peptide having the amino acid sequence MGWSCIILFLVATATGVHS (SEQ ID NO: 72) is used as a signal sequence. Meanwhile, other appropriate signal sequences may be attached. The expressed polypeptide is cleaved at the carboxyl terminus of the above sequence, and the resulting polypeptide is secreted to the outside of cells as a mature polypeptide. Then, appropriate host cells are transformed with the expression vector, and recombinant cells expressing the anti-GPC3 antibody-encoding DNA are obtained.

DNAs encoding the antibody heavy chain (H chain) and light chain (L chain) are separately inserted into different expression vectors to express the antibody gene. An antibody molecule having the H and L chains can be expressed by co-transfecting the same host cell with vectors into which the H-chain and L-chain genes are respectively inserted. Alternatively, host cells can be transformed with a single expression vector into which DNAs encoding the H and L chains are inserted (see WO 94/11523).

There are various known host cell/expression vector combinations for antibody preparation by introducing isolated antibody genes into appropriate hosts. All of these expression systems are applicable to isolation of the antigen-binding domains and CD3-binding domains of the present invention. Appropriate eukaryotic cells used as host cells include animal cells, plant cells, and fungal cells. Specifically, the animal cells include, for example, the following cells.

(1) mammalian cells: CHO, COS, myeloma, baby hamster kidney (BHK), HeLa, Vero, or such;
(2) amphibian cells: *Xenopus* oocytes, or such; and
(3) insect cells: sf9, sf21, Tn5, or such.

In addition, as a plant cell, an antibody gene expression system using cells derived from the *Nicotiana* genus such as *Nicotiana tabacum* is known. Callus cultured cells can be appropriately used to transform plant cells.

Furthermore, the following cells can be used as fungal cells:

yeasts: the *Saccharomyces* genus such as *Saccharomyces cerevisiae*, and the *Pichia* genus such as *Pichia pastoris*; and filamentous fungi: the *Aspergillus* genus such as *Aspergillus niger.*

Furthermore, antibody gene expression systems that utilize prokaryotic cells are also known. For example, when using bacterial cells, *E. coli* cells, *Bacillus subtilis* cells, and such can suitably be utilized in the present invention. Expression vectors carrying the antibody genes of interest are introduced into these cells by transfection. The transfected cells are cultured in vitro, and the desired antibody can be prepared from the culture of transformed cells.

In addition to the above-described host cells, transgenic animals can also be used to produce a recombinant antibody. That is, the antibody can be obtained from an animal into which the gene encoding the antibody of interest is introduced. For example, the antibody gene can be constructed as a fusion gene by inserting in frame into a gene that encodes a protein produced specifically in milk. Goat β-casein or such can be used, for example, as the protein secreted in milk. DNA fragments containing the fused gene inserted with the antibody gene is injected into a goat embryo, and then this embryo is introduced into a female goat. Desired antibodies can be obtained as a protein fused with the milk protein from milk produced by the transgenic goat born from the embryo-recipient goat (or progeny thereof). In addition, to increase the volume of milk containing the desired antibody produced by the transgenic goat, hormones can be administered to the transgenic goat as necessary (Ebert, K. M. et al., Bio/Technology (1994) 12 (7), 699-702).

When a polypeptide complex described herein is administered to human, an antigen-binding domain derived from a genetically recombinant antibody that has been artificially modified to reduce the heterologous antigenicity against human and such, can be appropriately used as the antigen-binding domain of the complex. Such genetically recombinant antibodies include, for example, humanized antibodies. These modified antibodies are appropriately produced by known methods.

An antibody variable region used to produce the antigen-binding domain of a polypeptide complex described herein is generally formed by three complementarity-determining regions (CDRs) that are separated by four framework regions (FRs). CDR is a region that substantially determines the binding specificity of an antibody. The amino acid sequences of CDRs are highly diverse. On the other hand, the FR-forming amino acid sequences often have high identity even among antibodies with different binding specificities. Therefore, generally, the binding specificity of a certain antibody can be introduced to another antibody by CDR grafting.

A humanized antibody is also called a reshaped human antibody. Specifically, humanized antibodies prepared by grafting the CDR of a non-human animal antibody such as a mouse antibody to a human antibody and such are known. Common genetic engineering techniques for obtaining humanized antibodies are also known. Specifically, for example, overlap extension PCR is known as a method for grafting a mouse antibody CDR to a human FR. In overlap extension PCR, a nucleotide sequence encoding a mouse antibody CDR to be grafted is added to primers for synthesizing a human antibody FR. Primers are prepared for each of the four FRs. It is generally considered that when grafting a mouse CDR to a human FR, selecting a human FR that has high identity to a mouse FR is advantageous for maintaining the CDR function. That is, it is generally preferable to use a human FR comprising an amino acid sequence which has high identity to the amino acid sequence of the FR adjacent to the mouse CDR to be grafted.

Nucleotide sequences to be ligated are designed so that they will be connected to each other in frame. Human FRs are individually synthesized using the respective primers. As a result, products in which the mouse CDR-encoding DNA is attached to the individual FR-encoding DNAs are obtained. Nucleotide sequences encoding the mouse CDR of each product are designed so that they overlap with each other. Then, complementary strand synthesis reaction is conducted to anneal the overlapping CDR regions of the products synthesized using a human antibody gene as template. Human FRs are ligated via the mouse CDR sequences by this reaction.

The full length V region gene, in which three CDRs and four FRs are ultimately ligated, is amplified using primers that anneal to its 5'- or 3'-end, which are added with suitable restriction enzyme recognition sequences. An expression vector for humanized antibody can be produced by inserting the DNA obtained as described above and a DNA that encodes a human antibody C region into an expression vector so that they will ligate in frame. After the recombinant vector is transfected into a host to establish recombinant cells, the recombinant cells are cultured, and the DNA encoding the humanized antibody is expressed to produce the humanized antibody in the cell culture (see, European Patent Publication No. EP 239400 and International Patent Publication No. WO 1996/002576).

By qualitatively or quantitatively measuring and evaluating the antigen-binding activity of the humanized antibody produced as described above, one can suitably select human antibody FRs that allow CDRs to form a favorable antigen-binding site when ligated through the CDRs. Amino acid residues in FRs may be substituted as necessary, so that the CDRs of a reshaped human antibody form an appropriate antigen-binding site. For example, amino acid sequence mutations can be introduced into FRs by applying the PCR method used for grafting a mouse CDR into a human FR. More specifically, partial nucleotide sequence mutations can be introduced into primers that anneal to the FR. Nucleotide sequence mutations are introduced into the FRs synthesized by using such primers. Mutant FR sequences having the desired characteristics can be selected by measuring and evaluating the activity of the amino acid-substituted mutant antibody to bind to the antigen by the above-mentioned method (Sato, K. et al., Cancer Res. (1993) 53:851-856).

Alternatively, desired human antibodies can be obtained by immunizing transgenic animals having the entire repertoire of human antibody genes (see WO 1993/012227; WO 1992/003918; WO 1994/002602; WO 1994/025585; WO 1996/034096; WO 1996/033735) by DNA immunization.

Furthermore, techniques for preparing human antibodies by panning using human antibody libraries are also known. For example, the V region of a human antibody is expressed as a single-chain antibody (scFv) on phage surface by the phage display method. Phages expressing an scFv that binds to the antigen can be selected. The DNA sequence encoding the human antibody V region that binds to the antigen can be determined by analyzing the genes of selected phages. The DNA sequence of the scFv that binds to the antigen is determined. An expression vector is prepared by fusing the V region sequence in frame with the C region sequence of a desired human antibody, and inserting this into an appropriate expression vector. The expression vector is introduced into cells appropriate for expression such as those described above. The human antibody can be produced by expressing the human antibody-encoding gene in the cells. These methods are already known (see WO 1992/001047; WO 1992/020791; WO 1993/006213; WO 1993/011236; WO 1993/019172; WO 1995/001438; WO 1995/015388).

Antigen-Binding Domain

Herein, "antigen-binding domain" refers to an antibody portion which comprises a region that specifically binds and is complementary to the whole or a portion of an antigen. When the molecular weight of an antigen is large, an antibody can only bind to a particular portion of the antigen. The particular portion is called "epitope". An antigen-binding domain can be provided from one or more antibody variable domains. Preferably, the antigen-binding domains contain both the antibody light chain variable region (VL) and antibody heavy chain variable region (VH). Such preferable antigen-binding domains include, for example, "single-chain Fv (scFv)", "single-chain antibody", "Fv", "single-chain Fv2 (scFv2)", "Fab", and "F(ab')2".

The antigen-binding domains of polypeptide complexes of the present invention may bind to the same epitope. The epitope can be present in a protein comprising the amino acid sequence of SEQ ID NO: 2 or 4. Alternatively, the antigen-binding domains of polypeptide complexes of the present invention may individually bind to different epitopes. The epitope can be present in a protein comprising the amino acid sequence of SEQ ID NO: 2 or 4.

Specificity

"Specific" means that a molecule that binds specifically to one or more binding partners does not show any significant binding to molecules other than the partners. Furthermore, "specific" is also used when an antigen-binding domain is specific to a particular epitope of multiple epitopes contained in an antigen. When an epitope bound by an antigen-binding domain is contained in multiple different antigens, a polypeptide complex containing the antigen-binding domain can bind to various antigens that have the epitope.

Antigen

Herein, there is no particular limitation on the antigen, and it is possible to use any antigen except for CD3. Such antigens include, for example, receptors, cancer antigens, MHC antigens, and differentiation antigens. The receptors include, for example, those belonging to the hematopoietic growth factor receptor family, cytokine receptor family, tyrosine kinase receptor family, serine/threonine kinase receptor family, TNF receptor family, G protein-coupled receptor family, GPI-anchored receptor family, tyrosine phosphatase receptor family, adhesion factor family, and hormone receptor family. Receptors belonging to these receptor families and their characteristics are described in various documents, for example, reviews such as Cooke B A., King R J B., van der Molen H J. ed. New Comprehensive Biochemistry Vol. 18B "Hormones and their Actions Part II" pp. 1-46 (1988) Elsevier Science Publishers BV.; and SAIBO KOGAKU (Cell Technology) Supplementary Volume Handbook Series "Secchaku Inshi Handbook (Handbook for Adhesion factors)" M. Miyasaka Ed. (1994) Shujunsha, Tokyo, Japan; and Patthy (Cell (1990) 61 (1), 13-14); Ullrich et al., (Cell (1990) 61 (2), 203-212); Massagué (Cell (1992) 69 (6), 1067-1070); Miyajima et al., (Annu. Rev. Immunol. (1992) 10, 295-331); Taga et al., (FASEB J. (1992) 6, 3387-3396); Fantl et al., (Annu. Rev. Biochem. (1993), 62, 453-481), Smith et al., (Cell (1994) 76 (6) 959-962), Flower D R. Biochim. Biophys. Acta, Flower (Biochim. Biophys. Acta (1999) 1422 (3) 207-234.

Specifically, receptors belonging to the above receptor families preferably include, for example, human and mouse erythropoietin (EPO) receptors (Blood (1990) 76 (1), 31-35; Cell (1989) 57 (2), 277-285), human and mouse granulocyte colony stimulating factor (G-CSF) receptors (Proc. Natl. Acad. Sci. USA. (1990) 87 (22), 8702-8706; mG-CSFR, Cell (1990) 61 (2), 341-350), human and mouse thrombopoietin (TPO) receptors (Proc. Natl. Acad. Sci. USA (1992) 89 (12), 5640-5644; EMBO J. (1993) 12 (7), 2645-53), human and mouse insulin receptors (Nature (1985) 313 (6005), 756-761), human and mouse Flt-3 ligand receptors (Proc. Natl. Acad. Sci. USA (1994) 91 (2), 459-463), human and mouse platelet-derived growth factor (PDGF) receptors (Proc. Natl. Acad. Sci. USA. (1988) 85 (10), 3435-3439), human and mouse interferon (IFN)-$\alpha$ and -$\beta$ receptors (Cell (1990) 60 (2), 225-234; and Cell (1994) 77 (3), 391-400), human and mouse leptin receptors, human and mouse growth hormone (GH) receptors, human and mouse interleukin (IL)-10 receptors, human and mouse insulin-like growth factor (IGF)-I receptors, human and mouse leukemia inhibitory factor (LIF) receptors, and human and mouse ciliary neurotrophic factor (CNTF) receptors.

Cancer antigens are antigens expressed as cells become malignant, and are also called "tumor-specific antigens". Furthermore, abnormal sugar chains that are expressed on cell surface or protein molecules when the cells become cancerous are also cancer antigens, and are called "cancer-associated carbohydrate antigen". Such cancer antigens include, for example, GPC3 (Int J Cancer. (2003) 103 (4), 455-65), Epithelial Cell Adhesion Molecule (EpCAM) (Proc. Natl. Acad. Sci. USA. (1989) 86 (1), 27-31), Epidermal Growth Factor Receptor (EGFR), CA19-9, CA15-3, and sialyl SSEA-1 (SLX). GPC3 belongs to the above-mentioned GPI-anchored receptor family and is expressed in several types of cancers including liver cancer. EpCAM is expressed in multiple types of cancers including lung cancer, and its polynucleotide and polypeptide sequences are disclosed in RefSeq accession numbers NM_002354.2 (SEQ ID NO: 3) and NP_002345.2 (SEQ ID NO: 4), respectively).

Generally, MHC antigens are categorized into MHC class I and class II antigens. The MHC class I antigens include HLA-A, -B, -C, -E, -F, -G, and -H, while the MHC class II antigens include HLA-DR, -DQ, and -DP.

Differentiation antigens include CD1, CD2, CD4, CD5, CD6, CD7, CD8, CD10, CD11a, CD11b, CD11c, CD13, CD14, CD15s, CD16, CD18, CD19, CD20, CD21, CD23, CD25, CD28, CD29, CD30, CD32, CD33, CD34, CD35, CD38, CD40, CD41a, CD41b, CD42a, CD42b, CD43, CD44, CD45, CD45RO, CD48, CD49a, CD49b, CD49c, CD49d, CD49e, CD49f, CD51, CD54, CD55, CD56, CD57, CD58, CD61, CD62E, CD62L, CD62P, CD64, CD69, CD71, CD73, CD95, CD102, CD106, CD122, CD126, and CDw130.

Epitope

"Epitope" means an antigenic determinant in an antigen, and refers to an antigen site to which the antigen-binding domain of a polypeptide complex disclosed herein binds. Thus, for example, the epitope can be defined according to its structure. Alternatively, the epitope may be defined according to the antigen-binding activity of a polypeptide complex that recognizes the epitope. When the antigen is a peptide or polypeptide, the epitope can be specified by the amino acid residues forming the epitope. Alternatively, when the epitope is a sugar chain, the epitope can be specified by its specific sugar chain structure.

A linear epitope is an epitope that contains an epitope whose primary amino acid sequence is recognized. Such a linear epitope typically contains at least three and most commonly at least five, for example, about 8 to 10 or 6 to 20 amino acids in its specific sequence.

In contrast to the linear epitope, "conformational epitope" is an epitope in which the primary amino acid sequence containing the epitope is not the only determinant of the recognized epitope (for example, the primary amino acid sequence of a conformational epitope is not necessarily recognized by an epitope-defining antibody). Conformational epitopes may contain a greater number of amino acids compared to linear epitopes. A conformational epitope-recognizing antibody recognizes the three-dimensional structure of a peptide or protein. For example, when a protein molecule folds and forms a three-dimensional structure, amino acids and/or polypeptide main chains that form a conformational epitope become aligned, and the epitope is made recognizable by the antibody. Methods for determining epitope conformations include, for example, X ray crystallography, two-dimensional nuclear magnetic resonance, site-specific spin labeling, and electron paramagnetic resonance, but are not limited thereto. See, for example, Epitope Mapping Protocols in Methods in Molecular Biology (1996), Vol. 66, Morris (ed.).

Examples of a method for assessing the epitope binding by a test polypeptide complex containing a GPC3 antigen-binding domain are described below. According to the examples below, methods for assessing the epitope binding by a test polypeptide complex containing an antigen-binding domain for an antigen other than GPC3, can also be appropriately conducted.

For example, whether a test polypeptide complex containing a GPC3 antigen-binding domain recognizes a linear epitope in the GPC3 molecule can be confirmed for example as mentioned below. A linear peptide comprising an amino acid sequence forming the extracellular domain of GPC3 is synthesized for the above purpose. The peptide can be synthesized chemically, or obtained by genetic engineering techniques using a region encoding the amino acid sequence corresponding to the extracellular domain in a GPC3 cDNA. Then, a test polypeptide complex containing a GPC3 antigen-binding domain is assessed for its binding activity towards a linear peptide comprising the amino acid sequence forming the extracellular domain. For example, an immobilized linear peptide can be used as an antigen by ELISA to evaluate the binding activity of the polypeptide complex towards the peptide. Alternatively, the binding activity towards a linear peptide can be assessed based on the level that the linear peptide inhibits the binding of the polypeptide complex to GPC3-expressing cells. These tests can demonstrate the binding activity of the polypeptide complex towards the linear peptide.

Whether a test polypeptide complex containing a GPC3 antigen-binding domain recognizes a conformational epitope can be assessed as follows. GPC3-expressing cells are prepared for the above purpose. A test polypeptide complex containing a GPC3 antigen-binding domain can be determined to recognize a conformational epitope when it strongly binds to GPC3-expressing cells upon contact, but does not substantially bind to an immobilized linear peptide comprising an amino acid sequence forming the extracellular domain of GPC3. Herein, "not substantially bind" means that the binding activity is 80% or less, generally 50% or less, preferably 30% or less, and particularly preferably 15% or less compared to the binding activity towards cells expressing human GPC3.

Methods for assaying the binding activity of a test polypeptide complex containing a GPC3 antigen-binding domain towards GPC3-expressing cells include, for example, the methods described in Antibodies: A Laboratory Manual (Ed Harlow, David Lane, Cold Spring Harbor Laboratory (1988) 359-420). Specifically, the assessment can be performed based on the principle of ELISA or fluorescence activated cell sorting (FACS) using GPC3-expressing cells as antigen.

In the ELISA format, the binding activity of a test polypeptide complex containing a GPC3 antigen-binding domain towards GPC3-expressing cells can be assessed quantitatively by comparing the levels of signal generated by enzymatic reaction. Specifically, a test polypeptide complex is added to an ELISA plate onto which GPC3-expressing cells are immobilized. Then, the test polypeptide complex bound to the cells is detected using an enzyme-labeled antibody that recognizes the test polypeptide complex. Alternatively, when FACS is used, a dilution series of a test polypeptide complex is prepared, and the antibody binding titer for GPC3-expressing cells can be determined to compare the binding activity of the test polypeptide complex towards GPC3-expressing cells.

The binding of a test polypeptide complex towards an antigen expressed on the surface of cells suspended in buffer or the like can be detected using a flow cytometer. Known flow cytometers include, for example, the following devices:

- FACSCanto™ II flow cytometer
- FACSAria™ fusion flow cytometer
- FACSArray™ bioanalyzer
- FACSVantage™ SE flow cytometer
- FACSCalibur™ flow cytometer (all are trade names of BD Biosciences)
- EPICS® ALTRA™ HyPerSort™ cell sorting system
- Cytomics™ FC 500 flow cytometer
- EPICS® XL-MCL™ flow cytometer with Expo 32 ADC™ analysis software
- EPICS® XL™ flow cytometer with Expo 32 ADC™ analysis software
- Cell Lab Quanta™ flow cytometer/Cell Lab Quanta™ SC flow cytometer (all are trade names of Beckman Coulter)

Preferable methods for assaying the binding activity of a test polypeptide complex containing a GPC3 antigen-binding domain towards an antigen include, for example, the following method. First, GPC3-expressing cells are reacted with a test polypeptide complex, and then this is stained with an FITC-labeled secondary antibody that recognizes the polypeptide complex. The test polypeptide complex is appropriately diluted with a suitable buffer to prepare the complex at a desired concentration. For example, the complex can be used at a concentration within the range of 10 μg/ml to 10 ng/ml. Then, the fluorescence intensity and cell count are determined using FACSCalibur™ flow cytometer (BD). The fluorescence intensity obtained by analysis using the CellQuest™ Software (BD), i.e., the Geometric Mean value, reflects the quantity of antibody bound to cells. That is, the binding activity of a test polypeptide complex, which is represented by the quantity of the test polypeptide complex bound, can be determined by measuring the Geometric Mean value.

Whether a test polypeptide complex containing a GPC3 antigen-binding domain shares a common epitope with another polypeptide complex can be assessed based on the competition between the two complexes for the same epitope. The competition between polypeptide complexes can be detected by cross-blocking assay or the like. For example, the competitive ELISA assay is a preferred cross-blocking assay.

Specifically, in cross-blocking assay, the GPC3 protein immobilized to the wells of a microtiter plate is pre-incubated in the presence or absence of a candidate competitor polypeptide complex, and then a test polypeptide complex is added thereto. The quantity of test polypeptide complex bound to the GPC3 protein in the wells is indirectly correlated with the binding ability of a candidate competitor polypeptide complex that competes for the binding to the same epitope. That is, the greater the affinity of the competitor polypeptide complex for the same epitope, the lower the binding activity of the test polypeptide complex towards the GPC3 protein-coated wells.

The quantity of the test polypeptide complex bound to the wells via the GPC3 protein can be readily determined by labeling the polypeptide complex in advance. For example, a biotin-labeled polypeptide complex is measured using an avidin/peroxidase conjugate and appropriate substrate. In particular, cross-blocking assay that uses enzyme labels such as peroxidase is called "competitive ELISA assay". The polypeptide complex can also be labeled with other labeling substances that enable detection or measurement. Specifically, radiolabels, fluorescent labels, and such are known.

When the candidate competitor polypeptide complex can block the binding by a test polypeptide complex containing a GPC3 antigen-binding domain by at least 20%, preferably at least 20 to 50%, and more preferably at least 50% compared to the binding activity in a control experiment conducted in the absence of the competitor polypeptide complex, the test polypeptide complex is determined to substantially bind to the same epitope bound by the competitor polypeptide complex, or compete for the binding to the same epitope.

When the structure of an epitope bound by a test polypeptide complex containing a GPC3 antigen-binding domain has already been identified, whether the test and control polypeptide complexes share a common epitope can be assessed by comparing the binding activities of the two polypeptide complexes towards a peptide prepared by introducing amino acid mutations into the peptide forming the epitope.

To measure the above binding activities, for example, the binding activities of test and control polypeptide complexes towards a linear peptide into which a mutation is introduced are compared in the above ELISA format. Besides the ELISA methods, the binding activity towards the mutant peptide bound to a column can be determined by flowing test and control polypeptide complexes in the column, and then quantifying the polypeptide complex eluted in the elution solution. Methods for adsorbing a mutant peptide to a column, for example, in the form of a GST fusion peptide, are known.

Alternatively, when the identified epitope is a conformational epitope, whether test and control polypeptide complexes share a common epitope can be assessed by the following method. First, GPC3-expressing cells and cells expressing GPC3 with a mutation introduced into the epitope are prepared. The test and control polypeptide complexes are added to a cell suspension prepared by suspending these cells in an appropriate buffer such as PBS. Then, the cell suspensions are appropriately washed with a buffer, and an FITC-labeled antibody that recognizes the test and control polypeptide complexes is added thereto. The fluorescence intensity and number of cells stained with the labeled antibody are determined using FACSCalibur™ flow cytometer (BD). The test and control polypeptide complexes are appropriately diluted using a suitable buffer, and used at desired concentrations. For example, they may be used at a concentration within the range of 10 μg/ml to 10 ng/ml. The fluorescence intensity determined by analysis using the CellQuest™ Software (BD), i.e., the Geometric Mean value, reflects the quantity of labeled antibody bound to cells. That is, the binding activities of the test and control polypeptide complexes, which are represented by the quantity of labeled antibody bound, can be determined by measuring the Geometric Mean value.

In the above method, whether a polypeptide complex does "not substantially bind to cells expressing mutant GPC3"

can be assessed, for example, by the following method. First, the test and control polypeptide complexes bound to cells expressing mutant GPC3 are stained with a labeled antibody. Then, the fluorescence intensity of the cells is determined. When FACSCalibur™ flow cytometer is used for fluorescence detection by flow cytometry, the determined fluorescence intensity can be analyzed using the CellQuest™ Software. From the Geometric Mean values in the presence and absence of the polypeptide complex, the comparison value (ΔGeo-Mean) can be calculated according to the following formula to determine the ratio of increase in fluorescence intensity as a result of the binding by the polypeptide complex.

ΔGeo-Mean=Geo-Mean(in the presence of the polypeptide complex)/Geo-Mean(in the absence of the polypeptide complex)

The Geometric Mean comparison value (ΔGeo-Mean value for the mutant GPC3 molecule) determined by the above analysis, which reflects the quantity of a test polypeptide complex bound to cells expressing mutant GPC3, is compared to the ΔGeo-Mean comparison value that reflects the quantity of the test polypeptide complex bound to GPC3-expressing cells. In this case, the concentrations of the test polypeptide complex used to determine the ΔGeo-Mean comparison values for GPC3-expressing cells and cells expressing mutant GPC3 are particularly preferably adjusted to be equal or substantially equal. A polypeptide complex that has been confirmed to recognize an epitope in GPC3 is used as a control polypeptide complex.

If the ΔGeo-Mean comparison value of a test polypeptide complex for cells expressing mutant GPC3 is smaller than the ΔGeo-Mean comparison value of the test polypeptide complex for GPC3-expressing cells by at least 80%, preferably 50%, more preferably 30%, and particularly preferably 15%, then the test polypeptide complex "does not substantially bind to cells expressing mutant GPC3". The formula for determining the Geo-Mean (Geometric Mean) value is described in the CellQuest™ Software User's Guide (BD biosciences). When the comparison shows that the comparison values are substantially equivalent, the epitope for the test and control polypeptide complexes can be determined to be the same.

Variable Fragment (Fv)

Herein, the term "variable fragment (Fv)" refers to the minimum unit of an antibody-derived antigen-binding domain that is composed of a pair of the antibody light chain variable region (VL) and antibody heavy chain variable region (VH). In 1988, Skerra and Pluckthun found that homogeneous and active antibodies can be prepared from the *E. coli* periplasm fraction by inserting an antibody gene downstream of a bacterial signal sequence and inducing expression of the gene in *E. coli* (Science (1988) 240 (4855), 1038-1041). In the Fv prepared from the periplasm fraction, VH associates with VL in a manner so as to bind to an antigen.

Herein, Fv preferably includes, for example, a pair of Fv which is a polypeptide complex or such comprising:

(1) a bivalent antigen-binding domain which is a bivalent scFv, wherein one monovalent scFv of the bivalent scFv is linked to one polypeptide forming an Fc domain by a heavy-chain Fv fragment forming a CD3-binding domain, and the other monovalent scFv is linked to the other polypeptide forming an Fc domain by a light-chain Fv fragment forming a CD3-binding domain;

(2) a domain comprising an Fc domain that has no Fcγ receptor-binding activity, and which is derived from amino acids forming the Fc domain of IgG1, IgG2a, IgG3, or IgG4; and (3) at least a monovalent CD3-binding domain, wherein the light-chain and heavy-chain Fv fragments associate to form a CD3-binding domain such that it can bind to the CD3 antigen.

scFv, Single-Chain Antibody, and Sc(Fv)2

Herein, the terms "scFv", "single-chain antibody", and "sc(Fv)2" all refer to an antibody fragment of a single polypeptide chain that contains variable regions derived from the heavy and light chains, but not the constant region. In general, a single-chain antibody also contains a polypeptide linker between the VH and VL domains, which enables formation of a desired structure that is thought to allow antigen binding. The single-chain antibody is discussed in detail by Pluckthun in "The Pharmacology of Monoclonal Antibodies, Vol. 113, Rosenburg and Moore, eds., Springer-Verlag, New York, 269-315 (1994)". See also International Patent Publication WO 1988/001649; U.S. Pat. Nos. 4,946,778 and 5,260,203. In a particular embodiment, the single-chain antibody can be bispecific and/or humanized.

scFv is an antigen-binding domain in which VH and VL forming Fv are linked together by a peptide linker (Proc. Natl. Acad. Sci. U.S.A. (1988) 85 (16), 5879-5883). VH and VL can be retained in close proximity by the peptide linker.

sc(Fv)2 is a single-chain antibody in which four variable regions of two VL and two VH are linked by linkers such as peptide linkers to form a single chain (J Immunol. Methods (1999) 231 (1-2), 177-189). The two VH and two VL may be derived from different monoclonal antibodies. Such sc(Fv)2 preferably includes, for example, a bispecific sc(Fv)2 that recognizes two epitopes present in a single antigen as disclosed in the Journal of Immunology (1994) 152 (11), 5368-5374. sc(Fv)2 can be produced by methods known to those skilled in the art. For example, sc(Fv)2 can be produced by linking scFv by a linker such as a peptide linker.

Herein, the form of an antigen-binding domain forming an sc(Fv)2 include an antibody in which the two VH units and two VL units are arranged in the order of VH, VL, VH, and VL ([VH]-linker-[VL]-linker-[VH]-linker-[VL]) beginning from the N terminus of a single-chain polypeptide.

The order of the two VH units and two VL units is not limited to the above form, and they may be arranged in any order. Example order of the form is listed below.

[VL]-linker-[VH]-linker-[VH]-linker-[VL]
[VH]-linker-[VL]-linker-[VL]-linker-[VH]
[VH]-linker-[VH]-linker-[VL]-linker-[VL]
[VL]-linker-[VL]-linker-[VH]-linker-[VH]
[VL]-linker-[VH]-linker-[VL]-linker-[VH]

The molecular form of sc(Fv)2 is also described in detail in WO 2006/132352. According to these descriptions, those skilled in the art can appropriately prepare desired sc(Fv)2 to produce the polypeptide complexes disclosed herein.

Furthermore, the polypeptide complexes of the present invention may be conjugated with a carrier polymer such as PEG or an organic compound such as an anticancer agent. Alternatively, a sugar chain addition sequence is preferably inserted into the polypeptide complexes such that the sugar chain produces a desired effect.

The linkers to be used for linking the variable regions of an antibody comprise arbitrary peptide linkers that can be introduced by genetic engineering, synthetic linkers, and linkers disclosed in, for example, Protein Engineering, 9(3), 299-305, 1996. However, peptide linkers are preferred in the present invention. The length of the peptide linkers is not particularly limited, and can be suitably selected by those skilled in the art according to the purpose. The length is preferably five amino acids or more (without particular limitation, the upper limit is generally 30 amino acids or less, preferably 20 amino acids or less), and particularly preferably 15 amino acids. When sc(Fv)2 contains three peptide linkers, their length may be all the same or different.

For example, such peptide linkers include:

```
Ser

Gly•Ser

Gly•Gly•Ser

Ser•Gly•Gly

Gly•Gly•Gly•Ser (SEQ ID NO: 5)

Ser•Gly•Gly•Gly (SEQ ID NO: 6)

Gly•Gly•Gly•Gly•Ser (SEQ ID NO: 7)

Ser•Gly•Gly•Gly•Gly (SEQ ID NO: 8)

Gly•Gly•Gly•Gly•Gly•Ser (SEQ ID NO: 9)

Ser•Gly•Gly•Gly•Gly•Gly (SEQ ID NO: 10)

Gly•Gly•Gly•Gly•Gly•Gly•Ser (SEQ ID NO: 11)

Ser•Gly•Gly•Gly•Gly•Gly•Gly (SEQ ID NO: 12)

(Gly•Gly•Gly•Gly•Ser (SEQ ID NO: 7))n

(Ser•Gly•Gly•Gly•Gly (SEQ ID NO: 8))n
```

where n is an integer of 1 or larger. The length or sequences of peptide linkers can be selected accordingly by those skilled in the art depending on the purpose.

Synthetic linkers (chemical crosslinking agents) is routinely used to crosslink peptides, and for example:

N-hydroxy succinimide (NHS),
disuccinimidyl suberate (DSS),
bis(sulfosuccinimidyl) suberate ($BS^3$),
dithiobis(succinimidyl propionate) (DSP),
dithiobis(sulfosuccinimidyl propionate) (DTSSP),
ethylene glycol bis(succinimidyl succinate) (EGS),
ethylene glycol bis(sulfosuccinimidyl succinate) (sulfo-EGS),
disuccinimidyl tartrate (DST), disulfosuccinimidyl tartrate (sulfo-DST),
bis[2-(succinimidoxycarbonyloxy)ethyl] sulfone (BSOCOES),
and bis[2-(sulfosuccinimidoxycarbonyloxy)ethyl] sulfone (sulfo-BSOCOES). These crosslinking agents are commercially available.

In general, three linkers are required to link four antibody variable regions together. The linkers to be used may be of the same type or different types.

Fab, F(ab')2, and Fab'

"Fab" consists of a single light chain, and a CH1 domain and variable region from a single heavy chain. The heavy chain of Fab molecule cannot form disulfide bonds with another heavy chain molecule.

"F(ab')2" or "Fab" is produced by treating an immunoglobulin (monoclonal antibody) with a protease such as pepsin and papain, and refers to an antibody fragment generated by digesting an immunoglobulin (monoclonal antibody) at near the disulfide bonds present between the hinge regions in each of the two H chains. For example, papain cleaves IgG upstream of the disulfide bonds present between the hinge regions in each of the two H chains to generate two homologous antibody fragments, in which an L chain comprising VL (L-chain variable region) and CL (L-chain constant region) is linked to an H-chain fragment comprising VH (H-chain variable region) and CHγ1 (γ1 region in an H-chain constant region) via a disulfide bond at their C-terminal regions. Each of these two homologous antibody fragments is called Fab'.

"F(ab')2" consists of two light chains and two heavy chains comprising the constant region of a CH1 domain and a portion of CH2 domains so that disulfide bonds are formed between the two heavy chains. The F(ab')2 forming a polypeptide complex disclosed herein can be preferably produced as follows. A whole monoclonal antibody or such comprising a desired antigen-binding domain is partially digested with a protease such as pepsin; and Fc fragments are removed by adsorption onto a Protein A column. The protease is not particularly limited, as long as it can cleave the whole antibody in a selective manner to produce F(ab')2 under an appropriate setup enzyme reaction condition such as pH. Such proteases include, for example, pepsin and ficin.

Fc Domain

An Fc domain that forms a polypeptide complex disclosed herein can be preferably produced in the following manner. An antibody such as a monoclonal antibody is partially digested with a protease such as pepsin. Then, the resulting fragment is adsorbed onto a Protein A or Protein G column, and eluted with an appropriate elution buffer. The protease is not particularly limited, as long as it can cleave antibodies such as monoclonal antibodies under an appropriate setup enzyme reaction condition such as pH. Such proteases include, for example, pepsin and ficin.

The polypeptide complexes described herein comprise an Fc domain with reduced Fcγ receptor-binding activity, which includes amino acids forming the Fc domain of IgG1, IgG2, IgG3, or IgG4.

Antibody isotype is determined according to the structure of the constant region. Constant regions of the isotypes IgG1, IgG2, IgG3, and IgG4 are called Cγ1, Cγ2, Cγ3, and Cγ4, respectively. The amino acid sequences of Fc domain polypeptides forming human Cγ1, Cγ2, Cγ3, and Cγ4 are exemplified in SEQ ID NO: 23, 24, 25, and 26, respectively. The relationship between amino acid residues forming each amino acid sequence and Kabat's EU numbering (herein also referred to as EU INDEX) are shown in FIG. 18.

The Fc domain refers to the region besides F(ab')2 which comprises two light chains and two heavy chains comprising a portion of the constant region that comprises a CH1 domain and a region between the CH1 and CH2 domains so that disulfide bonds are formed between the two heavy chains. The Fc domain forming a polypeptide complex disclosed herein can be preferably produced as follows. A monoclonal IgG1, IgG2, IgG3, or IgG4 antibody or the like is partially digested with a protease such as pepsin, followed by elution of the fraction adsorbed onto a Protein A column. The protease is not particularly limited, as long as it can cleave the whole antibody in a selective manner to produce F(ab')2 in an appropriate setup enzyme reaction condition such as pH. Such proteases include, for example, pepsin and ficin.

Fcγ Receptor

Fcγ receptor refers to a receptor capable of binding to the Fc domain of monoclonal IgG1, IgG2, IgG3, or IgG4 antibodies, and includes all members belonging to the family of proteins substantially encoded by an Fcγ receptor gene. In human, the family includes FcγRI (CD64) including isoforms FcγRIa, FcγRIb and FcγRIc; FcγRII (CD32) including isoforms FcγRIIa (including allotype H131 and R131), FcγRIIb (including FcγRIIb-1 and FcγRIIb-2), and FcγRIIc; and FcγRIII (CD16) including isoform FcγRIIIa (including allotype V158 and F158) and FcγRIIIb (including allotype FcγRIIIb-NA1 and FcγRIIIb-NA2); as well as all unidentified human FcγRs, FcγR isoforms, and allotypes thereof. However, Fcγ receptor is not limited to these examples. Without being limited thereto, FcγR includes those derived from humans, mice, rats, rabbits, and monkeys. FcγR may be derived from any organisms. Mouse FcγR includes, without being limited to, FcγRI (CD64), FcγRII (CD32), FcγRIII (CD16), and FcγRIII-2 (CD16-2), as well as all unidentified mouse FcγRs, FcγR isoforms, and allotypes thereof. Such preferred Fcγ receptors include, for example, human FcγI (CD64), FcγIIA (CD32), FcγIIB (CD32), FcγIIIA (CD16), and/or FcγIIIB (CD16). The polynucleotide sequence and amino acid sequence of FcγI are shown in SEQ ID NOs: 13 (NM_000566.3) and 14 (NP_000557.1), respectively; the polynucleotide sequence and amino acid sequence of FcγIIA are shown in SEQ ID NOs: 15 (BC020823.1) and 16 (AAH20823.1), respectively; the polynucleotide sequence and amino acid sequence of FcγIIB are shown in SEQ ID NOs: 17 (BC146678.1) and 18 (AAI46679.1), respectively; the polynucleotide sequence and amino acid sequence of FcγIIIA are shown in SEQ ID NOs: 19 (BC033678.1) and 20 (AAH33678.1), respectively; and the polynucleotide sequence and amino acid sequence of FcγIIIB are shown in SEQ ID NOs: 21 (BC128562.1) and 22 (AAI28563.1), respectively (RefSeq accession number is shown in each parentheses). Whether an Fcγ receptor has binding activity to the Fc domain of a monoclonal IgG1, IgG2, IgG3, or IgG4 antibody can be assessed by AlphaScreen® Amplified Luminescent Proximity Homogeneous Assay, Biacore™ surface plasmon resonance (SPR) system, and others (Proc. Natl. Acad. Sci. USA (2006) 103 (11), 4005-4010), in addition to the above-described FACS and ELISA formats.

Meanwhile, "Fc ligand" or "effector ligand" refers to a molecule and preferably a polypeptide that binds to an antibody Fc domain, forming an Fc/Fc ligand complex. The molecule may be derived from any organisms. The binding of an Fc ligand to Fc preferably induces one or more effector functions. Such Fc ligands include, but are not limited to, Fc receptors, FcγR, FcαR, FcεR, FcRn, C1q, and C3, mannan-binding lectin, mannose receptor, *Staphylococcus* Protein A, *Staphylococcus* Protein G, and viral FcγRs. The Fc ligands also include Fc receptor homologs (FcRH) (Davis et al., (2002) Immunological Reviews 190, 123-136), which are a family of Fc receptors homologous to FcγR. The Fc ligands also include unidentified molecules that bind to Fc.

Fcγ Receptor-Binding Activity

The impaired binding activity of Fc domain to any of the Fcγ receptors FcγI, FcγIIA, FcγIIB, FcγIIIA, and/or FcγIIIB can be assessed by using the above-described FACS and ELISA formats as well as AlphaScreen® Amplified Luminescent Proximity Homogeneous Assay and Biacore™ SPR system (Proc. Natl. Acad. Sci. USA (2006) 103 (11), 4005-4010).

AlphaScreen® Amplified Luminescent Proximity Homogeneous Assay (ALPHA) is performed by the ALPHA technology based on the principle described below using two types of beads: donor and acceptor beads. A luminescent signal is detected only when molecules linked to the donor beads interact biologically with molecules linked to the acceptor beads and when the two beads are located in close proximity. Excited by laser beam, the photosensitizer in a donor bead converts oxygen around the bead into excited singlet oxygen. When the singlet oxygen diffuses around the donor beads and reaches the acceptor beads located in close proximity, a chemiluminescent reaction within the acceptor beads is induced. This reaction ultimately results in light emission. If molecules linked to the donor beads do not interact with molecules linked to the acceptor beads, the singlet oxygen produced by donor beads do not reach the acceptor beads and chemiluminescent reaction does not occur.

For example, a biotin-labeled polypeptide complex is immobilized to the donor beads and glutathione S-transferase (GST)-tagged Fcγ receptor is immobilized to the acceptor beads. In the absence of a polypeptide complex comprising a competitive mutant Fc domain, Fcγ receptor interacts with a polypeptide complex comprising a wild-type Fc domain, inducing a signal of 520 to 620 nm as a result. The polypeptide complex having a non-tagged mutant Fc domain competes with the polypeptide complex comprising a wild-type Fc domain for the interaction with Fcγ receptor. The relative binding affinity can be determined by quantifying the reduction of fluorescence as a result of competition. Methods for biotinylating the polypeptide complexes such as antibodies using Sulfo-NHS-biotin or the like are known. Appropriate methods for adding the GST tag to an Fcγ receptor include methods that involve fusing polypeptides encoding Fcγ and GST in-frame, expressing the fused gene using cells introduced with a vector carrying the gene, and then purifying using a glutathione column. The induced signal can be preferably analyzed, for example, by fitting to a one-site competition model based on nonlinear regression analysis using software such as GRAPHPAD PRISM (GraphPad; San Diego).

One of the substances for observing their interaction is immobilized as a ligand onto the gold thin layer of a sensor chip. When light is shed on the rear surface of the sensor chip so that total reflection occurs at the interface between the gold thin layer and glass, the intensity of reflected light is partially reduced at a certain site (SPR signal). The other substance for observing their interaction is injected as an analyte onto the surface of the sensor chip. The mass of immobilized ligand molecule increases when the analyte binds to the ligand. This alters the refraction index of solvent on the surface of the sensor chip. The change in refraction index causes a positional shift of SPR signal (conversely, the dissociation shifts the signal back to the original position). In the Biacore™ SPR system, the amount of shift described above (i.e., the change of mass on the sensor chip surface) is plotted on the vertical axis, and thus the change of mass over time is shown as measured data (sensorgram). Kinetic parameters (association rate constant (ka) and dissociation rate constant (kd)) are determined from the curve of sensorgram, and affinity (KD) is determined from the ratio between these two constants. Inhibition assay is preferably used in the Biacore™ SPR system. Examples of such inhibition assay are described in Proc. Natl. Acad. Sci. USA (2006) 103(11), 4005-4010.

Herein, "Fcγ receptor-binding activity is reduced" means, for example, that based on the above-described analysis method the competitive activity of a test polypeptide complex is 50% or less, preferably 45% or less, 40% or less, 35% or less, 30% or less, 20% or less, or 15% or less, and particularly preferably 10% or less, 9% or less, 8% or less, 7% or less, 6% or less, 5% or less, 4% or less, 3% or less, 2% or less, or 1% or less than the competitive activity of a control polypeptide complex.

Polypeptide complexes comprising the Fc domain of a monoclonal IgG1, IgG2, IgG3, or IgG4 antibody can be appropriately used as control polypeptide complexes. The Fc domain structures are shown in SEQ ID NOs: 23 (A is added to the N terminus of RefSeq accession number AAC82527.1), 24 (A is added to the N terminus of RefSeq accession number AAB59393.1), 25 (A is added to the N terminus of RefSeq accession number CAA27268.1), and 26 (A is added to the N terminus of RefSeq accession number AAB59394.1). Furthermore, when a polypeptide complex comprising an Fc domain mutant of an antibody of a particular isotype is used as a test substance, the effect of the mutation of the mutant on the Fcγ receptor-binding activity is assessed using as a control a polypeptide complex comprising an Fc domain of the same isotype. As described above, polypeptide complexes comprising an Fc domain mutant whose Fcγ receptor-binding activity has been judged to be reduced are appropriately prepared.

Such known mutants include, for example, mutants having a deletion of amino acids 231A-238S (EU numbering) (WO 2009/011941), as well as mutants C226S, C229S, P238S, (C220S) (J. Rheumatol (2007) 34, 11); C226S and C229S (Hum. Antibod. Hybridomas (1990) 1 (1), 47-54); C226S, C229S, E233P, L234V, and L235A (Blood (2007) 109, 1185-1192).

Specifically, the preferred polypeptide complexes include those comprising an Fc domain with a substitution of the amino acid at position 220, 226, 229, 231, 232, 233, 234, 235, 236, 237, 238, 239, 240, 264, 265, 266, 267, 269, 270, 295, 296, 297, 298, 299, 300, 325, 327, 328, 329, 330, 331, or 332 (EU numbering) in the amino acids forming the Fc domain of an antibody of a particular isotype. The isotype of antibody from which the Fc domain originates is not particularly limited, and it is possible to use an appropriate Fc domain derived from a monoclonal IgG1, IgG2, IgG3, or IgG4 antibody. It is preferable to use Fc domains derived from IgG1 antibodies.

The preferred polypeptide complexes include, for example, those comprising an Fc domain which has any one of the substitutions shown below, whose positions are specified according to EU numbering (each number represents the position of an amino acid residue in the EU numbering; and the one-letter amino acid symbol before the number represents the amino acid residue before substitution, while the one-letter amino acid symbol after the number represents the amino acid residue before the substitution) in the amino acids forming the Fc domain of IgG1 antibody:

(a) L234F, L235E, P331S;
(b) C226S, C229S, P238S;
(c) C226S, C229S; or
(d) C226S, C229S, E233P, L234V, L235A;

as well as those having an Fc domain which has a deletion of the amino acid sequence at positions 231 to 238.

Furthermore, the preferred polypeptide complexes also include those comprising an Fc domain that has any one of the substitutions shown below, whose positions are specified according to EU numbering in the amino acids forming the Fc domain of an IgG2 antibody:

(e) H268Q, V309L, A330S, and P331S;
(f) V234A;
(g) G237A;
(h) V234A and G237A;
(i) A235E and G237A; or
(j) V234A, A235E, and G237A. Each number represents the position of an amino acid residue in EU numbering; and the one-letter amino acid symbol before the number represents the amino acid residue before substitution, while the one-letter amino acid symbol after the number represents the amino acid residue before the substitution.

Furthermore, the preferred polypeptide complexes also include those comprising an Fc domain that has any one of the substitutions shown below, whose positions are specified according to EU numbering in the amino acids forming the Fc domain of an IgG3 antibody:

(k) F241A;
(l) D265A; or
(m) V264A. Each number represents the position of an amino acid residue in EU numbering; and the one-letter amino acid symbol before the number represents the amino acid residue before substitution, while the one-letter amino acid symbol after the number represents the amino acid residue before the substitution.

Furthermore, the preferred polypeptide complexes also include those comprising an Fc domain that has any one of the substitutions shown below, whose positions are specified according to EU numbering in the amino acids forming the Fc domain of an IgG4 antibody:

(n) L235A, G237A, and E318A;
(o) L235E; or
(p) F234A and L235A. Each number represents the position of an amino acid residue in EU numbering; and the one-letter amino acid symbol before the number represents the amino acid residue before substitution, while the one-letter amino acid symbol after the number represents the amino acid residue before the substitution.

The other preferred polypeptide complexes include, for example, those comprising an Fc domain in which any amino acid at position 233, 234, 235, 236, 237, 327, 330, or 331 (EU numbering) in the amino acids forming the Fc domain of an IgG1 antibody is substituted with an amino acid of the corresponding position in EU numbering in the corresponding IgG2 or IgG4.

The preferred polypeptide complexes also include, for example, those comprising an Fc domain in which any one or more of the amino acids at positions 234, 235, and 297 (EU numbering) in the amino acids forming the Fc domain of an IgG1 antibody is substituted with other amino acids. The type of amino acid after substitution is not particularly limited; however, the polypeptide complexes comprising an Fc domain in which any one or more of the amino acids at positions 234, 235, and 297 are substituted with alanine are particularly preferred.

The preferred polypeptide complexes also include, for example, those comprising an Fc domain in which an amino acid at position 265 (EU numbering) in the amino acids forming the Fc domain of an IgG1 antibody is substituted with another amino acid. The type of amino acid after substitution is not particularly limited; however, polypeptide complexes comprising an Fc domain in which an amino acid at position 265 is substituted with alanine are particularly preferred.

Fc Domain Derived from Bispecific Antibody

Herein, appropriate Fc domains derived from bispecific antibody are also used as an Fc domain with reduced Fcγ receptor-binding activity. A bispecific antibody is an antibody having two different specificities. The IgG-type bispecific antibody can be secreted from hybrid hybridoma (quadroma) produced by fusing two types of IgG antibody-producing hybridomas (Milstein C et al., Nature (1983) 305, 537-540).

Alternatively, the IgG-type bispecific antibody can also be secreted by introducing a total of four genes, genes of the L chains and H chains forming two types of IgGs of interest, into cells and co-expressing them. However, in theory, there are ten combinations of IgG H chains and L chains produced by such methods. It is difficult to purify IgG consisting of a desired combination of H chain and L chain from ten types of IgGs. In addition, in theory the amount of secreted IgG with a desired combination is also significantly reduced, which requires large scale culture. This further increases the production cost.

In this case, an appropriate amino acid substitution can be introduced into the CH3 domain forming an H-chain Fc domain in order to preferentially secrete IgG with a heterologous combination of H chains. Specifically, this method is conducted by substituting an amino acid having a larger side chain (knob (which means “bulge”)) for an amino acid in the CH3 domain of one of the H chains, and substituting an amino acid having a smaller side chain (hole (which means “void”)) for an amino acid in the CH3 domain of the other H chain so that the knob is placed in the hole. This promotes heteromeric H chain formation and simultaneously inhibits homomeric H chain formation (WO 1996/027011; Ridgway J B et al., Protein Engineering (1996) 9, 617-621; Merchant A M et al., Nature Biotechnology (1998) 16, 677-681).

On the other hand, with respect to the L chain, the L-chain variable region is less polymorphic than the H-chain variable region, and thus obtaining a common L chain that can confer binding ability to both H chains is expected. Efficient expression of a bispecific IgG can be achieved by introducing the genes of such a common L chain and two H chains into cells to express the IgG (Nature Biotechnology (1998) 16, 677-681). However, it is difficult to realize this idea because the probability that two types of antibodies containing the same L chain are randomly selected is low. Thus, a method for selecting a common L chain which shows strong binding ability to any different H chains is proposed (WO 2004/065611).

Furthermore, there are also known techniques for producing a bispecific antibody by applying methods for controlling polypeptide association, or association of polypeptide-formed heteromeric multimers to the association between the two polypeptides that form an Fc domain. Specifically, methods for controlling polypeptide association may be employed to produce a bispecific antibody (WO 2006/106905), in which amino acid residues forming the interface between two polypeptides that form the Fc domain are altered to inhibit the association between Fc domains having the same sequence and to allow the formation of polypeptide complexes formed by two Fc domains of different sequences.

The above-described two polypeptides forming an Fc domain derived from a bispecific antibody can be appropriately used as a domain encompassing an Fc domain of the present invention. More specifically, such preferred two polypeptides forming an Fc domain include those in which amino acids at positions 349 and 366 (EU numbering) in the amino acid sequence of one polypeptide are cysteine and tryptophan, respectively, and amino acids at positions 356, 366, 368, and 407 (EU numbering) in the amino acid sequence of the other polypeptide are cysteine, serine, alanine, and valine, respectively.

In another embodiment, preferred domains encompassing an Fc domain of the present invention include two polypeptides forming an Fc domain, in which amino acid at position 409 (EU numbering) in the amino acid sequence of one polypeptide is aspartic acid, and amino acid at position 399 (EU numbering) in the amino acid sequence of the other polypeptide is lysine. In the above embodiment, amino acid at position 409 may be glutamic acid instead of aspartic acid, while the amino acid at position 399 may be arginine instead of lysine. Furthermore, aspartic acid at position 360 or 392 can also be preferably combined with lysine at position 399.

In another embodiment, preferred domains encompassing an Fc domain of the present invention include two polypeptides forming an Fc domain, in which the amino acid at position 370 (EU numbering) in the amino acid sequence of one polypeptide is glutamic acid, and the amino acid at position 357 (EU numbering) in the amino acid sequence of the other polypeptide is lysine.

In still another embodiment, preferred domains encompassing an Fc domain of the present invention include two polypeptides forming an Fc domain, in which amino acid at position 439 (EU numbering) in the amino acid sequence of one polypeptide is glutamic acid, and amino acid at position 356 (EU numbering) in the amino acid sequence of the other polypeptide is lysine.

In addition, preferred domains encompassing an Fc domain of the present invention include embodiments with a combination thereof:

two polypeptides forming an Fc domain, in which amino acids at positions 409 and 370 (EU numbering) in the amino acid sequence of one polypeptide are aspartic acid and glutamic acid, respectively, and amino acids at positions 399 and 357 (EU numbering) in the amino acid sequence of the other polypeptide are both lysine (in this embodiment, glutamic acid at position 370 may be replaced with aspartic acid, and glutamic acid at position 370 may be replaced with aspartic acid at position 392);

two polypeptides forming an Fc domain, in which amino acids at positions 409 and 439 (EU numbering) in the amino acid sequence of one polypeptide are aspartic acid and glutamic acid, respectively, and amino acids at positions 399 and 356 (EU numbering) in the amino acid sequence of the other polypeptide are both lysine (in this embodiment, glutamic acid position at 439 may be replaced with aspartic acid at position 360, 392, or 439);

two polypeptides forming an Fc domain, in which amino acids at positions 370 and 439 (EU numbering) in the amino acid sequence of one polypeptide are both glutamic acid, and amino acids at positions 357 and 356 (EU numbering) in the amino acid sequence of the other polypeptide are both lysine; and two polypeptides forming an Fc domain, in which amino acids at positions 409, 370, and 439 (EU numbering) in the amino acid sequence of one polypeptide are aspartic acid, glutamic acid, and glutamic acid, respectively, and amino acids at positions 399, 357, and 356 (EU numbering) in the amino acid sequence of the other polypeptide are all lysine (in this embodiment, the amino acid at position 370 may not be substituted with glutamic acid; alternatively, instead of substituting amino acid at position 370 with glutamic acid, glutamic acid at position 439 may be replaced with aspartic acid, or glutamic acid at position 439 may be replaced with aspartic acid at position 392).

In yet another embodiment, preferred domains encompassing an Fc domain of the present invention include two polypeptides forming an Fc domain, in which amino acid at position 356 (EU numbering) in the amino acid sequence of one polypeptide is lysine, and amino acids at positions 435 and 439 (EU numbering) in the amino acid sequence of the other polypeptide are arginine and glutamic acid, respectively.

When the above-described two polypeptides forming an Fc domain derived from a bispecific antibody are used as a domain encompassing an Fc domain of the present invention, antigen-binding domains and/or CD3-binding domains of the present invention can be arranged in a desired combination.

Fc Domain with Reduced C-Terminal Heterogeneity

Herein, Fc domains with improved Fc domain C-terminal heterogeneity in addition to the above-described characteristic are appropriately used as Fc domains with reduced Fcγ receptor-binding activity. More specifically, the present invention provides Fc domains in which glycine and lysine at positions 446 and 447 (EU numbering), respectively, in the amino acid sequences of two polypeptides forming an Fc domain derived from IgG1, IgG2, IgG3, or IgG4 are deleted.

T Cell Receptor Complex-Binding Domain

Herein, "T cell receptor complex-binding domain" refers to a portion of a T cell receptor complex antibody, which comprises a region that specifically binds and is complementary to the whole or a portion of a T cell receptor complex. Such T cell receptor complex may be T cell receptor itself, or an adaptor molecule that together with the T cell receptor forms the T cell receptor complex. A preferred adaptor is CD3.

T Cell Receptor-Binding Domain

Herein, "T cell receptor-binding domain" refers to a portion of a T cell receptor antibody, which comprises a region that specifically binds and is complementary to the whole or a portion of a T cell receptor.

It is possible to use the variable region or constant region of a T cell receptor. However, preferred epitopes to which a CD3-binding domain binds are those located in the constant region. Sequences of the constant region include, for example, those of the T cell receptor α chain (RefSeq accession number CAA26636.1; SEQ ID NO: 67), T cell receptor β chain (RefSeq accession number C25777; SEQ ID NO: 68), T cell receptor γ1 chain (RefSeq accession number A26659; SEQ ID NO: 69), T cell receptor γ2 chain (RefSeq accession number AAB63312.1; SEQ ID NO: 70), and T cell receptor δ chain (RefSeq accession number AAA61033.1; SEQ ID NO: 71).

CD3-Binding Domain

Herein, "CD3-binding domain" refers to a portion of a CD3 antibody, which comprises a region that specifically binds and is complementary to the whole or a portion of CD3. The CD3-binding domain can be derived from one or more antibody variable domains. Preferably, the CD3-binding domain includes both CD3 antibody light chain variable region (VL) and CD3 antibody heavy chain variable region (VH). Such preferred CD3-binding domains include, for example, "single-chain Fv (scFv)", "single chain antibody", "Fv", "single-chain Fv2 (scFv2)", "Fab", and "F(ab')2".

The CD3-binding domain of the present invention may bind to any epitope, as long as the epitope is located within the γ chain, δ chain, or ε chain sequence forming human CD3. In the present invention, preferred CD3-binding domains include those comprising a CD3 antibody light chain variable region (VL) and a CD3 antibody heavy chain variable region (VH), which bind to an epitope in the extracellular domain of the ε chain of a human CD3 complex. Such preferred CD3-binding domains include those comprising a CD3 antibody light chain variable region (VL) and a CD3 antibody heavy chain variable region (VH) of antibody OKT3 (Proc. Natl. Acad. Sci. USA (1980) 77, 4914-4917) or various known CD3 antibodies. Furthermore, such appropriate CD3-binding domains include those derived from a CD3 antibody with desired characteristics, which are obtained by immunizing a desired animal with the γ chain, δ chain, or ε chain forming human CD3 by the above-described methods. Appropriate anti-CD3 antibodies from which a CD3-binding domain is derived include human antibodies and antibodies appropriately humanized as described above. The structures of γ chain, ε chain, and ε chain forming CD3 are shown as polynucleotide sequences in SEQ ID NOs: 27 (NM_000073.2), 29 (NM_000732.4), and 31 (NM_000733.3), respectively, and as polypeptide sequences in SEQ ID NO: 28 (NP_000064.1), 30 (NP_000723.1), and 32 (NP_000724.1), respectively (RefSeq accession number is shown in parentheses).

Polypeptide Complex

The structure of a polypeptide complex of the present invention is not limited, as long as it contains (1) an antigen-binding domain;

(2) a domain comprising an Fc domain with reduced Fcγ receptor-binding activity; and (3) a T cell receptor complex-binding domain, as described above.

In the present invention, the preferred T cell receptor complex-binding domain is a T cell receptor-binding domain or CD3-binding domain. Each of the domains described above may be linked directly via peptide linkage. For example, (1) F(ab')2 is used as the antigen-binding domain, and (2) an Fc domain with reduced Fcγ receptor-binding activity is used as the domain comprising an Fc domain with reduced Fcγ receptor-binding activity. In this case, when the antigen-binding domain of (1) is linked via a peptide bond to the domain comprising an Fc domain of (2), the linked polypeptide forms an antibody structure. Such an antibody may be prepared by purifying the culture media of the above-described hybridoma or purifying culture media of desired host cells stably carrying the polynucleotide that encodes the antibody-forming polypeptide.

When the CD3-binding domain of (3) is linked to the antibody structure, the CD3-binding domain may be linked via peptide bond to the C terminus of the constant region of the antibody structure. In another embodiment, the CD3-binding domain is linked via peptide bond to the N terminus of the heavy chain variable region or light chain variable region of the antibody structure. In the other embodiment, the CD3-binding domain may be linked via peptide bond to the C terminus of the light chain constant region of the antibody structure. The CD3-binding domain to be linked may have any desired structure; however, such an appropriate CD3-binding domain includes preferably Fv, and more preferably scFv. The valency of the CD3-binding domain that binds to the antibody structure is not limited. To link a divalent CD3-binding domain to the antibody structure, a monovalent CD3-binding domain may be linked via peptide bond to the respective C termini of two Fc domains forming the constant region of the antibody structure. Alternatively, to link a divalent CD3-binding domain to the antibody structure, a divalent scFv (i.e., sc(Fv)2) may be linked via peptide bond to the C terminus of one of the two Fc domains. In this case, the polypeptide complex in which a divalent scFv (i.e., sc(Fv)2) is linked to the C terminus of only one of the two Fc domains forming the constant region of the antibody structure is efficiently produced by using an above-described Fc domain derived from a bispecific antibody. Alternatively, to link a monovalent CD3-binding domain to the antibody structure, a monovalent scFv may be linked via peptide bond to the C terminus of one of the two Fc domains.

In this case, a polypeptide complex of the present invention in which a monovalent scFv is linked to the C terminus of only one of the two Fc domains forming the constant region of the antibody structure is efficiently produced by using an above-described Fc domain derived from a bispecific antibody.

Furthermore, when the CD3-binding domain of (3) is linked via peptide bond to the C terminus of the constant region of the antibody structure, the appropriate polypeptide complexes include those in which the heavy chain Fv fragment forming the CD3-binding domain is linked to the C terminus of one constant region (CH3 domain) forming the Fc domain, and the light chain Fv fragment forming the CD3-binding domain is linked to the C terminus of the other constant region (CH3 domain) forming the Fc domain. In this case, an appropriate linker such as Gly-Gly-Gly-Gly-Ser (SEQ ID NO: 7) is inserted to link the heavy chain or light chain Fv fragment to the C terminus of the constant region (CH3 domain). The number of repeats in the linker is not limited; however, it is selected from 1 to 10, preferably 2 to 8, or more preferably 2 to 6. Specifically, it is possible to insert an appropriate linker in which the number of [Gly-Gly-Gly-Gly-Ser] (SEQ ID NO: 7) repeats is 1, 2, 3, 4, 5, 6, 7, 8, 9, or 10.

Alternatively, when a polypeptide complex is produced in which the heavy chain Fv fragment forming the CD3-binding domain is linked to the C terminus of one constant region (CH3 domain) forming the Fc domain and the light chain Fv fragment of the CD3-binding domain is linked to the C terminus of the other constant region (CH3 domain) forming the Fc domain, appropriate alterations of amino acid residues that allow formation of disulfide bonds between the heavy chain Fv fragment and light chain Fv fragment can be used to enhance the association between the heavy chain Fv fragment and light chain Fv fragment.

In another embodiment, when a polypeptide complex of the present invention in which the heavy chain Fv fragment forming the CD3-binding domain is linked to the C terminus of one constant region (CH3 domain) forming the Fc domain and the light chain Fv fragment forming the CD3-binding domain is linked to the C terminus of the other constant region (CH3 domain) forming the Fc domain is produced, antibody CH1 and CL domains can be linked to each of the heavy chain Fv fragment and light chain Fv fragment to enhance the association between the heavy chain Fv fragment and light chain Fv fragment.

In still another embodiment, in order to link a divalent CD3-binding domain to the antibody structure, a monovalent CD3-binding domain may be linked via peptide bond to the respective C termini of two light chain constant regions or the respective N termini of the light chain variable regions of the antibody structure. Alternatively, in order to link a divalent CD3-binding domain to the antibody structure, a divalent scFv (i.e., sc(Fv)2) may be linked via peptide bond to the respective C termini of two light chain constant regions or the respective N termini of light chain variable regions. In this case, polypeptide complexes in which a divalent scFv (i.e., sc(Fv)2) is linked to the C or N terminus of one of the two light chain variable regions of the antibody structure can be efficiently produced by using an above-described Fc domain derived from a bispecific antibody. Alternatively, in order to link a monovalent CD3-binding domain to the antibody structure, a monovalent scFv may be linked via peptide bond to the C or N terminus of one of the two light chain variable regions. In this case, polypeptide complexes of the present invention in which a monovalent scFv is linked to the N or C terminus of one light chain variable region of the two light chain variable regions of the antibody structure can be efficiently produced by using an above-described Fc domain derived from bispecific antibody.

In another embodiment, in order to link a divalent CD3-binding domain to the antibody structure, a monovalent CD3-binding domain may be linked via peptide bond to the respective N termini of two heavy chain variable regions of the antibody structure. Alternatively, in order to link a divalent CD3-binding domain to the antibody structure, a divalent scFv (i.e., sc(Fv)2) may be linked via peptide bond to the N terminus of one of the two heavy chain variable regions. In this case, polypeptide complexes in which a divalent scFv (i.e., sc(Fv)2) is linked to the N terminus of only one of two heavy chain variable regions of the antibody structure can be efficiently produced by using an above-described Fc domain derived from bispecific antibody. Alternatively, in order to link a monovalent CD3-binding domain to the antibody structure, a monovalent scFv may be linked via peptide bond to the N terminus of one of the two heavy chain variable regions. In this case, polypeptide complexes of the present invention in which a monovalent scFv is linked to the N terminus of one of the two heavy chain variable regions of the antibody structure can be efficiently produced by using an above-described Fc domain derived from a bispecific antibody.

Furthermore, an above-described polypeptide complex can be produced by linking each domain directly via peptide bond or by peptide binding via a peptide linker. In this case, the linker to be used includes the linker described above as an example and appropriate linkers with a peptide tag, for example, His-tag, HA-tag, myc-tag, or FLAG®-tag. In addition, it is preferred to use the property of mutual binding based on hydrogen bonding, disulfide linkage, covalent bonding, or ionic interaction, or a combination thereof. For example, it is possible to employ the affinity between antibody CH1 and CL, or the above-described Fc domains derived from a bispecific antibody may be used for the heteromeric association of Fc domains. Moreover, interdomain disulfide bonds can be preferably used as described in the Examples.

In another structure of the polypeptide complex of the present invention, for example, a monovalent Fv and a monovalent Fab are preferably used as (1) the antigen binding domain. In this case, the following structure is used. The heavy chain Fv fragment (VH) or light chain Fv fragment (VL) of monovalent Fv is linked via peptide bond to the heavy chain CH1 domain. The heavy chain CH1 domain is linked via peptide bond to one of (2) the two Fc domains with reduced Fcγ receptor-binding activity which form the polypeptide complex of the present invention. The other VL or VH fragment of the monovalent Fv is linked via peptide bond to the light chain CH domain which is linked via disulfide bond to the heavy chain CH1 domain. Thus, VH and VL respectively linked to the termini of heavy chain CH1 domain and light chain CL domain form an antibody-binding domain. sc(Fv)2 which forms both the (1) antibody-binding domain and (3) CD3-binding domain may be linked via peptide bond to the N terminus of the other Fc domain of the two described above. In this case, a polypeptide complex having a structure in which the heavy chain CH1 domain is linked via peptide bond to one of the two Fc domains forming the polypeptide complex, and sc(Fv)2 is linked via peptide bond to the other Fc domain can be produced by using an above-described Fc domain derived from a bispecific antibody. The above-described polypeptide complex can be produced by linking each domain directly via peptide bond or by peptide binding via a peptide linker. In this case, the linker to be used includes the linkers described above as an example and appropriate linkers with a peptide tag, for example, His-tag, HA-tag, myc-tag, or FLAG®-tag.

In another preferred structure of the polypeptide complex of the present invention, for example, a divalent scFv is also used as (1) the antigen-binding domain. In an embodiment of the structure, it is also possible to produce a polypeptide complex in which one of the divalent scFvs is linked via peptide bond through VH forming (3) the CD3-binding domain to one of the two (2) Fc domains with reduced Fcγ receptor-binding activity, and the other divalent scFv is linked via peptide bond through VL forming (3) the CD3-binding domain to one of the two (2) Fc domains with reduced Fcγ receptor-binding activity. In this case, it is possible to use an above-described Fc domain derived from a bispecific antibody. The above-described polypeptide complex can be produced by linking each domain directly via peptide bond or by peptide binding via a peptide linker. In this case, the linker to be used includes the linkers described above as an example and appropriate linkers with a peptide tag, for example, His-tag, HA-tag, myc-tag, or FLAG®-tag.

In another embodiment of the structure where a divalent scFv is used as (1) the antigen-binding domain, it is possible to produce a polypeptide complex in which one of the divalent scFv is linked via peptide bond scFv forming (3) the CD3-binding domain to one of the two (2) Fc domains with reduced Fcγ receptor-binding activity, and the other divalent scFv is linked via peptide bond to the other (2) Fc domain with reduced Fcγ receptor. In this case, a polypeptide complex in which scFv forming the antigen-binding domain is linked via peptide bond through scFv forming the CD3-binding domain to one of the two Fc domains forming the polypeptide complex, and scFv forming the antigen-binding domain is linked via peptide bond to the other Fc domain can be produced by using an above-described Fc domain derived from a bispecific antibody. The above-described polypeptide complex can be produced by linking each domain directly via peptide bond or by peptide binding via a peptide linker. In this case, the linker to be used includes the linkers described above as an example and appropriate linkers with a peptide tag, for example, His-tag, HA-tag, myc-tag, or FLAG®-tag.

In another preferred structure of the polypeptide complex of the present invention, for example, both antigen-binding domain and T cell receptor complex-binding domain are each a structure of monovalent Fab. In an embodiment of the structure, it is possible to produce a polypeptide complex in which a heavy chain Fv fragment of a monovalent Fab forming the antigen-binding domain is linked through a CH1 domain to one polypeptide forming an Fc domain and a light chain Fv fragment of the Fab is linked to a CL domain, while a heavy chain Fv fragment of Fab forming the T cell receptor-binding domain is linked through a CH1 domain to the other polypeptide forming the Fc domain and a light chain Fv fragment of the Fab is linked to a CL domain.

In another embodiment of the structure, it is also possible to produce a polypeptide complex in which a heavy chain Fv fragment of a monovalent Fab forming the antigen-binding domain is linked through a CH1 domain to one polypeptide forming an Fc domain and a light chain Fv fragment of the Fab is linked to a CL domain, while a light chain Fv fragment of an Fab forming the T cell receptor-binding domain is linked through a CH1 domain to the other polypeptide forming the Fc domain and a heavy chain Fv fragment of the Fab is linked to a CL domain. Alternatively, it is also possible to produce a polypeptide complex in which a heavy chain Fv fragment of monovalent Fab forming the T cell receptor-binding domain is linked through a CH1 domain to one polypeptide forming an Fc domain and a light chain Fv fragment of the Fab is linked to a CL domain, while a light chain Fv fragment of an Fab forming the antigen-binding domain is linked through a CH1 domain to the other polypeptide forming an Fc domain and a heavy chain Fv fragment of the Fab is linked to a CL domain.

In another embodiment of the structure, it is also possible to produce a polypeptide complex in which a heavy chain Fv fragment of a monovalent Fab forming the antigen-binding domain is linked through a CH1 domain to one polypeptide forming an Fc domain and a light chain Fv fragment of the Fab is linked to a CL domain, while a heavy chain Fv fragment of Fab forming the T cell receptor-binding domain is linked through a CL domain to the other polypeptide forming an Fc domain and a light chain Fv fragment of the Fab is linked to a CH1 domain. Alternatively, it is also possible to produce a polypeptide complex in which a heavy chain Fv fragment of a monovalent Fab forming the T cell receptor-binding domain is linked through a CH1 domain to one polypeptide forming an Fc domain and a light chain Fv fragment of the Fab is linked to a CL domain, while a heavy chain Fv fragment of Fab forming the antigen-binding domain is linked through a CL domain to the other polypeptide forming an Fc domain and a light chain Fv fragment of the Fab is linked to a CH1 domain.

In an embodiment of another structure of the polypeptide complex of the present invention in which both antigen-binding domain and T cell receptor complex-binding domain are each a structure of monovalent Fab, the preferred polypeptides of the present invention include those that have:

(1) an antigen-binding domain in which a heavy chain Fv fragment of a monovalent Fab structure that binds to an antigen is linked through a CH1 domain to one of the above-described polypeptides forming an Fc domain and a light chain Fv fragment of the Fab structure is linked to a CL domain; and (2) a T cell receptor complex-binding domain in which a heavy chain Fv fragment of a monovalent Fab structure that binds to an T cell receptor complex is linked through a CH1 domain to the other polypeptide forming an Fc domain and a light chain Fv fragment of the Fab structure is linked to a CL domain;

and in which the electric charges of the CH1 and CL domains are controlled so that the heavy chain Fv fragment of the antigen-binding domain is associated with the light chain Fv fragment of the antigen-binding domain, or the heavy chain Fv fragment of the T cell receptor-binding domain is associated with the light chain Fv fragment of the T cell receptor-binding domain. In this embodiment, the structure (structure with controlled association) of the polypeptide complex is not limited to a particular structure, as long as the electric charges of the CH1 and CL domains are controlled so that the heavy chain Fv fragment of the antigen-binding domain is associated with the light chain Fv fragment of the antigen-binding domain, or the heavy chain Fv fragment of the T cell receptor-binding domain is associated with the light chain Fv fragment of the T cell receptor-binding domain.

In an embodiment of the structure with controlled association, it is possible to produce a polypeptide complex in which amino acid residues of the CH1 domain linked to the heavy chain Fv fragment of the T cell receptor complex-binding domain have the same electric charges as amino acid residues of the CL domain linked to the light chain Fv fragment of the antigen-binding domain.

In an embodiment of the structure with controlled association, it is possible to produce a polypeptide complex in which amino acid residues of the CH1 domain linked to the heavy chain Fv fragment of the antigen-binding domain have the same electric charges as amino acid residues of the CL domain linked to the light chain Fv fragment of the T cell receptor complex-binding domain.

In an embodiment of the structure with controlled association, it is possible to produce a polypeptide complex in which amino acid residues of the CH1 domain linked to the heavy chain Fv fragment of the T cell receptor complex-binding domain have the same electric charges as amino acid residues of the CL domain linked to the light chain Fv fragment of the antigen-binding domain, and amino acid residues of the CH1 domain linked to the heavy chain Fv fragment of antigen-binding domain have the same electric charges as amino acid residues of the CL domain linked to the light chain Fv fragment of the T cell receptor complex-binding domain.

In another embodiment of the structure with controlled association, it is possible to produce a polypeptide complex in which amino acid residues of the CH1 domain linked to the heavy chain Fv fragment of the T cell receptor complex-binding domain have the same electric charges as amino acid residues of the CL domain linked to the light chain Fv fragment of the antigen-binding domain, and amino acid residues of the CH1 domain linked to the heavy chain Fv fragment of the T cell receptor complex-binding domain have electric charges opposite to those of amino acid residues of the CL domain linked to the light chain Fv fragment of the T cell receptor-binding domain.

In still another embodiment of the structure with controlled association, it is possible to produce a polypeptide complex in which amino acid residues of the CH1 domain linked to the heavy chain Fv fragment of the T cell receptor complex-binding domain have the same electric charges as amino acid residues of the CL domain linked to the light chain Fv fragment of the antigen-binding domain; amino acid residues of the CH1 domain linked to the heavy chain Fv fragment of the antigen-binding domain have the same electric charges as amino acid residues of the CL domain linked to the light chain Fv fragment of the T cell receptor complex-binding domain; and amino acid residues of the CH1 domain linked to the heavy chain Fv fragment of the T cell receptor complex-binding domain have electric charges opposite to those of amino acid residues of the CL domain linked to the light chain Fv fragment of the T cell receptor-binding domain.

In yet another embodiment of the structure with controlled association, it is possible to produce a polypeptide complex in which amino acid residues of the CH1 domain linked to the heavy chain Fv fragment of the antigen-binding domain have the same electric charges as amino acid residues of the CL domain linked to the light chain Fv fragment of the T cell receptor complex-binding domain, and amino acid residues of the CH1 domain linked to the heavy chain Fv fragment of the antigen-binding domain have electric charges opposite to those of amino acid residues of the CL domain linked to the light chain Fv fragment of the antigen-binding domain.

In an alternative embodiment of the structure with controlled association, it is possible to produce a polypeptide complex in which amino acid residues of the CH1 domain linked to the heavy chain Fv fragment of the T cell receptor complex-binding domain have the same electric charges as amino acid residues of the CL domain linked to the light chain Fv fragment of the antigen-binding domain; amino acid residues of the CH1 domain linked to the heavy chain Fv fragment of the antigen-binding domain have the same electric charges as amino acid residues of the CL domain linked to the light chain Fv fragment of the T cell receptor complex-binding domain; and amino acid residues of the CH1 domain linked to the heavy chain Fv fragment of the antigen-binding domain have electric charges opposite to those of amino acid residues of the CL domain linked to the light chain Fv fragment of the antigen-binding domain.

In still yet another embodiment of the structure with controlled association, it is possible to produce a polypeptide complex in which amino acid residues of the CH1 domain linked to the heavy chain Fv fragment of the T cell receptor complex-binding domain have the same electric charges as amino acid residues of the CL domain linked to the light chain Fv fragment of the antigen-binding domain; amino acid residues of the CH1 domain linked to heavy chain Fv fragment of the antigen-binding domain have the same electric charges as amino acid residues of the CL domain linked to the light chain Fv fragment of the T cell receptor complex-binding domain; amino acid residues of the CH1 domain linked to the heavy chain Fv fragment of the T cell receptor complex-binding domain have electric charges opposite to those of amino acid residues of the CL domain linked to the light chain Fv fragment of the T cell receptor-binding domain; and amino acid residues of the CH1 domain linked to the heavy chain Fv fragment of the antigen-binding domain have electric charges opposite to those of amino acid residues of the CL domain linked to the light chain Fv fragment of the antigen-binding domain.

Control of Electric Charges of CH1 and CL Domains

To obtain a bispecific polypeptide complex that recognizes an epitope of the T cell receptor-binding domain by the heavy and light chains of the T cell receptor-binding domain, and an epitope of an antigen by the heavy and light chains of the antigen-binding domain, theoretically ten types of polypeptide complex molecules are produced if each of the four chains is expressed when producing the polypeptide complex.

Nevertheless, the desired polypeptide complex molecule can be preferentially obtained, for example, by controlling the domains so as to inhibit the association between the heavy chain of the T cell receptor-binding domain and the light chain of the antigen-binding domain, and/or the association between the heavy chain of the antigen-binding domain and the light chain of the T cell receptor-binding domain.

Examples include alterations of amino acid residues that form an interface between the heavy chain CH1 of the T cell receptor-binding domain and the light chain CL of the antigen-binding domain to positively charged amino acid residues, and alterations of amino acid residues that form an interface between the heavy chain CH1 of the antigen-binding domain and the light chain CL of the T cell receptor-binding domain to negatively charged amino acid residues. As a result of such alterations, undesired association between the heavy chain CH1 of the T cell receptor-binding domain and the light chain CL of the antigen-binding domain is inhibited because the electric charges of the amino acid residues that form the interface are both positive, and undesired association between the heavy chain CH1 of the antigen-binding domain and the light chain CL of the T cell receptor-binding domain is also inhibited because the electric charges of the amino acid residues that form the interface are both negative. A desired polypeptide complex of the present invention can be efficiently produced as a result of the desired association between the heavy chain CH1 of T cell receptor-binding domain and the light chain CL of the T cell receptor-binding domain as well as the desired association between the heavy chain CH1 of the antigen-binding domain and the light chain CL of the antigen-binding domain. Furthermore, the desired association between the heavy light chains of the T cell receptor-binding domains is preferably promoted because the amino acid residues that form the interface have opposite electric charges from each other. The desired association between the heavy and light chains of the antigen-binding domains is also preferably promoted because the amino acid residues that form the interface have opposite electric charges from each other. This allows efficient production of a polypeptide complex of the present invention with the desired association.

Furthermore, control of the association in the present invention can also be used to inhibit the association between CH1s (the heavy chains of the T cell receptor-binding domain and antigen-binding domain) or between CLs (the light chains of the T cell receptor-binding domain and antigen-binding domain).

Those skilled in the art can appropriately find in a desired polypeptide complex whose association is controlled according to the present invention the types of amino acid residues locating in close proximity at the CH1/CL interface upon association.

Furthermore, by using public databases or such, those skilled in the art can appropriately find usable antibody CH1 and CL sequences in an organism such as human, monkey, mouse, or rabbit. More specifically, the amino acid sequence information of CH1 and CL can be obtained by methods described below in the Examples.

Specifically, as shown in the Examples described below, specific examples of combinations of amino acid residues locating in close proximity (facing or contacting) at the CH1/CL interface upon association between CH1 and CL which are respectively linked to the VH and VL forming the T cell receptor-binding domain or antigen-binding domain include:

- lysine (K) at position 147 (EU numbering) in CH1 (for example, position 147 in the amino acid sequence of SEQ ID NO: 1) and threonine (T) at position 180 (EU numbering) in the facing (contacting) CL;
- lysine (K) at position 147 (EU numbering) in CH1 and serine(S) at position 131 (EU numbering) in the facing (contacting) CL;
- lysine (K) at position 147 (EU numbering) in CH1 and threonine (T) at position 164 (EU numbering) in the facing (contacting) CL;
- lysine (K) at position 147 (EU numbering) in CH1 and asparagine (N) at position 138 (EU numbering) in CL, which face (contact with) each other;
- lysine (K) at position 147 (EU numbering) in CH1 and glutamic acid (E) at position 123 (EU numbering) in the facing (contacting) CL;
- glutamine (Q) at position 175 (EU numbering) in CH1 and glutamine (Q) at position 160 (EU numbering) in the facing (contacting) CL; or
- lysine (K) at position 213 (EU numbering) in CH1 and glutamic acid (E) at position 123 (EU numbering) in the facing (contacting) CL.

These positions are numbered according to the document by Kabat et al. (Kabat E A et al., 1991. Sequence of Proteins of Immunological Interest. NIH).

Herein, the numbers indicated by EU numbering are assigned according to EU numbering (Sequences of proteins of immunological interest, NIH Publication No. 91-3242). In the present invention, "amino acid residue at position X (EU numbering)" and "amino acid at position X (EU numbering)" (where X is an arbitrary number) are interchangeable with "amino acid residue corresponding to position X (EU numbering)", "amino acid corresponding to position X (EU numbering)".

As described in the Examples below, a desired polypeptide complex can be preferentially obtained by altering the amino acid residues and conducting the methods of the present invention.

The amino acid residues described above are known to be highly conserved in human and mouse (J. Mol. Recognit. (2003) 16, 113-120). Thus, the association between CH1 and CL in the constant region of a polypeptide complex of the present invention other than the polypeptide complexes described in the Examples can also be controlled by altering amino acid residues corresponding to the above-described amino acid residues.

Specifically, the present invention provides polypeptide complexes with controlled association between the heavy chain and light chain, in which one, two or more pairs selected from the group consisting of the pairs of amino acid residues described in (a) to (f) below have the same electric charges:

(a) the amino acid residue at position 147 (EU numbering) in CH1 and the amino acid residue at position 180 (EU numbering) in CL;
(b) the amino acid residue at position 147 (EU numbering) in CH1 and the amino acid residue at position 131 (EU numbering) in CL;
(c) the amino acid residue at position 147 (EU numbering) in CH1 and the amino acid residue at position 164 (EU numbering) in CL;
(d) the amino acid residue at position 147 (EU numbering) in CH1 and the amino acid residue at position 138 (EU numbering) in CL;
(e) the amino acid residue at position 147 (EU numbering) in CH1 and the amino acid residue at position 123 (EU numbering) in CL; and
(f) the amino acid residue at position 175 (EU numbering) in CH1 and the amino acid residue at position 160 (EU numbering) in CL.

Furthermore, in another embodiment, the present invention provides antibodies in which the amino acid residues in the pair of amino acid residues described in (g) below have the same electric charges:

(g) the amino acid residue at position 213 (EU numbering) in CH1 and the amino acid residue at position 123 (EU numbering) in CL.

The amino acid residues in each of the pairs described above are located in close proximity with each other upon association, as described in the EXAMPLES below. By homology modeling or other methods using commercially available software, those skilled in the art can appropriately find in a desired CH1 or CL amino acid positions corresponding to the amino acid residues described in (a) to (g) above, and can appropriately alter amino acid residues at those positions.

Such an "electrically charged amino acid residue" in an above-described antibody is preferably selected, for example, from the amino acid residues belonging to the group (X) or (Y) described below:

(X) glutamic acid (E) and aspartic acid (D); and (Y) lysine (K), arginine (R) and histidine (H).

In the above-described polypeptide complexes, "has the same electric charge" means that, for example, all of two or more amino acid residues belongs to one of groups (X) and (Y) described above. On the other hand, "has an opposite electric charge" means that, for example, at least one of two or more amino acid residues has an amino acid residue that belongs to one of groups (X) and (Y) described above, while the other amino acid residues have an amino acid residues that belongs to the other group.

Methods of producing the above-described polypeptide complexes and methods of the present invention for controlling the association by altering the amino acid residues in groups (a) to (g) above to amino acid residues having the same electric charge are also preferred embodiments of the present invention.

In the present invention, amino acid residues "to be altered" are not limited to the above-described amino acid residues of the constant region. By homology modeling or other methods using commercially available software, those skilled in the art can appropriately identify amino acid residues that form an interface in a mutant polypeptide or heteromeric multimer and appropriately alter amino acid residues at those positions to control association.

In the techniques for inhibiting undesired association between the heavy chain and light chain by introducing charge repulsion at the interface between the heavy chain and light chain variable regions, amino acid residues in contact with each other at the interface between the heavy chain variable region (VH) and light chain variable region (VL) include, for example, glutamine (Q) at position 39 (for example, position 39 in the amino acid sequence of SEQ ID NO: 6 in WO 2006/106905) in the heavy chain variable region FR2 and glutamine (Q) at position 38 (for example, position 44 in the amino acid sequence of SEQ ID NO: 8 in WO 2006/106905) in the facing (contacting) light chain variable region FR2. Such preferred amino acid residues also include, for example, leucine (L) at position 45 (for example, position 45 in the amino acid sequence of SEQ ID NO: 6 in WO 2006/106905) in the heavy chain variable region FR2 and proline (P) at position 44 (for example, position 44 in the amino acid sequence of SEQ ID NO: 8 in WO 2006/106905) in the facing light chain variable region FR2. These positions are numbered according to the document by Kabat et al. (Kabat E A et al. 1991. Sequence of Proteins of Immunological Interest. NIH).

The amino acid residues described above are known to be highly conserved in human and mouse (J. Mol. Recognit. (2003) 16, 113-120). Thus, the association between VH and VL in antibody variable regions other than the polypeptide complexes described in the Examples can also be controlled by altering amino acid residues corresponding to the above-described amino acid residues.

More specifically, such antibodies having heavy chain and light chain variable regions include those in which the amino acid residues of (1) and (2), or (3) and (4) described below have the same electric charges:

(1) the amino acid residue corresponding to position 39 (EU numbering) in the heavy chain variable region;

(2) the amino acid residue corresponding to position 38 (EU numbering) in the light chain variable region;

(3) the amino acid residue corresponding to position 45 (EU numbering) in the heavy chain variable region;

(4) the amino acid residue corresponding to position 44 (EU numbering) in the light chain variable region.

The amino acid residues of (1) and (2), or (3) and (4) described above are located in close proximity to each other upon association. By homology modeling or other methods using commercially available software, those skilled in the art can appropriately identify in a desired heavy chain or light chain variable region amino acid positions corresponding to the amino acid residues described in (1) to (4) above, and can appropriately alter amino acid residues at those positions.

In an above-described antibody, the "electrically charged amino acid residue" is preferably selected, for example, from the amino acid residues belonging to the group (X) or (Y) below:

(X) glutamic acid (E) and aspartic acid (D); and (Y) lysine (K), arginine (R), and histidine (H).

In human and mouse, generally, the amino acid residues of (1) to (4) described above are:

(1) glutamine (Q);

(2) glutamine (Q);

(3) leucine (L); and (4) proline (P), respectively.

In a preferred embodiment of the present invention, the above-described amino acid residues are altered (for example, substitution with a charged amino acid). The types of amino acid residues (1) to (4) described above are not limited to those described above. These amino acids may be any other amino acids corresponding to those described above. For example, in the case of human, an amino acid corresponding to the amino acid at position 38 (EU numbering) in light chain variable region may be histidine (H). By referring to published documents (for example, J. Mol. Recognit. (2003) 16, 113-120) or the like, those skilled in the art can find the type of amino acid residue corresponding to an arbitrary position in the light chain, and thus can appropriately alter the amino acid residue (for example, substitution with a charged amino acid).

In techniques for inhibiting undesired association between the heavy chain and light chain by substituting electrically charged polar amino acids for amino acid residues that form the hydrophobic core at the interface between the heavy chain and light chain variable regions, preferred amino acid residues capable of forming the hydrophobic core at the interface between the heavy chain variable region (VH) and light chain variable region (VL) include, for example, leucine (L) at position 45 in the heavy chain variable region and proline (P) at position 44 in the facing light chain variable region.

In general, a "hydrophobic core" refers to a portion where side chains of hydrophobic amino acids assemble inside the associated polypeptide. Hydrophobic amino acids include, for example, alanine, isoleucine, leucine, methionine, phenylalanine, proline, tryptophan, and valine. Meanwhile, amino acid residues other than the hydrophobic amino acids (for example, tyrosine) can also be involved in the formation of hydrophobic core. Together with the hydrophilic surface from outward exposure of the side chains of hydrophilic amino acids, the hydrophobic core serves as a driving force to promote the association of water-soluble polypeptides. When hydrophobic amino acids of two different domains are present on the molecular surface and exposed to water molecules, the entropy is increased, which results in an increase in the free energy. Therefore, the two domains associate with each other to decrease free energy for stabilization. The hydrophobic amino acids at the interface are buried inside of the molecule to form a hydrophobic core.

It is considered that when the hydrophobic amino acids that form a hydrophobic core in the polypeptide association are altered to polar amino acids with electric charge, the formation of hydrophobic core is inhibited. This results in inhibition of the polypeptide association.

Other known technologies are also applicable to the polypeptide complexes of the present invention. For example, to promote the association of the first VH (VH1) and first VL (VL1), and/or second VH (VH2) and second VL (VL2), in addition to the "alterations" of the present invention, amino acids in one of the H chain variable regions are substituted with those having a larger side chain (knob; bulge) and amino acids in the other H chain variable region are substituted with those having a smaller side chain (hole; void) so that the knob is placed in the hole. This promotes the association of VH1 and VL1, and/or VH2 and VL2, resulting in further inhibition of the association between VH1 and VL2 and/or between VH2 and VL1 polypeptides (WO 1996/027011; Ridgway J B et al., Protein Engineering (1996) 9, 617-621; Merchant A M et al., Nature Biotechnology (1998) 16, 677-681).

In the production of an above-described polypeptide complex, each domain may be linked directly via peptide bond or by peptide binding via a peptide linker. In this case, the linker to be used includes the linker described above as an example and appropriate linkers with a peptide tag, for example, His-tag, HA-tag, myc-tag, or FLAG®-tag. In addition, it is preferable to use the property of mutual binding based on hydrogen bonding, disulfide bond, covalent bonding, or ionic interaction, or a combination thereof. For example, it is possible to employ the affinity between antibody CH1 and CL, or the above-described Fc domains derived from a bispecific antibody may be used for heteromeric association of Fc domains. Moreover, interdomain disulfide bonds can be preferably used as described in the EXAMPLES.

Figure 17:
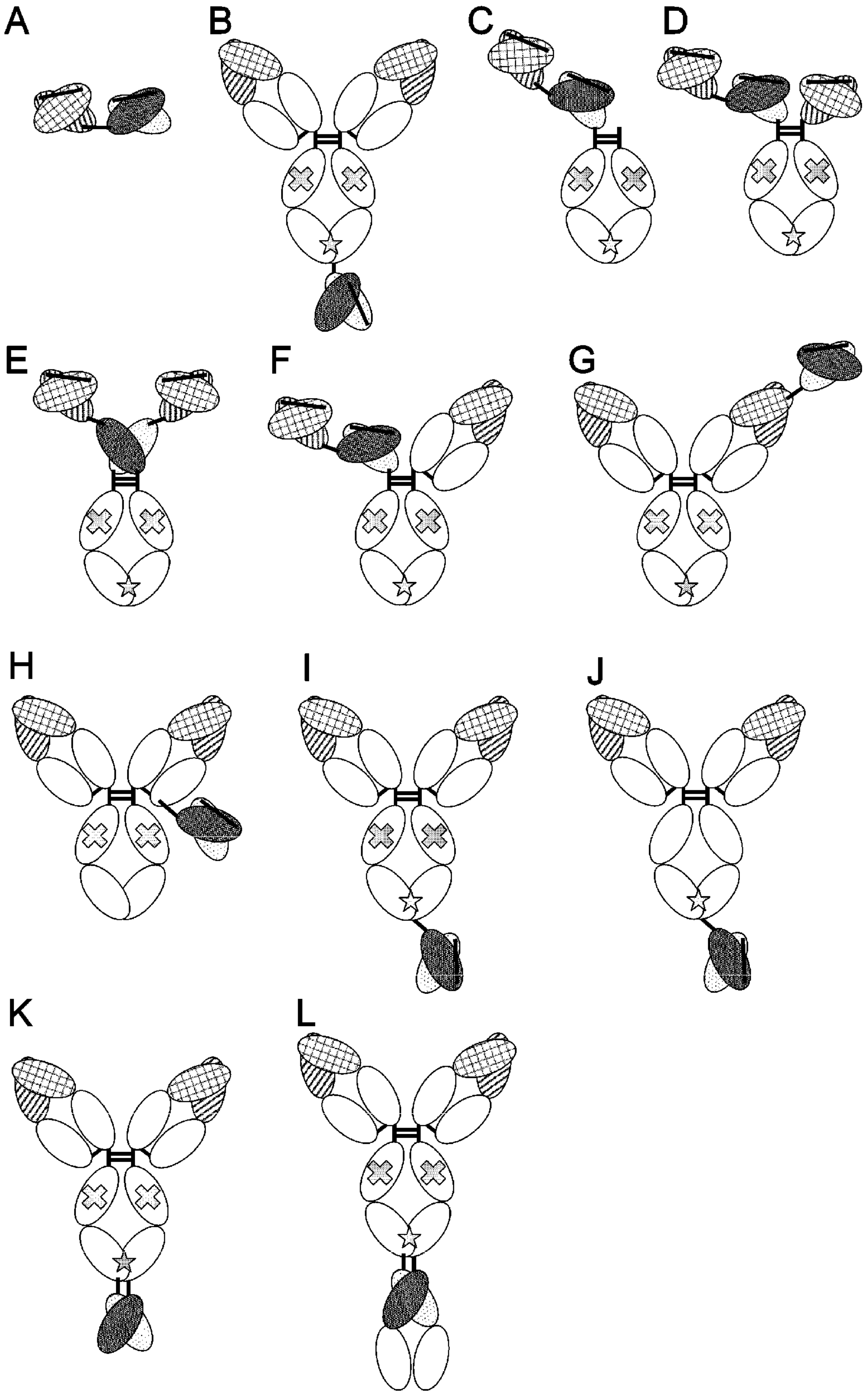
FIG. 17 shows diagrams of GPC3 BiTE (A); GPC3 ERY 10 (B); GPC3 ERY2 (C); GPC3 ERY5 (D); GPC3 ERY6 (E); GPC3 ERY7 (F); GPC3 ERY8-2 (G); GPC3 ERY9-1 (H); GPC3 ERY10-1 (I); GPC3 ERY15 (J); GPC3 ERY18 (K); and GPC3 ERY19-3 (L).
Figure 19:
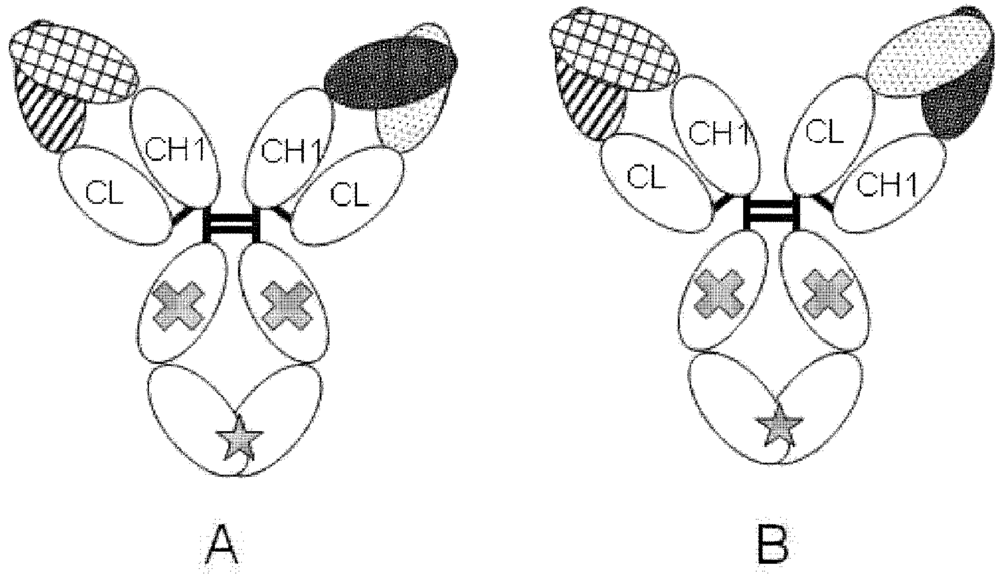
FIG. 19 shows diagrams A and B that represent domains forming the following polypeptide complexes described in the Examples herein: GPC3 ERY17-2, GPC3 ERY17-3, EpCAM ERY17-2, and EpCAM ERY17-3. The domain with cross-hatched lines represents the H-chain variable region of the anti-cancer antigen (GPC3, EpCAM, EGFR) antibody; the domain with diagonal lines represents the L-chain variable region of the anti-cancer antigen (GPC3, EpCAM, EGFR) antibody; the domain with dotted lines represents the H-chain variable region of the anti-CD3 antibody; the closed domain represents the L-chain variable region of the anti-CD3 antibody; the open domain represents the antibody constant region; the cross represents a silent Fc mutation; and the star represents a mutation promoting heteromeric Fc association.
Figure 24:
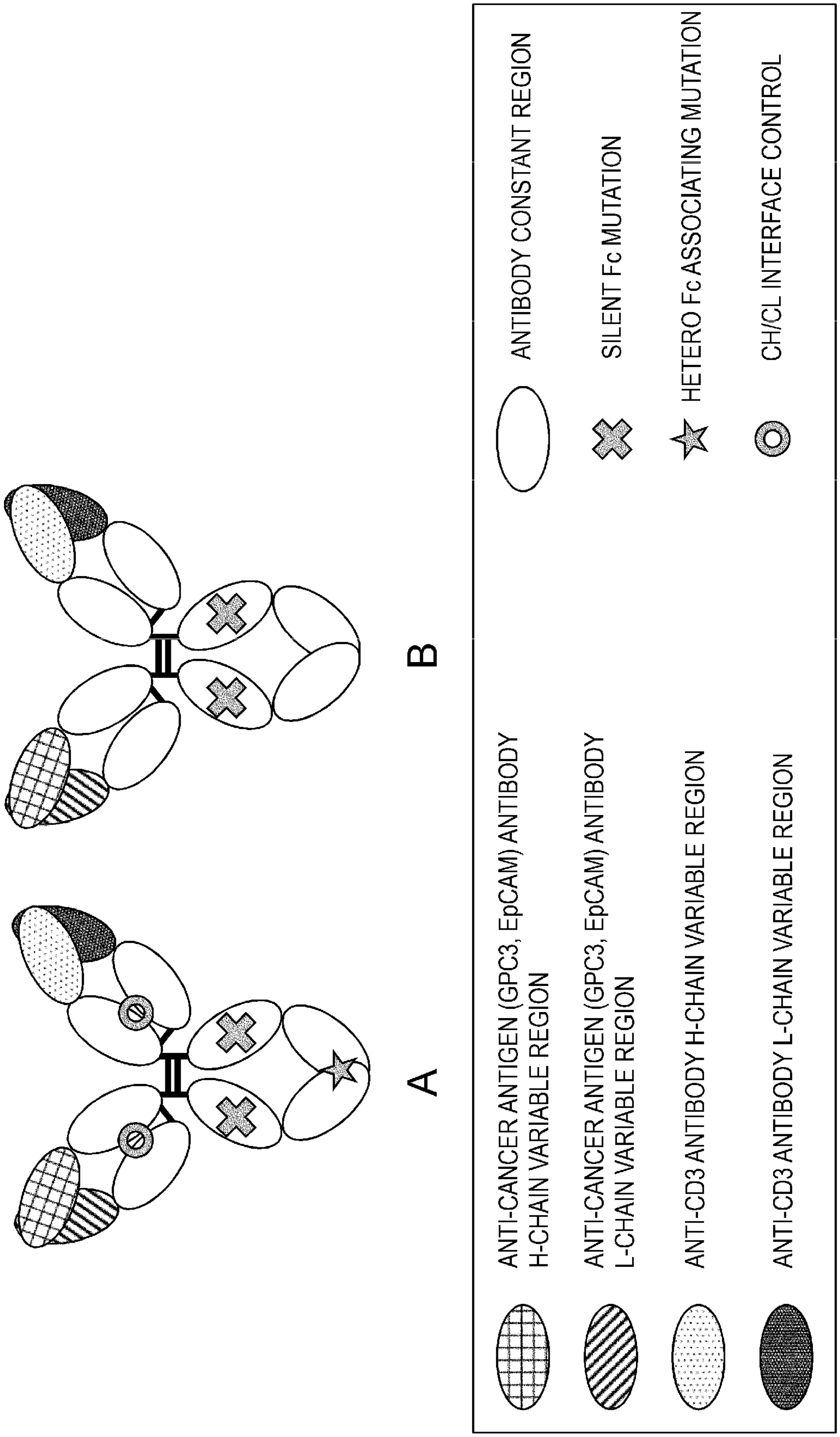
FIG. 24 shows diagrams that represent domains forming the following polypeptide complexes described in the Examples herein: GM1, GM2, and GM0. "A" shows a polypeptide complex in which the CH1/CL interface association is regulated, and Knobs-into-Holes (KiH) modifications are introduced. "B" shows a polypeptide complex that has no regulation of the CH1/CL interface association or introduction of KiH modifications. The domain with cross-hatched lines represents the H-chain variable region of the anti-cancer antigen (GPC3 or EpCAM) antibody; the domain with diagonal lines represents the L-chain variable region of the anti-cancer antigen (GPC3 or EpCAM) antibody; the domain with dotted lines represents the H-chain variable region of the anti-CD3 antibody; the closed domain represents the L-chain variable region of the anti-CD3 antibody; the open domain represents the antibody constant region; the cross represents a silent Fc mutation; the star represents a mutation promoting heteromeric Fc association; and the doughnut-shaped symbol represents a mutation regulating the CH1/CL interface interaction.

The polypeptide complexes of the present invention include, for example, the embodiments shown in FIGS. 17, 19, and 24.

The polypeptide complexes of the present invention can be produced by the same methods as the above-described methods for producing recombinant antibodies.

Furthermore, the present invention relates to polynucleotides encoding the polypeptide complex of the present invention. A polypeptide complex of the present invention can be inserted into any expression vectors. An appropriate host is transformed with the expression vector to obtain cells expressing the polypeptide complex. The polypeptide complex encoded by the polynucleotide can be obtained by culturing cells expressing the polypeptide complex and collecting the expression product from the culture supernatant. Specifically, the present invention relates to vectors carrying a polynucleotide encoding the polypeptide complex of the present invention, cells containing the vectors, and methods of producing the polypeptide complex of the present invention, in which the cells are cultured and the polypeptide complex is collected from the culture supernatant. Those described above can be obtained by the same technologies described above for the recombinant antibodies.

Pharmaceutical Composition

In another aspect, the present invention provides pharmaceutical compositions which comprise as an active ingredient a polypeptide complex comprising:

(1) an antigen-binding domain;

(2) a domain comprising an Fc domain with reduced Fcγ receptor-binding activity; and (3) a CD3-binding domain.

The present invention also relates to therapeutic agents to induce cellular cytotoxicity, which comprise the above-described complex as an active ingredient (therapeutic agents for inducing cellular cytotoxicity), cell growth-suppressing agents, and anticancer agents. The pharmaceutical compositions of the present invention can be used as a therapeutic or preventive agent for cancer. The therapeutic agents for inducing cellular cytotoxicity, cell growth-suppressing agents, and anticancer agents of the present invention are preferably administered to subjects with cancer or a likelihood of cancer recurrence.

In the present invention, the therapeutic agents for inducing cellular cytotoxicity, cell growth-suppressing agents, and anticancer agents, which comprise as an active ingredient a polypeptide complex comprising:

(1) an antigen-binding domain;

(2) a domain encompassing an Fc domain with reduced Fcγ receptor-binding activity; and (3) a CD3-binding domain may also be described as a method for preventing or treating cancer, which comprises the step of administering the polypeptide complex to a subject, or use of the polypeptide complex in producing therapeutic agents for inducing cellular cytotoxicity, cell growth-suppressing agents, or anticancer agents.

Herein, "comprising as an active ingredient a polypeptide complex comprising:

(1) an antigen-binding domain;

(2) a domain encompassing an Fc domain with reduced Fcγ receptor-binding activity; and (3) a CD3-binding domain"

means comprising the polypeptide complex as a major active ingredient; however, the content ratio of the polypeptide complex is not limited.

A pharmaceutical composition of the present invention, a therapeutic agent for inducing cellular cytotoxicity, a cell growth-suppressing agent, or an anticancer agent of the present invention may be formulated with different types of polypeptide complexes, if needed. For example, the cytotoxic action against cells expressing an antigen can be enhanced by a cocktail of multiple polypeptide complexes of the present invention that bind to the same antigen. Alternatively, the therapeutic effect can be increased by formulating a polypeptide complex of the present invention comprising an antigen-binding domain that binds to a cancer antigen in combination with other polypeptide complexes of the present invention comprising an antigen-binding domain against a different antigen.

If necessary, the polypeptide complexes of the present invention may be encapsulated in microcapsules (microcapsules made from hydroxymethylcellulose, gelatin, poly[m-ethylmethacrylate], and the like), and made into components of colloidal drug delivery systems (liposomes, albumin microspheres, microemulsions, nano-particles, and nano-capsules) (for example, see "Remington's Pharmaceutical Science 16th edition", Oslo Ed. (1980)). Moreover, methods for preparing agents as sustained-release agents are known, and these can be applied to the polypeptide complexes of the present invention (J. Biomed. Mater. Res. (1981) 15, 267-277; Chemtech. (1982) 12, 98-105; U.S. Pat. No. 3,773,719; European Patent Application (EP) Nos. EP58481 and EP133988; Biopolymers (1983) 22, 547-556).

The pharmaceutical compositions, cell growth-suppressing agents, or anticancer agents of the present invention may be administered either orally or parenterally to patients. Parental administration is preferred. Specifically, such administration methods include injection, nasal administration, transpulmonary administration, and percutaneous administration. Injections include, for example, intravenous injections, intramuscular injections, intraperitoneal injections, and subcutaneous injections. For example, pharmaceutical compositions, therapeutic agents for inducing cellular cytotoxicity, cell growth-suppressing agents, or anticancer agents of the present invention can be administered locally or systemically by injection. Furthermore, appropriate administration methods can be selected according to the patient's age and symptoms. The administered dose can be selected, for example, from the range of 0.0001 mg to 1,000 mg per kg of body weight for each administration. Alternatively, the dose can be selected, for example, from the range of 0.001 mg/body to 100,000 mg/body per patient. However, the dose of a pharmaceutical composition of the present invention is not limited to these doses.

The pharmaceutical compositions of the present invention can be formulated according to conventional methods (for example, Remington's Pharmaceutical Science, latest edition, Mark Publishing Company, Easton, U.S.A.), and may also contain pharmaceutically acceptable carriers and additives. Examples include, but are not limited to, surfactants, excipients, coloring agents, flavoring agents, preservatives, stabilizers, buffers, suspension agents, isotonic agents, binders, disintegrants, lubricants, fluidity promoting agents, and corrigents, and other commonly used carriers can be suitably used. Specific examples of the carriers include light anhydrous silicic acid, lactose, crystalline cellulose, mannitol, starch, carmellose calcium, carmellose sodium, hydroxypropyl cellulose, hydroxypropyl methylcellulose, polyvinylacetal diethylaminoacetate, polyvinylpyrrolidone, gelatin, medium-chain triglyceride, polyoxyethylene hardened castor oil 60, saccharose, carboxymethyl cellulose, corn starch, inorganic salt, and such.

The present invention also provides methods for damaging cells expressing a cancer antigen or for suppressing the cell growth by contacting the cells expressing the cancer antigen with a polypeptide complex of the present invention that binds to the cancer antigen. Monoclonal antibodies that bind to the cancer antigen are described above as a cancer antigen-binding polypeptide complex of the present invention, which is included in the therapeutic agents for inducing cellular cytotoxicity, cell growth-suppressing agents, and anticancer agents of the present invention. Cells to which a cancer antigen-binding polypeptide complex of the present invention binds are not particularly limited, as long as they express the cancer antigen. Specifically, in the present invention, the preferred cancer antigen-expressing cells include ovary cancer cells, prostate cancer cells, breast cancer cells, uterine cancer cells, liver cancer cells, lung cancer cells, pancreatic cancer cells, stomach cancer cells, urinary bladder cancer cells, and colon cancer cells. When the cancer antigen is GPC3, cells are not limited as long as they are cancer cells expressing GPC3. However, the preferred cancer cells include hepatocarcinoma cells, lung cancer cells, and ovary cancer cells.

In the present invention, "contact" can be carried out, for example, by adding a cancer antigen-binding polypeptide complex of the present invention to culture media of cells expressing the cancer antigen cultured in vitro. In this case, a polypeptide complex to be added can be used in an appropriate form, such as a solution or solid prepared by lyophilization or the like. When the polypeptide complex of the present invention is added as an aqueous solution, the solution may be a pure aqueous solution containing the polypeptide complex alone or a solution containing, for example, an above-described surfactant, excipient, coloring agent, flavoring agent, preservative, stabilizer, buffering agent, suspending agent, isotonizing agent, binder, disintegrator, lubricant, fluidity accelerator, and corrigent. The added concentration is not particularly limited; however, the final concentration in a culture medium is preferably in a range of 1 pg/ml to 1 g/ml, more preferably 1 ng/ml to 1 mg/ml, and still more preferably 1 μg/ml to 1 mg/ml.

In another embodiment of the present invention, "contact" can also be carried out by administration to nonhuman animals transplanted with cancer antigen-expressing cells in vivo or to animals having cancer cells expressing the cancer antigen endogenously. The administration method may be oral or parenteral. Parenteral administration is particularly preferred. Specifically, the parenteral administration method includes injection, nasal administration, pulmonary administration, and percutaneous administration. Injections include, for example, intravenous injections, intramuscular injections, intraperitoneal injections, and subcutaneous injections. For example, pharmaceutical compositions, therapeutic agents for inducing cellular cytotoxicity, cell growth-suppressing agents, or anticancer agents of the present invention can be administered locally or systemically by injection. Furthermore, an appropriate administration method can be selected according to the age and symptoms of an animal subject. When the polypeptide complex is administered as an aqueous solution, the solution may be a pure aqueous solution containing the polypeptide complex alone or a solution containing, for example, an above-described surfactant, excipient, coloring agent, flavoring agent, preservative, stabilizer, buffering agent, suspending agent, isotonizing agent, binder, disintegrator, lubricant, fluidity accelerator, and corrigent. The administered dose can be selected, for example, from the range of 0.0001 to 1,000 mg per kg of body weight for each administration. Alternatively, the dose can be selected, for example, from the range of 0.001 to 100,000 mg/body for each patient. However, the dose of a polypeptide complex of the present invention is not limited to these examples.

The methods described below are preferably used as a method for assessing or determining cellular cytotoxicity caused by contacting a polypeptide complex of the present invention with antigen-expressing cells to which the antigen-binding domain forming the polypeptide complex of the present invention binds. The methods for assessing or determining the cytotoxic activity in vitro include methods for determining the activity of cytotoxic T cells or the like. Whether a polypeptide complex of the present invention has the activity of inducing T-cell mediated cellular cytotoxicity can be determined by known methods (see, for example, Current protocols in Immunology, Chapter 7. Immunologic studies in humans, Editor, John E, Coligan et al., John Wiley & Sons, Inc., (1993)). In the cytotoxicity assay, a polypeptide complex whose antigen-binding domain binds to an antigen different from that recognized by the antigen-binding domain of the polypeptide complex of the present invention and which is not expressed in the cells is used as a control polypeptide complex. The control polypeptide complex is assayed in the same manner. Then, the activity is assessed by testing whether a polypeptide complex of the present invention exhibits a stronger cytotoxic activity than that of a control polypeptide complex.

Meanwhile, the in vivo cytotoxic activity is assessed or determined, for example, by the following procedure. Cells expressing the antigen to which the antigen-binding domain forming a polypeptide complex of the present invention binds are transplanted intracutaneously or subcutaneously to a nonhuman animal subject. Then, from the day of transplantation or thereafter, a test polypeptide complex is administered into vein or peritoneal cavity every day or at intervals of several days. The tumor size is measured over time. Difference in the change of tumor size can be defined as the cytotoxic activity. As in an in vitro assay, a control polypeptide complex is administered. The polypeptide complex of the present invention can be judged to have cytotoxic activity when the tumor size is smaller in the group administered with the polypeptide complex of the present invention than in the group administered with the control polypeptide complex.

An MTT method and measurement of isotope-labeled thymidine uptake into cells are preferably used to assess or determine the effect of contact with a polypeptide complex of the present invention to suppress the growth of cells expressing an antigen to which the antigen-binding domain forming the polypeptide complex binds. Meanwhile, the same methods described above for assessing or determining the in vivo cytotoxic activity can be used preferably to assess or determine the activity of suppressing cell growth in vivo.

The present invention also provides kits for use in a method of the present invention, which contain a polypeptide complex of the present invention or a polypeptide complex produced by a method of the present invention. The kits may be packaged with an additional pharmaceutically acceptable carrier or medium, or instruction manual describing how to use the kits, etc.

In addition, the present invention relates to polypeptide complexes of the present invention or polypeptide complexes produced by a method of the present invention for use in a method of the present invention.

All prior-art documents cited herein are incorporated herein by reference.

EXAMPLES

Hereinbelow, the present invention is specifically described with reference to the Examples, but it is not to be construed as being limited thereto.

[Example 1] Construction and Assessment of GPC3 ERY2

(1) Outline

There is a well-known method for prolonging the blood half-life of a protein administered in vivo, which is based on the FcRn-mediated recycling using a protein of interest conjugated to an antibody Fc domain. However, the conjugation of a natural type of Fc to BiTE could lead to induction of various cytokines, since a single molecule would bind to a T cell via the anti-CD3 scFv of its BiTE moiety and simultaneously to the FcgR (Fcγ receptor) on the cellular membrane of, for example, a NK cell or macrophage via its Fc domain, and the resulting cross-linking would activate these cells in a cancer antigen-independent manner. Thus, a molecule termed ERY2, in which a BiTE is linked via a polypeptide linker to an Fc domain having reduced Fcγ receptor-binding activity (silent Fc), was prepared, and the activity of ERY2 was assessed by comparing it to that of the BiTE. The scFv of an anti-CD3 epsilon antibody was linked via a short peptide linker to the scFv of an antibody against Glypican 3 (GPC3), which is a GPI-anchored protein known to be expressed at a high level in liver cancer cells, to produce BiTE against GPC3 (GPC3 BiTE) (FIG. 17A). This was then linked to a silent Fc to produce an ERY2 against GPC3 (GPC3 ERY2) (FIG. 17C). Furthermore, a normal IgG-type anti-GPC3 antibody was constructed for comparison. The IgG-type anti-GPC3 antibody was prepared as an antibody with reduced fucose content in its sugar chain moiety, i.e., a low-fucose antibody, which is known to have an enhanced ADCC activity.

(2) Construction of GPC3 BiTE

By PCR amplification using an expression vector for an anti-GPC3 antibody as a template, cDNAs each encoding an H chain variable region (anti-GPC3 VH) or an L chain variable region (anti-GPC3 VL) were obtained. PCR was performed using primers containing appropriate additional sequences and the above cDNAs as templates to construct a cDNA fragment encoding an anti-GPC3 scFv having an amino acid sequence in which the anti-GPC3 VH and anti-GPC3 VL were linked together via a linker with three repeats of Gly-Gly-Gly-Gly-Ser (SEQ ID NO: 7).

Furthermore, a series of oligonucleotides were prepared each of which had a nucleotide sequence encoding a partial sequence of the H chain variable region (M12 VH) or L chain variable region (M12 VL) of an anti-CD3 antibody (M12), and had complementary sequences at the ends. The oligonucleotides were designed such that they would be linked together via the complementary sequence portions by polymerase reaction to synthesize a polynucleotide corresponding to the H chain variable region (M12 VH) and L chain variable region (M12 VL). The oligonucleotides were mixed and then assembled together by PCR to give two cDNAs encoding the amino acid sequences of respective variable regions. PCR was performed using primers containing appropriate additional sequences and the above cDNAs as templates to produce a cDNA fragment encoding M12 scFv having an amino sequence in which M12 VL and M12 VH were linked together via a linker having three repeats of Gly-Gly-Gly-Gly-Ser (SEQ ID NO: 7).

Next, by PCR using primers containing appropriate additional sequences and the cDNA fragments each encoding anti-GPC3 scFv or M12 scFv as templates, a cDNA fragment was constructed which encoded an amino acid sequence in which anti-GPC3 scFv and M12 scFv were linked together via a linker composed of Gly-Gly-Gly-Gly-Ser (SEQ ID NO: 7) and its C terminus had a His tag (eight histidines) (the sequence of SEQ ID NO: 33 without its amino terminal 19 amino acids).

Using primers containing appropriate additional sequences and as a template the cDNA fragment encoding the amino acid sequence of SEQ ID NO: 33 lacking its amino terminal 19 amino acids, PCR was performed to produce a cDNA fragment in which an EcoRI cleavage sequence, kozac sequence, and a nucleotide sequence encoding a secretion signal sequence were attached to the 5' end of the above cDNA fragment and a NotI cleavage sequence to the 3' end. The resulting cDNA fragment was cleaved with EcoRI and NotI, and inserted into an mammalian cell expression vector to obtain an expression vector for GPC3 BiTE (SEQ ID NO: 33; the mature sequence does not contain the amino terminal 19 amino acids, which serve as a signal sequence).

The vector was introduced into CHO DG44 cells by electroporation. After limiting dilution, the cells were cultured in the presence of 1 mg/ml Geneticin to isolate drug-resistant cell lines. The culture supernatant of the obtained cell lines was analyzed by Western blotting using an anti-His tag antibody to select a cell line expressing GPC3 BiTE.

The culture supernatant obtained by large scale cell culture of the above-described cell line was loaded onto a SP Sepharose™ Fast Flow antibody purification resin column (GE Healthcare). After washing the column, a fraction containing GPC3 BiTE was eluted with a NaCl concentration gradient. The fraction was loaded onto a HisTrap™ High Performance (HP) column (GE Healthcare). After washing the column, a fraction containing GPC3 BiTE was eluted with an imidazole concentration gradient. The fraction was concentrated by ultrafiltration, and then the concentrate was loaded onto a Superdex™ 200 column (GE Healthcare). Only a monomeric GPC3 BiTE fraction was collected to obtain purified GPC3 BiTE.

(3) Construction of GPC3 ERY2

PCR using primers containing the same appropriate additional sequences as in the above-described method and a method well known to those skilled in the art such as a method using the QuikChange™ Site-Directed Mutagenesis Kit (Stratagene) were performed to produce expression vectors to which a polynucleotide encoding GPC3 ERY2_Hk (SEQ ID NO: 34; the mature sequence does not contain the amino terminal 19 amino acids, which serve as a signal sequence) or GPC3 ERY2_Hh (SEQ ID NO: 35; the mature sequence does not contain the amino terminal 19 amino acids, which serve as a signal sequence) was inserted.

These expression vectors were co-introduced into FreeStyle™ 293-F cells (Invitrogen) to express GPC3 ERY2 transiently. The resulting culture supernatant was loaded onto an Anti-FLAG® tag M2 column (Sigma). After washing, the column was eluted with 0.1 mg/ml FLAG® peptide (Sigma). A fraction containing GPC3 ERY2 was loaded onto a HisTrap™ HP column (GE Healthcare). After washing, the column was eluted with an imidazole concentration gradient. A fraction containing GPC3 ERY2 was concentrated by ultrafiltration, and the concentrate was loaded onto a Superdex™ 200 column (GE Healthcare). Only a monomeric GPC3 ERY2 fraction was collected from the eluate to obtain purified GPC3 ERY2.

(4) Construction of Low-Fucose Anti-GPC3 Antibody

An expression vector for an anti-GPC3 antibody (that is referred to as humanized GC33 antibody in WO 2006/006693) was introduced into GDP fucose-knockout CHO DXB11 cells (Cancer Sci. (2010) 101 (10), 2227-33) by electroporation. After limiting dilution, the cells were cultured in the presence of 0.5 mg/ml Geneticin to select drug resistant lines, and a cell line expressing a low-fucose anti-GPC3 antibody was obtained. From the culture supernatant obtained by culturing these cells, an antibody fraction was prepared by conventional affinity purification using a HiTrap™ Protein A purification column (Pharmacia). Then, the antibody fraction was subjected to gel filtration purification using a 26/60 Superdex™ 200 chromatography column (Pharmacia). A monomer fraction was collected from the eluate to obtain a low-fucose anti-GPC3 antibody.

(5) Cytotoxicity Assay Using Human Peripheral Blood Mononuclear Cells (5-1) Preparation of Human Peripheral Blood Mononuclear Cell (PBMC) Suspension From healthy volunteers (adult), 50 ml of peripheral blood was collected using syringes to which 100 μl of 1,000 units/ml heparin solution (Novo-Heparin® 5000 units for injection; Novo Nordisk) had been added in advance. The peripheral blood was diluted two fold with PBS (−), divided into four equal aliquots, and added to Leucosep™ lymphocyte separation tubes (Cat. No. 227290; Greiner bio-one) that had been injected with 15 ml of Ficoll-Paque™ PLUS media and centrifuged in advance. After centrifugation (2,150 rpm, 10 minutes, room temperature) of the separation tubes, a mononuclear cell fraction layer was collected. The cells in the mononuclear cell fraction were washed once with Dulbecco's Modified Eagle's Medium (SIGMA) containing 10% FBS (hereinafter referred to as 10% FBS/D-MEM), and then the cell density was adjusted to $4\times10^6$ cells/ml using 10% FBS/D-MEM. The cell suspension thus prepared was used as a human PBMC suspension in subsequent experiments.

(5-2) Cytotoxic Activity Assay

The cytotoxic activity was assessed based on the cell growth inhibition rate determined using xCELLigence® real-time cell analyzer (Roche Diagnostics). The target cell used was SK-pca13a cell line established by forcedly expressing human GPC3 in SK-HEP-1 cell line. SK-pca13a cells were detached from dishes, and seeded onto an E-Plate 96 (Roche Diagnostics) plate at $1\times10^4$ cells/well (100 μl/well). Then viable cell assay was started using xCELLigence® real-time cell analyzer. On the following day, the plate was removed from the xCELLigence® real-time cell analyzer, and 50 μl of each antibody prepared at various concentrations (0.004, 0.04, 0.4, and 4 nM) was added to the plate. After 15 minutes of reaction at room temperature, 50 μl of human PBMC suspension ($2\times10^5$ cells/well) prepared in (5-1) was added. The plate was placed in the xCELLigence® real-time cell analyzer again to start viable cell assay. The reaction was carried out under 5% carbon dioxide gas at 37° C. The cell growth inhibition rate (%) was determined according to the formula shown below using the Cell Index value at 72 hours after the addition of human PBMCs. The Cell Index value used in the calculation was normalized such that the Cell Index value immediately before the addition of antibody was taken as 1.

$$\text{Cell growth inhibition rate (\%)}=(A-B)\times100/(A-1)$$

A denotes the mean Cell Index value for the no-antibody well (the target cell and human PBMC only), while B denotes the mean Cell Index value for each well. The measurement was carried out in triplicate.

The cytotoxic activity of GPC3 BiTE, GPC3 ERY2, and IgG-type anti-GPC3 antibody was measured using PBMCs (peripheral blood mononuclear cells) prepared from human blood as effector cells. GPC3 BiTE showed a very strong activity (FIG. 1). This activity was much stronger than that of the low-fucose anti-GPC3 antibody. Thus, GPC3 BiTE may serve as an excellent cancer therapeutic agent that exceeds the IgG-type antibody. On the other hand, the activity of GPC3 ERY2 was not as strong as that of GPC3 BiTE, although it was greater than that of the IgG-type anti-GPC3 antibody. This suggests that the mere addition of Fc to BiTE does not enable creation of a desired molecule.

[Example 2] Construction and Assessment of GPC3 ERY5, GPC3 ERY6, and GPC3 ERY7

Next, in an attempt to improve the specific activity, the cancer antigen (GPC3)-binding domain was made bivalent to enhance the cancer cell-binding activity. Another anti-GPC3 scFv was added to GPC3 ERY2 to construct GPC3 ERY5 (FIG. 17D). Furthermore, instead of the scFv, a Fab-type GPC3-binding domain was added to produce GPC3 ERY7 (FIG. 17F). In addition, GPC3 ERY6 (FIG. 17E) was also constructed in which the anti-CD3 epsilon scFv of GPC3 ERY5 was split into two arms.

Specifically, a method known to those skilled in the art, such as PCR using primers containing the same appropriate additional sequences as in the above-described method, was performed to produce a series of expression vectors into which a polynucleotide encoding GPC3 ERY5_Hh, GPC3 ERY6_Hk, GPC3 ERY6_Hh, GPC3 ERY7_Hh, or GPC3 ERY7_L was inserted.

The following combinations of expression vectors were introduced into FreeStyle™ 293-F cells to express each designed molecule transiently.

A. Designed Molecule: GPC3 ERY5

Polypeptides encoded by polynucleotides inserted in expression vectors: GPC3 ERY5_Hh (SEQ ID NO: 36; the mature sequence does not contain the amino terminal 19 amino acids, which serves as a signal sequence) and GPC3 ERY2_Hk B. Designed Molecule: GPC3 ERY6

Polypeptides encoded by polynucleotides inserted in expression vectors: GPC3 ERY6_Hk (SEQ ID NO: 37; the mature sequence does not contain the amino terminal 19 amino acids, which serves as a signal sequence) and GPC3 ERY6_Hh (SEQ ID NO: 38; the mature sequence does not contain the amino terminal 19 amino acids, which serves as a signal sequence)

C. Designed Molecule: GPC3 ERY7

Polypeptides encoded by polynucleotides inserted in expression vectors: GPC3 ERY7_Hh (SEQ ID NO: 39; the mature sequence does not contain the amino terminal 19 amino acids, which serves as a signal sequence), GPC3 ERY7_L (SEQ ID NO: 40; the mature sequence does not contain the amino terminal 19 amino acids, which serves as a signal sequence), and GPC3 ERY2_Hk.

The resulting culture supernatant was loaded onto an Anti-FLAG® tag M2 column (Sigma). After washing, the column was eluted with 0.1 mg/ml FLAG® peptide (Sigma). A fraction containing the designed molecule was loaded onto a HisTrap™ HP column (GE Healthcare). After washing, the column was eluted with an imidazole concentration gradient. A fraction containing the designed molecule was concentrated by ultrafiltration. Then, the fraction was loaded onto a Superdex™ 200 column (GE Healthcare). Only a monomer fraction was collected from the eluate to obtain each purified designed molecule.

Figure 2:
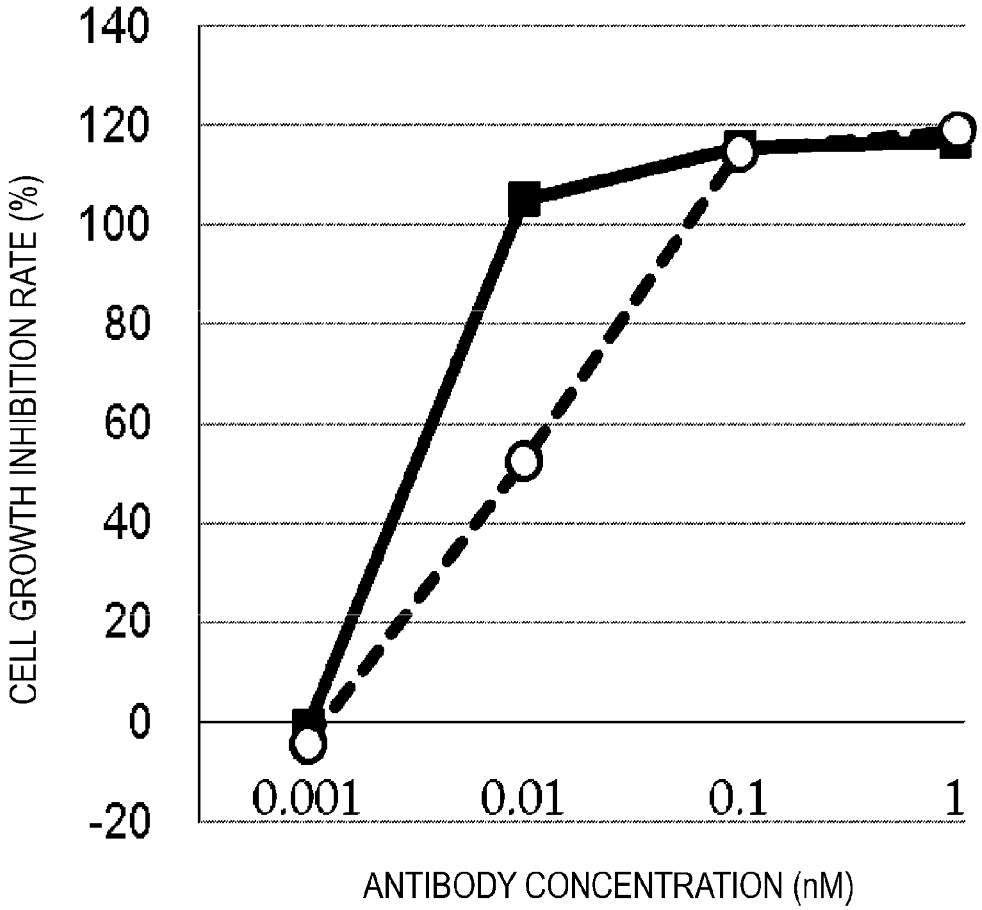
FIG. 2 is a graph showing comparison of the cytotoxic activities of GPC3 BiTE and GPC3 ERY5. Closed square (■) and open circle (○) represent the cytotoxic activities of GPC3 BiTE and GPC3 ERY5, respectively.
Figure 3:
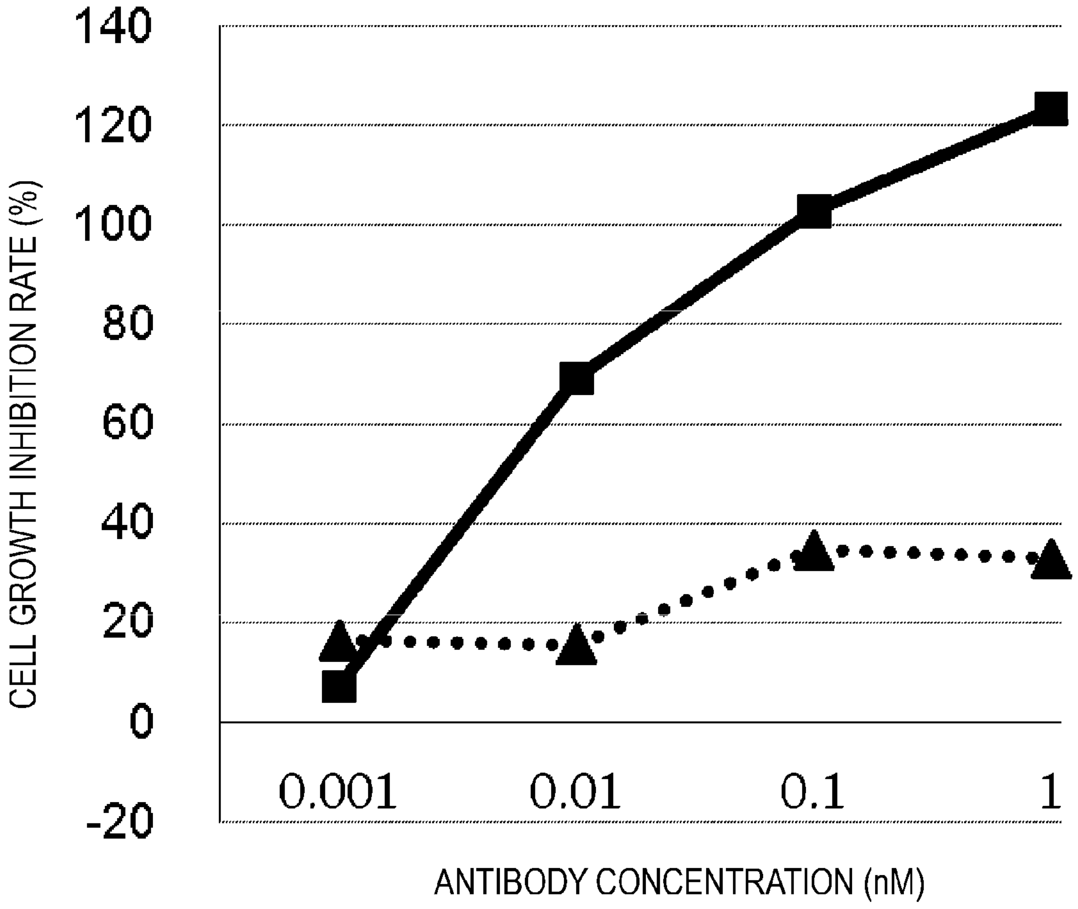
FIG. 3 is a graph showing comparison of the cytotoxic activities of GPC3 BiTE and GPC3 ERY6. Closed square (■) and closed triangle (▲) represent the cytotoxic activities of GPC3 BiTE and GPC3 ERY6, respectively.
Figure 4:
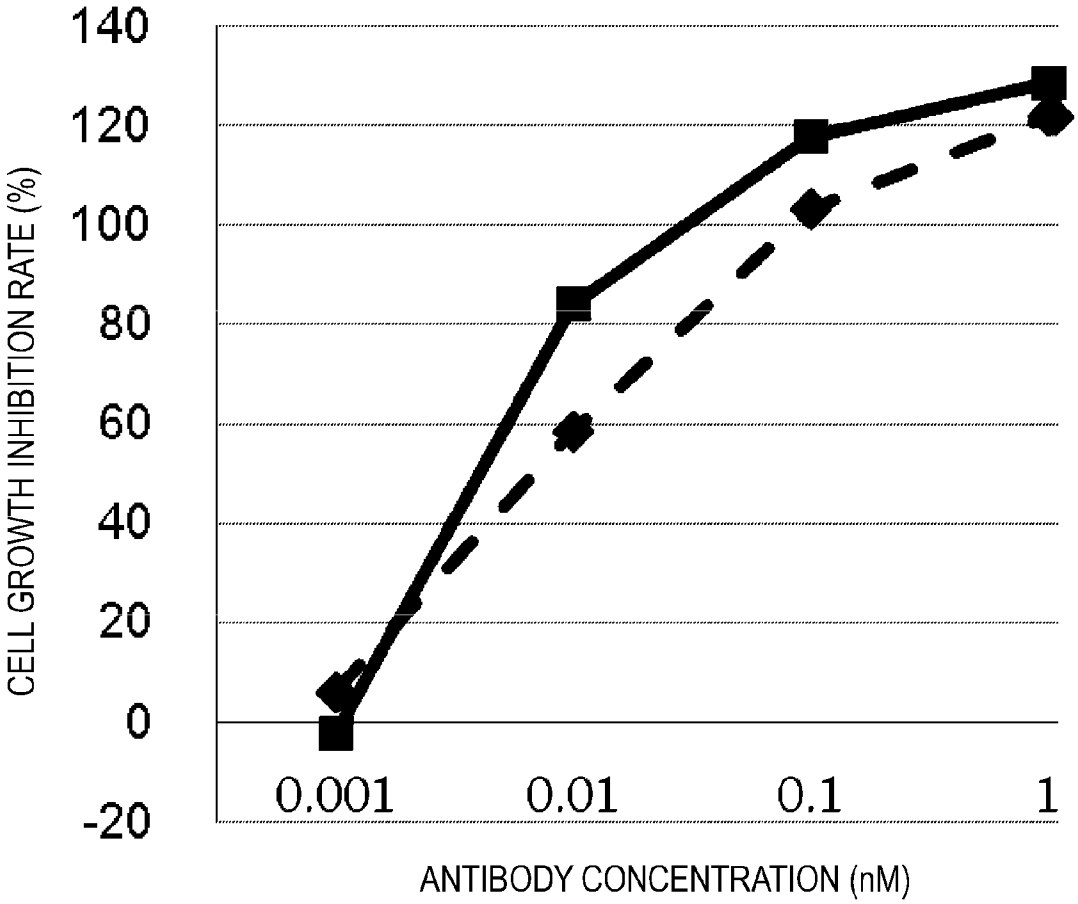
FIG. 4 is a graph showing comparison of the cytotoxic activities of GPC3 BiTE and GPC3 ERY7. Closed square (■) and closed diamond (♦) represent the cytotoxic activities of GPC3 BiTE and GPC3 ERY7, respectively.

These polypeptide complexes were compared to GPC3 BiTE in terms of the cytotoxic activity. The result showed that the cytotoxic activity of these polypeptide complexes was not as much as that of GPC3 BiTE (FIGS. 2 to 4). This finding suggests that the addition of Fc to the BiTE structure or its mimetic structure and the configuration that allows bivalent binding to a cancer antigen do not enable creation of a desired molecule.

[Example 3] Construction and Assessment of GPC3 ERY8-2, GPC3 ERY9-1, and GPC3 ERY10-1

(1) Construction of GPC3 ERY8-2, GPC3 ERY9-1, and GPC3 ERY10-1

Next, molecules having no BiTE structure but possessing the desired activity were designed. An anti-cancer antigen (GPC3) IgG was used as a backbone, and a molecule in which an anti-CD3 epsilon scFv was added to this backbone was constructed. The IgG Fc used as a backbone was a silent Fc having reduced FcgR (Fcγ receptor)-binding activity, as in the above-described cases. GPC3 ERY8-2 (FIG. 17G), GPC3 ERY10-1 (FIG. 17I), and GPC3 ERY9-1 (FIG. 17H) were constructed in which the anti-CD3 epsilon scFv was attached to the N terminus of the H chain, C terminus of the H chain, and C terminus of the L chain of the anti-GPC3 antibody IgG, respectively.

Specifically, by a method known to those skilled in the art, such as PCR using primers containing the same appropriate additional sequences as in the above-described method, a series of expression vectors were constructed into which a polynucleotide encoding GPC3 ERY8-2_Hk (SEQ ID NO: 41; the mature sequence does not contain the amino terminal 19 amino acids, which serve as a signal sequence), GPC3 ERY8-2_Hh (SEQ ID NO: 42; the mature sequence does not contain the amino terminal 19 amino acids, which serve as a signal sequence), GPC3 ERY9-1_H (SEQ ID NO: 43; the mature sequence does not contain the amino terminal 19 amino acids, which serve as a signal sequence), GPC3 ERY9-1_L-His (SEQ ID NO: 44; the mature sequence does not contain the amino terminal 19 amino acids, which serve as a signal sequence), GPC3 ERY9-1_L-FLAG (SEQ ID NO: 45; the mature sequence does not contain the amino terminal 19 amino acids, which serve as a signal sequence), or GPC3 ERY10-1_Hh (SEQ ID NO: 46; the mature sequence does not contain the amino terminal 19 amino acids, which serve as a signal sequence) was inserted.

The following combinations of expression vectors were introduced into FreeStyle™ 293-F cells to express each designed molecule transiently.

D. Designed Molecule: GPC3 ERY8-2

Polypeptides encoded by polynucleotides inserted in expression vectors: GPC3 ERY8-2_Hk (SEQ ID NO: 41; the mature sequence does not contain the amino terminal 19 amino acids, which serve as a signal sequence), GPC3 ERY8-2_Hh (SEQ ID NO: 42; the mature sequence does not contain the amino terminal 19 amino acids, which serve as a signal sequence), and GPC3 ERY7 L E. Designed Molecule: GPC3 ERY9-1

Polypeptides encoded by polynucleotides inserted in expression vectors: GPC3 ERY9-1_H (SEQ ID NO: 43; the mature sequence does not contain the amino terminal 19 amino acids, which serve as a signal sequence), GPC3 ERY9-1_L-His (SEQ ID NO: 44; the mature sequence does not contain the amino terminal 19 amino acids, which serves as a signal sequence), and GPC3 ERY9-1 L-FLAG (SEQ ID NO: 45; the mature sequence does not contain the amino terminal 19 amino acids, which serve as a signal sequence)

F. Designed Molecule: GPC3 ERY10-1

Polypeptides encoded by polynucleotides inserted in expression vectors: GPC3 ERY10-1_Hh (SEQ ID NO: 46; the mature sequence does not contain the amino terminal 19 amino acids, which serve as a signal sequence) and GPC3 ERY8-2_Hk, GPC3 ERY7_L The resulting culture supernatant was loaded onto an Anti-FLAG® tag M2 column (Sigma). After washing, the column was eluted with 0.1 mg/ml FLAG® peptide (Sigma). A fraction containing the designed molecule was loaded onto a HisTrap™ HP column (GE Healthcare). After washing, the column was eluted with an imidazole concentration gradient. A fraction containing the designed molecule was concentrated by ultrafiltration. Then, the fraction was loaded onto a Superdex™ 200 column (GE Healthcare). Only a monomer fraction was collected from the eluate to obtain each purified designed molecule.

Figure 5:
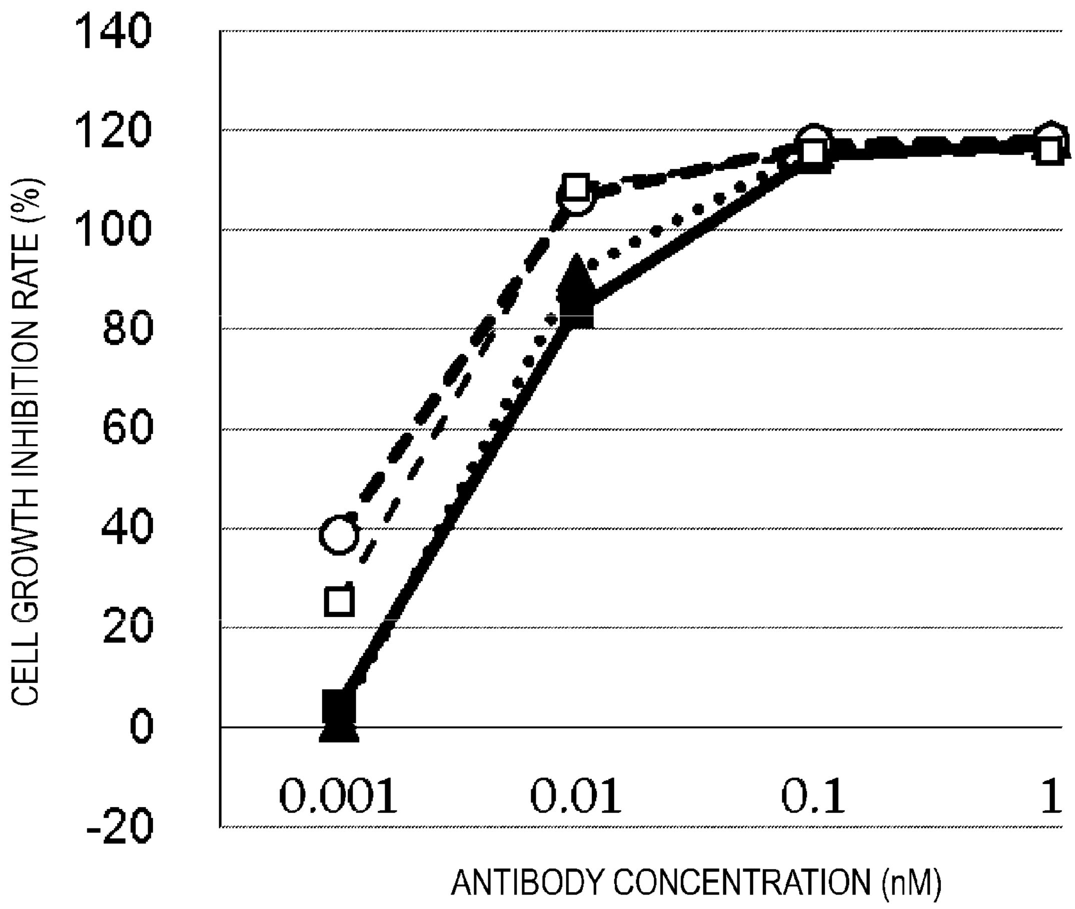
FIG. 5 is a graph showing comparison of the cytotoxic activities of GPC3 BiTE, GPC3 ERY8-2, GPC3 ERY9-1, and GPC3 ERY10-1. Closed square (■), closed triangle (▲), open circle (○), and open square (□) represent the cytotoxic activities of GPC3 BiTE, GPC3 ERY8-2, GPC3 ERY9-1, and GPC3 ERY10-1, respectively.

These molecules were assessed for the in vitro cytotoxic activity. The result revealed that all molecules exhibited a cytotoxic activity comparable to or greater than that of GPC3 BiTE (FIG. 5). In particular, GPC3 ERY9-1 and GPC3 ERY10-1 were found to clearly have a greater cytotoxic activity than GPC3 BiTE. The present invention for the first time demonstrates that molecules made by adding an anti-CD3 epsilon scFv to an anti-cancer antigen IgG also have a cytotoxic activity comparable to or greater than that of BiTE. Particularly, it is surprising that molecules such as GPC3 ERY9-1 and GPC3 ERY10-1 clearly exhibited a greater cytotoxic activity than BiTE although there was a large distance between their cancer antigen-binding domain and CD3 epsilon-binding domain.

(2) Assessment of the In Vivo Efficacy of GPC3 ERY8-2 and GPC3 ERY10-1:

GPC3 ERY8-2 and GPC3 ERY10-1, which were demonstrated to have a cytotoxic activity comparable to or greater than that of GPC3 BiTE in the in vitro assay described in (1), were assessed for the in vivo efficacy. Cells of GPC3-expressing human lung cancer cell line PC-10 were mixed with human PBMCs, and then transplanted to NOD scid mice. The mice were treated by administering GPC3 ERY8-2 or GPC3 ERY10-1 (referred to as pre-mix model).

Specifically, the efficacy test for GPC3 ERY8-2 using the PC-10 pre-mix model was conducted as follows. PBMCs were isolated from blood collected from healthy volunteers. NK cells were removed from the PBMCs using CD56 MicroBeads, human (MACS® Cell Separation portfolio, Miltenyi biotec). Human lung squamous carcinoma cell line PC-10 (Immuno-Biological Laboratories Co., Ltd.) ($5\times10^6$ cells), human PBMCs without NK cells ($4.5\times10^6$ cells), and Matrigel™ Basement Membrane Matrix (BD) were mixed, and then transplanted subcutaneously to the inguinal region of NOD scid mice (CLEA Japan Inc.; female, 7W). The day of transplantation was designated day 0. On the day before transplantation, an anti-asialo GM1 antibody (Wako Pure Chemical Industries) was intraperitoneally administered to the mice at 0.2 mg/head. After two hours of transplantation, GPC ERY8-2 was intraperitoneally administered at 30 μg/head. GPC ERY8-2 was administered five times in total during the period of days 0 to 4.

Furthermore, the efficacy test for GPC3 ERY10-1 using the PC-10 pre-mix model was conducted as follows. PBMCs were isolated from blood collected from healthy volunteers. NK cells were removed from the PBMCs using CD56 MicroBeads, human (MACS® Cell Separation portfolio, Miltenyi biotec). Human lung squamous carcinoma cell line PC-10 (Immuno-Biological Laboratories Co., Ltd.) ($5\times10^6$ cells), human PBMCs without NK cells ($4.5\times10^6$ cells), and Matrigel™ Basement Membrane Matrix (BD) were mixed, and then transplanted subcutaneously to the inguinal region of NOD scid mice (CLEA Japan Inc.; female, 7W). The day of transplantation was designated day 0. On the day before transplantation, an anti-asialo-GM1 antibody (Wako Pure Chemical Industries) was intraperitoneally administered to the mice at 0.2 mg/head. After two hours of transplantation, GPC ERY10-1 was intraperitoneally administered at 30 μg/head. GPC ERY10-1 was administered 13 times in total during the periods of days 0 to 4, days 7 to 11, and days 14 to 16.

Figure 6:
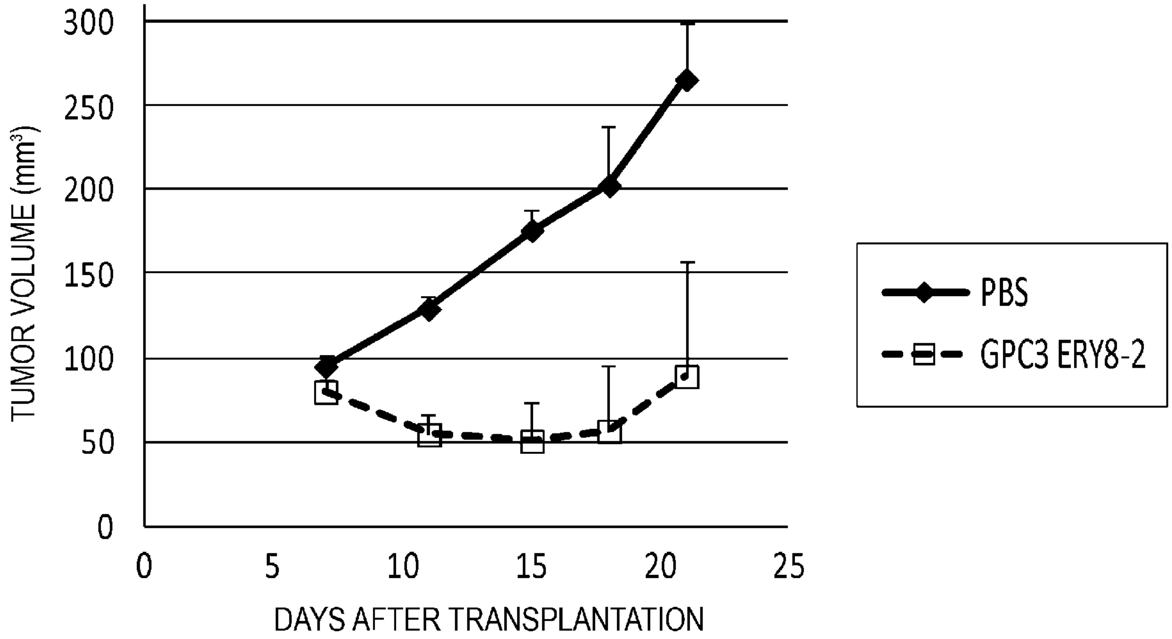
FIG. 6 is a graph showing the in vivo anti-tumor effect of GPC3 ERY8-2 in the PC-10 pre-mix model. Open square (□) and closed diamond (♦) indicate changes in the tumor volume of the GPC3 ERY7 administration group and control (PBS administration) group, respectively.
Figure 7:
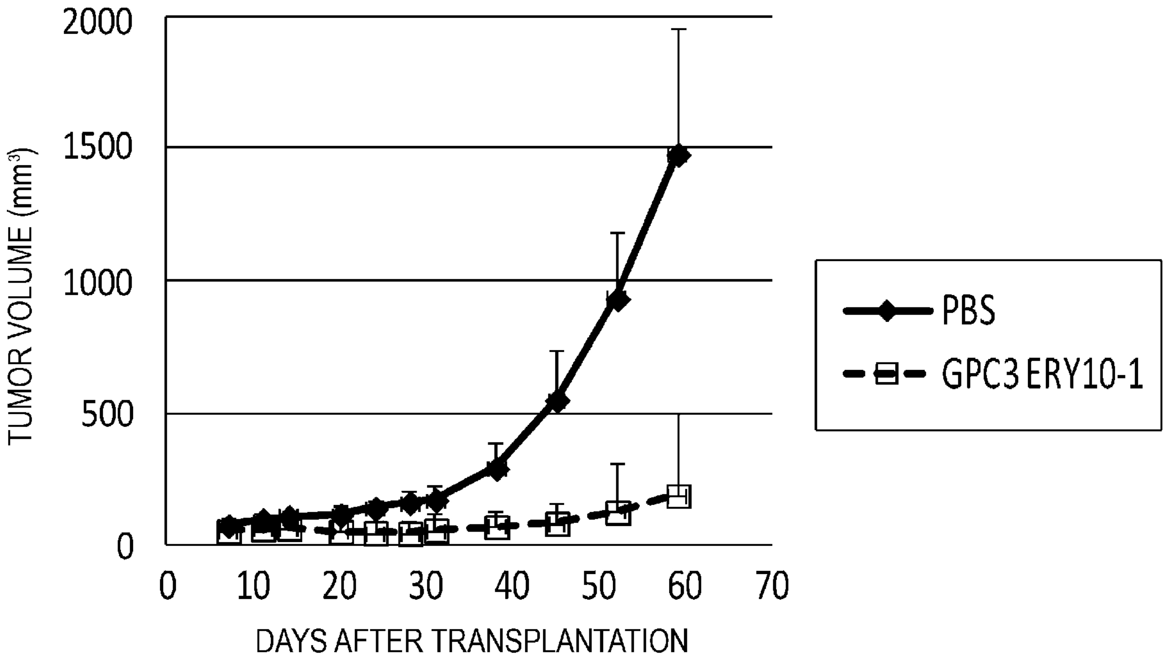
FIG. 7 is a graph showing the in vivo anti-tumor effect of GPC3 ERY10-1 in the PC-10 pre-mix model. Open square (□) and closed diamond (♦) indicate changes in the tumor volume of the GPC3 ERY10-1 administration group and control (PBS administration) group, respectively.

The result showed that in the GPC3 ERY8-2 and GPC3 ERY10-1 administration groups the tumor growth was clearly suppressed as compared to the solvent (PBS) administration group (FIGS. 6 and 7).

Furthermore, GPC3 ERY10-1 was also assessed for the in vivo efficacy using an alternative model. Specifically, T cells were grown by culturing human PBMCs in vitro and then introduced into NOD scid mice which had developed tumors originating from transplanted PC-10. The mice were treated by administering GPC3 ERY10-1 (referred to as T cell transfer model).

Specifically, the efficacy test for GPC3 ERY10-1 using the PC-10 T cell transfer model was conducted as follows. T cell expansion culture was carried out using T cell activation/expansion kit/human (MACS® Cell Culture and Stimulation portfolio, Miltenyilbiotec) and PBMCs isolated from blood collected from healthy volunteers. Human lung squamous carcinoma cell line PC-10 cells (Immuno-Biological Laboratories Co., Ltd.) ($1\times10^7$ cells) were mixed with Matrigel™ Basement Membrane Matrix (BD), and then transplanted subcutaneously to the inguinal region of NOD scid mice (CLEA Japan Inc.; female, 7W). The day of transplantation was designated day 0. On the day before transplantation and days 6, 8, 12, 16, and 20, an anti-asialo-GM1 antibody (Wako Pure Chemical Industries) was intraperitoneally administered to the mice at 0.2 mg/head. On day 6 of transplantation, the mice were grouped by the tumor size and body weight, and then T cells prepared by expansion culture as described above were transplanted at $1\times10^7$ cells/head into the peritoneal cavity. After two hours of transplantation, GPC ERY10-1 was intraperitoneally administered at 30 μg/head. GPC ERY10-1 was administered five times in total on days 7, 8, 12, 16, and 17.

Figure 8:
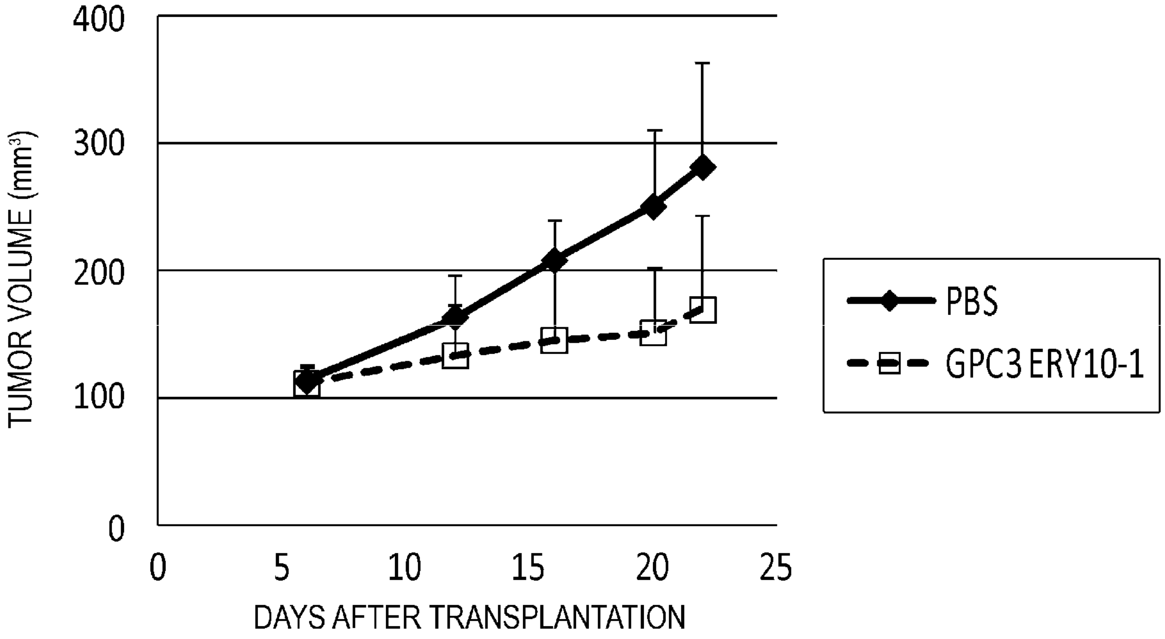
FIG. 8 is a graph showing the in vivo anti-tumor effect of GPC3 ERY10-1 in the PC-10 T cell transfer model. Open square (□) and closed diamond (♦) indicate changes in the tumor volume of the GPC3 ERY10-1 administration group and control (PBS administration) group, respectively.

The result showed that the GPC3 ERY10-1 administration group of this model also exhibited a clear anti-tumor effect as compared to the solvent administration group (FIG. 8).

The finding described above demonstrates that a series of molecules in which one scFv of an anti-CD3 epsilon antibody is added to an IgG backbone having a silent Fc exhibit a clear in vivo anti-tumor effect.

(3) Assessment of Plasma Retention

In order to assess whether molecules such as GPC3 ERY8-2, GPC3 ERY9-1, and GPC3 ERY10-1 have a considerably longer half-life in plasma than GPC3 BiTE, GPC3 ERY9-1 and GPC3 ERY10-1 were administered at 30 μg/head to NOD scid mice to which no cancer cells had been transplanted, and their plasma concentrations were measured over time.

Specifically, PK analysis was carried out in the following manner. GPC3 ERY9-1 and GPC3 ERY10-1 were intraperitoneally administered to NOD scid mice (CLEA Japan Inc.; female, 8W) at 30 μg/head. Blood was collected from the buccal vein of the mice using hematocrit capillaries (Terumo) at 15 minutes, two hours, 1 day, 2 days, and 7 days after administration. Plasma was prepared from the blood.

GPC3 ERY9-1 and GPC3 ERY10-1 were appropriately diluted and added to GPC3-expressing Ba/F3 cells (GPC3/BaF) or human CD3 epsilon-expressing Ba/F3 cells (CD3/BaF) to allow GPC3 ERY9-1 or GPC3 ERY10-1 to react with GPC3/BaF and CD3/BaF. After washing these cells, an FITC-labeled secondary antibody was added for further reaction. After washing the cells, the fluorescent intensity of the label on the cells was measured using Epics XL™ flow cytometer (Beckman coulter) to prepare a calibration curve for each antibody.

Blood was collected over time from the mice that had been given GPC3 ERY9-1 or GPC3 ERY10-1. Plasma was prepared from the blood and diluted appropriately. In the same manner as for the preparation of calibration curves described above, the plasma samples were reacted with GPC3/BaF or CD3/BaF to determine the amount of plasma GPC3 ERY9-1 and GPC3 ERY10-1 bound to each cell. The plasma concentration of each antibody was calculated using determined values and the calibration curves described above.

Figure 9:
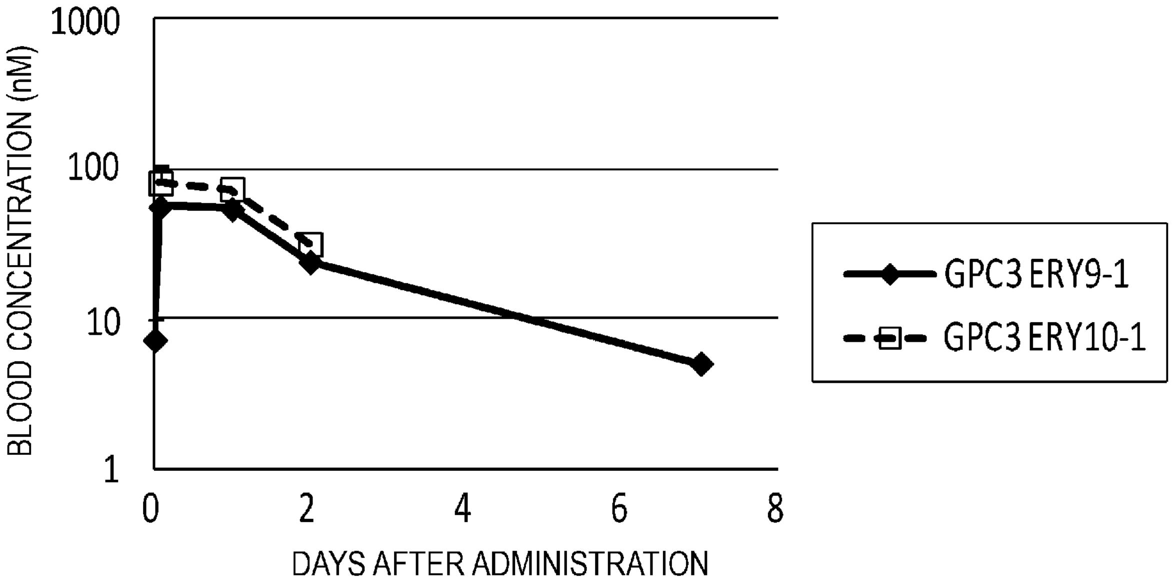
FIG. 9 is a graph showing a time course of the plasma concentrations of GPC3 ERY9-1 and GPC3 ERY10-1 determined using GPC3-expressing Ba/F3 cells. Closed diamond (♦) and open square (□) indicate the plasma concentration time course for GPC3 ERY9-1 and GPC3 ERY10-1, respectively.
Figure 10:
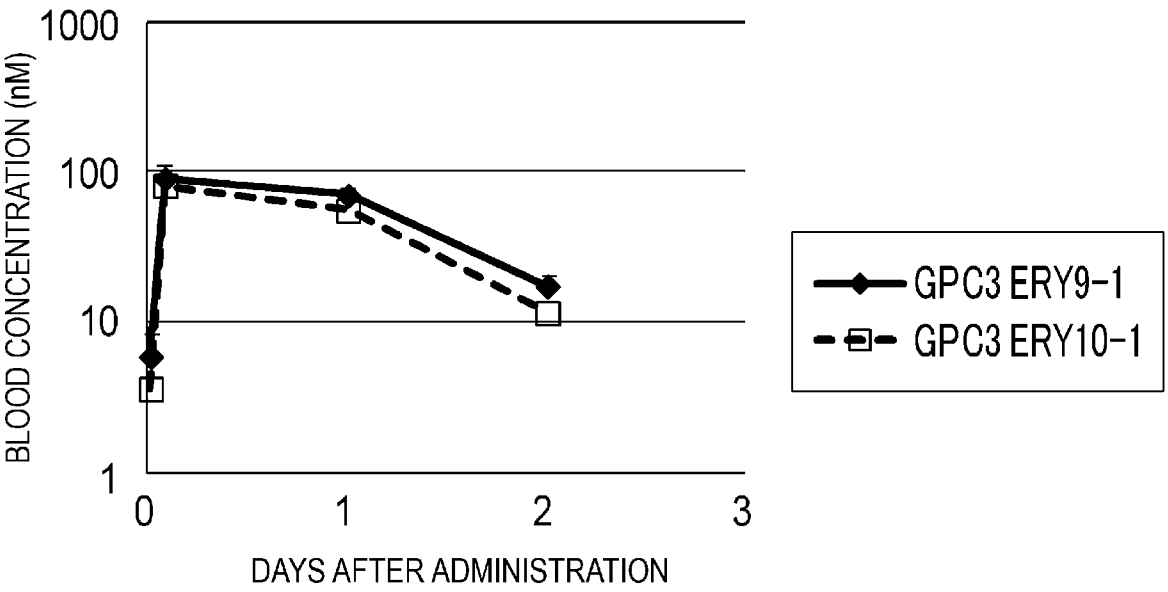
FIG. 10 is a graph showing time course of the plasma concentrations of GPC3 ERY9-1 and GPC3 ERY10-1 determined using CD3-expressing Ba/F3 cells. Closed diamond (♦) and open square (□) indicate the plasma concentration time course for GPC3 ERY9-1 and GPC3 ERY10-1, respectively.

The result showed that the blood concentration of both GPC3 ERY9-1 and GPC3 ERY10-1 remained higher than 10 nM after two days of the administration (FIGS. 9 and 10).

This finding demonstrates that molecules such as GPC3 ERY9-1 and GPC3 ERY10-1 have a significantly improved plasma half-life as compared to BiTE.

(4) Effect of Silent Fc on Cancer Antigen-Independent Cytokine Induction (4-1) Construction of GPC3 ERY15-1 Having FcgR-Binding Fc GPC3 ERY15-1 having an FcgR-binding Fc (FIG. 17J) was constructed to test whether molecules such as GPC3 ERY8-2, GPC3 ERY9-1, and GPC3 ERY10-1 would induce cytokines in a cancer antigen-independent manner.

Specifically, as in the above-described method, PCR using primers containing appropriate additional sequences and a method known to those skilled in the art such as a method using QuikChange™ Site-Directed Mutagenesis Kit (Stratagene) were performed to construct expression vectors into which a polynucleotide encoding GPC3 ERY15-1_Hh (SEQ ID NO: 47; the mature sequence does not contain the amino terminal 19 amino acids, which serve as a signal sequence) or GPC3 ERY15-1_Hk (SEQ ID NO: 48; the mature sequence does not contain the amino terminal 19 amino acids, which serve as a signal sequence) was inserted.

The expression vectors for GPC3 ERY15-1_Hh (SEQ ID NO: 47; the mature sequence does not contain the amino terminal 19 amino acids, which serve as a signal sequence), GPC3 ERY15-1_Hk (SEQ ID NO: 48; the mature sequence does not contain the amino terminal 19 amino acids, which serve as a signal sequence), and GPC3 ERY7_L were co-introduced into FreeStyle™ 293-F cells to express GPC3 ERY15-1 transiently. The resulting culture supernatant was loaded onto an Anti-FLAG® tag M2 column (Sigma). After washing, the column was eluted with 0.1 mg/ml FLAG® peptide (Sigma). A fraction containing GPC3 ERY15-1 was loaded onto a HisTrap™ HP column (GE Healthcare). After washing, the column was eluted with an imidazole concentration gradient. A fraction containing GPC3 ERY15-1 was concentrated by ultrafiltration. Then, the fraction was loaded onto a Superdex™ 200 column (GE Healthcare). Only a monomeric GPC3 ERY15-1 fraction was collected from the eluate to obtain purified GPC3 ERY15-1.

(4-2) Assay for Cancer Antigen-Independent Cytokine-Inducing Ability

The cancer antigen-independent cytokine-inducing ability of GPC3 ERY15-1 was compared to those of GPC3 BiTE, GPC3 ERY9-1, GPC3 ERY10-1, and catumaxomab. By using the method described above, PBMCs were prepared from blood collected from healthy volunteers. Fifty μl of each antibody adjusted to 40 nM was added to 50 μl of human PBMC suspension ($2\times10^5$ cells/well), and then 100 μl of 10% FBS/D-MEM was added thereto. The reaction mixture was incubated under 5% carbon dioxide gas at 37° C. After 72 hours of incubation, the culture supernatant was collected, and cytokines secreted in the culture supernatant were quantified using a BD™ Cytometric Bead Array (CBA) Human Th1/Th2/Th17 CBA Kit (BD). The assay was carried out in triplicate by the method according to the appended protocol.

Figure 11:
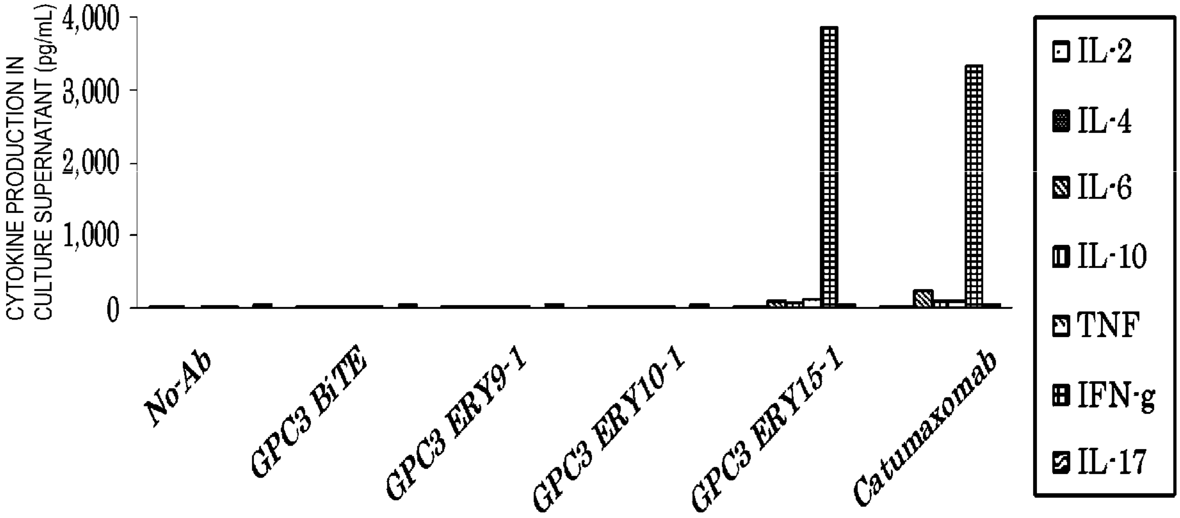
FIG. 11 is a graph showing assessment of GPC3 BiTE, GPC3 ERY9-1, GPC3 ERY10-1, GPC3 ERY15-1, and catumaxomab for their ability to induce cytokines in a cancer antigen-independent manner.

As a result, GPC3 ERY15-1 and catumaxomab, which have a FcgR-binding Fc, showed clear cytokine induction. In contrast, no cytokine induction was observed for GPC3 BiTE, which has no Fc, and GPC3 ERY9-1 and GPC3 ERY10-1, which possess a silent Fc (FIG. 11). This result suggests that molecules having a silent Fc such as GPC3 ERY8-2, GPC3 ERY9-1, and GPC3 ERY10-1 are highly safe molecules which do not induce cytokines in a cancer antigen-independent manner.

[Example 4] Construction and Assessment of GPC3 ERY18 L1, L2, L3, L4, and S1

Molecules having a CD3-binding domain different from the scFv structure were assessed. GPC3 ERY18 (FIG. 17K) was constructed in which the VH and VL domains of an anti-CD3 antibody were linked to the C termini of the two H chains of an anti-cancer antigen (GPC3) IgG. In this construction, a series of molecules (GPC3 ERY18 L1, L2, L3, and L4) having one to four linker units (Gly-Gly-Gly-Gly-Ser; SEQ ID NO: 7) at the junction were produced. At the same time, another molecule (GPC3 ERY18 S1) was constructed in which amino acids at appropriate positions were substituted with Cys to allow introduction of a disulfide bond.

Specifically, a method known to those skilled in the art, such as PCR using primers containing appropriate additional sequences as in the method described above, was performed to construct a series of expression vectors into which a polynucleotide encoding GPC3 ERY18 L1_Hh (SEQ ID NO: 49; the mature sequence does not contain the amino terminal 19 amino acids, which serve as a signal sequence), GPC3 ERY18 L1_Hk (SEQ ID NO: 50; the mature sequence does not contain the amino terminal 19 amino acids, which serve as a signal sequence), GPC3 ERY18 L2_Hh (SEQ ID NO: 51; the mature sequence does not contain the amino terminal 19 amino acids, which serve as a signal sequence), GPC3 ERY18 L2_Hk (SEQ ID NO:52; the mature sequence does not contain the amino terminal 19 amino acids, which serve as a signal sequence), GPC3 ERY18 L3_Hh (SEQ ID NO: 53; the mature sequence does not contain the amino terminal 19 amino acids, which serve as a signal sequence), GPC3 ERY18 L3_Hk (SEQ ID NO: 54; the mature sequence does not contain the amino terminal 19 amino acids, which serve as a signal sequence), GPC3 ERY18 L4_Hh (SEQ ID NO: 55; the mature sequence does not contain the amino terminal 19 amino acids, which serve as a signal sequence), GPC3 ERY18 L4_Hk (SEQ ID NO: 56; the mature sequence does not contain the amino terminal 19 amino acids, which serve as a signal sequence), GPC3 ERY18 S1_Hh (SEQ ID NO: 57; the mature sequence does not contain the amino terminal 19 amino acids, which serve as a signal sequence), or GPC3 ERY18 S1_Hk (SEQ ID NO: 58; the mature sequence does not contain the amino terminal 19 amino acids, which serve as a signal sequence) was inserted.

The following combinations of expression vectors were introduced into FreeStyle™ 293-F cells to express each designed molecule transiently.

G. Designed Molecule: GPC3 ERY18 L1

Expression vectors: GPC3 ERY18 L1_Hh (SEQ ID NO: 49; the mature sequence does not contain the amino terminal 19 amino acids, which serve as a signal sequence), GPC3 ERY18 L1_Hk (SEQ ID NO: 50; the mature sequence does not contain the amino terminal 19 amino acids, which serve as a signal sequence), and GPC3 ERY7 L H. Designed Molecule: GPC3 ERY18 L2

Expression vectors: GPC3 ERY18 L2_Hh (SEQ ID NO: 51; the mature sequence does not contain the amino terminal 19 amino acids, which serve as a signal sequence), GPC3 ERY18 L2_Hk (SEQ ID NO: 52; the mature sequence does not contain the amino terminal 19 amino acids, which serve as a signal sequence), and GPC3 ERY7 L I. Designed Molecule: GPC3 ERY18 L3

Expression vectors: GPC3 ERY18 L3_Hh (SEQ ID NO: 53; the mature sequence does not contain the amino terminal 19 amino acids, which serve as a signal sequence), GPC3 ERY18 L3_Hk (SEQ ID NO: 54; the mature sequence does not contain the amino terminal 19 amino acids, which serve as a signal sequence), and GPC3 ERY7 L J. Designed Molecule: GPC3 ERY18 L4

Expression vectors: GPC3 ERY18 L4_Hh (SEQ ID NO: 55; the mature sequence does not contain the amino terminal 19 amino acids, which serve as a signal sequence), GPC3 ERY18 L4_Hk (SEQ ID NO: 56; the mature sequence does not contain the amino terminal 19 amino acids, which serve as a signal sequence), and GPC3 ERY7 L K. Designed Molecule: GPC3 ERY18 S1

Expression vectors: GPC3 ERY18 S1_Hh (SEQ ID NO: 57; the mature sequence does not contain the amino terminal 19 amino acids, which serve as a signal sequence), GPC3 ERY18 S1_Hk (SEQ ID NO: 58; the mature sequence does not contain the amino terminal 19 amino acids, which serve as a signal sequence), and GPC3 ERY7 L The resulting culture supernatant was loaded onto an Anti-FLAG® tag M2 column (Sigma). After washing, the column was eluted with 0.1 mg/ml FLAG® peptide (Sigma). A fraction containing the designed molecule was loaded onto a HisTrap™ HP column (GE Healthcare). After washing, the column was eluted with an imidazole concentration gradient. A fraction containing the designed molecule was concentrated by ultrafiltration. Then, the fraction was loaded onto a Superdex™ 200 column (GE Healthcare). Only a monomer fraction was collected from the eluate to obtain each purified designed molecule.

Figure 12:
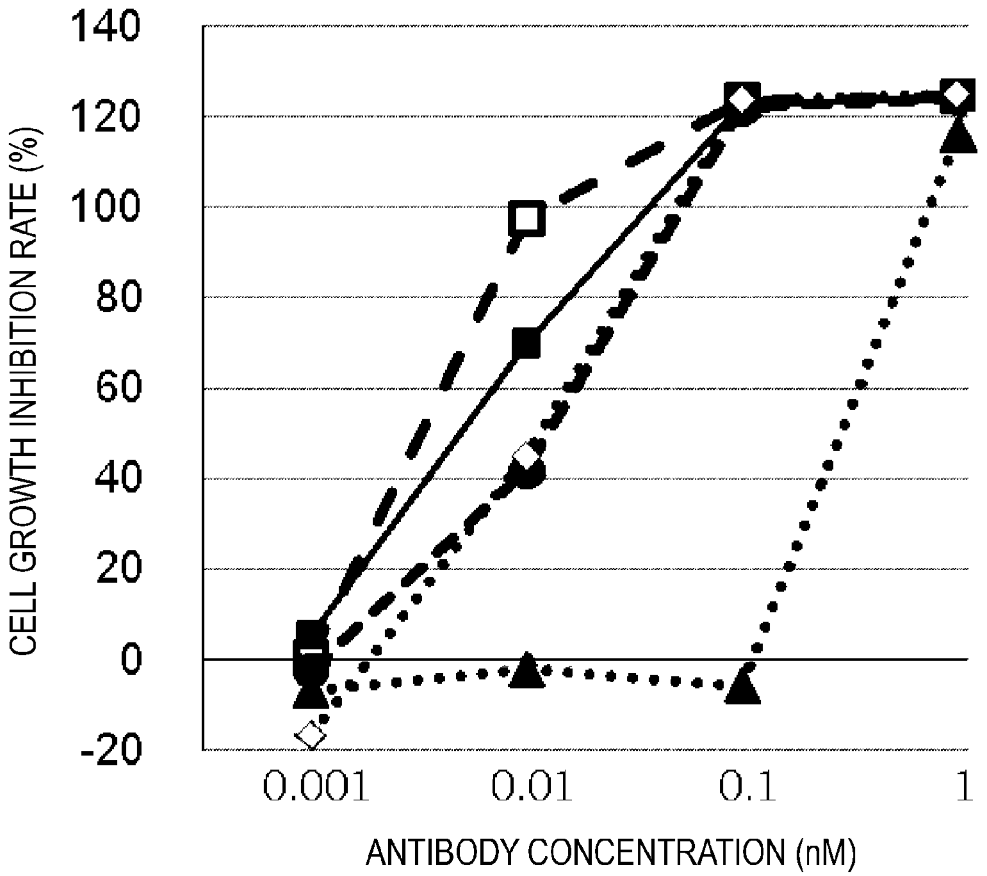
FIG. 12 is a graph showing the in vitro cytotoxicities of GPC3 ERY18 L1, GPC3 ERY18L2, GPC3 ERY18L3, GPC3 ERY18L4, and GPC3 ERY18S1. Closed triangle (▲), closed circle (●), closed square (■), open square (□), and open diamond (◇) represent the cytotoxic activities of GPC3 ERY18 L1, GPC3 ERY18 L2, GPC3 ERY18 L3, GPC3 ERY18 L4, and GPC3 ERY18 S1, respectively.
Figure 13:
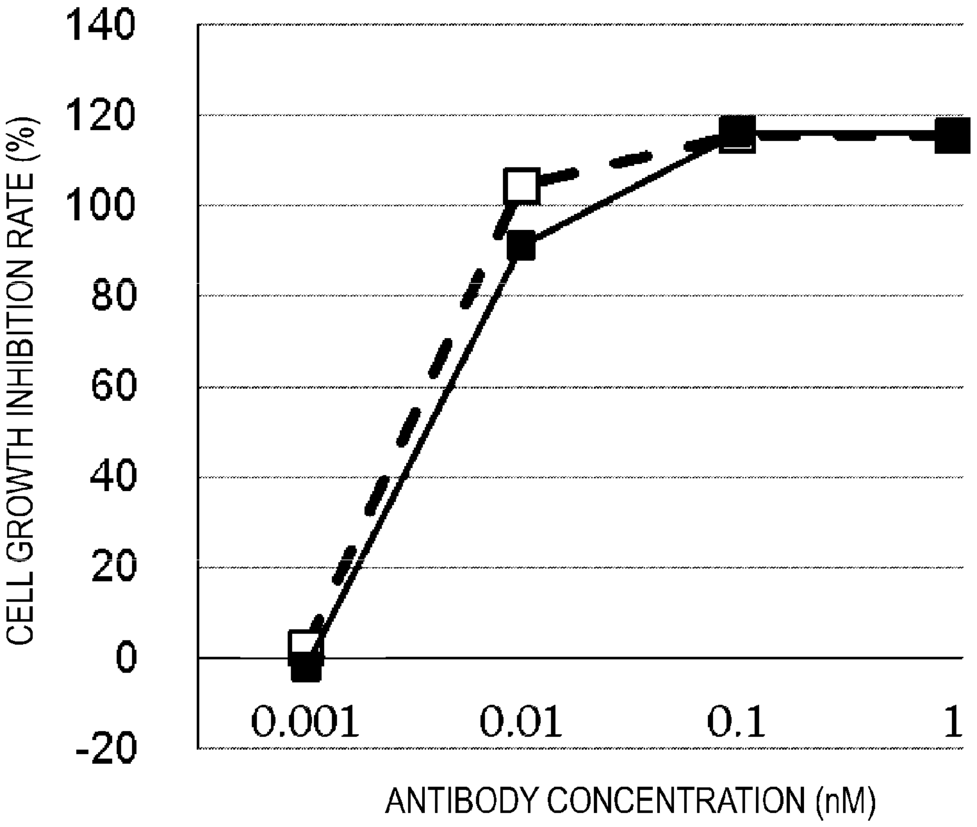
FIG. 13 is a graph showing comparison of the in vitro cytotoxic activities of GPC3 ERY18 L3 and GPC3 ERY10-1. Closed square (■) and open square (□) represent the cytotoxic activities of GPC3 ERY18 L3 and GPC3 ERY10-1, respectively.

GPC3 ERY18 L1, GPC3 ERY18L2, GPC3 ERY18L3, GPC3 ERY18L4, and GPC3 ERY18S1 molecules were each assessed for the in vitro cytotoxic activity (FIGS. 12 and 13). The result showed that all molecules except GPC3 ERY18 L1 had an activity comparable to that of GPC3 ERY10-1. This result demonstrates that molecules having a non-scFv structure have a comparable cytotoxic activity. The structure where the VH and VL domains of CD3 antibody are each linked to the C termini of two H chains of an anti-cancer antigen (GPC3) IgG is expected to contribute to stabilization of the polypeptide complexes of the present invention.

[Example 5] Construction and Assessment of GPC3 ERY19-3

Next, molecules having a Fab-like CD3-binding domain were assessed. GPC3 ERY19-3 (FIG. 17L) was constructed in which the VH and CH1 domains, and VL and CL domains of CD3 antibody were each linked to the C termini of the two H chains of an anti-cancer antigen (GPC3) IgG antibody. Specifically, by a method known to those skilled in the art, such as PCR using primers containing appropriate additional sequences in the same manner as in the method described above, expression vectors were constructed into which a polynucleotide encoding GPC3 ERY19-3_Hh (SEQ ID NO: 59; the mature sequence does not contain the amino terminal 19 amino acids, which serve as a signal sequence) or GPC3 ERY19-3_Hk (SEQ ID NO: 60; the mature sequence does not contain the amino terminal 19 amino acids, which serve as a signal sequence) was inserted.

The expression vectors for GPC3 ERY19-3_Hh (SEQ ID NO: 59; the mature sequence does not contain the amino terminal 19 amino acids, which serve as a signal sequence), GPC3 ERY19-3_Hk (SEQ ID NO: 60; the mature sequence does not contain the amino terminal 19 amino acids, which serve as a signal sequence), and GPC3 ERY7_L were co-introduced into FreeStyle™ 293-Fcells to express GPC3 ERY19-3 transiently. The resulting culture supernatant was loaded onto a HiTrap™ rProtein A Fast Flow column (GE Healthcare). After washing, the column was eluted with an acid. A fraction containing GPC3 ERY19-3 was concentrated by ultrafiltration, and then loaded onto a Superdex™ 200 column (GE Healthcare). Only a monomeric GPC3 ERY19-3 fraction was collected from the eluate to obtain purified GPC3 ERY19-3.

Figure 14:
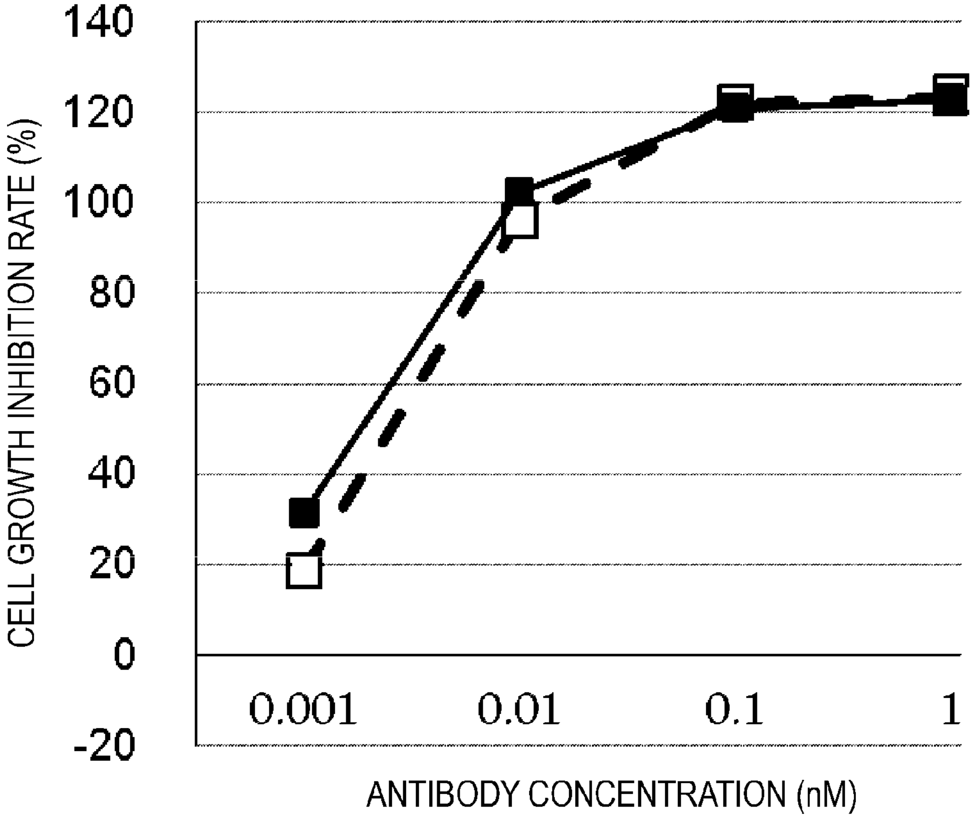
FIG. 14 is a graph showing comparison of the in vitro cytotoxic activities of GPC3 ERY19-3 and GPC3 BITE. Open square (□) and closed square (■) represent the cytotoxic activities of GPC3 ERY19-3 and GPC3 BiTE, respectively.

The GPC3 ERY19-3 molecule was assessed for the in vitro cytotoxic activity. The result showed that the molecule had an activity comparable to GPC3 BiTE (FIG. 14). The CD3-binding domain with a Fab-like structure is expected to contribute to stabilization of the polypeptide complex molecules of the present invention.

[Example 6] Preparation of Polypeptide Complexes Using a Protein a Purification Step Alone by Introduction of Mutation into the CH3 Domain of GPC3 ERY 10-1

(1) Outline

In GPC3 ERY10-1 prepared in Example 3, the CH3 domain has the knobs-into-holes structure. The desired GPC3 ERY10-1 molecule, in which the two H chains were heteromerically associated together, was purified by two types of affinity purification using the His tag and FLAG® tag attached to the C terminus of each H chain. If the GPC3 ERY10-1 molecule is produced as a pharmaceutical, Protein A chromatography is first performed on the culture supernatant of GPC3 ERY10-1-expressing cells to purify a polypeptide complex having a Fc domain. This step has to be followed by an additional chromatographic purification step using His tag affinity chromatography and FLAG® tag affinity chromatography. This results in increased costs for the purification process. Thus, this Example examined molecular modifications that enable purification of the desired GPC3 ERY10-1 molecule having the two heteromerically associated H chains by Protein A chromatography only without using a His tag and FLAG® tag.

Specifically, modifications to eliminate the Protein A binding in one of the two H chains were examined. As a result of such modifications, when non-Protein A-binding H chains are homomerically associated, the molecule cannot bind to Protein A and therefore passes through Protein A chromatography. On the other hand, a molecule in which a non-Protein A-binding H chain is heteromerically associated with a Protein A-binding H chain, and a molecule in which Protein A-binding H chains are homomerically associated, may be separated using Protein A chromatography based on difference in the affinity for Protein A. However, in the antibody Fc domain, the binding site for Protein A overlaps with the binding site for FcRn, which is crucial for the plasma retention of antibody. Thus, it is necessary to selectively reduce the Protein A-binding activity only, while maintaining the FcRn-binding activity. As such a modification, substitution of His at position 435 (EU numbering) with Arg was discovered. The combination of this mutation with the mutations described in WO 2006/106905 (substituting Asp at position 356 (EU numbering) in one of the H chains with Lys, and Lys at position 439 (EU numbering) in the other H chain with Glu), which promote heteromeric association of the two H chains, was tested as to whether it could enable purification of polypeptide complexes such as GPC3 ERY10-1 using Protein A chromatography only.

(2) Construction of Antibody Gene Expression Vectors and Expression of Respective Antibodies For the antibody H chain variable region, a gene encoding GC33 (2) H (anti-human Glypican-3 antibody H chain variable region, SEQ ID NO: 61; the mature sequence does not contain the amino terminal 19 amino acids, which serve as a signal sequence) was constructed by a method known to those skilled in the art. Similarly, for the antibody L chain, a gene encoding GC33-k0 (anti-human Glypican-3 antibody L chain, SEQ ID NO: 62; the mature sequence does not contain the amino terminal 19 amino acids, which serve as a signal sequence) was constructed by a method known to those skilled in the art. Next, for the antibody H chain constant region, the genes described below were constructed by a method known to those skilled in the art.

L. Designed Molecule: LALA-G1d

LALA-G1d (SEQ ID NO: 63; the mature sequence does not contain the amino terminal 19 amino acids, which serve as a signal sequence), in which Leu at positions 234 and 235 (EU numbering) have been substituted with Ala, Asn at position 297 has been substituted with Ala, and Gly and Lys at the C-terminal have been removed in the sequence of IgG1

M. Designed Molecule: LALA-G1d-CD3

LALA-G1d-CD3 (SEQ ID NO: 64; the mature sequence does not contain the amino terminal 19 amino acids, which serve as a signal sequence), in which a CD3 scFv (anti-human CD3 antibody H chain variable region and anti-human CD3 antibody L chain variable region are linked together via a polypeptide linker) has been linked to the C terminus of LALA-G1d (SEQ ID NO: 63; the mature sequence does not contain the amino terminal 19 amino acids, which serve as a signal sequence)

N. Designed Molecule: LALA-G3S3E-G1d

LALA-G3S3E-G1d (SEQ ID NO: 65; the mature sequence does not contain the amino terminal 19 amino acids, which serve as a signal sequence), in which His at position 435 (EU numbering) has been substituted with Arg, and Lys at position 439 (EU numbering) has been substituted with Glu in the sequence of LALA-G1d (SEQ ID NO: 63; the mature sequence does not contain the amino terminal 19 amino acids, which serve as a signal sequence)

O. Designed Molecule: LALA-S3K-G1d-CD3

LALA-S3K-G1d-CD3 (SEQ ID NO: 66; the mature sequence does not contain the amino terminal 19 amino acids, which serve as a signal sequence), in which Asp at position 356 (EU numbering) has been substituted with Lys in the sequence of LALA-G1d-CD3 (SEQ ID NO: 64; the mature sequence does not contain the amino terminal 19 amino acids, which serve as a signal sequence)

Anti-human GPC3 antibody H chain genes NTA1L and NTA1R were constructed by linking LALA-G1d-CD3 or LALA-G1d downstream of GC33 (2) H, respectively. Meanwhile, anti-human GPC3 antibody H chain genes NTA2L and NTA2R were constructed by linking LALA-S3K-G1d-CD3 or LALA-G3S3E-G1d downstream of GC33 (2) H, respectively.

Expression vectors for NTA1L, NTA1R, NTA2L, NTA2R (H chains), and GC33-k0 (L chain) were constructed by inserting each gene into an animal cell expression vector. These vectors were combined as shown below and introduced into FreeStyle™ 293 cells (Invitrogen) by a method known to those skilled in the art to transiently express the polypeptide complexes described below. As shown below, the polypeptide complexes are referred to by the names of introduced genes combined in the order of [first H chain/second H chain/L chain].

NTA1L/NTA1R/GC33-k0
NTA2L/NTA2R/GC33-k0

(3) Purification of Expressed Samples and Assessment for Heteromeric Complex Formation Culture supernatant of FreeStyle™ 293 cells (hereinafter referred to as CM) containing a polypeptide complex shown below was used as a sample.

NTA1L/NTA1R/GC33-k0
NTA2L/NTA2R/GC33-k0

CM was filtered through a ø0.22-μm filter and loaded onto a rProtein A Sepharose™ Fast Flow antibody purification resin column (GE Healthcare) equilibrated with D-PBS. Washing steps 1 and 2, and elution step 1 were carried out using the buffers shown in Table 1. The loading amount of CM was adjusted so that the loading amount of antibody was 20 mg/ml resin. Eluted fractions were collected and analyzed by size exclusion chromatography to identify the components in the fractions.

TABLE 1

| EQUILIBRATION | D-PBS |
|---|---|
| WASH 1 | 1 mM sodium acetate, 150 mM NaCl, pH 6.5 |
| WASH 2 | 0.3 mM HCl, 150 mM NaCl, pH 3.7 |
| ELUTION 1 | 2 mM HCl, pH 2.7 |

Figure 15:
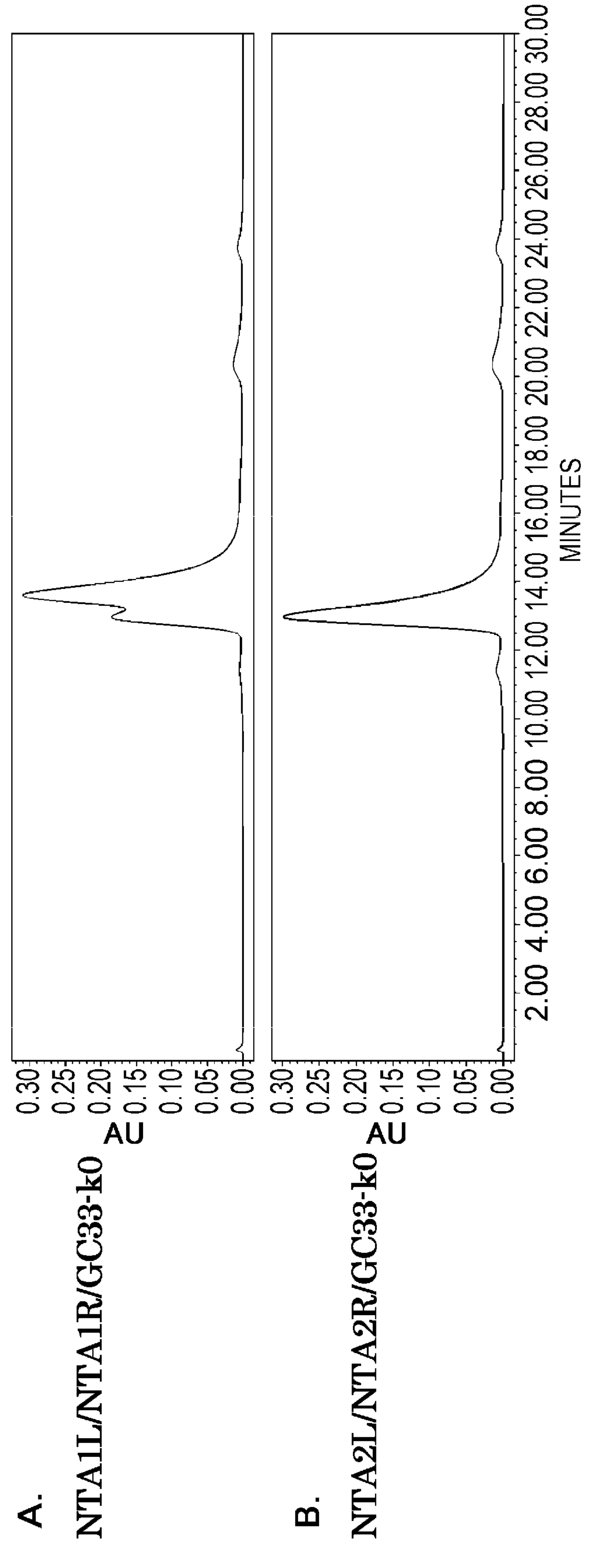
FIG. 15 shows a set of chromatograms. Diagram A is a chromatogram showing results of the size exclusion chromatography analysis of CM in which NTA1L/NTA1R/GC33-k0 was expressed. Diagram B is a chromatogram showing results of the size exclusion chromatography analysis of CM in which NTA2L/NTA2R/GC33-k0 was expressed.
Figure 16:
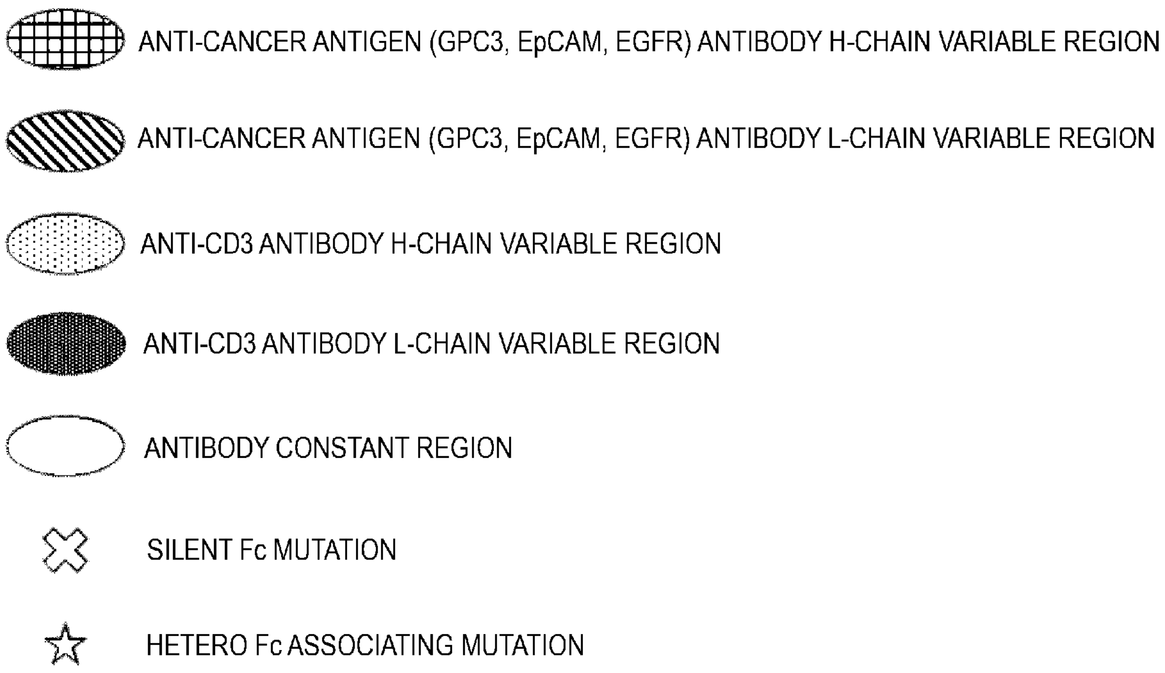
FIG. 16 shows diagrams that represent domains forming the following polypeptide complexes described in the Examples herein: GPC3 BiTE, GPC3 ERY2, GPC3 ERY5, GPC3 ERY6, GPC3 ERY7, GPC3 ERY8-2, GPC3 ERY9-1, GPC3 ERY 10-1, GPC3 ERY15, GPC3 ERY18, and GPC3 ERY19-3. The domain with cross-hatched lines represents the H-chain variable region of the anti-cancer antigen (GPC3, EpCAM, EGFR) antibody; the domain with diagonal lines represents the L-chain variable region of the anti-cancer antigen (GPC3, EpCAM, EGFR) antibody; the domain with dotted lines represents the H-chain variable region of the anti-CD3 antibody; the closed domain represents the L-chain variable region of the anti-CD3 antibody; the open domain represents the antibody constant region; the cross represents a silent Fc mutation; and the star represents a mutation promoting heteromeric Fc association.

The result of size exclusion chromatography analysis of each eluted fraction is shown in FIG. 15 and Table 2. The values indicate percent area of elution peak. When NTA1L/NTA1R/GC33-k0 or NTA2L/NTA2R/GC33-k0 was expressed, the anti-GPC3 homomeric antibody (NTA1L/GC33-k0 or NTA2L/GC33-k0) was almost undetectable in CM. Meanwhile, the anti-GPC3 homomeric antibody (NTA2R/GC33-k0) was only about 2% in CM where NTA2L/NTA2R/GC33-k0 was expressed, whereas it was about 76% in CM where NTA1L/NTA1R/GC33-k0 was expressed. This result demonstrates that, when His at position 435 (EU numbering) is substituted with Arg and, in order to allow efficient formation of the heteromeric molecule of the respective H chains, Asp at position 356 (EU numbering) in the polypeptide sequence of one of the H chains is substituted with Lys and Lys at position 439 (EU numbering) in the polypeptide sequence of the other H chain is substituted with Glu, heteromeric polypeptide complexes having the same molecular form as GPC3 ERY10-1 can be efficiently purified with a purity of more than 98% by only the purification step using Protein A.

TABLE 2

| | CD3 homomeric antibody | Heteromeric antibody | GPC3 homomeric antibody |
|---|---|---|---|
| NTA1L/NTA1R/GC33-k0 | 0.7 | 23.5 | 75.8 |
| NTA2L/NTA2R/GC33-k0 | — | 98.2 | 1.8 |

[Example 7] Construction and Assessment of GPC3 ERY 17-2 and GPC3 ERY 17-3

(1) Construction of GPC3 ERY 17-2 and GPC3 ERY 17-3

Next, a molecule was constructed by using an anti-cancer antigen (GPC3) IgG as a backbone and substituting one of the Fabs with a CD3 epsilon-binding domain. As in the above-described cases, the Fc of the backbone IgG was silent Fc having a reduced FcgR (Fcγ receptor)-binding activity. For the CD3 epsilon-binding domains, the VH and VL domains of anti-CD3 epsilon Fab were exchanged to produce GPC3 ERY17-2 (FIG. 19, diagram A), and the CH1 and CL domains were exchanged to produce GPC3 ERY17-3 (FIG. 19, diagram B).

Specifically, by a method known to those skilled in the art, such as PCR using primers containing the same appropriate additional sequences as in the method described above, a series of expression vectors were constructed into which a polynucleotide encoding ERY17-2_Hh (SEQ ID NO: 73; the mature sequence does not contain the amino terminal 19 amino acids, which serve as a signal sequence), ERY17-2_L (SEQ ID NO: 74; the mature sequence does not contain the amino terminal 19 amino acids, which serve as a signal sequence), ERY17-3_Hh (SEQ ID NO: 75; the mature sequence does not contain the amino terminal 19 amino acids, which serve as a signal sequence), or ERY17-3_L (SEQ ID NO: 76; the mature sequence does not contain the amino terminal 19 amino acids, which serve as a signal sequence) was inserted.

The following combinations of expression vectors were introduced into FreeStyle™ 293-F cells to express each designed molecule transiently.

P. Designed Molecule: GPC3 ERY17-2

Polypeptides encoded by polynucleotides inserted in expression vectors: GPC3 ERY8-2_Hk, GPC3 ERY7_L, ERY17-2_Hh (SEQ ID NO: 73; the mature sequence does not contain the amino terminal 19 amino acids, which serve as a signal sequence), and ERY17-2_L (SEQ ID NO: 74; the mature sequence does not contain the amino terminal 19 amino acids, which serve as a signal sequence)

Q. Designed Molecule: GPC3 ERY17-3

Polypeptides encoded by polynucleotides inserted in expression vectors: GPC3 ERY8-2_Hk, GPC3 ERY7 L, ERY17-3_Hh (SEQ ID NO: 75; the mature sequence does not contain the amino terminal 19 amino acids, which serve as a signal sequence), and ERY17-3_L (SEQ ID NO: 76; the mature sequence does not contain the amino terminal 19 amino acids, which serve as a signal sequence)

(2) Purification of GPC3 ERY 17-2 and GPC3 ERY 17-3

The resulting culture supernatant was loaded onto an Anti-FLAG® tag M2 column (Sigma). After washing, the column was eluted with 0.1 mg/ml FLAG® peptide (Sigma). A fraction containing the designed molecule was loaded onto a HisTrap™ HP column (GE Healthcare). After washing, the column was eluted with an imidazole concentration gradient. A fraction containing the designed molecule was concentrated by ultrafiltration. Then, the fraction was loaded onto a Superdex™ 200 column (GE Healthcare). Only a monomer fraction was collected from the eluate to obtain each purified designed molecule.

(3) Cytotoxic Activity of GPC3 ERY 17-2 and GPC3 ERY 17-3

Figure 20:
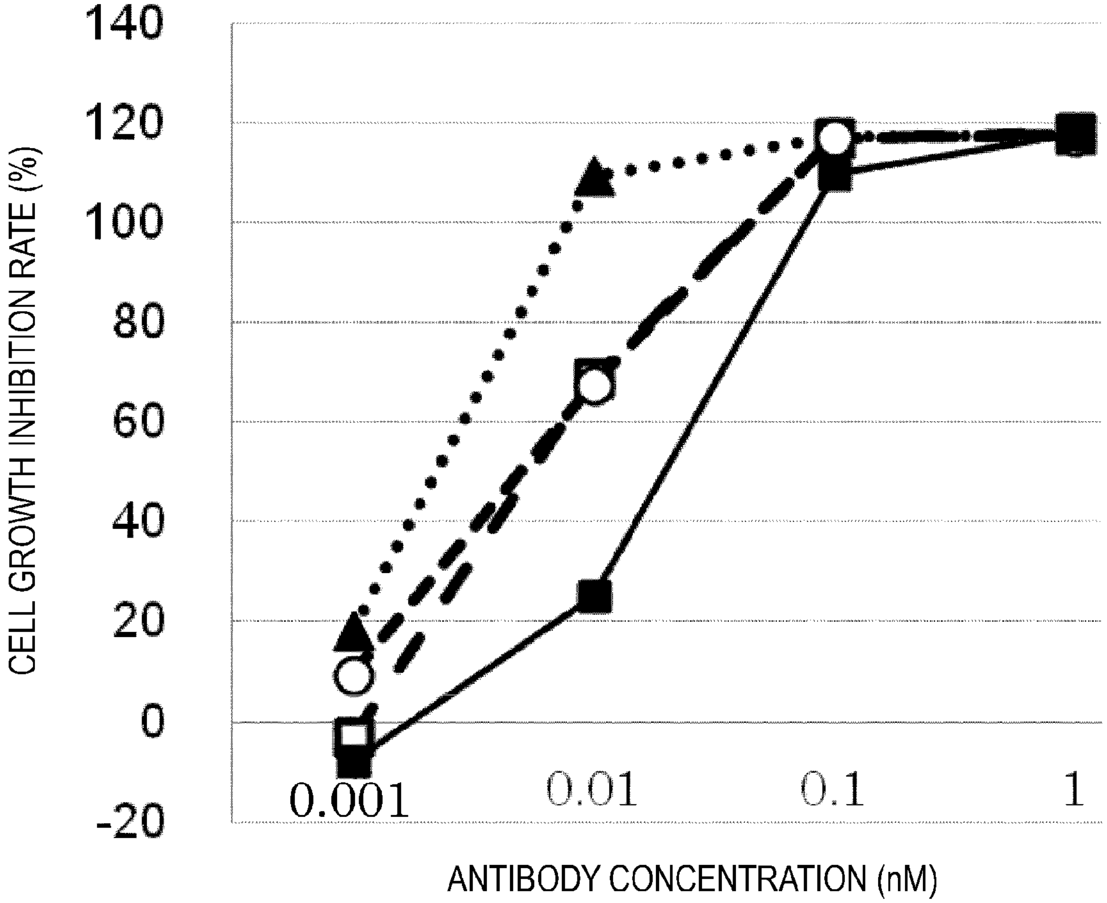
FIG. 20 is a graph showing comparison of the cytotoxic activities of GPC3 BiTE, GPC3 ERY17-2, GPC3 ERY17-3, and GPC3 ERY10-1. Closed square (■), closed triangle (▲), open circle (○), and open square (□) represent the cytotoxic activities of GPC3 BiTE, GPC3 ERY17-2, GPC3 ERY17-3, and GPC3 ERY10-1, respectively.

GPC3 ERY 17-2 and GPC3 ERY 17-3 were assessed for the in vitro cytotoxic activity (FIG. 20). The result showed that both molecules clearly exhibited a greater cytotoxic activity than GPC3 BITE. Thus, the present invention for the first time demonstrates that molecules in which an anti-cancer antigen IgG is used as a backbone and one of the Fabs is substituted with a CD3 epsilon-binding domain exhibit a cytotoxic activity comparable to or greater than that of BiTE.

(4) Efficacy Test for GPC3 ERY17-2 using PC-10 T Cell Transfer Model

GPC3 ERY17-2, which was demonstrated to have a cytotoxic activity comparable to or greater than that of GPC3 BiTE in the in vitro assay, was assessed for the in vivo efficacy using the PC-10 T cell transfer model. Specifically, the efficacy test of GPC3 ERY17-2 using the PC-10 T cell transfer model was carried out as follows. T cell expansion culture was carried out using T cell activation/expansion kit/human (MACS® Cell Culture and Stimulation portfolio, Miltenyi biotec) and PBMCs isolated from blood collected from healthy volunteers. Human lung squamous carcinoma cell line PC-10 cells (Immuno-Biological Laboratories Co., Ltd.) ($1\times10^7$ cells) were mixed with Matrigel™ Basement Membrane Matrix (BD), and then transplanted subcutaneously to the inguinal region of NOD scid mice (CLEA Japan Inc.; female, 7W). The day of transplantation was designated day 0. On the day before transplantation and days 13, 17, 21, and 25, an anti-asialo-GM1 antibody (Wako Pure Chemical Industries) was intraperitoneally administered to the mice at 0.2 mg/head. On day 13 after transplantation, the mice were grouped by the tumor size and body weight. On day 14 after transplantation, T cells prepared by expansion culture as described above were transplanted at $3\times10^7$ cells/head to the peritoneal cavity. After two hours of transplantation, GPC ERY17-2 was intravenously administered at 30 μg/head. GPC ERY17-2 was administered five times in total on days 14, 15, 16, 17, and 18.

Figure 21:
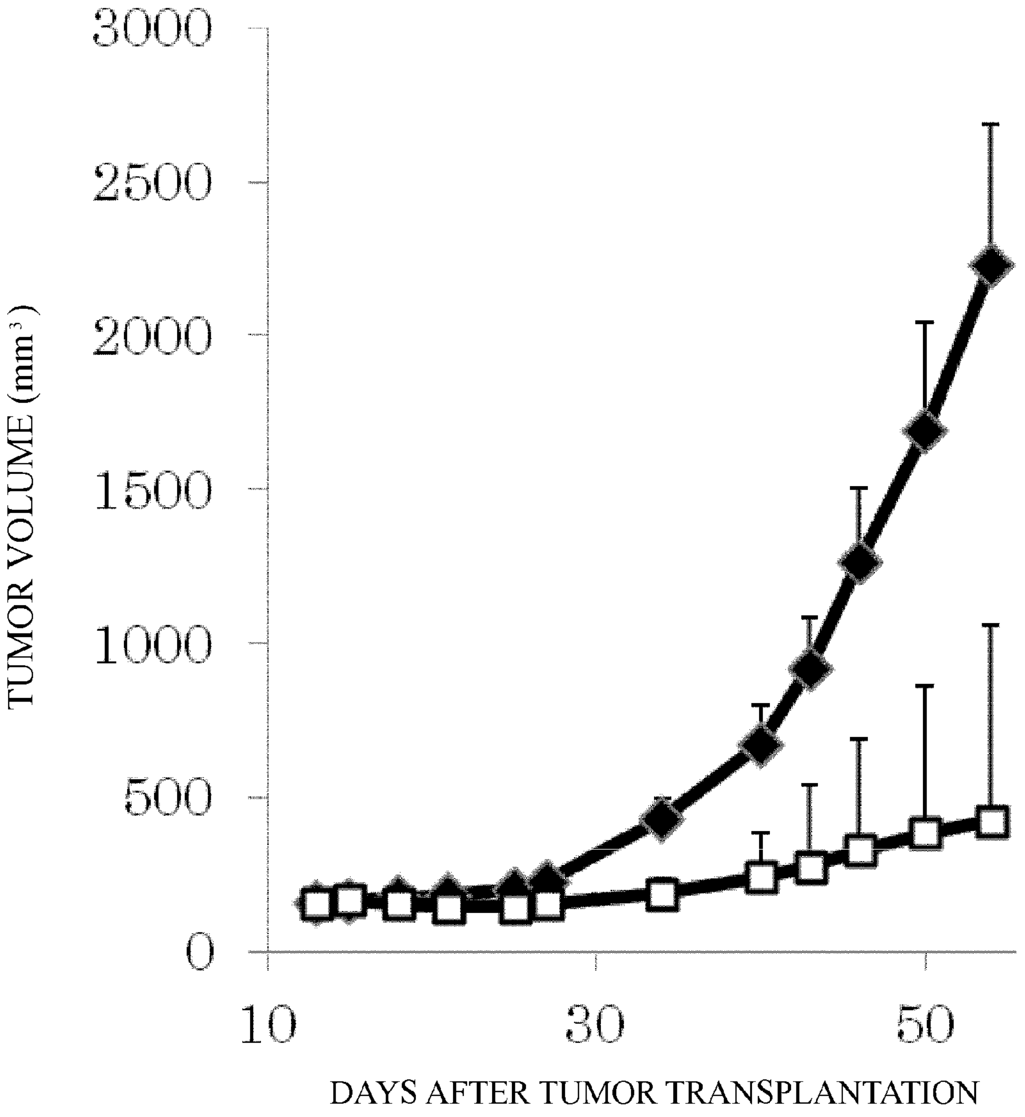
FIG. 21 is a graph showing the in vivo anti-tumor effect of GPC3 ERY17-2 in the PC-10 T cell transfer model. Open square (□) and closed diamond (◆) indicate changes in the tumor volume of the GPC3 ERY17-2 administration group and control (PBS administration) group, respectively.

The result showed that a clear anti-tumor effect was also observed in the GPC3 ERY17-2 administration group of this model, as compared to the solvent administration group (FIG. 21).

The finding described above demonstrates that molecules in which an anti-cancer antigen IgG is used as a backbone and one of the Fabs is substituted with a CD3 epsilon-binding domain produce a clear anti-tumor effect in vivo.

[Example 8] Construction and Assessment of GPC3 ERY17-2-M20

(1) Construction of GPC3 ERY17-2-M20

Next, a molecule retaining the desired activity even after alterations to the CD3 epsilon-binding domain was constructed. GPC3 ERY17-2-M20 (FIG. 19, diagram A) was constructed in which the sequence of the CD3 epsilon-binding domain was altered. Specifically, using as a template an expression vector for an anti-CD3 antibody (M20), a method known to a person skilled in the art such as PCR using primers containing the same appropriate sequences as in the above-described methods was performed to produce a series of expression vectors into which a polynucleotide encoding ERY17-2-M20_Hh (SEQ ID NO: 77; the mature sequence does not contain the amino terminal 19 amino acids, which serve as a signal sequence) or ERY17-2-M20_L (SEQ ID NO: 78; the mature sequence does not contain the amino terminal 19 amino acids, which serve as a signal sequence) was inserted.

(2) Purification of GPC3 ERY17-2-M20

The expression vectors for GPC3 ERY8-2_Hk, GPC3 ERY7_L, ERY17-2-M20_Hh (SEQ ID NO: 77), and ERY17-2-M20_L (SEQ ID NO: 78) were co-introduced into FreeStyle™ 293-F cells to express GPC3 ERY17-2-M20 transiently. The resulting culture supernatant was filtered through a ø0.22-μm filter, and then loaded onto an equilibrated rProtein A Sepharose™ Fast Flow antibody purification resin column (GE Healthcare). Purified GPC3 ERY17-2-M20 was obtained by washing steps 1 and 2, and elution step 1 using the buffers shown in Table 3.

TABLE 3

| | |
|---|---|
| EQUILIBRATION | FreeStyle ™ 293 Expression Medium (Invitrogen), 1% Pen Strep (Invitrogen) |
| WASH 1 | 1 mM sodium acetate, 150 mM NaCl, pH 6.5 |
| WASH 2 | 0.3 mM HCl, 150 mM NaCl, pH 3.7 |
| ELUTION 1 | 2 mM HCl, pH 2.7 |

(3) Cytotoxic Activity of GPC3 ERY17-2-M20

Figure 22:
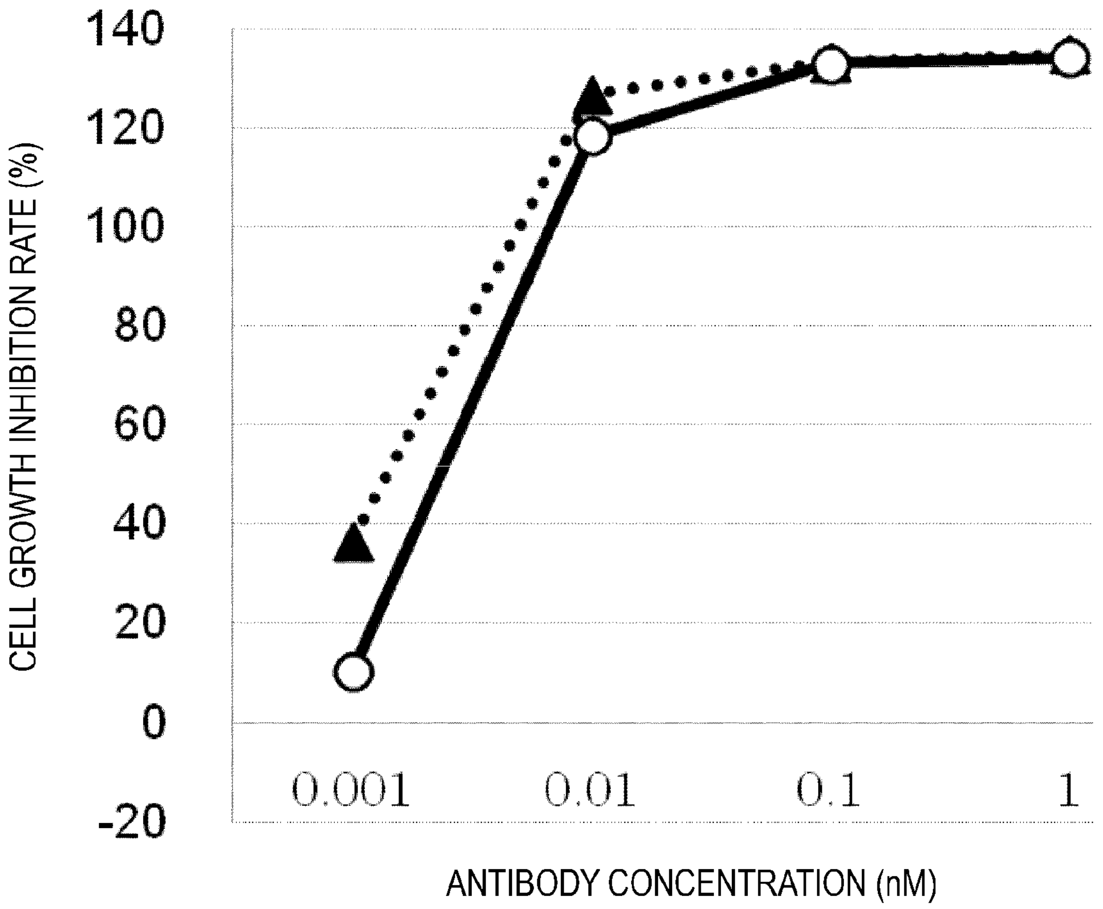
FIG. 22 is a graph showing comparison of the cytotoxic activities of GPC3 ERY17-2 and GPC3 ERY17-2-M20. Closed triangle (▲) and open circle (○) represent the cytotoxic activities of GPC3 ERY17-2 and GPC3 ERY17-2-M20, respectively.

GPC3 ERY17-2-M20 was tested for the in vitro cytotoxic activity, and showed a cytotoxic activity comparable to that of GPC3 ERY17-2 (FIG. 22). This finding demonstrates that even molecules having an altered sequence in the CD3 epsilon-binding domain have a comparable cytotoxic activity.

[Example 9] Construction and Assessment of EpCAM ERY17-2 and EpCAM ERY17-3

(1) Construction of EpCAM ERY17-2 and EpCAM ERY17-3

Next, molecules targeting a different cancer antigen but retaining the desired activity were constructed. EpCAM ERY17-2 (FIG. 19, diagram A), in which the anti-GPC3 Fab in GPC3 ERY17-2 was replaced with an anti-EpCAM Fab, and EpCAM ERY17-3 (FIG. 19, diagram B), in which the anti-GPC3 Fab in GPC3 ERY17-3 was replaced with an anti-EpCAM Fab, were produced. Specifically, using as a template an expression vector for an anti-EpCAM antibody, a method known to those skilled in the art such as PCR using primers containing the same appropriate sequences as in the above-described method was performed to produce a series of expression vectors into which a polynucleotide encoding EpCAM ERY17_Hk (SEQ ID NO: 79; the mature sequence does not contain the amino terminal 19 amino acids, which serve as a signal sequence) or EpCAM ERY17_L (SEQ ID NO: 80; the mature sequence does not contain the amino terminal 19 amino acids, which serve as a signal sequence) was inserted.

The following combinations of expression vectors were introduced into FreeStyle™ 293-F cells to express each designed molecule transiently.

R. Designed Molecule: EpCAM ERY17-2

Polypeptides encoded by polynucleotides inserted in expression vectors: EpCAM ERY17_Hk (SEQ ID NO: 79; the mature sequence does not contain the amino terminal 19 amino acids, which serve as a signal sequence), EpCAM ERY17_L (SEQ ID NO: 80; the mature sequence does not contain the amino terminal 19 amino acids, which serve as a signal sequence), ERY17-2_Hh, and ERY17-2_L S. Designed Molecule: EpCAM ERY17-3

Polypeptides encoded by polynucleotides inserted in expression vectors: EpCAM ERY17_Hk, EpCAM ERY17_L, ERY17-3_Hh, and ERY17-3_L (2) Purification of EpCAM ERY17-2 and EpCAM ERY17-3

The resulting culture supernatant was loaded onto an Anti-FLAG® tag M2 column (Sigma). After washing, the column was eluted with 0.1 mg/ml FLAG® peptide (Sigma). A fraction containing the designed molecule was loaded onto a HisTrap™ HP column (GE Healthcare). After washing, the column was eluted with an imidazole concentration gradient. A fraction containing the designed molecule was concentrated by ultrafiltration. Then, the fraction was loaded onto a Superdex™ 200 column (GE Healthcare). Only a monomer fraction was collected from the eluate to obtain each purified designed molecule.

(3) Cytotoxic Activity of EpCAM ERY17-2 and EpCAM ERY17-3

Figure 23:
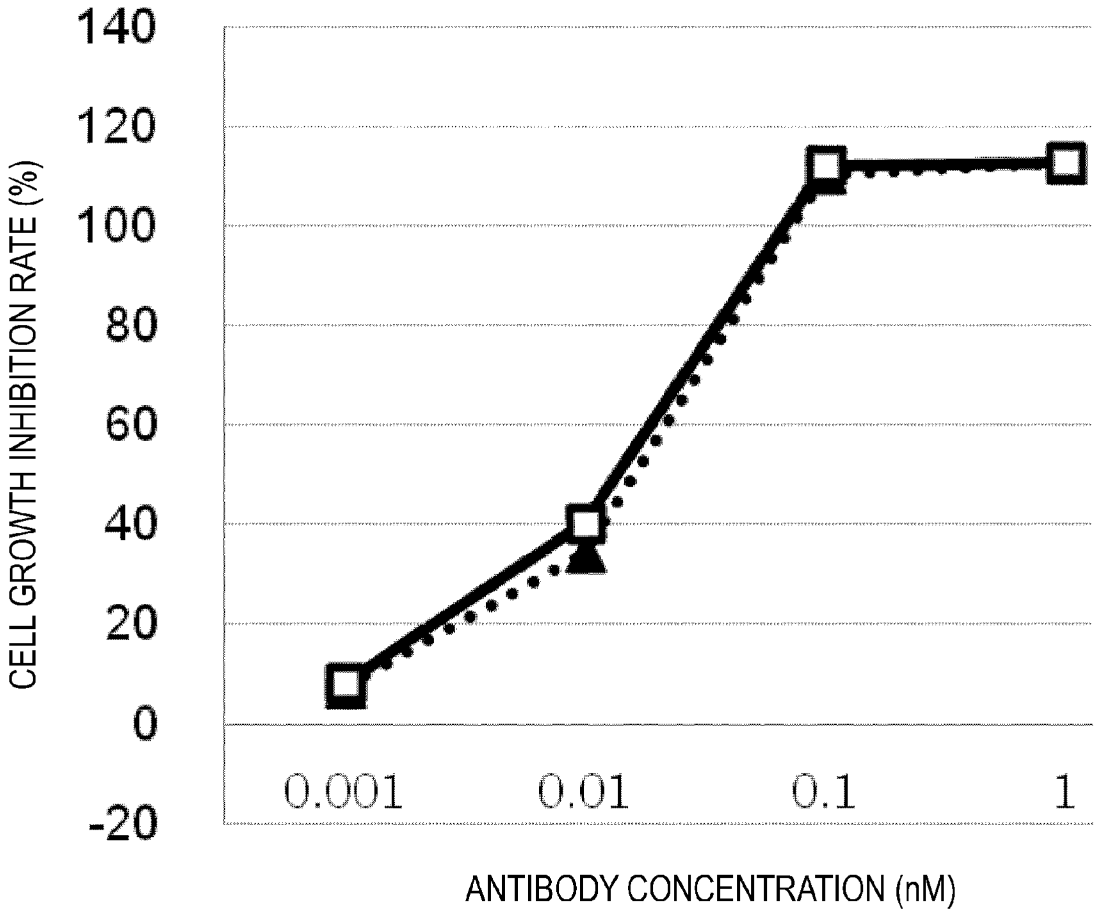
FIG. 23 is a graph showing comparison of the cytotoxic activities of EpCAM ERY17-2 and EpCAM ERY17-3. Closed triangle (▲) and open square (□) represent the cytotoxic activities of EpCAM ERY17-2 and EpCAM ERY17-3, respectively.

EpCAM ERY17-2 and EpCAM ERY17-3 were tested for the in vitro cytotoxic activity, and both showed a strong cytotoxic activity (FIG. 23). Thus, the present invention demonstrates that molecules in which an anti-cancer antigen IgG is used as a backbone and one of the Fabs is substituted with a CD3 epsilon-binding domain have a cytotoxic activity even when the type of cancer antigen has been changed.

[Example 10] Construction and Assessment of Bispecific Antibodies with Modulated CH1/CL Interfacial Association (1) Design of Bispecific Antibody By introducing mutations into each of the CH1 and CL domains of an bispecific antibody and thereby modulating the CH1/CL interfacial association with the use of electric charge repulsion at the CH1/CL interface, specific association may be allowed to occur between the anti-GPC3 H chain and L chain and between the anti-CD3 H chain and L chain. In order to modulate the CH1/CL interfacial association using electric charge repulsion, amino acid residues in CH1 of the H chains or CL of the L chains were substituted with Lys, which is positively charged, or with Glu, which is negatively charged.

(2) Construction of Expression Vectors for Antibody Genes and Expression of Respective Antibodies A bispecific antibody (FIG. 24A) was created by modulating the CH1/CL interfacial association of anti-CD3 antibody M12 (H chain, SEQ ID NO: 81; L chain, SEQ ID NO: 82) and anti-GPC3 antibody GC33 (2) (H chain, SEQ ID NO: 83; L chain, SEQ ID NO: 84) and further introducing Knobs-into-Holes (KiH) modifications (WO 1996/027011; Ridgway J B et al. (Protein Engineering (1996) 9, 617-621), Merchant A M et al. (Nat. Biotechnol. (1998) 16, 677-681)) into them to avoid the H chains from associating with each other. A control bispecific antibody (FIG. 24B), in which neither the CH1/CL interfacial association modulation nor the Knobs-into-Holes (KiH) modifications were introduced, was also constructed. Specifically, expression vectors having as an insert a polynucleotide encoding M12_TH2h (SEQ ID NO: 85), in which several amino acids in CH1 of the H chain of M12 (SEQ ID NO: 81) were substituted with Lys, or M12_TL17 (SEQ ID NO: 86), in which several amino acids in CL of the L chain (SEQ ID NO: 82) were substituted with Glu, were constructed by a method known to those skilled in the art. Likewise, expression vectors having as an insert a polynucleotide encoding GC33 (2)_TH13k (SEQ ID NO: 87) or GC33 (2)_TH15k (SEQ ID NO: 88), in which several amino acids in CH1 of the H chain of GC33 (2) (SEQ ID NO: 83) were substituted with Glu, or GC33 (2)_TL16 (SEQ ID NO: 89) or GC33 (2)_TL19 (SEQ ID NO: 90), in which several amino acids in CL of the L chain (SEQ ID NO: 84) were substituted with Lys, were constructed by a method known to those skilled in the art.

The following combinations of expression vectors were introduced into FreeStyle™ 293-F cells to express each designed molecule transiently.

T. Designed Molecule: GM1

Expression vectors: M12_TH2h (SEQ ID NO: 85), M12_TL17 (SEQ ID NO: 86), GC33 (2)_TH13k (SEQ ID NO: 87), and GC33 (2)_TL16 (SEQ ID NO: 89)

U. Designed Molecule: GM2 Expression vectors: M12_TH2h (SEQ ID NO: 85), M12_TL17 (SEQ ID NO: 86), GC33 (2)_TH15k (SEQ ID NO: 88), and GC33 (2)_TL19 (SEQ ID NO: 90)

V. Designed Molecule: GM0

Expression vectors: H chain of M12 (SEQ ID NO: 81), L chain of M12 (SEQ ID NO: 82), H chain of GC33 (2) (SEQ ID NO: 83), and L chain of GC33 (2) (SEQ ID NO: 84)

From the resulting culture supernatant, antibodies were purified by a method known to those skilled in the art using rProtein A Sepharose™ Fast Flow (GE Healthcare) antibody purification resin columns.

(3) Cytotoxic Activity of GM1, GM2, and GM0

Figure 25:
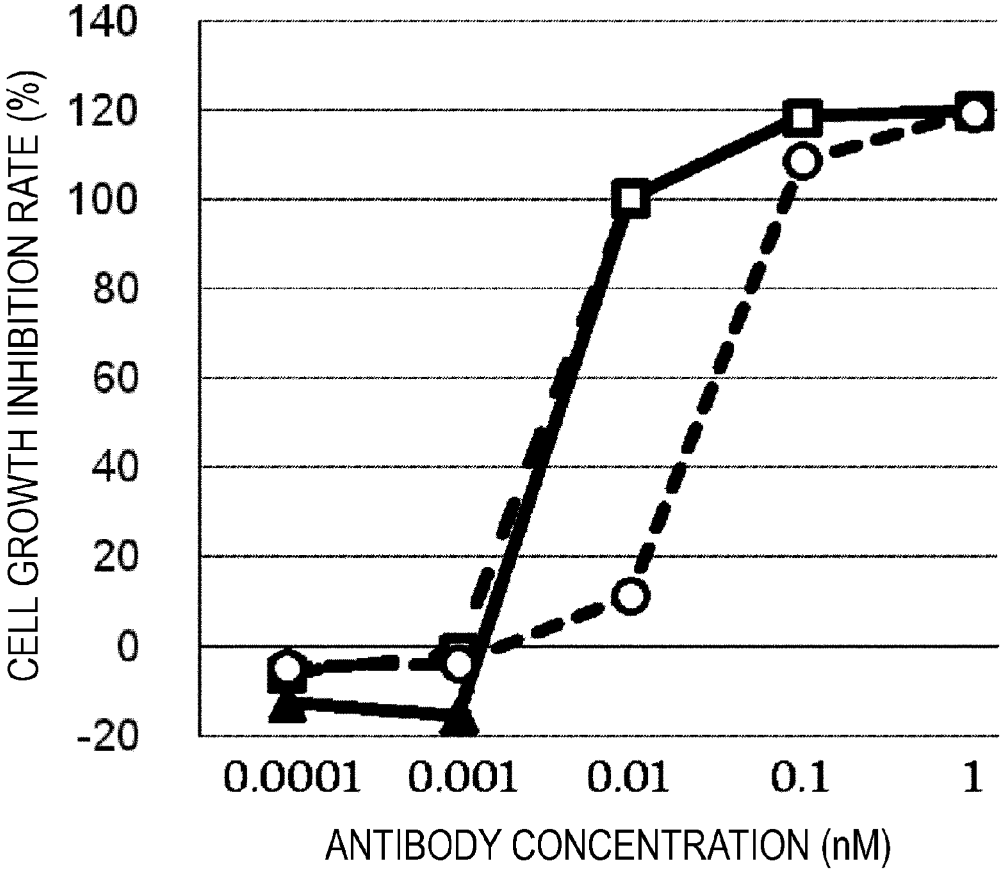
FIG. 25 is a graph showing comparison of the cytotoxic activities of GM1, GM2, and GM0. Closed triangle (▲), open square (□), and open circle (○) represent the cytotoxic activities of GM1, GM2, and GM3, respectively.

Polypeptide complexes GM1, GM2, and GM0 were assessed for the in vitro cytotoxic activity. The result showed that GM1 and GM2 exhibited a comparable cytotoxic activity, and this activity was clearly greater than that of GM0 (FIG. 25). Thus, the present invention demonstrates that the combination of the modulation of CH1/CL interfacial association and the KiH modifications allows efficient production of bispecific antibodies.

[Example 11] Construction and Assessment of EGFR ERY17-2

(1) Construction of EGFR ERY17-2

Furthermore, a molecule having the desired activity that targets another cancer antigen was prepared. EGFR ERY17-2 (FIG. 19, diagram A) was constructed by replacing the anti-GPC3 Fab of GPC3 ERY17-2 with the anti-EGFR Fab. Specifically, using as a template an expression vector for an anti-EGFR antibody, a method known to those skilled in the art such as PCR using primers containing the same appropriate sequences as in the above-described method was performed to produce a series of expression vectors into which the polynucleotide encoding EGFR ERY17_Hk (SEQ ID NO: 91: the mature sequence does not contain the amino terminal 19 amino acids, which serve as a signal sequence) or EGFR ERY17_L (SEQ ID NO: 92: the mature sequence does not contain the amino terminal 19 amino acids, which serve as a signal sequence) was inserted.

The following combinations of expression vectors were introduced into FreeStyle™ 293-F cells to express each designed molecule transiently.

W. Designed Molecule: EGFR ERY17-2

Polypeptides encoded by polynucleotides inserted in expression vectors: EGFR ERY17 Hk (SEQ ID NO: 91: the mature sequence does not contain the amino terminal 19 amino acids, which serve as a signal sequence), EGFR ERY17_L (SEQ ID NO: 92: the mature sequence does not contain the amino terminal 19 amino acids, which serve as a signal sequence), ERY17-2_Hh, and ERY17-2_L.

(2) Purification of EGFR ERY17-2

The resulting culture supernatants were loaded onto an Anti-FLAG® tag M2 column (Sigma). After washing, the column was eluted with 0.1 mg/mL FLAG® peptide (Sigma). A fraction containing the designed molecule was loaded onto a HisTrap™ HP column (GE Healthcare). After washing, the column was eluted with an imidazole concentration gradient. A fraction containing the designed molecule was concentrated by ultrafiltration. Then, the fraction was loaded onto a Superdex™ 200 column (GE Healthcare). Only a monomer fraction was collected from the eluate to obtain each purified designed molecule.

(3) Cytotoxic Activity of EGFR ERY17-2

Figure 26:
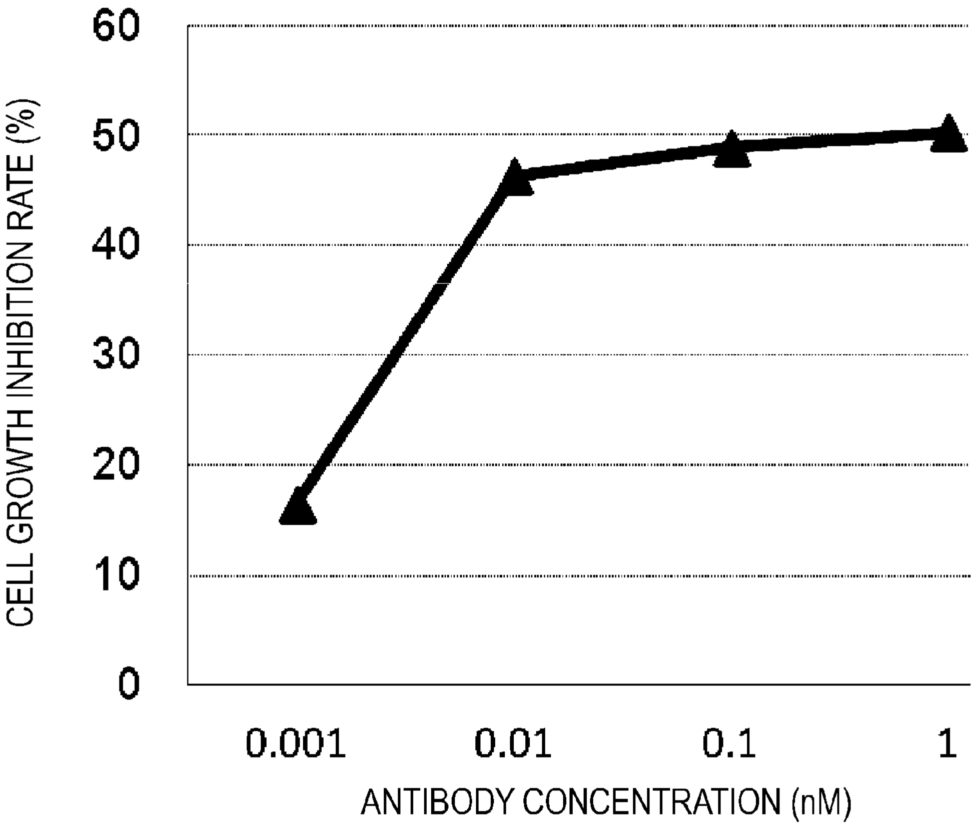
FIG. 26 is a graph showing the cytotoxic activity of EGFR ERY17-2. Closed triangle (▲) represents the cytotoxic activity of EGFR ERY17-2.

EGFR ERY17-2 was tested for the in vitro cytotoxic activity, and it showed a strong cytotoxic activity (FIG. 26). Thus, the present invention demonstrates that molecules in which an anti-cancer antigen IgG is used as a backbone and one of the Fabs is substituted with a CD3 epsilon-binding domain have a cytotoxic activity even when the cancer antigen is GPC3 or EpCAM or the type of cancer antigen has been further changed.

Industrial Applicability

The present invention provides novel polypeptide complexes that retain the strong anti-tumor activity of BiTE and have a long half-life in blood, as well as excellent safety properties that result in no induction of cancer antigen-independent cytokine storm or such. When the antigen-binding domain of a polypeptide complex of the present invention is substituted, therapeutic agents that comprise the polypeptide complex as an active ingredient for inducing cellular cytotoxicity, can target and damage various cells including cancer cells. Thus, various cancers can be treated or prevented. This allows desirable treatments that are highly safe and convenient, and reduce the physical burden for patients.

The invention claimed is:

1. A bispecific antibody that comprises:

a first light chain comprising a first light chain variable region (VL) and a first light chain constant region;

a second light chain comprising a second VL and a second light chain constant region;

a first heavy chain comprising a first heavy chain variable region (VH) and a first heavy chain constant region, wherein the first heavy chain constant region is a non-wild-type heavy chain constant region comprising the sequence of SEQ ID NO: 23 with one or more amino acid substitutions and optionally a deletion of one or both of the amino acids at EU numbering positions 446 and 447; and a second heavy chain comprising a second VH and a second heavy chain constant region, wherein the second heavy chain constant region is a non-wild-type heavy chain constant region comprising the sequence of SEQ ID NO: 23 with one or more amino acid substitutions and optionally a deletion of one or both of the amino acids at EU numbering positions 446 and 447, wherein the first light chain and the first heavy chain associate to form a first antigen-binding domain that binds to CD3, wherein the second light chain and the second heavy chain associate to form a second antigen-binding domain that binds to CD20, wherein the first VL and second VL each contains a light chain CDR1, a light chain CDR2, and a light chain CDR3, wherein the first VH and second VH each contains a heavy chain CDR1, a heavy chain CDR2, and a heavy chain CDR3, wherein the first heavy chain constant region associates with the second heavy chain constant region, wherein, when assessed by surface plasmon resonance, the ability of the associated first and second heavy chain constant regions to bind to a given human Fcγ receptor is reduced, compared to the ability of a wild-type human IgG1 antibody to bind to the human Fcγ receptor, as a result of at least one of the one or more amino acid substitutions within the first and second heavy chain constant regions, wherein at least one of the amino acid substitutions that result in the reduced ability to bind to the human Fcγ receptor is selected from L234F, L235E, and D265A in each of the first and second heavy chain constant regions, wherein all positions are by EU numbering, and wherein the human Fcγ receptor is a human FcγRI receptor, a human FcγRIIA receptor, or a human FcγRIIIA receptor.

2. The bispecific antibody of claim 1, wherein at least two of the following amino acid substitutions are present in both the first and second heavy chain constant regions:

(a) L234F;

(b) L235E; and (c) D265A, wherein all position numbers are by EU numbering.

3. The bispecific antibody of claim 1, wherein all three of the following amino acid substitutions are present in both the first and second heavy chain constant regions:

(a) L234F;

(b) L235E; and (c) D265A, wherein all position numbers are by EU numbering.

4. The bispecific antibody of claim 3, further comprising one or more additional amino acid substitutions, compared to SEQ ID NO: 23, in the CH3 domain of one or both of the first and second heavy chain constant regions.

5. The bispecific antibody of claim 4, wherein the one or more additional amino acid substitutions include a substitution, compared to SEQ ID NO: 23, at EU numbering position 356 in the first heavy chain constant region.

6. The bispecific antibody of claim 5, wherein the one or more additional amino acid substitutions further include a substitution, compared to SEQ ID NO: 23, at EU numbering position 356 in the second heavy chain constant region.

7. The bispecific antibody of claim 6, wherein the sequence of the CH3 domain of the first heavy chain constant region differs from the sequence of the CH3 domain of the second heavy chain constant region at one or more positions, and the difference results in a higher percentage of heterodimers formed in a mixture of the first and second heavy chains than if the first and second heavy chains comprise identical CH3 domains.

8. The bispecific antibody of claim 7, wherein the amino acid at EU numbering position 409 in the first heavy chain constant region is different from the amino acid at EU numbering position 409 in the second heavy chain constant region.

9. A bispecific antibody that comprises:

a first light chain comprising a first VL and a first light chain constant region;

a second light chain comprising a second VL and a second light chain constant region;

a first heavy chain comprising a first VH and a first heavy chain constant region, wherein the first heavy chain constant region comprises the sequence of SEQ ID NO: 23 with (a) amino acid substitutions comprising a Phe substitution at EU numbering position 234, a Glu substitution at EU numbering position 235, and substitutions at EU numbering positions 265 and 356, and (b) optionally a deletion of one or both of the amino acids at EU numbering position 446 and 447; and a second heavy chain comprising a second VH and a second heavy chain constant region, wherein the second heavy chain constant region comprises the sequence of SEQ ID NO: 23 with (A) amino acid substitutions comprising a Phe substitution at EU numbering position 234, a Glu substitution at EU numbering position 235, and substitutions at EU numbering positions 265, 356, and 409; and (B) optionally a deletion of one or both of the amino acids at EU numbering positions 446 and 447, wherein the first heavy chain constant region associates with the second heavy chain constant region, wherein, when assessed by surface plasmon resonance, the ability of the associated first and second heavy chain constant regions to bind to a given human Fcγ receptor is reduced, compared to the ability of a wild-type human IgG1 antibody to bind to the human Fcγ receptor, wherein the human Fcγ receptor is a human FcγRI receptor, a human FcγRIIA receptor, or a human FcγRIIIA receptor, wherein the first VL and second VL each contains a light chain CDR1, a light chain CDR2, and a light chain CDR3, wherein the first VH and second VH each contains a heavy chain CDR1, a heavy chain CDR2, and a heavy chain CDR3, and wherein the bispecific antibody is a T cell engager.

10. The bispecific antibody of claim 9, wherein each of the first and second heavy chain constant regions comprises an Ala substitution at EU numbering position 265.

11. The bispecific antibody of claim 9, wherein the sequence of the CH3 domain of the first heavy chain constant region differs from the sequence of the CH3 domain of the second heavy chain constant region at one or more positions, and the difference results in a higher percentage of heterodimers formed in a mixture of the first and second heavy chains than if the first and second heavy chains comprise identical CH3 domains.

12. The bispecific antibody of claim 11, wherein the amino acid at EU numbering position 409 in the first heavy chain constant region is different from the amino acid at EU numbering position 409 in the second heavy chain constant region.

13. The bispecific antibody of claim 9, wherein each of the first and second heavy chain constant regions comprises a deletion of one or both of the amino acids at EU numbering positions 446 and 447.

14. An antibody that comprises:

a first heavy chain constant region associated with a second heavy chain constant region, each comprising the sequence of SEQ ID NO: 23 with at least one mutation, including one or more mutations selected from a Phe substitution at EU numbering position 234, a Glu substitution at EU numbering position 235, and an Ala substitution at EU numbering position 265; and a means for binding to CD3 that comprises an antigen binding domain comprising three VH CDRs present in SEQ ID NO: 81 and three VL CDRs present in SEQ ID NO: 82, wherein, when assessed by surface plasmon resonance, the ability of the associated first and second heavy chain constant regions to bind to a given human Fcγ receptor is reduced, compared to the ability of two associated wild-type human IgG1 heavy chain constant regions to bind to the human Fcγ receptor, as a result of the at least one mutation, wherein the human Fcγ receptor is a human FcγRI receptor, a human FcγRIIA receptor, or a human FcγRIIIA receptor.

15. The antibody of claim 14, wherein either or both of the first and second heavy chain constant regions further comprise a mutation, compared to SEQ ID NO: 23, at EU numbering position 356.

16. The antibody of claim 14, wherein each of the first and second heavy chain constant regions comprises the following mutations, compared to SEQ ID NO: 23:

(a) L234F;

(b) L235E; and (c) D265A, wherein all positions are numbered by EU numbering.

17. The antibody of claim 14, wherein the sequence of the CH3 domain of the first heavy chain constant region differs from the sequence of the CH3 domain of the second heavy chain constant region at one or more positions, and the difference results in a higher percentage of heterodimers formed in a mixture of a first heavy chain comprising the first heavy chain constant region and a second heavy chain comprising the second heavy chain constant region than if the first and second heavy chains comprise identical CH3 domains.

18. The antibody of claim 17, wherein the amino acid at EU numbering position 409 in the first heavy chain constant region is different from the amino acid at EU numbering position 409 in the second heavy chain constant region.

19. The antibody of claim 1, wherein the first VH comprises three CDRs present in SEQ ID NO: 81 and the first VL comprises three CDRs present in SEQ ID NO: 82.

20. The bispecific antibody of claim 9, wherein the first VH comprises three CDRs present in SEQ ID NO: 81, and the first VL comprises three CDRs present in SEQ ID NO: 82.

21. An antibody that binds to human CD3, comprising:

a first light chain comprising a VL comprising three CDRs of SEQ ID NO: 82 and a light chain constant region;

a first heavy chain comprising a VH comprising three CDRs of SEQ ID NO: 81 and a first heavy chain constant region;

a second light chain comprising a VL and a light chain constant region; and a second heavy chain comprising a VH and a second heavy chain constant region, wherein the first and second heavy chain constant regions each comprises the sequence of SEQ ID NO: 23 with one or more amino acid substitutions and optionally a deletion of one or both of the amino acids at EU numbering positions 446 and 447, wherein all three of the following amino acid substitutions are present in both heavy chain constant regions, with all positions by EU numbering:

(a) L234F;

(b) L235E; and (c) D265A, and wherein the sequence of the CH3 domain of the first heavy chain constant region differs from the sequence of the CH3 domain of the second heavy chain constant region at one or more positions, and the difference results in a higher percentage of heterodimers formed in a mixture of the first and second heavy chains than if the first and second heavy chains comprise identical CH3 domains.

22. The antibody of claim 21, wherein the antibody is a bispecific antibody.

23. The antibody of claim 21, wherein the amino acid at EU numbering position 409 in the first heavy chain constant region is different from the amino acid at EU numbering position 409 in the second heavy chain constant region.

24. The antibody of claim 23, wherein the one or more amino acid substitutions further include a substitution, compared to SEQ ID NO: 23, at EU numbering position 356 in the first heavy chain constant region.

25. The antibody of claim 24, wherein the one or more amino acid substitutions further include a substitution, compared to SEQ ID NO: 23, at EU numbering position 356 in the second heavy chain constant region.

* * * * *

SEQUENCE LISTING

```
Sequence total quantity: 92
SEQ ID NO: 1           moltype = DNA  length = 1812
FEATURE                Location/Qualifiers
source                 1..1812
                       mol_type = genomic DNA
                       organism = Homo sapiens
SEQUENCE: 1
atggccggga ccgtgcgcac cgcgtgcttg gtggtggcga tgctgctcag cttggacttc  60
ccgggacagg cgcagccccc gccgccgccg ccggacgcca cctgtcacca agtccgctcc  120
ttcttccaga gactgcagcc cggactcaag tgggtgccag aaactcccgt gccaggatca  180
gatttgcaag tatgtctccc taagggccca acatgctgct caagaaagat ggaagaaaaa  240
taccaactaa cagcacgatt gaacatggaa cagctgcttc agtctgcaag tatggagctc  300
aagttcttaa ttattcagaa tgctgcggtt ttccaagagg cctttgaaat tgttgttcgc  360
catgccaaga actacaccaa tgccatgttc aagaacaact acccaagcct gactccacaa  420
gcttttgagt ttgtgggtga atttttcaca gatgtgtctc tctacatctt gggttctgac  480
atcaatgtag atgacatggt caatgaattg tttgacagcc tgtttccagt catctatacc  540
cagctaatga acccaggcct gcctgattca gccttggaca tcaatgagtg cctccgagga  600
gcaagacgtg acctgaaagt atttgggaat ttccccaagc ttattatgac ccaggtttcc  660
aagtcactgc aagtcactag gatcttcctt caggctctga atcttggaat tgaagtgatc  720
aacacaactg atcacctgaa gttcagtaag gactgtggcc gaatgctcac cagaatgtgg  780
tactgctctt actgccaggg actgatgatg gttaaaccct gtggcggtta ctgcaatgtg  840
gtcatgcaag gctgtatggc aggtgtggtg gagattgaca agtactggag agaatacatt  900
```

```
ctgtcccttg aagaacttgt gaatggcatg tacagaatct atgacatgga gaacgtactg  960
cttggtctct tttcaacaat ccatgattct atccagtatg tccagaagaa tgcaggaaag  1020
ctgaccacca ctgaaactga gaagaaaata tggcacttca aatatcctat cttcttcctg  1080
tgtatagggc tagacttaca gattggcaag ttatgtgccc attctcaaca acgccaatat  1140
agatctgctt attatcctga agatctcttt attgacaaga aagtattaaa agttgctcat  1200
gtagaacatg aagaaacctt atccagccga agaagggaac taattcagaa gttgaagtct  1260
ttcatcagct tctatagtgc tttgcctggc tacatctgca gccatagccc tgtggcggaa  1320
aacgacaccc tttgctggaa tggacaagaa ctcgtggaga gatacagcca aaaggcagca  1380
aggaatggaa tgaaaaacca gttcaatctc catgagctga aaatgaaggg ccctgagcca  1440
gtggtcagtc aaattattga caaactgaag cacattaacc agctcctgag aaccatgtct  1500
atgcccaaag gtagagttct ggataaaaac ctggatgagg aagggtttga aagtggagac  1560
tgcggtgatg atgaagatga gtgcattgga ggctctggtg atggaatgat aaaagtgaag  1620
aatcagctcc gcttccttgc agaactggcc tatgatctgg atgtggatga tgcgcctgga  1680
aacagtcagc aggcaactcc gaaggacaac gagataagca cctttcacaa cctcgggaac  1740
gttcattccc cgctgaagct tctcaccagc atggccatct cggtggtgtg cttcttcttc  1800
ctggtgcact ga                                                      1812

SEQ ID NO: 2            moltype = AA  length = 603
FEATURE                 Location/Qualifiers
source                  1..603
                        mol_type = protein
                        organism = Homo sapiens
SEQUENCE: 2
MAGTVRTACL VVAMLLSLDF PGQAQPPPPP PDATCHQVRS FFQRLQPGLK WVPETPVPGS  60
DLQVCLPKGP TCCSRKMEEK YQLTARLNME QLLQSASMEL KFLIIQNAAV FQEAFEIVVR  120
HAKNYTNAMF KNNYPSLTPQ AFEFVGEFFT DVSLYILGSD INVDDMVNEL FDSLFPVIYT  180
QLMNPGLPDS ALDINECLRG ARRDLKVFGN FPKLIMTQVS KSLQVTRIFL QALNLGIEVI  240
NTTDHLKFSK DCGRMLTRMW YCSYCQGLMM VKPCGGYCNV VMQGCMAGVV EIDKYWREYI  300
LSLEELVNGM YRIYDMENVL LGLFSTIHDS IQYVQKNAGK LTTTETEKKI WHFKYPIFFL  360
CIGLDLQIGK LCAHSQQRQY RSAYYPEDLF IDKKVLKVAH VEHEETLSSR RRELIQKLKS  420
FISFYSALPG YICSHSPVAE NDTLCWNGQE LVERYSQKAA RNGMKNQFNL HELKMKGPEP  480
VVSQIIDKLK HINQLLRTMS MPKGRVLDKN LDEEGFESGD CGDDEDECIG GSGDGMIKVK  540
NQLRFLAELA YDLDVDDAPG NSQQATPKDN EISTFHNLGN VHSPLKLLTS MAISVVCFFF  600
LVH                                                                603

SEQ ID NO: 3            moltype = DNA  length = 945
FEATURE                 Location/Qualifiers
source                  1..945
                        mol_type = genomic DNA
                        organism = Homo sapiens
SEQUENCE: 3
atggcgcccc cgcaggtcct cgcgttcggg cttctgcttg ccgcggcgac ggcgactttt  60
gccgcagctc aggaagaatg tgtctgtgaa aactacaagc tggccgtaaa ctgctttgtg  120
aataataatc gtcaatgcca gtgtacttca gttggtgcac aaaatactgt catttgctca  180
aagctggctg ccaaatgttt ggtgatgaag gcagaaatga atggctcaaa acttgggaga  240
agagcaaaac ctgaaggggc cctccagaac aatgatgggc tttatgatcc tgactgcgat  300
gagagcgggc tctttaaggc caagcagtgc aacggcacct ccatgtgctg gtgtgtgaac  360
actgctgggg tcagaagaac agacaaggac actgaaataa cctgctctga gcgagtgaga  420
acctactgga tcatcattga actaaaacac aaagcaagag aaaaacctta tgatagtaaa  480
agtttgcgga ctgcacttca gaaggagatc acaacgcgtt atcaactgga tccaaaattt  540
atcacgagta ttttgtatga gaataatgtt atcactattg atctggttca aaattcttct  600
caaaaaactc agaatgatgt ggacatagct gatgtggctt attattttga aaaagatgtt  660
aaaggtgaat ccttgtttca ttctaagaaa atggacctga cagtaaatgg ggaacaactg  720
gatctggatc ctggtcaaac tttaatttat tatgttgatg aaaaagcacc tgaattctca  780
atgcagggtc taaaagctgg tgttattgct gttattgtgg ttgtggtgat agcagttgtt  840
gctggaattg ttgtgctggt tatttccaga aagaagagaa tggcaaagta tgagaaggct  900
gagataaagg agatgggtga gatgcatagg gaactcaatg cataa                  945

SEQ ID NO: 4            moltype = AA  length = 314
FEATURE                 Location/Qualifiers
source                  1..314
                        mol_type = protein
                        organism = Homo sapiens
SEQUENCE: 4
MAPPQVLAFG LLLAAATATF AAAQEECVCE NYKLAVNCFV NNNRQCQCTS VGAQNTVICS  60
KLAAKCLVMK AEMNGSKLGR RAKPEGALQN NDGLYDPDCD ESGLFKAKQC NGTSMCWCVN  120
TAGVRRTDKD TEITCSERVR TYWIIIELKH KAREKPYDSK SLRTALQKEI TTRYQLDPKF  180
ITSILYENNV ITIDLVQNSS QKTQNDVDIA DVAYYFEKDV KGESLFHSKK MDLTVNGEQL  240
DLDPGQTLIY YVDEKAPEFS MQGLKAGVIA VIVVVVIAVV AGIVVLVISR KKRMAKYEKA  300
EIKEMGEMHR ELNA                                                    314

SEQ ID NO: 5            moltype = AA  length = 4
FEATURE                 Location/Qualifiers
source                  1..4
                        mol_type = protein
                        organism = synthetic construct
SEQUENCE: 5
GGGS                                                               4
```

```
SEQ ID NO: 6            moltype = AA  length = 4
FEATURE                 Location/Qualifiers
source                  1..4
                        mol_type = protein
                        organism = synthetic construct
SEQUENCE: 6
SGGG                                                          4

SEQ ID NO: 7            moltype = AA  length = 5
FEATURE                 Location/Qualifiers
source                  1..5
                        mol_type = protein
                        organism = synthetic construct
SEQUENCE: 7
GGGGS                                                         5

SEQ ID NO: 8            moltype = AA  length = 5
FEATURE                 Location/Qualifiers
source                  1..5
                        mol_type = protein
                        organism = synthetic construct
SEQUENCE: 8
SGGGG                                                         5

SEQ ID NO: 9            moltype = AA  length = 6
FEATURE                 Location/Qualifiers
source                  1..6
                        mol_type = protein
                        organism = synthetic construct
SEQUENCE: 9
GGGGGS                                                        6

SEQ ID NO: 10           moltype = AA  length = 6
FEATURE                 Location/Qualifiers
source                  1..6
                        mol_type = protein
                        organism = synthetic construct
SEQUENCE: 10
SGGGGG                                                        6

SEQ ID NO: 11           moltype = AA  length = 7
FEATURE                 Location/Qualifiers
source                  1..7
                        mol_type = protein
                        organism = synthetic construct
SEQUENCE: 11
GGGGGGS                                                       7

SEQ ID NO: 12           moltype = AA  length = 7
FEATURE                 Location/Qualifiers
source                  1..7
                        mol_type = protein
                        organism = synthetic construct
SEQUENCE: 12
SGGGGGG                                                       7

SEQ ID NO: 13           moltype = DNA  length = 1125
FEATURE                 Location/Qualifiers
source                  1..1125
                        mol_type = genomic DNA
                        organism = Homo sapiens
SEQUENCE: 13
atgtggttct tgacaactct gctcctttgg gttccagttg atgggcaagt ggacaccaca  60
aaggcagtga tcactttgca gcctccatgg gtcagcgtgt tccaagagga aaccgtaacc  120
ttgcactgtg aggtgctcca tctgcctggg agcagctcta cacagtggtt tctcaatggc  180
acagccactc agacctcgac ccccagctac agaatcacct ctgccagtgt caatgacagt  240
ggtgaataca ggtgccagag aggtctctca gggcgaagtg accccataca gctggaaatc  300
cacagaggct ggctactact gcaggtctcc agcagagtct tcacggaagg agaacctctg  360
gccttgaggt gtcatgcgtg gaaggataag ctggtgtaca atgtgcttta ctatcgaaat  420
ggcaaagcct ttaagttttt ccactggaat tctaacctca ccattctgaa aaccaacata  480
agtcacaatg gcacctacca ttgctcaggc atgggaaagc atcgctacac atcagcagga  540
atatctgtca ctgtgaaaga gctatttcca gctccagtgc tgaatgcatc tgtgacatcc  600
ccactcctgg aggggaatct ggtcaccctg agctgtgaaa caaagttgct cttgcagagg  660
cctggtttgc agctttactt ctccttctac atgggcagca agaccctgcg aggcaggaac  720
acatcctctg aataccaaat actaactgct agaagagaag actctgggtt atactggtgc  780
gaggctgcca cagaggatgg aaatgtcctt aagcgcagcc ctgagttgga gcttcaagtg  840
cttggcctcc agttaccaac tcctgtctgg tttcatgtcc ttttctatct ggcagtggga  900
ataatgtttt tagtgaacac tgttctctgg gtgacaatac gtaaagaact gaaaagaaag  960
aaaaagtggg atttagaaat ctctttggat tctggtcatg agaagaaggt aatttccagc  1020
```

```
cttcaagaag acagacattt agaagaagag ctgaaatgtc aggaacaaaa agaagaacag  1080
ctgcaggaag gggtgcaccg gaaggagccc caggggggcca cgtag                 1125

SEQ ID NO: 14          moltype = AA  length = 374
FEATURE                Location/Qualifiers
source                 1..374
                       mol_type = protein
                       organism = Homo sapiens
SEQUENCE: 14
MWFLTTLLLW VPVDGQVDTT KAVITLQPPW VSVFQEETVT LHCEVLHLPG SSSTQWFLNG  60
TATQTSTPSY RITSASVNDS GEYRCQRGLS GRSDPIQLEI HRGWLLLQVS SRVFTEGEPL  120
ALRCHAWKDK LVYNVLYYRN GKAFKFFHWN SNLTILKTNI SHNGTYHCSG MGKHRYTSAG  180
ISVTVKELFP APVLNASVTS PLLEGNLVTL SCETKLLLQR PGLQLYFSFY MGSKTLRGRN  240
TSSEYQILTA RREDSGLYWC EAATEDGNVL KRSPELELQV LGLQLPTPVW FHVLFYLAVG  300
IMFLVNTVLW VTIRKELKRK KKWDLEISLD SGHEKKVISS LQEDRHLEEE LKCQEQKEEQ  360
LQEGVHRKEP QGAT                                                    374

SEQ ID NO: 15          moltype = DNA  length = 951
FEATURE                Location/Qualifiers
source                 1..951
                       mol_type = genomic DNA
                       organism = Homo sapiens
SEQUENCE: 15
atgactatgg agacccaaat gtctcagaat gtatgtccca gaaacctgtg gctgcttcaa  60
ccattgacag ttttgctgct gctggcttct gcagacagtc aagctgctcc cccaaaggct  120
gtgctgaaac ttgagccccc gtggatcaac gtgctccagg aggactctgt gactctgaca  180
tgccaggggg ctcgcagccc tgagagcgac tccattcagt ggttccacaa tgggaatctc  240
attcccaccc acacgcagcc cagctacagg ttcaaggcca acaacaatga cagcggggag  300
tacacgtgcc agactggcca gaccagcctc agcgaccctg tgcatctgac tgtgctttcc  360
gaatggctgg tgctccagac ccctcacctg gagttccagg agggagaaac catcatgctg  420
aggtgccaca gctggaagga caagcctctg gtcaaggtca cattcttcca gaatggaaaa  480
tcccagaaat tctcccattt ggatcccacc ttctccatcc cacaagcaaa ccacagtcac  540
agtggtgatt accactgcac aggaaacata ggctacacgc tgttctcatc caagcctgtg  600
accatcactg tccaagtgcc cagcatgggc agctcttcac caatgggggt cattgtggct  660
gtggtcattg cgactgctgt agcagccatt gttgctgctg tagtggcctt gatctactgc  720
aggaaaaagc ggatttcagc caattccact gatcctgtga aggctgccca atttgagcca  780
cctggacgtc aaatgattgc catcagaaag agacaacttg aagaaaccaa caatgactat  840
gaaacagctg acggcggcta catgactctg aaccccaggg cacctactga cgatgataaa  900
aacatctacc tgactcttcc tcccaacgac catgtcaaca gtaataacta a           951

SEQ ID NO: 16          moltype = AA  length = 316
FEATURE                Location/Qualifiers
source                 1..316
                       mol_type = protein
                       organism = Homo sapiens
SEQUENCE: 16
MTMETQMSQN VCPRNLWLLQ PLTVLLLLAS ADSQAAPPKA VLKLEPPWIN VLQEDSVTLT  60
CQGARSPESD SIQWFHNGNL IPTHTQPSYR FKANNNDSGE YTCQTGQTSL SDPVHLTVLS  120
EWLVLQTPHL EFQEGETIML RCHSWKDKPL VKVTFFQNGK SQKFSHLDPT FSIPQANHSH  180
SGDYHCTGNI GYTLFSSKPV TITVQVPSMG SSSPMGVIVA VVIATAVAAI VAAVVALIYC  240
RKKRISANST DPVKAAQFEP PGRQMIAIRK RQLEETNNDY ETADGGYMTL NPRAPTDDDK  300
NIYLTLPPND HVNSNN                                                  316

SEQ ID NO: 17          moltype = DNA  length = 876
FEATURE                Location/Qualifiers
source                 1..876
                       mol_type = genomic DNA
                       organism = Homo sapiens
SEQUENCE: 17
atgggaatcc tgtcattctt acctgtcctt gccactgaga gtgactgggc tgactgcaag  60
tccccccagc cttggggtca tatgcttctg tggacagctg tgctattcct ggctcctgtt  120
gctgggacac ctgcagctcc cccaaaggct gtgctgaaac tcgagcccca gtggatcaac  180
gtgctccagg aggactctgt gactctgaca tgccggggga ctcacagccc tgagagcgac  240
tccattcagt ggttccacaa tgggaatctc attcccaccc acacgcagcc cagctacagg  300
ttcaaggcca acaacaatga cagcggggag tacacgtgcc agactggcca gaccagcctc  360
agcgaccctg tgcatctgac tgtgctttct gagtggctgg tgctccagac ccctcacctg  420
gagttccagg agggagaaac catcgtgctg aggtgccaca gctggaagga caagcctctg  480
gtcaaggtca cattcttcca gaatggaaaa tccaagaaat tttcccgttc ggatcccaac  540
ttctccatcc cacaagcaaa ccacagtcac agtggtgatt accactgcac aggaaacata  600
ggctacacgc tgtactcatc caagcctgtg accatcactg tccaagctcc cagctcttca  660
ccgatgggga tcattgtggc tgtggtcact gggattgctg tagcggccat tgttgctgct  720
gtagtggcct tgatctactg caggaaaaag cggatttcag ccaatcccac taatcctgat  780
gaggctgaca aagttggggc tgagaacaca atcacctatt cacttctcat gcacccggat  840
gctctggaag agcctgatga ccagaaccgt atttag                            876

SEQ ID NO: 18          moltype = AA  length = 291
FEATURE                Location/Qualifiers
source                 1..291
                       mol_type = protein
```

```
                         organism = Homo sapiens
SEQUENCE: 18
MGILSFLPVL ATESDWADCK SPQPWGHMLL WTAVLFLAPV AGTPAAPPKA VLKLEPQWIN  60
VLQEDSVTLT CRGTHSPESD SIQWFHNGNL IPTHTQPSYR FKANNNDSGE YTCQTGQTSL  120
SDPVHLTVLS EWLVLQTPHL EFQEGETIVL RCHSWKDKPL VKVTFFQNGK SKKFSRSDPN  180
FSIPQANHSH SGDYHCTGNI GYTLYSSKPV TITVQAPSSS PMGIIVAVVT GIAVAAIVAA  240
VVALIYCRKK RISANPTNPD EADKVGAENT ITYSLLMHPD ALEEPDDQNR I          291

SEQ ID NO: 19            moltype = DNA  length = 765
FEATURE                  Location/Qualifiers
source                   1..765
                         mol_type = genomic DNA
                         organism = Homo sapiens
SEQUENCE: 19
atgtggcagc tgctcctccc aactgctctg ctacttctag tttcagctgg catgcggact  60
gaagatctcc caaaggctgt ggtgttcctg gagcctcaat ggtacagggt gctcgagaag  120
gacagtgtga ctctgaagtg ccagggagcc tactcccctg aggacaattc cacacagtgg  180
tttcacaatg agagcctcat ctcaagccag gcctcgagct acttcattga cgctgccaca  240
gttgacgaca gtggagagta caggtgccag acaaacctct ccaccctcag tgacccggtg  300
cagctagaag tccatatcgg ctggctgttg ctccaggccc ctcggtgggt gttcaaggag  360
gaagacccta ttcacctgag gtgtcacagc tggaagaaca ctgctctgca taaggtcaca  420
tatttacaga atggcaaagg caggaagtat tttcatcata attctgactt ctacattcca  480
aaagccacac tcaaagacag cggctcctac ttctgcaggg ggcttgttgg gagtaaaaat  540
gtgtcttcag agactgtgaa catcaccatc actcaaggtt tgtcagtgtc aaccatctca  600
tcattctttc cacctgggta ccaagtctct ttctgcttgg tgatggtact cctttttgca  660
gtggacacag gactatattt ctctgtgaag acaaacattc gaagctcaac aagagactgg  720
aaggaccata aatttaaatg gagaaaggac cctcaagaca aatga                 765

SEQ ID NO: 20            moltype = AA  length = 254
FEATURE                  Location/Qualifiers
source                   1..254
                         mol_type = protein
                         organism = Homo sapiens
SEQUENCE: 20
MWQLLLPTAL LLLVSAGMRT EDLPKAVVFL EPQWYRVLEK DSVTLKCQGA YSPEDNSTQW  60
FHNESLISSQ ASSYFIDAAT VDDSGEYRCQ TNLSTLSDPV QLEVHIGWLL LQAPRWVFKE  120
EDPIHLRCHS WKNTALHKVT YLQNGKGRKY FHHNSDFYIP KATLKDSGSY FCRGLVGSKN  180
VSSETVNITI TQGLSVSTIS SFFPPGYQVS FCLVMVLLFA VDTGLYFSVK TNIRSSTRDW  240
KDHKFKWRKD PQDK                                                   254

SEQ ID NO: 21            moltype = DNA  length = 702
FEATURE                  Location/Qualifiers
source                   1..702
                         mol_type = genomic DNA
                         organism = Homo sapiens
SEQUENCE: 21
atgtggcagc tgctcctccc aactgctctg ctacttctag tttcagctgg catgcggact  60
gaagatctcc caaaggctgt ggtgttcctg gagcctcaat ggtacagcgt gcttgagaag  120
gacagtgtga ctctgaagtg ccagggagcc tactcccctg aggacaattc cacacagtgg  180
tttcacaatg agagcctcat ctcaagccag gcctcgagct acttcattga cgctgccaca  240
gtcaacgaca gtggagagta caggtgccag acaaacctct ccaccctcag tgacccggtg  300
cagctagaag tccatatcgg ctggctgttg ctccaggccc ctcggtgggt gttcaaggag  360
gaagacccta ttcacctgag gtgtcacagc tggaagaaca ctgctctgca taaggtcaca  420
tatttacaga atggcaaaga caggaagtat tttcatcata attctgactt ccacattcca  480
aaagccacac tcaaagatag cggctcctac ttctgcaggg ggcttgttgg gagtaaaaat  540
gtgtcttcag agactgtgaa catcaccatc actcaaggtt tggcagtgtc aaccatctca  600
tcattctctc cacctgggta ccaagtctct ttctgcttgg tgatggtact cctttttgca  660
gtggacacag gactatattt ctctgtgaag acaaacattt ga                    702

SEQ ID NO: 22            moltype = AA  length = 233
FEATURE                  Location/Qualifiers
source                   1..233
                         mol_type = protein
                         organism = Homo sapiens
SEQUENCE: 22
MWQLLLPTAL LLLVSAGMRT EDLPKAVVFL EPQWYSVLEK DSVTLKCQGA YSPEDNSTQW  60
FHNESLISSQ ASSYFIDAAT VNDSGEYRCQ TNLSTLSDPV QLEVHIGWLL LQAPRWVFKE  120
EDPIHLRCHS WKNTALHKVT YLQNGKDRKY FHHNSDFHIP KATLKDSGSY FCRGLVGSKN  180
VSSETVNITI TQGLAVSTIS SFSPPGYQVS FCLVMVLLFA VDTGLYFSVK TNI        233

SEQ ID NO: 23            moltype = AA  length = 330
FEATURE                  Location/Qualifiers
source                   1..330
                         mol_type = protein
                         organism = synthetic construct
SEQUENCE: 23
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
```

```
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                   330

SEQ ID NO: 24          moltype = AA  length = 326
FEATURE                Location/Qualifiers
source                 1..326
                       mol_type = protein
                       organism = synthetic construct
SEQUENCE: 24
ASTKGPSVFP LAPCSRSTSE STAALGCLVK DYFPEPVTVS WNSGALTSGV HTFPAVLQSS  60
GLYSLSSVVT VPSSNFGTQT YTCNVDHKPS NTKVDKTVER KCCVECPPCP APPVAGPSVF  120
LFPPKPKDTL MISRTPEVTC VVVDVSHEDP EVQFNWYVDG VEVHNAKTKP REEQFNSTFR  180
VVSVLTVVHQ DWLNGKEYKC KVSNKGLPAP IEKTISKTKG QPREPQVYTL PPSREEMTKN  240
QVSLTCLVKG FYPSDIAVEW ESNGQPENNY KTTPPMLDSD GSFFLYSKLT VDKSRWQQGN  300
VFSCSVMHEA LHNHYTQKSL SLSPGK                                       326

SEQ ID NO: 25          moltype = AA  length = 377
FEATURE                Location/Qualifiers
source                 1..377
                       mol_type = protein
                       organism = synthetic construct
SEQUENCE: 25
ASTKGPSVFP LAPCSRSTSG GTAALGCLVK DYFPEPVTVS WNSGALTSGV HTFPAVLQSS  60
GLYSLSSVVT VPSSSLGTQT YTCNVNHKPS NTKVDKRVEL KTPLGDTTHT CPRCPEPKSC  120
DTPPPCPRCP EPKSCDTPPP CPRCPEPKSC DTPPPCPRCP APELLGGPSV FLFPPKPKDT  180
LMISRTPEVT CVVVDVSHED PEVQFKWYVD GVEVHNAKTK PREEQYNSTF RVVSVLTVLH  240
QDWLNGKEYK CKVSNKALPA PIEKTISKTK GQPREPQVYT LPPSREEMTK NQVSLTCLVK  300
GFYPSDIAVE WESSGQPENN YNTTPPMLDS DGSFFLYSKL TVDKSRWQQG NIFSCSVMHE  360
ALHNRFTQKS LSLSPGK                                                 377

SEQ ID NO: 26          moltype = AA  length = 327
FEATURE                Location/Qualifiers
source                 1..327
                       mol_type = protein
                       organism = synthetic construct
SEQUENCE: 26
ASTKGPSVFP LAPCSRSTSE STAALGCLVK DYFPEPVTVS WNSGALTSGV HTFPAVLQSS  60
GLYSLSSVVT VPSSSLGTKT YTCNVDHKPS NTKVDKRVES KYGPPCPSCP APEFLGGPSV  120
FLFPPKPKDT LMISRTPEVT CVVVDVSQED PEVQFNWYVD GVEVHNAKTK PREEQFNSTY  180
RVVSVLTVLH QDWLNGKEYK CKVSNKGLPS SIEKTISKAK GQPREPQVYT LPPSQEEMTK  240
NQVSLTCLVK GFYPSDIAVE WESNGQPENN YKTTPPVLDS DGSFFLYSRL TVDKSRWQEG  300
NVFSCSVMHE ALHNHYTQKS LSLSLGK                                      327

SEQ ID NO: 27          moltype = DNA  length = 549
FEATURE                Location/Qualifiers
source                 1..549
                       mol_type = genomic DNA
                       organism = Homo sapiens
SEQUENCE: 27
atggaacagg ggaagggcct ggctgtcctc atcctggcta tcattcttct tcaaggtact  60
ttggcccagt caatcaaagg aaaccacttg gttaaggtgt atgactatca agaagatggt  120
tcggtacttc tgacttgtga tgcagaagcc aaaaatatca catggtttaa agatgggaag  180
atgatcggct tcctaactga agataaaaaa aaatggaatc tgggaagtaa tgccaaggac  240
cctcgaggga tgtatcagtg taaaggatca cagaacaagt caaaaccact ccaagtgtat  300
tacagaatgt gtcagaactg cattgaacta aatgcagcca ccatatctgg ctttctcttt  360
gctgaaatcg tcagcatttt cgtccttgct gttggggtct acttcattgc tggacaggat  420
ggagttcgcc agtcgagagc ttcagacaag cagactctgt tgcccaatga ccagctctac  480
cagcccctca aggatcgaga agatgaccag tacagccacc ttcaaggaaa ccagttgagg  540
aggaattga                                                          549

SEQ ID NO: 28          moltype = AA  length = 182
FEATURE                Location/Qualifiers
source                 1..182
                       mol_type = protein
                       organism = Homo sapiens
SEQUENCE: 28
MEQGKGLAVL ILAIILLQGT LAQSIKGNHL VKVYDYQEDG SVLLTCDAEA KNITWFKDGK  60
MIGFLTEDKK KWNLGSNAKD PRGMYQCKGS QNKSKPLQVY YRMCQNCIEL NAATISGFLF  120
AEIVSIFVLA VGVYFIAGQD GVRQSRASDK QTLLPNDQLY QPLKDREDDQ YSHLQGNQLR  180
RN                                                                 182

SEQ ID NO: 29          moltype = DNA  length = 516
FEATURE                Location/Qualifiers
source                 1..516
                       mol_type = genomic DNA
                       organism = Homo sapiens
SEQUENCE: 29
atggaacata gcacgtttct ctctggcctg gtactggcta cccttctctc gcaagtgagc  60
```

```
cccttcaaga tacctataga ggaacttgag gacagagtgt ttgtgaattg caataccagc  120
atcacatggg tagagggaac ggtgggaaca ctgctctcag acattacaag actggacctg  180
ggaaaacgca tcctggaccc acgaggaata tataggtgta atgggacaga tatatacaag  240
gacaaagaat ctaccgtgca agttcattat cgaatgtgcc agagctgtgt ggagctggat  300
ccagccaccg tggctggcat cattgtcact gatgtcattg ccactctgct ccttgctttg  360
ggagtcttct gctttgctgg acatgagact ggaaggctgt ctggggctgc cgacacacaa  420
gctctgttga ggaatgacca ggtctatcag cccctccgag atcgagatga tgctcagtac  480
agccaccttg gaggaaactg ggctcggaac aagtga                            516

SEQ ID NO: 30          moltype = AA  length = 171
FEATURE                Location/Qualifiers
source                 1..171
                       mol_type = protein
                       organism = Homo sapiens
SEQUENCE: 30
MEHSTFLSGL VLATLLSQVS PFKIPIEELE DRVFVNCNTS ITWVEGTVGT LLSDITRLDL  60
GKRILDPRGI YRCNGTDIYK DKESTVQVHY RMCQSCVELD PATVAGIIVT DVIATLLLAL  120
GVFCFAGHET GRLSGAADTQ ALLRNDQVYQ PLRDRDDAQY SHLGGNWARN K           171

SEQ ID NO: 31          moltype = DNA  length = 624
FEATURE                Location/Qualifiers
source                 1..624
                       mol_type = genomic DNA
                       organism = Homo sapiens
SEQUENCE: 31
atgcagtcgg gcactcactg gagagttctg ggcctctgcc tcttatcagt tggcgtttgg  60
gggcaagatg gtaatgaaga aatgggtggt attacacaga caccatataa agtctccatc  120
tctggaacca cagtaatatt gacatgccct cagtatcctg gatctgaaat actatggcaa  180
cacaatgata aaaacatagg cggtgatgag gatgataaaa acataggcag tgatgaggat  240
cacctgtcac tgaaggaatt ttcagaattg gagcaaagtg gttattatgt ctgctacccc  300
agaggaagca aaccagaaga tgcgaacttt tatctctacc tgagggcaag agtgtgtgag  360
aactgcatgg agatggatgt gatgtcggtg gccacaattg tcatagtgga catctgcatc  420
actgggggct tgctgctgct ggtttactac tggagcaaga atagaaaggc caaggccaag  480
cctgtgacac gaggagcggg tgctggcggc aggcaaaggg gacaaaacaa ggagaggcca  540
ccacctgttc ccaacccaga ctatgagccc atccggaaag gccagcggga cctgtattct  600
ggcctgaatc agagacgcat ctga                                        624

SEQ ID NO: 32          moltype = AA  length = 207
FEATURE                Location/Qualifiers
source                 1..207
                       mol_type = protein
                       organism = Homo sapiens
SEQUENCE: 32
MQSGTHWRVL GLCLLSVGVW GQDGNEEMGG ITQTPYKVSI SGTTVILTCP QYPGSEILWQ  60
HNDKNIGGDE DDKNIGSDED HLSLKEFSEL EQSGYYVCYP RGSKPEDANF YLYLRARVCE  120
NCMEMDVMSV ATIVIVDICI TGGLLLLVYY WSKNRKAKAK PVTRGAGAGG RQRGQNKERP  180
PPVPNPDYEP IRKGQRDLYS GLNQRRI                                      207

SEQ ID NO: 33          moltype = AA  length = 523
FEATURE                Location/Qualifiers
source                 1..523
                       mol_type = protein
                       organism = synthetic construct
SEQUENCE: 33
MGWSCIILFL VATATGVHSQ VQLVQSGAEV KKPGASVKVS CKASGYTFTD YEMHWIRQPP  60
GQGLEWIGAI DPKTGDTAYS QKFKGRVTLT ADKSTSTAYM ELSSLTSEDT AVYYCTRFYS  120
YTYWGQGTLV TVSSGGGGSG GGGSGGGGSD IVMTQSPLSL PVTPGEPASI SCRSSQSLVH  180
SNRNTYLHWY QQKPGQAPRL LIYKVSNRFS GVPDRFSGSG SGTDFTLKIS RVEAEDVGVY  240
YCSQNTHVPP TFGQGTKLEI KGGGGSQAVV TQESALTTSP GETVTLTCRS STGAVTTSNY  300
ANWVQEKPDH LFTGLIGGTN KRAPGVPARF SGSLIGDKAA LTITGAQTED EAIYFCALWY  360
SNLWVFGGGT KLTVLGGGGS GGGGSGGGGS EVKLLESGGG LVQPKGSLKL SCAASGFTFN  420
TYAMNWVRQA PGKGLEWVAR IRSKYNNYAT YYADSVKDRF TISRDDSQSI LYLQMNNLKT  480
EDTAMYYCVR HGNFGNSYVS WFAYWGQGTL VTVSAHHHHH HHH                    523

SEQ ID NO: 34          moltype = AA  length = 753
FEATURE                Location/Qualifiers
source                 1..753
                       mol_type = protein
                       organism = synthetic construct
SEQUENCE: 34
MGWSCIILFL VATATGVHSQ VQLVQSGAEV KKPGASVKVS CKASGYTFTD YEMHWIRQPP  60
GQGLEWIGAI DPKTGDTAYS QKFKGRVTLT ADKSTSTAYM ELSSLTSEDT AVYYCTRFYS  120
YTYWGQGTLV TVSSGGGGSG GGGSGGGGSD IVMTQSPLSL PVTPGEPASI SCRSSQSLVH  180
SNRNTYLHWY QQKPGQAPRL LIYKVSNRFS GVPDRFSGSG SGTDFTLKIS RVEAEDVGVY  240
YCSQNTHVPP TFGQGTKLEI KGGGGSQAVV TQESALTTSP GETVTLTCRS STGAVTTSNY  300
ANWVQEKPDH LFTGLIGGTN KRAPGVPARF SGSLIGDKAA LTITGAQTED EAIYFCALWY  360
SNLWVFGGGT KLTVLGGGGS GGGGSGGGGS EVKLLESGGG LVQPKGSLKL SCAASGFTFN  420
TYAMNWVRQA PGKGLEWVAR IRSKYNNYAT YYADSVKDRF TISRDDSQSI LYLQMNNLKT  480
EDTAMYYCVR HGNFGNSYVS WFAYWGQGTL VTVSAEPKSS DKTHTCPPCP APEAAGGPSV  540
```

-continued

```
FLFPPKPKDT LMISRTPEVT CVVVDVSHED PEVKFNWYVD GVEVHNAKTK PREEQYASTY  600
RVVSVLTVLH QDWLNGKEYK CKVSNKALPA PIEKTISKAK GQPREPQVCT LPPSRDELTK  660
NQVSLWCLVK GFYPSDIAVE WESNGQPENN YKTTPPVLDS DGSFFLYSKL TVDKSRWQQG  720
NVFSCSVMHE ALHNHYTQKS LSLSPHHHHH HHH                              753

SEQ ID NO: 35          moltype = AA  length = 257
FEATURE                Location/Qualifiers
source                 1..257
                       mol_type = protein
                       organism = synthetic construct
SEQUENCE: 35
MGWSCIILFL VATATGVHSE PKSSDKTHTC PPCPAPEAAG GPSVFLFPPK PKDTLMISRT  60
PEVTCVVVDV SHEDPEVKFN WYVDGVEVHN AKTKPREEQY ASTYRVVSVL TVLHQDWLNG  120
KEYKCKVSNK ALPAPIEKTI SKAKGQPREP QVYTLPPSRC ELTKNQVSLS CAVKGFYPSD  180
IAVEWESNGQ PENNYKTTPP VLDSDGSFFL VSKLTVDKSR WQQGNVFSCS VMHEALHNHY  240
TQKSLSLSPD YKDDDDK                                                257

SEQ ID NO: 36          moltype = AA  length = 514
FEATURE                Location/Qualifiers
source                 1..514
                       mol_type = protein
                       organism = synthetic construct
SEQUENCE: 36
MGWSCIILFL VATATGVHSQ VQLVQSGAEV KKPGASVKVS CKASGYTFTD YEMHWIRQPP  60
GQGLEWIGAI DPKTGDTAYS QKFKGRVTLT ADKSTSTAYM ELSSLTSEDT AVYYCTRFYS  120
YTYWGQGTLV TVSSGGGGSG GGGSGGGGSD IVMTQSPLSL PVTPGEPASI SCRSSQSLVH  180
SNRNTYLHWY QQKPGQAPRL LIYKVSNRFS GVPDRFSGSG SGTDFTLKIS RVEAEDVGVY  240
YCSQNTHVPP TFGQGTKLEI KGGGGSGGGG SGGGGSEPKS SDKTHTCPPC PAPEAAGGPS  300
VFLFPPKPKD TLMISRTPEV TCVVVDVSHE DPEVKFNWYV DGVEVHNAKT KPREEQYAST  360
YRVVSVLTVL HQDWLNGKEY KCKVSNKALP APIEKTISKA KGQPREPQVY TLPPSRCELT  420
KNQVSLSCAV KGFYPSDIAV EWESNGQPEN NYKTTPPVLD SDGSFFLVSK LTVDKSRWQQ  480
GNVFSCSVMH EALHNHYTQK SLSLSPDYKD DDDK                              514

SEQ ID NO: 37          moltype = AA  length = 629
FEATURE                Location/Qualifiers
source                 1..629
                       mol_type = protein
                       organism = synthetic construct
SEQUENCE: 37
MGWSCIILFL VATATGVHSQ VQLVQSGAEV KKPGASVKVS CKASGYTFTD YEMHWIRQPP  60
GQGLEWIGAI DPKTGDTAYS QKFKGRVTLT ADKSTSTAYM ELSSLTSEDT AVYYCTRFYS  120
YTYWGQGTLV TVSSGGGGSG GGGSGGGGSD IVMTQSPLSL PVTPGEPASI SCRSSQSLVH  180
SNRNTYLHWY QQKPGQAPRL LIYKVSNRFS GVPDRFSGSG SGTDFTLKIS RVEAEDVGVY  240
YCSQNTHVPP TFGQGTKLEI KGGGGSEVKL LESGGGLVQP KGSLKLSCAA SGFTFNTYAM  300
NWVRQAPGKG LEWVARIRSK YNNYATYYAD SVKDRFTISR DDSQSILYLQ MNNLKTEDTA  360
MYYCVRHGNF GNSYVSWFAY WGQGTLVTVS AEPKSSDKTH TCPPCPAPEA AGGPSVFLFP  420
PKPKDTLMIS RTPEVTCVVV DVSHEDPEVK FNWYVDGVEV HNAKTKPREE QYASTYRVVS  480
VLTVLHQDWL NGKEYKCKVS NKALPAPIEK TISKAKGQPR EPQVCTLPPS RDELTKNQVS  540
LWCLVKGFYP SDIAVEWESN GQPENNYKTT PPVLDSDGSF FLYSKLTVDK SRWQQGNVFS  600
CSVMHEALHN HYTQKSLSLS PHHHHHHHH                                   629

SEQ ID NO: 38          moltype = AA  length = 613
FEATURE                Location/Qualifiers
source                 1..613
                       mol_type = protein
                       organism = synthetic construct
SEQUENCE: 38
MGWSCIILFL VATATGVHSQ VQLVQSGAEV KKPGASVKVS CKASGYTFTD YEMHWIRQPP  60
GQGLEWIGAI DPKTGDTAYS QKFKGRVTLT ADKSTSTAYM ELSSLTSEDT AVYYCTRFYS  120
YTYWGQGTLV TVSSGGGGSG GGGSGGGGSD IVMTQSPLSL PVTPGEPASI SCRSSQSLVH  180
SNRNTYLHWY QQKPGQAPRL LIYKVSNRFS GVPDRFSGSG SGTDFTLKIS RVEAEDVGVY  240
YCSQNTHVPP TFGQGTKLEI KGGGGSQAVV TQESALTTSP GETVTLTCRS STGAVTTSNY  300
ANWVQEKPDH LFTGLIGGTN KRAPGVPARF SGSLIGDKAA LTITGAQTED EAIYFCALWY  360
SNLWVFGGGT KLTVLEPKSS DKTHTCPPCP APEAAGGPSV FLFPPKPKDT LMISRTPEVT  420
CVVVDVSHED PEVKFNWYVD GVEVHNAKTK PREEQYASTY RVVSVLTVLH QDWLNGKEYK  480
CKVSNKALPA PIEKTISKAK GQPREPQVYT LPPSRCELTK NQVSLSCAVK GFYPSDIAVE  540
WESNGQPENN YKTTPPVLDS DGSFFLVSKL TVDKSRWQQG NVFSCSVMHE ALHNHYTQKS  600
LSLSPDYKDD DDK                                                    613

SEQ ID NO: 39          moltype = AA  length = 470
FEATURE                Location/Qualifiers
source                 1..470
                       mol_type = protein
                       organism = synthetic construct
SEQUENCE: 39
MGWSCIILFL VATATGVHSQ VQLVQSGAEV KKPGASVKVS CKASGYTFTD YEMHWIRQPP  60
GQGLEWIGAI DPKTGDTAYS QKFKGRVTLT ADKSTSTAYM ELSSLTSEDT AVYYCTRFYS  120
YTYWGQGTLV TVSSASTKGP SVFPLAPSSK STSGGTAALG CLVKDYFPEP VTVSWNSGAL  180
TSGVHTFPAV LQSSGLYSLS SVVTVPSSSL GTQTYICNVN HKPSNTKVDK KVEPKSCDKT  240
```

-continued

```
HTCPPCPAPE AAGGPSVFLF PPKPKDTLMI SRTPEVTCVV VDVSHEDPEV KFNWYVDGVE  300
VHNAKTKPRE EQYASTYRVV SVLTVLHQDW LNGKEYKCKV SNKALPAPIE KTISKAKGQP  360
REPQVYTLPP SRCELTKNQV SLSCAVKGFY PSDIAVEWES NGQPENNYKT TPPVLDSDGS  420
FFLVSKLTVD KSRWQQGNVF SCSVMHEALH NHYTQKSLSL SPDYKDDDDK             470

SEQ ID NO: 40          moltype = AA  length = 238
FEATURE                Location/Qualifiers
source                 1..238
                       mol_type = protein
                       organism = synthetic construct
SEQUENCE: 40
MGWSCIILFL VATATGVHSD IVMTQSPLSL PVTPGEPASI SCRSSQSLVH SNRNTYLHWY  60
QQKPGQAPRL LIYKVSNRFS GVPDRFSGSG SGTDFTLKIS RVEAEDVGVY YCSQNTHVPP  120
TFGQGTKLEI KRTVAAPSVF IFPPSDEQLK SGTASVVCLL NNFYPREAKV QWKVDNALQS  180
GNSQESVTEQ DSKDSTYSLS STLTLSKADY EKHKVYACEV THQGLSSPVT KSFNRGEC    238

SEQ ID NO: 41          moltype = AA  length = 470
FEATURE                Location/Qualifiers
source                 1..470
                       mol_type = protein
                       organism = synthetic construct
SEQUENCE: 41
MGWSCIILFL VATATGVHSQ VQLVQSGAEV KKPGASVKVS CKASGYTFTD YEMHWIRQPP  60
GQGLEWIGAI DPKTGDTAYS QKFKGRVTLT ADKSTSTAYM ELSSLTSEDT AVYYCTRFYS  120
YTYWGQGTLV TVSSASTKGP SVFPLAPSSK STSGGTAALG CLVKDYFPEP VTVSWNSGAL  180
TSGVHTFPAV LQSSGLYSLS SVVTVPSSSL GTQTYICNVN HKPSNTKVDK KVEPKSCDKT  240
HTCPPCPAPE AAGGPSVFLF PPKPKDTLMI SRTPEVTCVV VDVSHEDPEV KFNWYVDGVE  300
VHNAKTKPRE EQYASTYRVV SVLTVLHQDW LNGKEYKCKV SNKALPAPIE KTISKAKGQP  360
REPQVCTLPP SRDELTKNQV SLWCLVKGFY PSDIAVEWES NGQPENNYKT TPPVLDSDGS  420
FFLYSKLTVD KSRWQQGNVF SCSVMHEALH NHYTQKSLSL SPHHHHHHHH             470

SEQ ID NO: 42          moltype = AA  length = 734
FEATURE                Location/Qualifiers
source                 1..734
                       mol_type = protein
                       organism = synthetic construct
SEQUENCE: 42
MGWSCIILFL VATATGVHSQ AVVTQESALT TSPGETVTLT CRSSTGAVTT SNYANWVQEK  60
PDHLFTGLIG GTNKRAPGVP ARFSGSLIGD KAALTITGAQ TEDEAIYFCA LWYSNLWVFG  120
GGTKLTVLGG GGSGGGGSGG GGSEVKLLES GGGLVQPKGS LKLSCAASGF TFNTYAMNWV  180
RQAPGKGLEW VARIRSKYNN YATYYADSVK DRFTISRDDS QSILYLQMNN LKTEDTAMYY  240
CVRHGNFGNS YVSWFAYWGQ GTLVTVSAGG GGSGGGGSGG GGSQVQLVQS GAEVKKPGAS  300
VKVSCKASGY TFTDYEMHWI RQPPGQGLEW IGAIDPKTGD TAYSQKFKGR VTLTADKSTS  360
TAYMELSSLT SEDTAVYYCT RFYSYTYWGQ GTLVTVSSAS TKGPSVFPLA PSSKSTSGGT  420
AALGCLVKDY FPEPVTVSWN SGALTSGVHT FPAVLQSSGL YSLSSVVTVP SSSLGTQTYI  480
CNVNHKPSNT KVDKKVEPKS CDKTHTCPPC PAPEAAGGPS VFLFPPKPKD TLMISRTPEV  540
TCVVVDVSHE DPEVKFNWYV DGVEVHNAKT KPREEQYAST YRVVSVLTVL HQDWLNGKEY  600
KCKVSNKALP APIEKTISKA KGQPREPQVY TLPPSRCELT KNQVSLSCAV KGFYPSDIAV  660
EWESNGQPEN NYKTTPPVLD SDGSFFLVSK LTVDKSRWQQ GNVFSCSVMH EALHNHYTQK  720
SLSLSPDYKD DDDK                                                    734

SEQ ID NO: 43          moltype = AA  length = 462
FEATURE                Location/Qualifiers
source                 1..462
                       mol_type = protein
                       organism = synthetic construct
SEQUENCE: 43
MGWSCIILFL VATATGVHSQ VQLVQSGAEV KKPGASVKVS CKASGYTFTD YEMHWIRQPP  60
GQGLEWIGAI DPKTGDTAYS QKFKGRVTLT ADKSTSTAYM ELSSLTSEDT AVYYCTRFYS  120
YTYWGQGTLV TVSSASTKGP SVFPLAPSSK STSGGTAALG CLVKDYFPEP VTVSWNSGAL  180
TSGVHTFPAV LQSSGLYSLS SVVTVPSSSL GTQTYICNVN HKPSNTKVDK KVEPKSCDKT  240
HTCPPCPAPE AAGGPSVFLF PPKPKDTLMI SRTPEVTCVV VDVSHEDPEV KFNWYVDGVE  300
VHNAKTKPRE EQYASTYRVV SVLTVLHQDW LNGKEYKCKV SNKALPAPIE KTISKAKGQP  360
REPQVYTLPP SRDELTKNQV SLTCLVKGFY PSDIAVEWES NGQPENNYKT TPPVLDSDGS  420
FFLYSKLTVD KSRWQQGNVF SCSVMHEALH NHYTQKSLSL SP                     462

SEQ ID NO: 44          moltype = AA  length = 246
FEATURE                Location/Qualifiers
source                 1..246
                       mol_type = protein
                       organism = synthetic construct
SEQUENCE: 44
MGWSCIILFL VATATGVHSD IVMTQSPLSL PVTPGEPASI SCRSSQSLVH SNRNTYLHWY  60
QQKPGQAPRL LIYKVSNRFS GVPDRFSGSG SGTDFTLKIS RVEAEDVGVY YCSQNTHVPP  120
TFGQGTKLEI KRTVAAPSVF IFPPSDEQLK SGTASVVCLL NNFYPREAKV QWKVDNALQS  180
GNSQESVTEQ DSKDSTYSLS STLTLSKADY EKHKVYACEV THQGLSSPVT KSFNRGECHH  240
HHHHHH                                                             246

SEQ ID NO: 45          moltype = AA  length = 505
```

```
FEATURE                Location/Qualifiers
source                 1..505
                       mol_type = protein
                       organism = synthetic construct
SEQUENCE: 45
MGWSCIILFL VATATGVHSD IVMTQSPLSL PVTPGEPASI SCRSSQSLVH SNRNTYLHWY  60
QQKPGQAPRL LIYKVSNRFS GVPDRFSGSG SGTDFTLKIS RVEAEDVGVY YCSQNTHVPP  120
TFGQGTKLEI KRTVAAPSVF IFPPSDEQLK SGTASVVCLL NNFYPREAKV QWKVDNALQS  180
GNSQESVTEQ DSKDSTYSLS STLTLSKADY EKHKVYACEV THQGLSSPVT KSFNRGECGG  240
GGSGGGGSQA VVTQESALTT SPGETVTLTC RSSTGAVTTS NYANWVQEKP DHLFTGLIGG  300
TNKRAPGVPA RFSGSLIGDK AALTITGAQT EDEAIYFCAL WYSNLWVFGG GTKLTVLGGG  360
GSGGGGSGGG GSEVKLLESG GGLVQPKGSL KLSCAASGFT FNTYAMNWVR QAPGKGLEWV  420
ARIRSKYNNY ATYYADSVKD RFTISRDDSQ SILYLQMNNL KTEDTAMYYC VRHGNFGNSY  480
VSWFAYWGQG TLVTVSADYK DDDDK                                        505

SEQ ID NO: 46          moltype = AA  length = 729
FEATURE                Location/Qualifiers
source                 1..729
                       mol_type = protein
                       organism = synthetic construct
SEQUENCE: 46
MGWSCIILFL VATATGVHSQ VQLVQSGAEV KKPGASVKVS CKASGYTFTD YEMHWIRQPP  60
GQGLEWIGAI DPKTGDTAYS QKFKGRVTLT ADKSTSTAYM ELSSLTSEDT AVYYCTRFYS  120
YTYWGQGTLV TVSSASTKGP SVFPLAPSSK STSGGTAALG CLVKDYFPEP VTVSWNSGAL  180
TSGVHTFPAV LQSSGLYSLS SVVTVPSSSL GTQTYICNVN HKPSNTKVDK KVEPKSCDKT  240
HTCPPCPAPE AAGGPSVFLF PPKPKDTLMI SRTPEVTCVV VDVSHEDPEV KFNWYVDGVE  300
VHNAKTKPRE EQYASTYRVV SVLTVLHQDW LNGKEYKCKV SNKALPAPIE KTISKAKGQP  360
REPQVYTLPP SRCELTKNQV SLSCAVKGFY PSDIAVEWES NGQPENNYKT TPPVLDSDGS  420
FFLVSKLTVD KSRWQQGNVF SCSVMHEALH NHYTQKSLSL SPGGGGSGGG GSQAVVTQES  480
ALTTSPGETV TLTCRSSTGA VTTSNYANWV QEKPDHLFTG LIGGTNKRAP GVPARFSGSL  540
IGDKAALTIT GAQTEDEAIY FCALWYSNLW VFGGGTKLTV LGGGGSGGGG SGGGGSEVKL  600
LESGGGLVQP KGSLKLSCAA SGFTFNTYAM NWVRQAPGKG LEWVARIRSK YNNYATYYAD  660
SVKDRFTISR DDSQSILYLQ MNNLKTEDTA MYYCVRHGNF GNSYVSWFAY WGQGTLVTVS  720
ADYKDDDDK                                                          729

SEQ ID NO: 47          moltype = AA  length = 729
FEATURE                Location/Qualifiers
source                 1..729
                       mol_type = protein
                       organism = synthetic construct
SEQUENCE: 47
MGWSCIILFL VATATGVHSQ VQLVQSGAEV KKPGASVKVS CKASGYTFTD YEMHWIRQPP  60
GQGLEWIGAI DPKTGDTAYS QKFKGRVTLT ADKSTSTAYM ELSSLTSEDT AVYYCTRFYS  120
YTYWGQGTLV TVSSASTKGP SVFPLAPSSK STSGGTAALG CLVKDYFPEP VTVSWNSGAL  180
TSGVHTFPAV LQSSGLYSLS SVVTVPSSSL GTQTYICNVN HKPSNTKVDK KVEPKSCDKT  240
HTCPPCPAPE LLGGPSVFLF PPKPKDTLMI SRTPEVTCVV VDVSHEDPEV KFNWYVDGVE  300
VHNAKTKPRE EQYNSTYRVV SVLTVLHQDW LNGKEYKCKV SNKALPAPIE KTISKAKGQP  360
REPQVYTLPP SRCELTKNQV SLSCAVKGFY PSDIAVEWES NGQPENNYKT TPPVLDSDGS  420
FFLVSKLTVD KSRWQQGNVF SCSVMHEALH NHYTQKSLSL SPGGGGSGGG GSQAVVTQES  480
ALTTSPGETV TLTCRSSTGA VTTSNYANWV QEKPDHLFTG LIGGTNKRAP GVPARFSGSL  540
IGDKAALTIT GAQTEDEAIY FCALWYSNLW VFGGGTKLTV LGGGGSGGGG SGGGGSEVKL  600
LESGGGLVQP KGSLKLSCAA SGFTFNTYAM NWVRQAPGKG LEWVARIRSK YNNYATYYAD  660
SVKDRFTISR DDSQSILYLQ MNNLKTEDTA MYYCVRHGNF GNSYVSWFAY WGQGTLVTVS  720
ADYKDDDDK                                                          729

SEQ ID NO: 48          moltype = AA  length = 470
FEATURE                Location/Qualifiers
source                 1..470
                       mol_type = protein
                       organism = synthetic construct
SEQUENCE: 48
MGWSCIILFL VATATGVHSQ VQLVQSGAEV KKPGASVKVS CKASGYTFTD YEMHWIRQPP  60
GQGLEWIGAI DPKTGDTAYS QKFKGRVTLT ADKSTSTAYM ELSSLTSEDT AVYYCTRFYS  120
YTYWGQGTLV TVSSASTKGP SVFPLAPSSK STSGGTAALG CLVKDYFPEP VTVSWNSGAL  180
TSGVHTFPAV LQSSGLYSLS SVVTVPSSSL GTQTYICNVN HKPSNTKVDK KVEPKSCDKT  240
HTCPPCPAPE LLGGPSVFLF PPKPKDTLMI SRTPEVTCVV VDVSHEDPEV KFNWYVDGVE  300
VHNAKTKPRE EQYNSTYRVV SVLTVLHQDW LNGKEYKCKV SNKALPAPIE KTISKAKGQP  360
REPQVCTLPP SRDELTKNQV SLWCLVKGFY PSDIAVEWES NGQPENNYKT TPPVLDSDGS  420
FFLYSKLTVD KSRWQQGNVF SCSVMHEALH NHYTQKSLSL SPHHHHHHHH             470

SEQ ID NO: 49          moltype = AA  length = 600
FEATURE                Location/Qualifiers
source                 1..600
                       mol_type = protein
                       organism = synthetic construct
SEQUENCE: 49
MGWSCIILFL VATATGVHSQ VQLVQSGAEV KKPGASVKVS CKASGYTFTD YEMHWIRQPP  60
GQGLEWIGAI DPKTGDTAYS QKFKGRVTLT ADKSTSTAYM ELSSLTSEDT AVYYCTRFYS  120
YTYWGQGTLV TVSSASTKGP SVFPLAPSSK STSGGTAALG CLVKDYFPEP VTVSWNSGAL  180
```

```
TSGVHTFPAV LQSSGLYSLS SVVTVPSSSL GTQTYICNVN HKPSNTKVDK KVEPKSCDKT  240
HTCPPCPAPE AAGGPSVFLF PPKPKDTLMI SRTPEVTCVV VDVSHEDPEV KFNWYVDGVE  300
VHNAKTKPRE EQYASTYRVV SVLTVLHQDW LNGKEYKCKV SNKALPAPIE KTISKAKGQP  360
REPQVYTLPP SRCELTKNQV SLSCAVKGFY PSDIAVEWES NGQPENNYKT TPPVLDSDGS  420
FFLVSKLTVD KSRWQQGNVF SCSVMHEALH NHYTQKSLSL SPGGGGSEVK LLESGGGLVQ  480
PKGSLKLSCA ASGFTFNTYA MNWVRQAPGK GLEWVARIRS KYNNYATYYA DSVKDRFTIS  540
RDDSQSILYL QMNNLKTEDT AMYYCVRHGN FGNSYVSWFA YWGQGTLVTV SADYKDDDDK  600

SEQ ID NO: 50          moltype = AA  length = 584
FEATURE                Location/Qualifiers
source                 1..584
                       mol_type = protein
                       organism = synthetic construct
SEQUENCE: 50
MGWSCIILFL VATATGVHSQ VQLVQSGAEV KKPGASVKVS CKASGYTFTD YEMHWIRQPP  60
GQGLEWIGAI DPKTGDTAYS QKFKGRVTLT ADKSTSTAYM ELSSLTSEDT AVYYCTRFYS  120
YTYWGQGTLV TVSSASTKGP SVFPLAPSSK STSGGTAALG CLVKDYFPEP VTVSWNSGAL  180
TSGVHTFPAV LQSSGLYSLS SVVTVPSSSL GTQTYICNVN HKPSNTKVDK KVEPKSCDKT  240
HTCPPCPAPE AAGGPSVFLF PPKPKDTLMI SRTPEVTCVV VDVSHEDPEV KFNWYVDGVE  300
VHNAKTKPRE EQYASTYRVV SVLTVLHQDW LNGKEYKCKV SNKALPAPIE KTISKAKGQP  360
REPQVCTLPP SRDELTKNQV SLWCLVKGFY PSDIAVEWES NGQPENNYKT TPPVLDSDGS  420
FFLYSKLTVD KSRWQQGNVF SCSVMHEALH NHYTQKSLSL SPGGGGSQAV VTQESALTTS  480
PGETVTLTCR SSTGAVTTSN YANWVQEKPD HLFTGLIGGT NKRAPGVPAR FSGSLIGDKA  540
ALTITGAQTE DEAIYFCALW YSNLWVFGGG TKLTVLHHHH HHHH                  584

SEQ ID NO: 51          moltype = AA  length = 605
FEATURE                Location/Qualifiers
source                 1..605
                       mol_type = protein
                       organism = synthetic construct
SEQUENCE: 51
MGWSCIILFL VATATGVHSQ VQLVQSGAEV KKPGASVKVS CKASGYTFTD YEMHWIRQPP  60
GQGLEWIGAI DPKTGDTAYS QKFKGRVTLT ADKSTSTAYM ELSSLTSEDT AVYYCTRFYS  120
YTYWGQGTLV TVSSASTKGP SVFPLAPSSK STSGGTAALG CLVKDYFPEP VTVSWNSGAL  180
TSGVHTFPAV LQSSGLYSLS SVVTVPSSSL GTQTYICNVN HKPSNTKVDK KVEPKSCDKT  240
HTCPPCPAPE AAGGPSVFLF PPKPKDTLMI SRTPEVTCVV VDVSHEDPEV KFNWYVDGVE  300
VHNAKTKPRE EQYASTYRVV SVLTVLHQDW LNGKEYKCKV SNKALPAPIE KTISKAKGQP  360
REPQVYTLPP SRCELTKNQV SLSCAVKGFY PSDIAVEWES NGQPENNYKT TPPVLDSDGS  420
FFLVSKLTVD KSRWQQGNVF SCSVMHEALH NHYTQKSLSL SPGGGGSGGG GSEVKLLESG  480
GGLVQPKGSL KLSCAASGFT FNTYAMNWVR QAPGKGLEWV ARIRSKYNNY ATYYADSVKD  540
RFTISRDDSQ SILYLQMNNL KTEDTAMYYC VRHGNFGNSY VSWFAYWGQG TLVTVSADYK  600
DDDDK                                                             605

SEQ ID NO: 52          moltype = AA  length = 589
FEATURE                Location/Qualifiers
source                 1..589
                       mol_type = protein
                       organism = synthetic construct
SEQUENCE: 52
MGWSCIILFL VATATGVHSQ VQLVQSGAEV KKPGASVKVS CKASGYTFTD YEMHWIRQPP  60
GQGLEWIGAI DPKTGDTAYS QKFKGRVTLT ADKSTSTAYM ELSSLTSEDT AVYYCTRFYS  120
YTYWGQGTLV TVSSASTKGP SVFPLAPSSK STSGGTAALG CLVKDYFPEP VTVSWNSGAL  180
TSGVHTFPAV LQSSGLYSLS SVVTVPSSSL GTQTYICNVN HKPSNTKVDK KVEPKSCDKT  240
HTCPPCPAPE AAGGPSVFLF PPKPKDTLMI SRTPEVTCVV VDVSHEDPEV KFNWYVDGVE  300
VHNAKTKPRE EQYASTYRVV SVLTVLHQDW LNGKEYKCKV SNKALPAPIE KTISKAKGQP  360
REPQVCTLPP SRDELTKNQV SLWCLVKGFY PSDIAVEWES NGQPENNYKT TPPVLDSDGS  420
FFLYSKLTVD KSRWQQGNVF SCSVMHEALH NHYTQKSLSL SPGGGGSGGG GSQAVVTQES  480
ALTTSPGETV TLTCRSSTGA VTTSNYANWV QEKPDHLFTG LIGGTNKRAP GVPARFSGSL  540
IGDKAALTIT GAQTEDEAIY FCALWYSNLW VFGGGTKLTV LHHHHHHHH             589

SEQ ID NO: 53          moltype = AA  length = 610
FEATURE                Location/Qualifiers
source                 1..610
                       mol_type = protein
                       organism = synthetic construct
SEQUENCE: 53
MGWSCIILFL VATATGVHSQ VQLVQSGAEV KKPGASVKVS CKASGYTFTD YEMHWIRQPP  60
GQGLEWIGAI DPKTGDTAYS QKFKGRVTLT ADKSTSTAYM ELSSLTSEDT AVYYCTRFYS  120
YTYWGQGTLV TVSSASTKGP SVFPLAPSSK STSGGTAALG CLVKDYFPEP VTVSWNSGAL  180
TSGVHTFPAV LQSSGLYSLS SVVTVPSSSL GTQTYICNVN HKPSNTKVDK KVEPKSCDKT  240
HTCPPCPAPE AAGGPSVFLF PPKPKDTLMI SRTPEVTCVV VDVSHEDPEV KFNWYVDGVE  300
VHNAKTKPRE EQYASTYRVV SVLTVLHQDW LNGKEYKCKV SNKALPAPIE KTISKAKGQP  360
REPQVYTLPP SRCELTKNQV SLSCAVKGFY PSDIAVEWES NGQPENNYKT TPPVLDSDGS  420
FFLVSKLTVD KSRWQQGNVF SCSVMHEALH NHYTQKSLSL SPGGGGSGGG GSGGGGSEVK  480
LLESGGGLVQ PKGSLKLSCA ASGFTFNTYA MNWVRQAPGK GLEWVARIRS KYNNYATYYA  540
DSVKDRFTIS RDDSQSILYL QMNNLKTEDT AMYYCVRHGN FGNSYVSWFA YWGQGTLVTV  600
SADYKDDDDK                                                        610

SEQ ID NO: 54          moltype = AA  length = 594
```

```
FEATURE                 Location/Qualifiers
source                  1..594
                        mol_type = protein
                        organism = synthetic construct
SEQUENCE: 54
MGWSCIILFL VATATGVHSQ VQLVQSGAEV KKPGASVKVS CKASGYTFTD YEMHWIRQPP  60
GQGLEWIGAI DPKTGDTAYS QKFKGRVTLT ADKSTSTAYM ELSSLTSEDT AVYYCTRFYS  120
YTYWGQGTLV TVSSASTKGP SVFPLAPSSK STSGGTAALG CLVKDYFPEP VTVSWNSGAL  180
TSGVHTFPAV LQSSGLYSLS SVVTVPSSSL GTQTYICNVN HKPSNTKVDK KVEPKSCDKT  240
HTCPPCPAPE AAGGPSVFLF PPKPKDTLMI SRTPEVTCVV VDVSHEDPEV KFNWYVDGVE  300
VHNAKTKPRE EQYASTYRVV SVLTVLHQDW LNGKEYKCKV SNKALPAPIE KTISKAKGQP  360
REPQVCTLPP SRDELTKNQV SLWCLVKGFY PSDIAVEWES NGQPENNYKT TPPVLDSDGS  420
FFLYSKLTVD KSRWQQGNVF SCSVMHEALH NHYTQKSLSL SPGGGGSGGG GSGGGGSQAV  480
VTQESALTTS PGETVTLTCR SSTGAVTTSN YANWVQEKPD HLFTGLIGGT NKRAPGVPAR  540
FSGSLIGDKA ALTITGAQTE DEAIYFCALW YSNLWVFGGG TKLTVLHHHH HHHH        594

SEQ ID NO: 55           moltype = AA  length = 615
FEATURE                 Location/Qualifiers
source                  1..615
                        mol_type = protein
                        organism = synthetic construct
SEQUENCE: 55
MGWSCIILFL VATATGVHSQ VQLVQSGAEV KKPGASVKVS CKASGYTFTD YEMHWIRQPP  60
GQGLEWIGAI DPKTGDTAYS QKFKGRVTLT ADKSTSTAYM ELSSLTSEDT AVYYCTRFYS  120
YTYWGQGTLV TVSSASTKGP SVFPLAPSSK STSGGTAALG CLVKDYFPEP VTVSWNSGAL  180
TSGVHTFPAV LQSSGLYSLS SVVTVPSSSL GTQTYICNVN HKPSNTKVDK KVEPKSCDKT  240
HTCPPCPAPE AAGGPSVFLF PPKPKDTLMI SRTPEVTCVV VDVSHEDPEV KFNWYVDGVE  300
VHNAKTKPRE EQYASTYRVV SVLTVLHQDW LNGKEYKCKV SNKALPAPIE KTISKAKGQP  360
REPQVYTLPP SRCELTKNQV SLSCAVKGFY PSDIAVEWES NGQPENNYKT TPPVLDSDGS  420
FFLVSKLTVD KSRWQQGNVF SCSVMHEALH NHYTQKSLSL SPGGGGSGGG GSGGGGSGGG  480
GSEVKLLESG GGLVQPKGSL KLSCAASGFT FNTYAMNWVR QAPGKGLEWV ARIRSKYNNY  540
ATYYADSVKD RFTISRDDSQ SILYLQMNNL KTEDTAMYYC VRHGNFGNSY VSWFAYWGQG  600
TLVTVSADYK DDDDK                                                  615

SEQ ID NO: 56           moltype = AA  length = 599
FEATURE                 Location/Qualifiers
source                  1..599
                        mol_type = protein
                        organism = synthetic construct
SEQUENCE: 56
MGWSCIILFL VATATGVHSQ VQLVQSGAEV KKPGASVKVS CKASGYTFTD YEMHWIRQPP  60
GQGLEWIGAI DPKTGDTAYS QKFKGRVTLT ADKSTSTAYM ELSSLTSEDT AVYYCTRFYS  120
YTYWGQGTLV TVSSASTKGP SVFPLAPSSK STSGGTAALG CLVKDYFPEP VTVSWNSGAL  180
TSGVHTFPAV LQSSGLYSLS SVVTVPSSSL GTQTYICNVN HKPSNTKVDK KVEPKSCDKT  240
HTCPPCPAPE AAGGPSVFLF PPKPKDTLMI SRTPEVTCVV VDVSHEDPEV KFNWYVDGVE  300
VHNAKTKPRE EQYASTYRVV SVLTVLHQDW LNGKEYKCKV SNKALPAPIE KTISKAKGQP  360
REPQVCTLPP SRDELTKNQV SLWCLVKGFY PSDIAVEWES NGQPENNYKT TPPVLDSDGS  420
FFLYSKLTVD KSRWQQGNVF SCSVMHEALH NHYTQKSLSL SPGGGGSGGG GSGGGGSGGG  480
GSQAVVTQES ALTTSPGETV TLTCRSSTGA VTTSNYANWV QEKPDHLFTG LIGGTNKRAP  540
GVPARFSGSL IGDKAALTIT GAQTEDEAIY FCALWYSNLW VFGGGTKLTV LHHHHHHHH   599

SEQ ID NO: 57           moltype = AA  length = 610
FEATURE                 Location/Qualifiers
source                  1..610
                        mol_type = protein
                        organism = synthetic construct
SEQUENCE: 57
MGWSCIILFL VATATGVHSQ VQLVQSGAEV KKPGASVKVS CKASGYTFTD YEMHWIRQPP  60
GQGLEWIGAI DPKTGDTAYS QKFKGRVTLT ADKSTSTAYM ELSSLTSEDT AVYYCTRFYS  120
YTYWGQGTLV TVSSASTKGP SVFPLAPSSK STSGGTAALG CLVKDYFPEP VTVSWNSGAL  180
TSGVHTFPAV LQSSGLYSLS SVVTVPSSSL GTQTYICNVN HKPSNTKVDK KVEPKSCDKT  240
HTCPPCPAPE AAGGPSVFLF PPKPKDTLMI SRTPEVTCVV VDVSHEDPEV KFNWYVDGVE  300
VHNAKTKPRE EQYASTYRVV SVLTVLHQDW LNGKEYKCKV SNKALPAPIE KTISKAKGQP  360
REPQVYTLPP SRCELTKNQV SLSCAVKGFY PSDIAVEWES NGQPENNYKT TPPVLDSDGS  420
FFLVSKLTVD KSRWQQGNVF SCSVMHEALH NHYTQKSLSL SPGGGGSGGG GSGGGGSEVK  480
LLESGGGLVQ PKGSLKLSCA ASGFTFNTYA MNWVRQAPGK CLEWVARIRS KYNNYATYYA  540
DSVKDRFTIS RDDSQSILYL QMNNLKTEDT AMYYCVRHGN FGNSYVSWFA YWGQGTLVTV  600
SADYKDDDDK                                                        610

SEQ ID NO: 58           moltype = AA  length = 594
FEATURE                 Location/Qualifiers
source                  1..594
                        mol_type = protein
                        organism = synthetic construct
SEQUENCE: 58
MGWSCIILFL VATATGVHSQ VQLVQSGAEV KKPGASVKVS CKASGYTFTD YEMHWIRQPP  60
GQGLEWIGAI DPKTGDTAYS QKFKGRVTLT ADKSTSTAYM ELSSLTSEDT AVYYCTRFYS  120
YTYWGQGTLV TVSSASTKGP SVFPLAPSSK STSGGTAALG CLVKDYFPEP VTVSWNSGAL  180
TSGVHTFPAV LQSSGLYSLS SVVTVPSSSL GTQTYICNVN HKPSNTKVDK KVEPKSCDKT  240
```

```
HTCPPCPAPE AAGGPSVFLF PPKPKDTLMI SRTPEVTCVV VDVSHEDPEV KFNWYVDGVE  300
VHNAKTKPRE EQYASTYRVV SVLTVLHQDW LNGKEYKCKV SNKALPAPIE KTISKAKGQP  360
REPQVCTLPP SRDELTKNQV SLWCLVKGFY PSDIAVEWES NGQPENNYKT TPPVLDSDGS  420
FFLYSKLTVD KSRWQQGNVF SCSVMHEALH NHYTQKSLSL SPGGGGSGGG GSGGGGSQAV  480
VTQESALTTS PGETVTLTCR SSTGAVTTSN YANWVQEKPD HLFTGLIGGT NKRAPGVPAR  540
FSGSLIGDKA ALTITGAQTE DEAIYFCALW YSNLWVFGCG TKLTVLHHHH HHHH        594

SEQ ID NO: 59          moltype = AA  length = 704
FEATURE                Location/Qualifiers
source                 1..704
                       mol_type = protein
                       organism = synthetic construct
SEQUENCE: 59
MGWSCIILFL VATATGVHSQ VQLVQSGAEV KKPGASVKVS CKASGYTFTD YEMHWIRQPP  60
GQGLEWIGAI DPKTGDTAYS QKFKGRVTLT ADKSTSTAYM ELSSLTSEDT AVYYCTRFYS  120
YTYWGQGTLV TVSSASTKGP SVFPLAPSSK STSGGTAALG CLVKDYFPEP VTVSWNSGAL  180
TSGVHTFPAV LQSSGLYSLS SVVTVPSSSL GTQTYICNVN HKPSNTKVDK KVEPKSCDKT  240
HTCPPCPAPE AAGGPSVFLF PPKPKDTLMI SRTPEVTCVV VDVSHEDPEV KFNWYVDGVE  300
VHNAKTKPRE EQYASTYRVV SVLTVLHQDW LNGKEYKCKV SNKALPAPIE KTISKAKGQP  360
REPQVYTLPP SRCELTKNQV SLSCAVKGFY PSDIAVEWES NGQPENNYKT TPPVLDSDGS  420
FFLVSKLTVD KSRWQQGNVF SCSVMHEALH NHYTQKSLSL SPGGGGSGGG GSGGGGSEVK  480
LLESGGGLVQ PKGSLKLSCA ASGFTFNTYA MNWVRQAPGK GLEWVARIRS KYNNYATYYA  540
DSVKDRFTIS RDDSQSILYL QMNNLKTEDT AMYYCVRHGN FGNSYVSWFA YWGQGTLVTV  600
SAASTKGPSV FPLAPSSKST SGGTAALGCL VKDYFPEPVT VSWNSGALTS GVHTFPAVLQ  660
SSGLYSLSSV VTVPSSSLGT QTYICNVNHK PSNTKVDKKV EPKS                  704

SEQ ID NO: 60          moltype = AA  length = 692
FEATURE                Location/Qualifiers
source                 1..692
                       mol_type = protein
                       organism = synthetic construct
SEQUENCE: 60
MGWSCIILFL VATATGVHSQ VQLVQSGAEV KKPGASVKVS CKASGYTFTD YEMHWIRQPP  60
GQGLEWIGAI DPKTGDTAYS QKFKGRVTLT ADKSTSTAYM ELSSLTSEDT AVYYCTRFYS  120
YTYWGQGTLV TVSSASTKGP SVFPLAPSSK STSGGTAALG CLVKDYFPEP VTVSWNSGAL  180
TSGVHTFPAV LQSSGLYSLS SVVTVPSSSL GTQTYICNVN HKPSNTKVDK KVEPKSCDKT  240
HTCPPCPAPE AAGGPSVFLF PPKPKDTLMI SRTPEVTCVV VDVSHEDPEV KFNWYVDGVE  300
VHNAKTKPRE EQYASTYRVV SVLTVLHQDW LNGKEYKCKV SNKALPAPIE KTISKAKGQP  360
REPQVCTLPP SRDELTKNQV SLWCLVKGFY PSDIAVEWES NGQPENNYKT TPPVLDSDGS  420
FFLYSKLTVD KSRWQQGNVF SCSVMHEALH NHYTQKSLSL SPGGGGSGGG GSGGGGSQAV  480
VTQESALTTS PGETVTLTCR SSTGAVTTSN YANWVQEKPD HLFTGLIGGT NKRAPGVPAR  540
FSGSLIGDKA ALTITGAQTE DEAIYFCALW YSNLWVFGGG TKLTVLRTVA APSVFIFPPS  600
DEQLKSGTAS VVCLLNNFYP REAKVQWKVD NALQSGNSQE SVTEQDSKDS TYSLSSTLTL  660
SKADYEKHKV YACEVTHQGL SSPVTKSFNR GE                              692

SEQ ID NO: 61          moltype = AA  length = 115
FEATURE                Location/Qualifiers
source                 1..115
                       mol_type = protein
                       organism = synthetic construct
SEQUENCE: 61
QVQLVQSGAE VKKPGASVKV SCKASGYTFT DYEMHWIRQP PGQGLEWIGA IDPKTGDTAY  60
SQKFKGRVTL TADKSTSTAY MELSSLTSED TAVYYCTRFY SYTYWGQGTL VTVSS       115

SEQ ID NO: 62          moltype = AA  length = 219
FEATURE                Location/Qualifiers
source                 1..219
                       mol_type = protein
                       organism = synthetic construct
SEQUENCE: 62
DVVMTQSPLS LPVTPGEPAS ISCRSSQSLV HSNRNTYLHW YLQKPGQSPQ LLIYKVSNRF  60
SGVPDRFSGS GSGTDFTLKI SRVEAEDVGV YYCSQNTHVP PTFGQGTKLE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                        219

SEQ ID NO: 63          moltype = AA  length = 328
FEATURE                Location/Qualifiers
source                 1..328
                       mol_type = protein
                       organism = synthetic construct
SEQUENCE: 63
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEAAGG  120
PSVFLFPPKP KDTLMISRTP EVTCVVVDVS HEDPEVKFNW YVDGVEVHNA KTKPREEQYA  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSP                                    328

SEQ ID NO: 64          moltype = AA  length = 587
```

```
FEATURE                 Location/Qualifiers
source                  1..587
                        mol_type = protein
                        organism = synthetic construct
SEQUENCE: 64
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEAAGG  120
PSVFLFPPKP KDTLMISRTP EVTCVVVDVS HEDPEVKFNW YVDGVEVHNA KTKPREEQYA  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGG GGSGGGGSQA VVTQESALTT SPGETVTLTC  360
RSSTGAVTTS NYANWVQEKP DHLFTGLIGG TNKRAPGVPA RFSGSLIGDK AALTITGAQT  420
EDEAIYFCAL WYSNLWVFGG GTKLTVLGGG GSGGGGSGGG GSEVKLLESG GGLVQPKGSL  480
KLSCAASGFT FNTYAMNWVR QAPGKGLEWV ARIRSKYNNY ATYYADSVKD RFTISRDDSQ  540
SILYLQMNNL KTEDTAMYYC VRHGNFGNSY VSWFAYWGQG TLVTVSA               587

SEQ ID NO: 65           moltype = AA  length = 328
FEATURE                 Location/Qualifiers
source                  1..328
                        mol_type = protein
                        organism = synthetic construct
SEQUENCE: 65
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEAAGG  120
PSVFLFPPKP KDTLMISRTP EVTCVVVDVS HEDPEVKFNW YVDGVEVHNA KTKPREEQYA  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNRYT QESLSLSP                                    328

SEQ ID NO: 66           moltype = AA  length = 587
FEATURE                 Location/Qualifiers
source                  1..587
                        mol_type = protein
                        organism = synthetic construct
SEQUENCE: 66
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEAAGG  120
PSVFLFPPKP KDTLMISRTP EVTCVVVDVS HEDPEVKFNW YVDGVEVHNA KTKPREEQYA  180
STYRVVSVLT VLHQDWLNGK EYKCKVSNKA LPAPIEKTIS KAKGQPREPQ VYTLPPSRKE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGG GGSGGGGSQA VVTQESALTT SPGETVTLTC  360
RSSTGAVTTS NYANWVQEKP DHLFTGLIGG TNKRAPGVPA RFSGSLIGDK AALTITGAQT  420
EDEAIYFCAL WYSNLWVFGG GTKLTVLGGG GSGGGGSGGG GSEVKLLESG GGLVQPKGSL  480
KLSCAASGFT FNTYAMNWVR QAPGKGLEWV ARIRSKYNNY ATYYADSVKD RFTISRDDSQ  540
SILYLQMNNL KTEDTAMYYC VRHGNFGNSY VSWFAYWGQG TLVTVSA               587

SEQ ID NO: 67           moltype = AA  length = 141
FEATURE                 Location/Qualifiers
source                  1..141
                        mol_type = protein
                        organism = Homo sapiens
SEQUENCE: 67
DIQNPDPAVY QLRDSKSSDK SVCLFTDFDS QTNVSQSKDS DVYITDKTVL DMRSMDFKSN  60
SAVAWSNKSD FACANAFNNS IIPEDTFFPS PESSCDVKLV EKSFETDTNL NFQNLSVIGF  120
RILLLKVAGF NLLMTLRLWS S                                           141

SEQ ID NO: 68           moltype = AA  length = 179
FEATURE                 Location/Qualifiers
source                  1..179
                        mol_type = protein
                        organism = Homo sapiens
SEQUENCE: 68
EDLKNVFPPE VAVFEPSEAE ISHTQKATLV CLATGFYPDH VELSWWVNGK EVHSGVSTDP  60
QPLKEQPALN DSRYCLSSRL RVSATFWQNP RNHFRCQVQF YGLSENDEWT QDRAKPVTQI  120
VSAEAWGRAD CGFTSESYQQ GVLSATILYE ILLGKATLYA VLVSALVLMA MVKRKDSRG   179

SEQ ID NO: 69           moltype = AA  length = 173
FEATURE                 Location/Qualifiers
source                  1..173
                        mol_type = protein
                        organism = Homo sapiens
SEQUENCE: 69
DKQLDADVSP KPTIFLPSIA ETKLQKAGTY LCLLEKFFPD VIKIHWQEKK SNTILGSQEG  60
NTMKTNDTYM KFSWLTVPEK SLDKEHRCIV RHENNKNGVD QEIIFPPIKT DVITMDPKDN  120
CSKDANDTLL LQLTNTSAYY MYLLLLLKSV VYFAIITCCL LRRTAFCCNG EKS         173

SEQ ID NO: 70           moltype = AA  length = 204
FEATURE                 Location/Qualifiers
source                  1..204
```

```
                        mol_type = protein
                        organism = Homo sapiens
SEQUENCE: 70
KQLDADVSPK PTIFLPSIAE TKLQKAGTYL CLLEKFFPDI IKIHWQEKKS NTILGSQEGN  60
TMKTNDTYMK FSWLTVPEES LDKEHRCIVR HENNKNGIDQ EIIFPPIKTD VTTVDPKDSY  120
SKDANDVTTV DPKYNYSKDA NDVITMDPKD NWSKDANDTL LLQLTNTSAY YMYLLLLLKS  180
VVYFAIITCC LLGRTAFCCN GEKS                                        204

SEQ ID NO: 71           moltype = AA  length = 177
FEATURE                 Location/Qualifiers
source                  1..177
                        mol_type = protein
                        organism = Homo sapiens
SEQUENCE: 71
PSYTGGYADK LIFGKGTRVT VEPRSQPHTK PSVFVMKNGT NVACLVKEFY PKDIRINLVS  60
SKKITEFDPA IVISPSGKYN AVKLGKYEDS NSVTCSVQHD NKTVHSTDFE VKTDSTDHVK  120
PKETENTKQP SKSCHKPKAI VHTEKVNMMS LTVLGLRMLF AKTVAVNFLL TAKLFFL     177

SEQ ID NO: 72           moltype = AA  length = 19
FEATURE                 Location/Qualifiers
source                  1..19
                        mol_type = protein
                        organism = synthetic construct
SEQUENCE: 72
MGWSCIILFL VATATGVHS                                              19

SEQ ID NO: 73           moltype = AA  length = 466
FEATURE                 Location/Qualifiers
source                  1..466
                        mol_type = protein
                        organism = synthetic construct
SEQUENCE: 73
MGWSCIILFL VATATGVHSQ AVVTQESALT TSPGETVTLT CRSSTGAVTT SNYANWVQEK  60
PDHLFTGLIG GTNKRAPGVP ARFSGSLIGD KAALTITGAQ TEDEAIYFCA LWYSNLWVFG  120
GGTKLTVLSS ASTKGPSVFP LAPSSKSTSG GTAALGCLVK DYFPEPVTVS WNSGALTSGV  180
HTFPAVLQSS GLYSLSSVVT VPSSSLGTQT YICNVNHKPS NTKVDKKVEP KSCDKTHTCP  240
PCPAPEAAGG PSVFLFPPKP KDTLMISRTP EVTCVVVDVS HEDPEVKFNW YVDGVEVHNA  300
KTKPREEQYA STYRVVSVLT VLHQDWLNGK EYKCKVSNKA LPAPIEKTIS KAKGQPREPQ  360
VYTLPPSRCE LTKNQVSLSC AVKGFYPSDI AVEWESNGQP ENNYKTTPPV LDSDGSFFLV  420
SKLTVDKSRW QQGNVFSCSV MHEALHNHYT QKSLSLSPDY KDDDDK                466

SEQ ID NO: 74           moltype = AA  length = 251
FEATURE                 Location/Qualifiers
source                  1..251
                        mol_type = protein
                        organism = synthetic construct
SEQUENCE: 74
MGWSCIILFL VATATGVHSE VKLLESGGGL VQPKGSLKLS CAASGFTFNT YAMNWVRQAP  60
GKGLEWVARI RSKYNNYATY YADSVKDRFT ISRDDSQSIL YLQMNNLKTE DTAMYYCVRH  120
GNFGNSYVSW FAYWGQGTLV TVSAASVAAP SVFIFPPSDE QLKSGTASVV CLLNNFYPRE  180
AKVQWKVDNA LQSGNSQESV TEQDSKDSTY SLSSTLTLSK ADYEKHKVYA CEVTHQGLSS  240
PVTKSFNRGE C                                                      251

SEQ ID NO: 75           moltype = AA  length = 484
FEATURE                 Location/Qualifiers
source                  1..484
                        mol_type = protein
                        organism = synthetic construct
SEQUENCE: 75
MGWSCIILFL VATATGVHSE VKLLESGGGL VQPKGSLKLS CAASGFTFNT YAMNWVRQAP  60
GKGLEWVARI RSKYNNYATY YADSVKDRFT ISRDDSQSIL YLQMNNLKTE DTAMYYCVRH  120
GNFGNSYVSW FAYWGQGTLV TVSAASVAAP SVFIFPPSDE QLKSGTASVV CLLNNFYPRE  180
AKVQWKVDNA LQSGNSQESV TEQDSKDSTY SLSSTLTLSK ADYEKHKVYA CEVTHQGLSS  240
PVTKSFNRGE CDKTHTCPPC PAPEAAGGPS VFLFPPKPKD TLMISRTPEV TCVVVDVSHE  300
DPEVKFNWYV DGVEVHNAKT KPREEQYAST YRVVSVLTVL HQDWLNGKEY KCKVSNKALP  360
APIEKTISKA KGQPREPQVY TLPPSRCELT KNQVSLSCAV KGFYPSDIAV EWESNGQPEN  420
NYKTTPPVLD SDGSFFLVSK LTVDKSRWQQ GNVFSCSVMH EALHNHYTQK SLSLSPDYKD  480
DDDK                                                              484

SEQ ID NO: 76           moltype = AA  length = 233
FEATURE                 Location/Qualifiers
source                  1..233
                        mol_type = protein
                        organism = synthetic construct
SEQUENCE: 76
MGWSCIILFL VATATGVHSQ AVVTQESALT TSPGETVTLT CRSSTGAVTT SNYANWVQEK  60
PDHLFTGLIG GTNKRAPGVP ARFSGSLIGD KAALTITGAQ TEDEAIYFCA LWYSNLWVFG  120
GGTKLTVLSS ASTKGPSVFP LAPSSKSTSG GTAALGCLVK DYFPEPVTVS WNSGALTSGV  180
HTFPAVLQSS GLYSLSSVVT VPSSSLGTQT YICNVNHKPS NTKVDKKVEP KSC         233
```

```
SEQ ID NO: 77          moltype = AA  length = 466
FEATURE                Location/Qualifiers
source                 1..466
                       mol_type = protein
                       organism = synthetic construct
SEQUENCE: 77
MGWSCIILFL VATATGVHSQ TVVTQEPSLT VSPGGTVTLT CGSSTGAVTS GNYPNWVQQK  60
PGQAPRGLIG GTKFLAPGTP ARFSGSLLGG KAALTLSGVQ PEDEAEYYCV LWYSNRWVFG  120
GGTKLTVLSS ASTKGPSVFP LAPSSKSTSG GTAALGCLVK DYFPEPVTVS WNSGALTSGV  180
HTFPAVLQSS GLYSLSSVVT VPSSSLGTQT YICNVNHKPS NTKVDKKVEP KSCDKTHTCP  240
PCPAPEAAGG PSVFLFPPKP KDTLMISRTP EVTCVVVDVS HEDPEVKFNW YVDGVEVHNA  300
KTKPREEQYA STYRVVSVLT VLHQDWLNGK EYKCKVSNKA LPAPIEKTIS KAKGQPREPQ  360
VYTLPPSRCE LTKNQVSLSC AVKGFYPSDI AVEWESNGQP ENNYKTTPPV LDSDGSFFLV  420
SKLTVDKSRW QQGNVFSCSV MHEALHNHYT QKSLSLSPDY KDDDDK                 466

SEQ ID NO: 78          moltype = AA  length = 251
FEATURE                Location/Qualifiers
source                 1..251
                       mol_type = protein
                       organism = synthetic construct
SEQUENCE: 78
MGWSCIILFL VATATGVHSE VQLVESGGGL VQPGGSLKLS CAASGFTFNK YAMNWVRQAP  60
GKGLEWVARI RSKYNNYATY YADSVKDRFT ISRDDSKNTA YLQMNNLKTE DTAVYYCVRH  120
GNFGNSYISY WAYWGQGTLV TVSSASVAAP SVFIFPPSDE QLKSGTASVV CLLNNFYPRE  180
AKVQWKVDNA LQSGNSQESV TEQDSKDSTY SLSSTLTLSK ADYEKHKVYA CEVTHQGLSS  240
PVTKSFNRGE C                                                       251

SEQ ID NO: 79          moltype = AA  length = 475
FEATURE                Location/Qualifiers
source                 1..475
                       mol_type = protein
                       organism = synthetic construct
SEQUENCE: 79
MGWSCIILFL VATATGVHSE VQLLEQSGAE LVRPGTSVKI SCKASGYAFT NYWLGWVKQR  60
PGHGLEWIGD IFPGSGNIHY NEKFKGKATL TADKSSSTAY MQLSSLTFED SAVYFCARLR  120
NWDEPMDYWG QGTTVTVSSA STKGPSVFPL APSSKSTSGG TAALGCLVKD YFPEPVTVSW  180
NSGALTSGVH TFPAVLQSSG LYSLSSVVTV PSSSLGTQTY ICNVNHKPSN TKVDKKVEPK  240
SCDKTHTCPP CPAPEAAGGP SVFLFPPKPK DTLMISRTPE VTCVVVDVSH EDPEVKFNWY  300
VDGVEVHNAK TKPREEQYAS TYRVVSVLTV LHQDWLNGKE YKCKVSNKAL PAPIEKTISK  360
AKGQPREPQV CTLPPSRDEL TKNQVSLWCL VKGFYPSDIA VEWESNGQPE NNYKTTPPVL  420
DSDGSFFLYS KLTVDKSRWQ QGNVFSCSVM HEALHNHYTQ KSLSLSPHHH HHHHH       475

SEQ ID NO: 80          moltype = AA  length = 239
FEATURE                Location/Qualifiers
source                 1..239
                       mol_type = protein
                       organism = synthetic construct
SEQUENCE: 80
MGWSCIILFL VATATGVHSE LVMTQSPSSL TVTAGEKVTM SCKSSQSLLN SGNQKNYLTW  60
YQQKPGQPPK LLIYWASTRE SGVPDRFTGS GSGTDFTLTI SSVQAEDLAV YYCQNDYSYP  120
LTFGAGTKLE IKRTVAAPSV FIFPPSDEQL KSGTASVVCL LNNFYPREAK VQWKVDNALQ  180
SGNSQESVTE QDSKDSTYSL SSTLTLSKAD YEKHKVYACE VTHQGLSSPV TKSFNRGEC   239

SEQ ID NO: 81          moltype = AA  length = 453
FEATURE                Location/Qualifiers
source                 1..453
                       mol_type = protein
                       organism = synthetic construct
SEQUENCE: 81
EVKLLESGGG LVQPKGSLKL SCAASGFTFN TYAMNWVRQA PGKGLEWVAR IRSKYNNYAT  60
YYADSVKDRF TISRDDSQSI LYLQMNNLKT EDTAMYYCVR HGNFGNSYVS WFAYWGQGTL  120
VTVSAASTKG PSVFPLAPSS KSTSGGTAAL GCLVKDYFPE PVTVSWNSGA LTSGVHTFPA  180
VLQSSGLYSL SSVVTVPSSS LGTQTYICNV NHKPSNTKVD KKVEPKSCDK THTCPPCPAP  240
EAAGGPSVFL FPPKPKDTLM ISRTPEVTCV VVDVSHEDPE VKFNWYVDGV EVHNAKTKPR  300
EEQYASTYRV VSVLTVLHQD WLNGKEYKCK VSNKALPAPI EKTISKAKGQ PREPQVYTLP  360
PSRDELTKNQ VSLTCLVKGF YPSDIAVEWE SNGQPENNYK TTPPVLDSDG SFFLYSKLTV  420
DKSRWQQGNV FSCSVMHEAL HNHYTQKSLS LSP                               453

SEQ ID NO: 82          moltype = AA  length = 216
FEATURE                Location/Qualifiers
source                 1..216
                       mol_type = protein
                       organism = synthetic construct
SEQUENCE: 82
QAVVTQESAL TTSPGETVTL TCRSSTGAVT TSNYANWVQE KPDHLFTGLI GGTNKRAPGV  60
PARFSGSLIG DKAALTITGA QTEDEAIYFC ALWYSNLWVF GGGTKLTVLR TVAAPSVFIF  120
PPSDEQLKSG TASVVCLLNN FYPREAKVQW KVDNALQSGN SQESVTEQDS KDSTYSLSST  180
LTLSKADYEK HKVYACEVTH QGLSSPVTKS FNRGEC                            216
```

```
SEQ ID NO: 83          moltype = AA  length = 443
FEATURE                Location/Qualifiers
source                 1..443
                       mol_type = protein
                       organism = synthetic construct
SEQUENCE: 83
QVQLVQSGAE VKKPGASVKV SCKASGYTFT DYEMHWIRQP PGQGLEWIGA IDPKTGDTAY  60
SQKFKGRVTL TADKSTSTAY MELSSLTSED TAVYYCTRFY SYTYWGQGTL VTVSSASTKG  120
PSVFPLAPSS KSTSGGTAAL GCLVKDYFPE PVTVSWNSGA LTSGVHTFPA VLQSSGLYSL  180
SSVVTVPSSS LGTQTYICNV NHKPSNTKVD KKVEPKSCDK THTCPPCPAP EAAGGPSVFL  240
FPPKPKDTLM ISRTPEVTCV VVDVSHEDPE VKFNWYVDGV EVHNAKTKPR EEQYASTYRV  300
VSVLTVLHQD WLNGKEYKCK VSNKALPAPI EKTISKAKGQ PREPQVYTLP PSRDELTKNQ  360
VSLTCLVKGF YPSDIAVEWE SNGQPENNYK TTPPVLDSDG SFFLYSKLTV DKSRWQQGNV  420
FSCSVMHEAL HNHYTQKSLS LSP                                         443

SEQ ID NO: 84          moltype = AA  length = 219
FEATURE                Location/Qualifiers
source                 1..219
                       mol_type = protein
                       organism = synthetic construct
SEQUENCE: 84
DIVMTQSPLS LPVTPGEPAS ISCRSSQSLV HSNRNTYLHW YQQKPGQAPR LLIYKVSNRF  60
SGVPDRFSGS GSGTDFTLKI SRVEAEDVGV YYCSQNTHVP PTFGQGTKLE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                        219

SEQ ID NO: 85          moltype = AA  length = 453
FEATURE                Location/Qualifiers
source                 1..453
                       mol_type = protein
                       organism = synthetic construct
SEQUENCE: 85
EVKLLESGGG LVQPKGSLKL SCAASGFTFN TYAMNWVRQA PGKGLEWVAR IRSKYNNYAT  60
YYADSVKDRF TISRDDSQSI LYLQMNNLKT EDTAMYYCVR HGNFGNSYVS WFAYWGQGTL  120
VTVSAASTKG PSVFPLAPSS KSTSGGTAAL GCLVKDYFPE PVTVSWNSGA LTSGVHTFPA  180
VLKSSGLYSL SSVVTVPSSS LGTQTYICNV NHKPSNTKVD KKVEPKSCDK THTCPPCPAP  240
EAAGGPSVFL FPPKPKDTLM ISRTPEVTCV VVDVSHEDPE VKFNWYVDGV EVHNAKTKPR  300
EEQYASTYRV VSVLTVLHQD WLNGKEYKCK VSNKALPAPI EKTISKAKGQ PREPQVYTLP  360
PSRCELTKNQ VSLSCAVKGF YPSDIAVEWE SNGQPENNYK TTPPVLDSDG SFFLVSKLTV  420
DKSRWQQGNV FSCSVMHEAL HNHYTQKSLS LSP                              453

SEQ ID NO: 86          moltype = AA  length = 216
FEATURE                Location/Qualifiers
source                 1..216
                       mol_type = protein
                       organism = synthetic construct
SEQUENCE: 86
QAVVTQESAL TTSPGETVTL TCRSSTGAVT TSNYANWVQE KPDHLFTGLI GGTNKRAPGV  60
PARFSGSLIG DKAALTITGA QTEDEAIYFC ALWYSNLWVF GGGTKLTVLR TVAAPSVFIF  120
PPSDEQLKSG TAEVVCLLNN FYPREAKVQW KVDNALQSGN SEESVTEQDS KDSTYSLSST  180
LELSKADYEK HKVYACEVTH QGLSSPVTKS FNRGEC                           216

SEQ ID NO: 87          moltype = AA  length = 443
FEATURE                Location/Qualifiers
source                 1..443
                       mol_type = protein
                       organism = synthetic construct
SEQUENCE: 87
QVQLVQSGAE VKKPGASVKV SCKASGYTFT DYEMHWIRQP PGQGLEWIGA IDPKTGDTAY  60
SQKFKGRVTL TADKSTSTAY MELSSLTSED TAVYYCTRFY SYTYWGQGTL VTVSSASTKG  120
PSVFPLAPSS KSTSGGTAAL GCLVEDYFPE PVTVSWNSGA LTSGVHTFPA VLESSGLYSL  180
SSVVTVPSSS LGTQTYICNV NHKPSNTKVD KKVEPKSCDK THTCPPCPAP EAAGGPSVFL  240
FPPKPKDTLM ISRTPEVTCV VVDVSHEDPE VKFNWYVDGV EVHNAKTKPR EEQYASTYRV  300
VSVLTVLHQD WLNGKEYKCK VSNKALPAPI EKTISKAKGQ PREPQVCTLP PSRDELTKNQ  360
VSLWCLVKGF YPSDIAVEWE SNGQPENNYK TTPPVLDSDG SFFLYSKLTV DKSRWQQGNV  420
FSCSVMHEAL HNHYTQKSLS LSP                                         443

SEQ ID NO: 88          moltype = AA  length = 443
FEATURE                Location/Qualifiers
source                 1..443
                       mol_type = protein
                       organism = synthetic construct
SEQUENCE: 88
QVQLVQSGAE VKKPGASVKV SCKASGYTFT DYEMHWIRQP PGQGLEWIGA IDPKTGDTAY  60
SQKFKGRVTL TADKSTSTAY MELSSLTSED TAVYYCTRFY SYTYWGQGTL VTVSSASTKG  120
PSVFPLAPSS KSTSGGTAAL GCLVEDYFPE PVTVSWNSGA LTSGVHTFPA VLESSGLYSL  180
SSVVTVPSSS LGTQTYICNV NHKPSNTKVD EKVEPKSCDK THTCPPCPAP EAAGGPSVFL  240
FPPKPKDTLM ISRTPEVTCV VVDVSHEDPE VKFNWYVDGV EVHNAKTKPR EEQYASTYRV  300
```

```
VSVLTVLHQD WLNGKEYKCK VSNKALPAPI EKTISKAKGQ PREPQVCTLP PSRDELTKNQ  360
VSLWCLVKGF YPSDIAVEWE SNGQPENNYK TTPPVLDSDG SFFLYSKLTV DKSRWQQGNV  420
FSCSVMHEAL HNHYTQKSLS LSP                                          443

SEQ ID NO: 89          moltype = AA  length = 219
FEATURE                Location/Qualifiers
source                 1..219
                       mol_type = protein
                       organism = synthetic construct
SEQUENCE: 89
DIVMTQSPLS LPVTPGEPAS ISCRSSQSLV HSNRNTYLHW YQQKPGQAPR LLIYKVSNRF  60
SGVPDRFSGS GSGTDFTLKI SRVEAEDVGV YYCSQNTHVP PTFGQGTKLE IKRTVAAPSV  120
FIFPPSDEQL KSGTAKVVCL LNNFYPREAK VQWKVDNALQ SGNSKESVTE QDSKDSTYSL  180
SSTLKLSKAD YEKHKVYACE VTHQGLSSPV TKSFNRGEC                         219

SEQ ID NO: 90          moltype = AA  length = 219
FEATURE                Location/Qualifiers
source                 1..219
                       mol_type = protein
                       organism = synthetic construct
SEQUENCE: 90
DIVMTQSPLS LPVTPGEPAS ISCRSSQSLV HSNRNTYLHW YQQKPGQAPR LLIYKVSNRF  60
SGVPDRFSGS GSGTDFTLKI SRVEAEDVGV YYCSQNTHVP PTFGQGTKLE IKRTVAAPSV  120
FIFPPSDKQL KSGTAKVVCL LNNFYPREAK VQWKVDNALQ SGNSKESVTE QDSKDSTYSL  180
SSTLKLSKAD YEKHKVYACE VTHQGLSSPV TKSFNRGEC                         219

SEQ ID NO: 91          moltype = AA  length = 474
FEATURE                Location/Qualifiers
source                 1..474
                       mol_type = protein
                       organism = synthetic construct
SEQUENCE: 91
MGWSCIILFL VATATGVHSQ VQLKQSGPGL VQPSQSLSIT CTVSGFSLTN YGVHWVRQSP  60
GKGLEWLGVI WSGGNTDYNT PFTSRLSINK DNSKSQVFFK MNSLQSNDTA IYYCARALTY  120
YDYEFAYWGQ GTLVTVSAAS TKGPSVFPLA PSSKSTSGGT AALGCLVKDY FPEPVTVSWN  180
SGALTSGVHT FPAVLQSSGL YSLSSVVTVP SSSLGTQTYI CNVNHKPSNT KVDKKVEPKS  240
CDKTHTCPPC PAPEAAGGPS VFLFPPKPKD TLMISRTPEV TCVVVDVSHE DPEVKFNWYV  300
DGVEVHNAKT KPREEQYAST YRVVSVLTVL HQDWLNGKEY KCKVSNKALP APIEKTISKA  360
KGQPREPQVC TLPPSRDELT KNQVSLWCLV KGFYPSDIAV EWESNGQPEN NYKTTPPVLD  420
SDGSFFLYSK LTVDKSRWQQ GNVFSCSVMH EALHNHYTQK SLSLSPHHHH HHHH        474

SEQ ID NO: 92          moltype = AA  length = 233
FEATURE                Location/Qualifiers
source                 1..233
                       mol_type = protein
                       organism = synthetic construct
SEQUENCE: 92
MGWSCIILFL VATATGVHSD ILLTQSPVIL SVSPGERVSF SCRASQSIGT NIHWYQQRTN  60
GSPRLLIKYA SESISGIPSR FSGSGSGTDF TLSINSVESE DIADYYCQQN NNWPTTFGAG  120
TKLELKRTVA APSVFIFPPS DEQLKSGTAS VVCLLNNFYP REAKVQWKVD NALQSGNSQE  180
SVTEQDSKDS TYSLSSTLTL SKADYEKHKV YACEVTHQGL SSPVTKSFNR GEC          233
```